United States Patent
Metcalf et al.

(10) Patent No.: US 10,100,043 B2
(45) Date of Patent: Oct. 16, 2018

(54) SUBSTITUTED ALDEHYDE COMPOUNDS AND METHODS FOR THEIR USE IN INCREASING TISSUE OXYGENATION

(71) Applicants: Global Blood Therapeutics, Inc., South San Francisco, CA (US); CYTOKINETICS, INC., South San Francisco, CA (US)

(72) Inventors: Brian Metcalf, South San Francisco, CA (US); Chihyuan Chuang, Millbrae, CA (US); Zhe Li, South San Francisco, CA (US)

(73) Assignees: Global Blood Therapeutics, Inc., South San Francisco, CA (US); Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 14/776,723

(22) PCT Filed: Mar. 14, 2014

(86) PCT No.: PCT/US2014/029682
§ 371 (c)(1),
(2) Date: Sep. 14, 2015

(87) PCT Pub. No.: WO2014/145040
PCT Pub. Date: Sep. 18, 2014

(65) Prior Publication Data
US 2016/0039801 A1    Feb. 11, 2016

Related U.S. Application Data
(60) Provisional application No. 61/799,120, filed on Mar. 15, 2013.

(51) Int. Cl.
| | | |
|---|---|---|
| C07C 47/575 | (2006.01) | |
| C07D 213/63 | (2006.01) | |
| A61K 31/05 | (2006.01) | |
| A61K 31/055 | (2006.01) | |
| A61K 31/11 | (2006.01) | |
| A61K 31/4402 | (2006.01) | |
| A61K 31/4406 | (2006.01) | |
| A61K 31/4409 | (2006.01) | |
| A61K 31/4427 | (2006.01) | |
| C07D 405/14 | (2006.01) | |
| C07D 413/14 | (2006.01) | |
| C07D 231/12 | (2006.01) | |
| C07D 233/60 | (2006.01) | |
| C07D 401/12 | (2006.01) | |

(Continued)

(52) U.S. Cl.
CPC .......... *C07D 405/14* (2013.01); *C07C 47/565* (2013.01); *C07C 47/575* (2013.01); *C07C 62/36* (2013.01); *C07C 69/757* (2013.01); *C07D 213/61* (2013.01); *C07D 213/63* (2013.01); *C07D 213/64* (2013.01); *C07D 213/65* (2013.01); *C07D 213/69* (2013.01); *C07D 231/12* (2013.01); *C07D 233/60* (2013.01); *C07D 233/64* (2013.01); *C07D 401/12* (2013.01); *C07D 405/04* (2013.01); *C07D 413/14* (2013.01); C07C 2601/14 (2017.05); C07C 2601/16 (2017.05)

(58) Field of Classification Search
CPC .............. C07C 47/575; C07C 2101/16; C07C 2101/14; A61K 31/05; A61K 31/055; A61K 31/11; A61K 31/4402; A61K 31/4406; A61K 31/4409; A61K 31/4427; C07D 213/63
USPC ........... 560/67; 568/442; 514/570, 699, 350; 546/298
See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |

(Continued)

FOREIGN PATENT DOCUMENTS

| | | |
|---|---|---|
| CA | 2720096 | 10/2009 |
| CN | 101113148 | 1/2008 |

(Continued)

OTHER PUBLICATIONS

Yang et al. "Structural requirement of chalcones for the inhibitory activity of interleukin-5" Bioorg. & Med. Chem (2007), 15: pp. 104-111.*

(Continued)

*Primary Examiner* — Matthew P Coughlin
*Assistant Examiner* — Sagar Patel
(74) *Attorney, Agent, or Firm* — Sheppard Mullin Richter & Hampton LLP

(57) ABSTRACT

Provided are cycloalkyl- and cycloalkenyl-substituted benzaldehydes and heteroaldehydes of formula (I) that act as allosteric modulators of hemoglobin, methods and intermediates for their preparation, pharmaceutical compositions containing the modulators, and methods for their use in treating disorders mediated by hemoglobin and disorders that would benefit from increased tissue oxygenation.

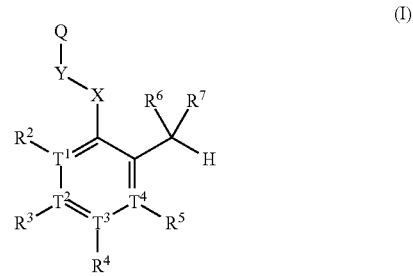

(I)

26 Claims, No Drawings

(51) Int. Cl.

| | |
|---|---|
| C07D 405/04 | (2006.01) |
| C07C 47/565 | (2006.01) |
| C07D 213/61 | (2006.01) |
| C07D 213/65 | (2006.01) |
| C07D 213/69 | (2006.01) |
| C07C 62/36 | (2006.01) |
| C07C 69/757 | (2006.01) |
| C07D 213/64 | (2006.01) |
| C07D 233/64 | (2006.01) |

(56) References Cited

U.S. PATENT DOCUMENTS

| | | |
|---|---|---|
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Balani |
| 5,266,582 A | 11/1993 | De Nanteuil et al. |
| 5,290,941 A | 3/1994 | Volante et al. |
| 5,403,816 A | 4/1995 | Takabe et al. |
| 5,521,202 A | 5/1996 | Yano et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 10/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,593,472 B2 | 7/2003 | Hoffman et al. |
| 6,608,076 B1 | 8/2003 | Greenwald et al. |
| 6,627,646 B2 | 9/2003 | Bakale |
| 6,630,496 B1 | 10/2003 | Seehra et al. |
| 7,160,910 B2 | 1/2007 | Safo et al. |
| 7,411,083 B2 | 8/2008 | Gopalsamy et al. |
| 8,846,694 B2 | 9/2014 | Heinrich et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,248,199 B2 | 2/2016 | Metcalf et al. |
| 9,422,279 B2 | 8/2016 | Metcalf et al. |
| 9,447,071 B2 | 9/2016 | Li et al. |
| 9,458,139 B2 | 10/2016 | Xu et al. |
| 9,604,999 B2 | 3/2017 | Harris et al. |
| 9,776,960 B2 | 10/2017 | Xu et al. |
| 9,802,900 B2 | 10/2017 | Li et al. |
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1* | 9/2003 | Lee ............ C09K 11/06 428/690 |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann |
| 2009/0163512 A1 | 6/2009 | Chen et al. |
| 2009/0312315 A1 | 12/2009 | Yamaguchi et al. |
| 2010/0204235 A1 | 8/2010 | Lizos et al. |
| 2010/0210651 A1 | 8/2010 | Hernandez et al. |
| 2010/0311748 A1 | 12/2010 | Dakin et al. |
| 2012/0220569 A1 | 8/2012 | Ohashi et al. |
| 2012/0245344 A1 | 9/2012 | Endo et al. |
| 2013/0045251 A1 | 2/2013 | Cen et al. |
| 2013/0072472 A1 | 3/2013 | Gless et al. |
| 2013/0190315 A1 | 7/2013 | Metcalf et al. |
| 2013/0190316 A1 | 7/2013 | Metcalf et al. |
| 2013/0190375 A1 | 7/2013 | Dunkel et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0259296 A1 | 9/2015 | Li et al. |
| 2015/0336908 A1 | 11/2015 | Shioda et al. |
| 2015/0344472 A1 | 12/2015 | Metcalf et al. |
| 2015/0344483 A1 | 12/2015 | Metcalf et al. |
| 2016/0024127 A1* | 1/2016 | Harris ............ C07F 9/65583 514/89 |
| 2016/0031865 A1 | 2/2016 | Li et al. |
| 2016/0031904 A1 | 2/2016 | Li et al. |
| 2016/0038474 A1 | 2/2016 | Sinha et al. |
| 2016/0046613 A1 | 2/2016 | Metcalf et al. |
| 2016/0083343 A1 | 3/2016 | Xu et al. |
| 2016/0303099 A1 | 3/2016 | Dufu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0332984 A1 | 11/2016 | Metcalf et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0327484 A1 | 11/2017 | Li et al. |

FOREIGN PATENT DOCUMENTS

| | | |
|---|---|---|
| CN | 102116772 | 7/2011 |
| DE | 2238734 | 2/1973 |
| DE | 2238628 | 3/1973 |
| DE | 2853765 | 6/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| EP | 010063 | 4/1980 |
| EP | 0054924 | 6/1982 |
| EP | 236140 | 9/1987 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0365328 | 4/1990 |
| EP | 0401517 | 12/1990 |

(56) References Cited

FOREIGN PATENT DOCUMENTS

| | | |
|---|---|---|
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0632036 | 1/1995 |
| EP | 0637586 | 2/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| FR | 2217016 | 9/1974 |
| FR | 2909379 | 6/2008 |
| GB | 1409865 | 10/1975 |
| GB | 1593417 | 7/1981 |
| IL | 64573 | 4/1985 |
| JP | 57-145844 | 6/1905 |
| JP | 59029667 | 2/1984 |
| JP | 61-040236 | 2/1986 |
| JP | 63230687 | 9/1988 |
| JP | S-63258463 | 10/1988 |
| JP | 01190688 | 7/1989 |
| JP | 06-041118 | 2/1994 |
| JP | 07-025882 | 1/1995 |
| JP | 2002-523469 | 7/2002 |
| JP | 2002-528537 | 9/2002 |
| JP | 2003-075970 | 3/2003 |
| JP | 2003-513060 | 4/2003 |
| JP | 2006-342115 | 12/2006 |
| JP | 2009-203230 | 9/2009 |
| WO | WO-91/19697 | 12/1991 |
| WO | WO-1992/02503 | 2/1992 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO-97/41120 | 11/1997 |
| WO | WO-97/44306 | 11/1997 |
| WO | WO-98/08818 | 3/1998 |
| WO | WO-98/21199 | 5/1998 |
| WO | WO-99/29694 | 6/1999 |
| WO | WO-99/43672 | 9/1999 |
| WO | WO-99/48490 | 9/1999 |
| WO | WO-1999/047529 | 9/1999 |
| WO | WO-99/59978 | 11/1999 |
| WO | WO-99/62908 | 12/1999 |
| WO | WO-00/12121 | 3/2000 |
| WO | WO-00/26202 | 5/2000 |
| WO | WO-00/35858 | 6/2000 |
| WO | WO-00/40564 | 7/2000 |
| WO | WO-00/71123 A1 | 11/2000 |
| WO | WO-00/75145 | 12/2000 |
| WO | WO-00/78746 | 12/2000 |
| WO | WO-01/00612 | 1/2001 |
| WO | WO-01/19823 | 3/2001 |
| WO | WO-01/23383 | 4/2001 |
| WO | WO-01/32596 | 5/2001 |
| WO | WO-01/36375 | 5/2001 |
| WO | WO-01/57006 | 8/2001 |
| WO | WO-01/57044 | 8/2001 |
| WO | WO-01/62705 | 8/2001 |
| WO | WO-01/70663 | 9/2001 |
| WO | WO-02/00622 | 1/2002 |
| WO | WO-02/12235 | 2/2002 |
| WO | WO-02/24635 | 3/2002 |
| WO | WO-02/24679 | 3/2002 |
| WO | WO-02/051849 | 7/2002 |
| WO | WO-02/053547 | 7/2002 |
| WO | WO-03/051366 | 6/2003 |
| WO | WO-03/053368 | 7/2003 |
| WO | WO-2003/101959 | 12/2003 |
| WO | WO-2004/014899 | 2/2004 |
| WO | WO-2004/018430 | 3/2004 |
| WO | WO-2004/024705 | 3/2004 |
| WO | WO-2004/050030 | 6/2004 |
| WO | WO-2004/056727 | 7/2004 |
| WO | WO-2004/058790 | 7/2004 |
| WO | WO-2004/087075 | 10/2004 |
| WO | WO-2004/111031 | 12/2004 |
| WO | WO-2005/047249 | 5/2005 |
| WO | WO-2005/074513 | 8/2005 |
| WO | WO-2005/077932 | 8/2005 |
| WO | WO-2005/086951 | 9/2005 |
| WO | WO-2005/087766 | 9/2005 |
| WO | WO-2005/096337 | 10/2005 |
| WO | WO-2006/011469 | 2/2006 |
| WO | WO-2006/065204 | 6/2006 |
| WO | WO-2006/088173 | 8/2006 |
| WO | WO-2006/103463 | 10/2006 |
| WO | WO-2006/106711 | 10/2006 |
| WO | WO-2006/116764 | 11/2006 |
| WO | WO-2006/003923 | 12/2006 |
| WO | WO-2007/003962 | 1/2007 |
| WO | WO-2007/009389 | 1/2007 |
| WO | WO-2007/017267 | 2/2007 |
| WO | WO-2007/047204 | 4/2007 |
| WO | WO-2007/049675 | 5/2007 |
| WO | WO-2007/061923 | 5/2007 |
| WO | WO-2007/084914 | 7/2007 |
| WO | WO-2007/117180 | 10/2007 |
| WO | WO-2008/013414 | 1/2008 |
| WO | WO-2008/016132 | 2/2008 |
| WO | WO-2008/029200 | 3/2008 |
| WO | WO-2008/041118 | 4/2008 |
| WO | WO-2008/051532 | 5/2008 |
| WO | WO-2008/060391 | 5/2008 |
| WO | WO-2008/066145 | 6/2008 |
| WO | WO-2008/081096 | 7/2008 |
| WO | WO-2008/101682 | 8/2008 |
| WO | WO-2008/116620 | 10/2008 |
| WO | WO-2009/001214 | 12/2008 |
| WO | WO-2009/011850 | 1/2009 |
| WO | WO-2009/050183 | 4/2009 |
| WO | WO-2009/125606 | 10/2009 |
| WO | WO-2009/128537 | 10/2009 |
| WO | WO-2009/130560 | 10/2009 |
| WO | WO-2009/136889 | 11/2009 |
| WO | WO-2009/146555 | 12/2009 |
| WO | WO-2010/031589 | 3/2010 |
| WO | WO-2010/056631 | 5/2010 |
| WO | WO-2010/129055 | 11/2010 |
| WO | WO-2011/033045 | 3/2011 |
| WO | WO-2011/088201 | 7/2011 |
| WO | WO-2011/136459 | 11/2011 |
| WO | WO-2012/020060 | 2/2012 |
| WO | WO-2012/138981 | 10/2012 |
| WO | WO-2012/141228 | 10/2012 |
| WO | WO-2013/052803 | 4/2013 |
| WO | WO-2013/102142 | 7/2013 |
| WO | WO-2013/102145 | 7/2013 |
| WO | WO-2014/104384 | 7/2014 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO-2015/031284 | 3/2015 |
| WO | WO-2015/031285 | 3/2015 |

OTHER PUBLICATIONS

STN Registry database entry: CAS RN 1039927-57-5 (Entered STN: Aug. 20, 2008).*
STN Registry database entry: CAS RN 1243541-58-3 (Entered STN: Sep. 29, 2010).*
Abdulmalik et al., "Sickle Cell Disease: Current Therapeutic Approaches", Expert Opinion on Therapeutic Patents, vol. 15, No. 11, 2005, pp. 1497-1506.

(56) References Cited

OTHER PUBLICATIONS

Abraham et al., "Vanillin, a potential agent for the treatment of Sickle Cell Anemia", Blood, American Society of Hematology, vol. 77, No. 6, 1991, pp. 1334-1341.
Cherian et al., "Structure-Activity Relationships of Antitubercular Nitroimidazoles. 3. Exploration of the Linker and Lipophilic Tail of ((S)-2-Nitro-6,7-dihydro-5 H-imidazo [2,1-b] [1,3]oxazin-6-yl)-(4-trifluoromethoxybenzyl)amine (6-Amino PA-824)", Journal of Medicinal Chemistry, vol. 54, No. 16, August, pp. 5639-5659.
Database CA [Online] Chemical Abstracts Service, Columbus, Ohio, US; Li, Zhuorong et al: "Substituted-benzoheterocycle derivatives, preparation, and application for preparation of antiviral or antineoplastic drugs", XP002726578, retrieved from STN Database accession No. 2013:366779 abstract RN: 1427163-92-5 & CN 102 952 062 A (Institute of Medicinal Biotechnology, Chinese Academy of Medical Scien) Mar. 6, 2013 (Mar. 6, 2013).
International Search Report and Written Opinion for PCT/US2014/029682 dated Jul. 30, 2014, 16 pages.
Marchetti et al., "Synthesis and biological evaluation of 5-substituted 04-alkylpyrimidines as CDK2 inhibitors", Organic & Biomolecular Chemistry, vol. 8, No. 10, 2010, p. 2397.
Mesguiche et al., "4-Alkoxy-2,6-diaminopyrimidine Derivatives: Inhibitors of cyclin dependent kinases 1 and 2", Bioorganic & Medicinal Chemistry Letters, vol. 13, 2003, pp. 217-222.
U.S. Appl. No. 61/581,053, filed Dec. 28, 2011, Metcalf et al.
U.S. Appl. No. 61/661,320, filed Jun. 18, 2012, Metcalf et al.
Abdulmalik et al., "Crystallographic analysis of human hemoglobin elucidates the structural basis of the potent and dual antisickling activity of pyridyl derivatives of vanillin", Acta Cryst. 2011, D67, 920-928.
Adhikary, P.K., et al., "A new antisickling agent: In vitro studies of its effect on S/S erythrocytes and on hemoglobin S", Experientia. 1978, vol. 34, No. 6, pp. 804-806.
Appendix A provided with Israel office action dated Aug. 11, 2016 for IL 233329.
Arya R, et al. "Tucaresol increases oxygen affinity and reduces haemolysis in subjects with sickle cell anaemia," Br. J. Haematol., 93(4):817-21 (1996).
Australian Examination Report dated Nov. 7, 2016 for AU 2016203755.
Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.
Bacsa et al., "Novel products from Baylis-Hillman reactions of salicylaldehydes", South African Journal of Chemistry (1998), 51(1), 47-54 CODEN: SAJCDG; ISSN: 0379-4350.
Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.
Ballet et al., Novel selective human melanocortin-3 receptor ligands: Use of the 4-amino-1,2,4,5-tetrahydro-2-benzazepin-3-one (Aba) scaffold, Bioorganic & Medicinal Chemistry Letters (2007), 17(9), 2492-2498 CODEN: BMCLES; ISSN: 0960-894X.
Barnes, et al., "Prospects for new drugs for chronic obstructive pulmonary disease." The Lancet, 2004, 364, 985-996.
Barnes. "COPD: is there light at the end of the tunnel?" Current Opinion in Pharmacology, 2004, 4:263-272.
Baxter et al., "Reductive aminations of carbonyl compounds with borohydride and borane reducing agents", Organic Reactions (Hoboken, NJ, United States) (2002), 59, No pp. given bin/mrwhome/107610747/HOME.
Beaumont et al., Design of ester prodrugs to enhance oral absorption of poorly permeable compounds: challenges to the discovery scientist. Curr. Drug Metab. 2003, 4:461-85.
Beddell, Substituted benzaldehydes designed to increase the oxygen affinity of human haemoglobin and inhibit the sickling of sickle erythrocycles, Br. J. Pharmac., 82:397-407, 1984.
Beena et al., "Synthesis and antibacterial activity evaluation of metronidazole-triazole conjugates", Bioorganic & Medicinal Chemistry Letters, 2009, 19(5):1396-1398.
Berge et al., "Pharmaceutical Salts", Journal of Pharmaceutical Science, 1977, 66:1-19.
Bernstein. Crystals in Supramolecular Chemistry. ACA Transactions. 2004; 39:1-14.
Bernstein. Polymorphism in Molecular Crystals. Clarendon Press, Oxford. 2002. 115-118, 272.
Bode et al.,"Novel synthesis and x-ray crystal structure of a coumarin derivative", South African Journal of Chemistry (1992), 45(1), 25-7 CODEN: SAJCDG; ISSN:0379-4350.
Bonaventura, et al., "Molecular Controls of the Oxygenation and Redox Reactions of Hemoglobin." Antioxidants & Redox Signaling, 18(17), 2013, 2298-2313.
Bradbury et al., "New nonpeptide angiotensin II receptor antagonists", Journal of Medicinal Chemistry, 1993, vol. 36, pp. 1245-1254.
Braga, et al. Making crystals from crystals: a green route to crystal engineering and polymorphism. Chem Commun (Camb). Aug. 7, 2005;(29):3635-45. Epub Jun. 15, 2005.
Britton et al., "Structure-activity relationships of a series of benzothlophens-derived NPY Y1 antagonists: optimization of the C-2 side chain". Bioorganic & Medicinal Chemistry Letters (1999), 9(3), 475-480 CODEN:BMCLE8;ISSN: 0960-894X.
Brown et al., "1,2-Dihydroisoquinollnes. III, Dimerization", Tetrahedron (1966), 22(8), 2437-43 CODEN: TETRAB; ISSN;0040-4020.
Caira. Crystalline Polymorphism of Organic Compounds. Topics in Current Chemistry, Springer, Berlin, DE. 1998; 198:163-208.
CAS Registry No. 1039841-20-7; entry dated Aug. 10, 2008.
CAS Registry No. 1096911-11-3; entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 631858-40-7; entry dated Dec. 29, 2003.
Chemical Abstract Registry No. 1142191-55-6, indexed in the Registry File on STN CA Online May 4, 2009.
Ciganek, "The catalyzed a-hydroxyalkylation and a-aminoalkylation of activated olefins (the Morita-Baylis-Hillman reaction", Organic Reactions (Hoboken, NJ, United States) (1997), 51, No pp given CODEN:ORHNBA URL:http://www3.Interscience.wiley.com/cgi-bin/mnwhome/107610747/HOME.
CMU Pharmaceutical polymorphism, internet p. 1-3 (2002) printout Apr. 3, 2008.
Concise Encyclopedia Chemistry, NY: Walter de Gruyter, 1993, 872-873.
Congreve et al. Application of Fragment Screening by X-ray Crystallography to the Discovery of Aminopyridines as Inhibitors of Beta-Secretase. J. Med. Chem. 50:1124-1132 (2007).
Cos et al., "Structure-Activity Relationship and Classification of Flavonoids as Inhibitors of Xanthine Oxidase and Superoxide Scavengers," J. Nat. Prod., (1998), 61:71-76.
Database Pubchem Compound Dec. 4, 2011 XP 003033770 (11 pages).
Davidovich, et al. Detection of polymorphism by powder x-ray diffraction: interference by preferred orientation. Am. Pharm. Rev. 2004; 10, 12, 14, 16, 100.
Dean. Analytical Chemistry Handbook. University of Tennese, Knoxville. McGraw-Hill, Inc. 1995; 10.24-10.26.
Deem. "Red Blood Cells and Hemoglobin in Hypoxic Pulmonary Vasoconstriction" Advances in experimental medicine and biology, (2006) 588, 217-231.
Desai et al. Preparation of N-[ro-(4-aryl-1-piperazinyl)ethyl/propyl]-3-hydroxyphthalimidines. Indian Journal of Chemistry. 39:455-457 (2000).
Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.
Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).

(56) References Cited

OTHER PUBLICATIONS

Ding et al., "Crystal structure of bis[μ2-2-(2-formylphenoxy)acetato-O,O]-bis[μ2-2-2-formylphynoxy)acetato-O,O]-octakis(n-butyl)tetratin(IV), Sn4O2(C9H7O4)4(C4H9)8", Zeitschrift fuer Kristallographie—New Crystal Structures (2011), 226(1), 31-32 CODEN:ZKNSFT; ISSN: 1433-7266.

Doelker, English translation of S.T.P, Pratiques (1999), 9(5), 399-409.

Doelker. English translation of Ann. Pharm. Fr., 2002, 60: 161-176. Einfalt, et al. Methods of amorphization and investigation of the amorphous state. Acta Pharm. 2013; 63:305-334.

Elwahy, "Synthesis of new benzo-substituted macrocyclic containing quinoxaline subunits" Tetrahedron (2000), 56(6), 897-907 CODEN:TETRAB; ISSN:0040-4020.

Epsztajn et al., "Application of organolithium", Tetrahedron, Elsevier Science Publishers, Amsterdam, NL, 1991, vol. 47, No. 9, pp. 1697-1706.

European Search Report and Search Opinion dated Aug. 4, 2015 for EP Application No. 12862525.8. 9 pages.

European Search Report and Search Opinion dated Jul. 21, 2016 for EP Application No. 14769616.5. 8 pages.

European Search Report and Search Opinion dated May 28, 2015 for EP Application No. 12862096.0. 13 pages.

European Search Report and Search Opinion dated Nov. 16, 2016 for EP Application No. 16194019.2. 13 pages.

European Search Report and Search Opinion dated Sep. 26, 2016 for EP Application No. 14768759.4. 6 pages.

Extended European Search Report and opinion dated Jul. 20, 2016 for EP Application No. 14768414.6. 10 pages.

Extended European Search Report and Search Opinion dated Jul. 18, 2016 for EP Application No. 14770695.6. 13 pages.

Extended European Search Report and Search Opinion dated Jul. 7, 2016 for EP Application No. 14768317.1. 7 pages.

Extended European Search Report and Search Opinion dated May 17, 2017 for EP Application No. 15746995.8. 8 pages.

Extended European Search Report and Search Opinion dated Nov. 23, 2015 for EP Application No. 12862525.8. 16 pages.

Gadaginamath, et al., "Synthesis and antibacterial activity of novel 1-butyl-2-phenoxyl2-phenylthlol2-aminomethyl-5-methoxyindole derivatives", Polish Journal of Chemistry (1997), 71(7), 923-928 CODEN: PJCHDQ; ISSN:0137-5083.

Gao et al, "A novel one-pot three-step synthesis of 2-(1-benzofuran-2-yl)quinoline-3-carboxylic acid derivatives", Journal of the Brazilian Chemical Society (2010), 21(5). 806-812 CODEN:JOCSET; ISSN: 0103-5053.

Ghate et al., "Synthesis of vanillin ethers from 4-(bromomethyl) coumarins as anti-inflammatory agents," European Journal of Medicinal Chemistry (2003), 38(3), 297-302 CODEN: EJMCAS; ISSN: 0223-5234.

Gibson et al., "Novel small molecule bradykinin B2 receptor antagonists", Journal of Medicinal Chemistry, 2009, vol. 52, pp. 4370-4379.

Glasson et al. Metal Template Synthesis of a Tripodal Tris(bipyridyl) Receptor that Encapsulates a Proton and an Iron (ii) Centre in a Pseudo Cage. Aust. J. Chem. 65:1371-1376 (2012).

Grashey, "The nitro group as a 1,3-dipole in cycloadditions" Angewandte Chemie (1962), 74, 155 CODEN: ANCEAD; ISSN: 0044-8249.

Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.

Guillory (in Brittain ed.) Polymorphism in Pharmaceutical Solids. NY, Marcel Dekker, Inc. 1999; 1-2:183-226.

Gunter et al., "Structural control of co-receptor binding in porphyrin-bipyridinium supramolecular assemblies", Journal of the Chemical Society, Perkin Transactions 1: Organic and Bio-Organic Chemistry (1998), (12), 1945-1958 CODEN: JCPRB4; ISSN: 0300-922X.

Hanmantgad et al., "Synthesis and pharmacological properties of some r-(2-benzo[b]furanyl)coumarins" Indian Journal of Chemistry, Section B: Organic Chemistry Including Medicinal Chemistry (1986), 25B(7), 779-81 CODEN: IJSBDB; ISSN: 0376-4699.

He et al., "Prodrugs of Phosphonates, Phosphinates, and Phosphates", Prodrugs: Challenges and rewards Part 2, edited by Stella et al., 2007, pp. 223-264.

Heimbach et al., "Enzyme-mediated precipitation of patent drugs from their phosphate prodrugs", International Journal of Pharmaceutics, 261, p. 81-92, 2003.

Heimbach et al., "Prodrugs: Challenges and Rewards Part I," New York, NY, Singer:AAPS Press, (2007), 5(Chapter 2.2.1):157-215 Overcoming Poor Aqueous Solubility of Drugs for Oral Delivery.

Heimgartner et al., "Stereoselective synthesis of swainsonines from pyridines", Tetrahedron, Elsevier Science Publishers, Amsterdam, NL, 2005, vol. 61, No. 3, pp. 643-655.

Hoffman, et al. 3-Hydroxy-3-methylglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).

Hong et al., "Potential Anticancer Agents VI: 5-Substituted Pyrimidine-6-Carboxaldehydes", Journal of Pharmaceutical Sciences, American Pharmaceutical Association, Washington, US, 1970, vol. 59, No. 11, pp. 1637-1645.

Huckauf, et al., "Oxygen Affinity of Haemoglobin and Red Cell Acid-Base Status in Patients with Severe Chronic Obstructive Lung Disease" Bull. Europe Physiopath. Resp., 1976, 12, 129-142.

International Preliminary Report on Patentability for PCT/US2014/022846 dated Sep. 15, 2015. 7 pages.

International Preliminary Report on Patentability for PCT/US2014/022742 dated Sep. 15, 2015. 7 pages.

International Preliminary Report on Patentability for PCT/US2014/022733 dated Sep. 15, 2015. 11 pages.

International Preliminary Report on Patentability for PCT/US2014/022769 dated Sep. 15, 2015. 8 pages.

International Search Report and Written Opinion dated Aug. 19, 2014 for PCT Application No. PCT/US2014/022736. 14 pages.

International Search Report and Written Opinion dated Aug. 27, 2014 for PCT Application No. PCT/US2014/022742. 11 pages.

International Search Report and Written Opinion dated Dec. 8, 2014 for PCT Application No. PCT/US2014/052575. 10 pages.

International Search Report and Written Opinion dated Jul. 22, 2014 for PCT Application No. PCT/US2014/022846. 11 pages.

International Search Report and Written Opinion dated Jul. 31, 2014 for PCT Application No. PCT/US2014/022789. 13 pages.

International Search Report and Written Opinion dated Jul. 4, 2014 for PCT Application No. PCT/US2014/022769. 11 pages.

International Search Report and Written Opinion dated Mar. 5, 2013 for PCT Application No. PCT/US2012/072177. 7 pages.

International Search Report and Written Opinion dated May 11, 2015 for PCT Application No. PCT/US2015/014589. 5 pages.

International Search Report and Written Opinion dated May 20, 2013 for PCT Application No. PCT/US2012/072183. 11 pages.

International Search Report and Written Opinion dated Nov. 28, 2014 for PCT Application No. PCT/US2014/052576. 10 pages.

International Search Report and Written Opinion dated Oct. 31, 2014 for PCT Application No. PCT/US2014/013575. 10 pages.

Israel office action dated Aug. 11, 2016 for Israeli Patent Application No. 233329.

Ito et al., A medium-term rat liver bioassay for rapid in vivo detection of carcinogenic potential of chemicals,01D Cancer Science, Jan. 2003, 94, pp. 3-8.

Ivanisevic, et al. Uses of x-ray powder diffraction in the pharmaceutical industry. Pharm. Sci. Encycl. 2010; 1-42.

Jain, et al., "Polymorphism in Pharmacy", Indian Drugs, 1986, 23(6) 315-329.

Jarvest et al., "Discovery and optimisation of potent, selective, ethanolamine Inhibitors of bacterial phenylalanyl tRNA synthetase", Bioorganic & Medicinal Chemistry Letter (2005), 15(9), 2305-2309 CODEN: BMCLES; ISSN: 0960-894X.

(56) References Cited

OTHER PUBLICATIONS

Karche et al., "Electronic Effects in Migratory Groups [1,4]-versus [1,2]—Rearrangement in Rhodium Carbenoid Generated Bicyclic Oxonium Ylides", Journal of Organic Chemistry (2001), 66(19), 6323-6332 CODEN: JOCEAH; ISSN: 0022-3263.
Katritzky et al., "Syntheses of 3-hydroxymethyl-2-3-dihydrobenzofurans and 3-hydroxymethylbenzofurans", ARKIVOC (Gainesville, FL, United States) (2003), (6), 49-61 CODEN: AGFUAR URL: http://www.arkat-usa.org/ark/journa1/2003/Vargoglis/AV-622A/6ss.pdf.
Kaye et al., "DABCO-catalyzed reactions of salicylaldehydes with acrylate derivatives", Synthetic Communications (1996), 26(11), 2085-97 CODEN: SYNCAV; ISSN: 0039-7911.
Kaye et al., "Does the DABCO-catalyzed reaction of 2-hydroxybenzaldehydes with methyl acrylate follow a Baylis-Hillman pathway?", Organic & Biomolecular Chemistry (2003), 1(7), 1133-1138 CODEN: OBCRAK; ISSN: 1477-0520.
Keidan, et al. Effect of BW12C on oxygen affinity of hemoglobin in sickle-cell disease. The Lancet. 1986; 327(8485):831-834.
Kessar et al., "Synthesis of Isoindolobenzazepines via photocyclisation of N-(2-formylphenethyl)phthalimide derivatives", Indian Journal of Chemistry, Section B: Organic Chemistry Including Medicinal Chemistry (1991), 30B(11), 999-1005 CODEN: JSBDB; ISSN:3076-4699.
Kessar et al., An Interesting Application of Photocyclisation in Apophdeadane Alkaloid Synthesis. Tetrahedron Letters (1987), 28(44), 5323-5326. CODEN: TELEAY; ISSN: 0040-4039.
Kirk-Othmer Encyclopedia of Chemical Technology. 2002; 8:95-147.
Kise et al., "Electroreductive Intramolecular Coupling of Phthalimides with Aromatic Aldehydes: Application to the Synthesis of Lennoxamine". Journal of Organic Chemistry (2011), 76(23), 9856-9880 CODEN:JOCEAH; ISSN: 0022-3263.
Klis, et al. Halogen-lithium exchange versus deprotonation: synthesis of diboronic acids derived from aryl-benzyl ethers. Tetrahedron Letters, 48(7):1169-1173 (2007).
Kratochvil. Chapter 8 Solid Forms of Pharmaceutical Molecules. J. Sestak et al. (eds.), Glassy, Amorphous and Nano-Crystalline Materials. Hot Topics in Thermal Analysis and Calorimetry 8, 2011, pp. 129-140.
Krow,"The Baeyer-Villiger oxidation of ketones and aldehydes", Organic Reactions (Hoboken, NJ, United States) (1993), 43, No pp. given CODEN: ORHNBA URL: http://www3.interscience.wiley.com/cgi- bin/mrwhome/107610747/HOME.
Lakkannavar et al., "4-[2'-benzylideneanlino aryloxymethyl] coumarins E and Z isomers". Indian Journal of Heterocyclic Chemistry (1995), 4(4), 303-4 CODEN: IJCHEI; ISSN: 0971-1627.
Lin et al. Synthesis and anticancer activity of benzyloxybenzaldehyde derivatives against HL-60 cells. Bioorganic & Medicinal Chemistry. 13(5), 1537-1544 (2005).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Liu et al., "Synthesis of Double-Armed Benzo-15-crown-5 and Their Complexation Thermodynamics with Alkali Cations", Journal of Inclusion Phenomena and Macrocyclic Chemistry (2005), 52(3-4), 229-235 CODEN: JIPCF5; ISSN: 1388-3127.
Luan, et al. TOPS-MODE model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.
Mahoney et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters (2009), 50(33), 4706-4709 CODEN: TELEAY; ISSN: 0040-4039.
Majhi et al., "An efficient synthesis of novel dibenzo-fused nine-membered oxacycles using a sequential Baylis-Hillman reaction and radical cyclization", Synthesis (2008), (1), 94-100 CODEN: SYNTBF; ISSN: 0039-7881.

Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL FARMACO, 1996, vol . 51, No. 8, 9, pp. 579-587.
Mantyla et al., Synthesis, in vitro evaluation, and antileishmanial activity of water-soluble prodrugs of buparvaquone. J. Med. Chem. 2004, 47:188-195.
McKay et al., 7,11,15,28-Tetrakis[(2-formylphenoxy)methyl]-1,21,23,25-tetramethylresorcin[4]arene cavitand ethyl acetate clathrate at 173 K, Acta Crystallographica, Section E: Structure Reports Online (2009), E65(4), 692-693 CODEN: ACSEBH; ISSN: 1600-5368 URL: http://journals.lucr.org/e/issues/2009/04/00fl22 33/fl2233.pdf.
McKay et al., "Microwave-assisted synthesis of a new series of resorcin[4]arene cavitand-capped porphyrin capsules", Organic & Biomolecular Chemistry (2009), 7(19), 3958-3968 CODEN: OBC-CRAK; ISSN: 1477-0520.
Merlino et al., "Development of second generation amidinohydrazones, thio- and semicarbazones as Trypanosoma cruzi-inhibitors bearing benzofuroxan and benzimidazole 1,3-dioxide core scaffolds" , MedChemComm (2010), 1(3), 216-228 CODEN: MCCEAY; ISSN: 2040-2503.
Mitra et al., "Synthesis and biological evaluation of dibenz[b,f][1,5]oxazocine derivatives for agonist activity at x-opioid receptor", European Journal of Medicinal Chemistry (2011), 46(5), 1713-1720 CODEN: EJMCAS; ISSN: 0223-5234.
Mulwad et al., "Synthesis and antimicrobial activity of [6'-methyl-4'-methoxy-2-oxo-2H-[1]- benzopyran)-2",4" dihydro-[1",2",4"}-triazol-3'-one and 3'phenylthiazolidin-4'-one-phenoxymethyl derivatives of dipyranoquinoline", Pharmaceutical Chemistry Journal Ahead of Print CODEN: PCJOAU; ISSN: 0091-150, 2011; pp. 427-432.
Muzaffar, et al., "Polymorphism and Drug Availability: a Review" J of Pharm. (Lahore), 1979, 1(1), 59-66.
Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.
Neelima et al., "A novel annelation reaction: synthesis of 6H-[1]benzopyrano[4,3-b]quinolines" Chemistry & Industry (London, United Kingdom) (1986), (4), 141-2 CODEN: CHINAG; ISSN: 0009-3068.
Nnamani, et al., "Pyridyl derivatives of benzaldehyde as potential antisickling agents," Chem. Biodivers., (2008), 5(9):1762-1769.
Nogrady, Medicinal Chemistry a Biochemical Approach, Oxford University Press, New York, pp. 388-393 (1985).
Nonoyama et al.,"Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron 1999, 533-543 CODEN: PLYHDE; ISSN: 0277-5387.
Notice of Allowance dated Dec. 19, 2014 for U.S. Appl. No. 13/730,730. 11 pages.
Nyerges et al, "Synthesis of Indazole N-oxides via the 1,7-electrocyclization of azomethine ylides", Tetrahedron Letters (2001), 42(30), 5081-5083 CODEN: TELEAY; ISSN:0040-4039.
Nyerges et al, "Synthesis of Indazole N-oxides via the 1,7-electrocyclization of azomethine ylides", Tetrahedron Letters (2004), 60(44), 9937-9944 CODEN: TETRAB; ISSN:0040-4020.
OECD SIDS "SIDS Initial Assessment Report for 13th SIAM," Nov. 2001, pp. 1-95.
Office Action dated Aug. 29, 2014 for U.S. Appl. No. 13/730,730. 17 pages.
Office Action dated Dec. 3, 2013 for U.S. Appl. No. 13/730,674. 8 pages.
Office Action dated Jul. 6, 2015 for U.S. Appl. No. 13/815,874. 14 pages.
Office Action dated Jun. 12, 2015 for CN Application No. 201280070743.5. 13 pages.
Office Action dated Jun. 29, 2015 for U.S. Appl. No. 13/815,810. 19 pages.

(56) References Cited

OTHER PUBLICATIONS

Office Action dated Jun. 30, 2014 for U.S. Appl. No. 13/730,674. 9 pages.
Office Action dated Sep. 18, 2013 for U.S. Appl. No. 13/730,674. 10 pages.
O'Reilly, "Metal-phenoxyalkanoic acid interactions, XXV. The crystal structures of (2-formyl-6-methoxyphenoxy)acetic acid and its zinc(II)complex and the lithium, zinc(II) and cadmium(II) complexes of (2-chlorophenoxy)acetic acid", Australian Journal of Chemistry (1987), 40(7)m 1146-59 CODEN; AJCHAS; ISSN:0004-9425.
Otsuka, et al., "Effect of Polymorphic Forms of Bulk Powders on Pharmaceutical Properties of Carbamazepine Granules." Chem. Pharm. Bull., 47(6) 852-856 (1999).
Patani, et al. Bioisosterism: A Rational Approach in Drug Design. J. Chem Rev. 1996, 96(8), pp. 3147-3176.
Perez et al., "Preparation of new 1,2-disubstituted ferrocenyl ammonium salt", Polyhedron (2009), 28(14), 3115-3119 CODEN: PLYHE; ISSN:0277-5387.
Perkins et al., "Manganese(II), Iron(II), cobalt(II), and cooper(II)complexes of an extended inherently chiral tris-bipyridyl cage", Proceedings of the National Academy of Sciences of the United States of America (2006), 103(3), 532-537 CODEN: PNASA6; ISSN: 0027-8424.
Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.
Prohens, et al. Polymorphism in pharmaceutical industry. The Pharmacist. Apr. 1, 2007; 373:58-68. (in Spanish with English abstract).
PUBCHEM CID 54009805 Create Date: Dec. 4, 2011 p. 1.
PUBCHEM CID 54883281 Create Date: Aug. 19, 2012 p. 1.
Remington's Pharmaceutical Sciences, 17th Edition, A. Gennaro editor, Easton Pennsylvania. Table of Contents. (1985).
Rodriguez-Spong, et al. General principles of pharmaceutical solid polymorphism: a supramolecular perspective. Adv Drug Deliv Rev. Feb. 23, 2004;56(3):241-74.
Rolan et al., "The pharmacokinetics, tolerability and pharmacodynamics of tucaresol (589C80); 4[2-formyl-3-hydroxyphenoxymethyl] benzoic acid), a potential anti-sickling agent, following oral administration to healthy subjects", British Journal of Clinical Pharmacology, 1993, 35(4):419-425.
Rooseboom et al., Enzyme-catalyzed activation of anticancer prodrugs. Pharmacol. Rev. 2004, 56:53-102.
Ruchirawat et al., "A novel synthesis of aporhoeadanes", Tetrahedron Letters (1984), 25(32), 3485-8 CODEN: TELEAY; ISSN: 0040-4039.
Safo, et al. Structural basis for the potent antisickling effect of a novel class of five-membered heterocyclic aldehydic compounds. J Med Chem. Sep. 9, 2004;47(19):4665-76.
Sahakitpichan et al., "A practical and highly efficient synthesis of lennoxamine and related isoindoloenzazepines" Tetrahedron (2004), 60(19), 4169-4172 CODEN: TETRAB; ISSN: 0040-4020.
Sahm et al., "Synthesis of 2-arylbenzofurans" Justus Liebigs Annalen der Chemie (1974), (4), 523-38 CODEN: JLACBF; ISSN: 0075-4617.
Sainsbury et al., "1,2-Dihydroisoquinolines, IV. Acylation" Tetrahedron (1966), 22(8), 2445-52 CODEN: TETRAB; ISSN: 0040-4020.
Sarodnick et al., "Quinoxalines XV, Convenient Synthesis and Structural Study of Pyrazolo[1,5-a]quinoxalines", Journal of Organic Chemistry (2009), 74(3), 1282-1287 CODEN: JOCEAH; ISSN: 0022-3263.
Schudel, et al. Uber die Chemie des Vitamins E. Helvetica Chimica Acta. 1963; 66:636-649.
Seddon. Pseudopolymorph: A Polemic. The QUILL Centre, The Queen's University of Belfast, United Kingdom. Jul. 26, 2004. 2 pages.

Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).
Siddiqui et al., "The Presence of Substitutents on the Aryl Moiety of the Aryl Phosphoramidate Derivative of d4T Enhances Anti-HIV Efficacy in Cell Culture-Activity Relationship," J. Med. Chem., (1999), 42:393-399.
Silva et al., "Advances in prodrug design," Mini Rev. Med. Chem., (2005), 5(10):893-914.
Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.
Singhal, et al., "Drug Polymorphism and Dosage Form Design: a Practical Perspective" Advanced Drug Delivery reviews 56, p. 335-347 (2004).
Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.
Srivastava et al., "Synthesis and biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.
Starke et al., "Quinoxalines, Part 13: Synthesis and mass spectrometric study of aryloxymethylquinoxalines and benzo[b]furylquinoxalines" Tetrahedron (2004), 60(29), 6063-6078 CODEN: TETRAB; ISSN:0040-4020.
Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
Swann et al., "Rates of reductive elimination of substituted nitrophenols from the (indol-3-yl)methyl position of indolequinones", Journal of the Chemical Society, Perkin Transactions 2 (2001), (8), 1340-1345.
Table of Compounds, each of which can be found either in Table 1 of U.S. Pat. No. 9,018,210 or Table 1 of U.S. Pat. No. 9,012,450.
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.
Testa et al., Hydrolysis in Drug and Prodrug Metabolism, Jun. 2003, Wiley-VCH, Zurich, 419-534.
Tome et al., "Product class 13: 1,2,3-triazoles", Science of Synthesis (2004), 13, 415-601 CODEN: SSCYJ9.
U.S. Pharmacopia #23, National Formulary #18, 1995, 1843-1844.
VanRompaey et al., "A versatile synthesis of 2-substituted 4-amino-1,2,4,5-tetrahydro-2-benzazepine-3-ones", Tetrahedron (2003), 59(24), 4421-4432 CODEN: TETRAB; ISSN:0040-4020.
VanRompaey et al., "Synthesis and evaluation of the 3B2-turn properties of 4-amino-1,2,4,5-tetrahydro-2-benzazepin-3-ones and of their spirocyclic derivative", European Journal of Organic Chemistry (2006), (13), 2899-2911 CODEN: EJOCFK; ISSN: 1434-193X.
Vicente et al., "Carbopalladation of Maleate and Fumarate Esters and 1,1-Dimethylallene with Ortho-Substituted Aryl Palladium Complexes" Organometallics (2010), 29(2), 409-416.
Vichinsky. "Emerging 'A' therapies in hemoglobinopathies: agonists, antagonists, antioxidants, and arginine." Hematology 2012, 271-275.
Vippagunta, et al. Crystalline Solids. Advanced Drug Delivery Reviews. 2001; 48:3-26.
Wang et al., "Studies of Benzothiophene Template as Potent Factor IXa (FIXa) Inhibitors in Thrombosis", Journal of Medicinal Chemistry (2010), 53, 1465-1472.
Warshawsky et al., "The synthesis of aminobenzazespinones as anti-phenylalanine dipeptide mimics and their use in NEP inhibition", Bioorganic & Medicinal Chemistry Letter (1996), 6(8), 957-962 CODEN: BMCLE8; ISSN: 0960-894X.

(56) References Cited

OTHER PUBLICATIONS

Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.
Wermuth, Camille G., "Molecular Variations Based on Isosteric Replacements", The Practice of Medicinal Chemistry, 1996, pp. 203-232.
Yan et al., "Synthesis, crystal structure and antibacterial activity of dibutyltin carboxylate", Huaxue Tongbao (2007), 70(4), 313-316 CODEN: HHTPAU; ISSN: 0441-3776.
Yan et al., "Synthesis, crystal structure and antibacterial activity of di-n-butyltin di-2(2-formylphenoxy)acetic ester", Yingyong Huaxue (2007), 24(6), 660-664.
Yoon et al., The Chirality Conversion Reagent for Amino Acids Based on Salicyl Aldehyde. Bull. Korean Chem. Soc., (2012), 33:1715-1718.
Zhang et al., "DFT study on RuII-catalyzed cyclization of terminal alkynals to cycloalkenes", International Journal of Quantum Chemistry (2009), 109(4), 679-687 CODEN: IJQCB2; ISSN:0020-7608.
Zhang, et al. Current prodrug strategies for improving oral absorption of nucleoside analogues. Asian Journal of Pharmaceutical Sciences. Apr. 2014; 9(2):65-74.
Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.
Zwaagstra et al., "Synthesis and Structure-Activity Relationships of Carboxylated Chalcones: A Novel Series of Cys-LT1 (LTD4) Receptor Antagonists", Journal of Medicinal Chemistry (1997), 40(7), 1075-1089 CODEN: JMCMAR; ISSN: 0022-2623.
Bottino, et al. Study on the scope of tert-amino effect: new extensions of type 2 reactions to bridged biaryls. J. Phys. Org. Chem. 2012; 25(11):1033-1041.
Cheng, et al. Vilsmeier formylation of tert-anilines: dibenzo[b,f][1,5]diazocines and quinazolinium salts via the 't-amino effect'. J. Chem. Soc., Perkin Trans 1. 1998; 1257-1262.
Database Registry, 2011, RN 1289869-72-2, 1027970-95-1, 959671-57-9.
Database Registry, 2012, RN 1390863-18-9, 1390573-58-6, 1389652-57-6, 1387166-17-7, 1318517-26-8, 1318395-05-9, 933829-46-0, 879919-21-8.
Hang, Song. "Pharmaceutical Separation Engineering" East China University of Technology Press. Aug. 31, 2011; 270-272. (in Chinese with English abstract).
International Search Report and Written Opinion dated Aug. 4, 2017 for PCT Application No. PCT/US2017/032104. 10 pages.
"Master of Engineering Education Chemical Engineering Development Report" National Engineering Education Master in Chemical Engineering Cooperation Group, Zhejiang University Press. Mar. 31, 2011; 241-245. (in Chinese with English abstract).
Metcalf, et al., "Discovery of GBT440, an Orally Bioavailable R-State Stabilizer of Sickle Cell Hemoglobin," ACS Med. Chem. Lett., 2017, 8, 321-326.
Oh, et al. Solid-phase synthesis of 1,3-oxazolidine derivatives. Tetrahedron Letters. 2000; 41:5069-5072.
Strickley. Solubilizing excipients in oral and injectable formulations. Pharm Res. Feb. 2004;21(2):201-30.
Tsuge, et al. Suppressive Effect of Vitamin B6-Sugar Derivatives on The Proliferation of Feline Mammary Tumor Cell, FRM. Vitamins (Japan), 2006; 80(11):537-542. (In Japanese with English Abstract).
Van Halbeek, et al., "Sialic Acid in Permethylation Analysis: Prepared and Identification of Partially O-Methylated Derivatives of methyl N-Acetyl-N-Methyl-beta-D-Neurominate Methyl Glycoside", Carbohydrate Research, vol. 60, No. 1, 1978, pp. 51-62, 53, and 59.
Zhang, et al. A selective fluorescent chemosensor with 1, 2, 4-triazole as subunit for Cu (II) and its application in imaging Cu (II) in living cells. Dyes and Pigments. 2012; 92(3):1370-1375.

* cited by examiner

SUBSTITUTED ALDEHYDE COMPOUNDS AND METHODS FOR THEIR USE IN INCREASING TISSUE OXYGENATION

CROSS REFERENCE TO RELATED APPLICATIONS

This application is the U.S. 371 national stage application of International Patent Application No. PCT/US2014/029682, filed on Mar. 14, 2014; which claims the benefit of U.S. Provisional Patent Application No. 61/799,120, filed Mar. 15, 2013; the entire disclosures of which are incorporated herein by reference in their entirety.

FIELD OF THE INVENTION

The present invention generally relates to substituted benzaldehydes and heteroarylaldehydes and derivatives thereof that act as allosteric modulators of hemoglobin, methods and intermediates for their preparation, pharmaceutical compositions containing the modulators, and methods for their use in treating disorders mediated by hemoglobin and disorders that would benefit from increased tissue oxygenation.

BACKGROUND OF THE INVENTION

Hemoglobin (Hb) is a tetrameric protein in red blood cells that transports up to four oxygen molecules from the lungs to various tissues and organs throughout the body. Hemoglobin binds and releases oxygen through conformational changes, and is in the tense (T) state when it is unbound to oxygen and in the relaxed (R) state when it is bound to oxygen. The equilibrium between the two conformational states is under allosteric regulation. Natural compounds such as 2,3-bisphosphoglycerate (2,3-BPG), protons, and carbon dioxide stabilize hemoglobin in its de-oxygenated T state, while oxygen stabilizes hemoglobin in its oxygenated R state. Other relaxed R states have also been found, however their role in allosteric regulation has not been fully elucidated.

Sickle cell disease is a prevalent disease particularly among those of African and Mediterranean descent. Sickle hemoglobin (HbS) contains a point mutation where glutamic acid is replaced with valine, allowing the T state to become susceptible to polymerization to give the HbS containing red blood cells their characteristic sickle shape. The sickled cells are also more rigid than normal red blood cells, and their lack of flexibility can lead to blockage of blood vessels. Certain synthetic aldehydes have been found to shift the equilibrium from the polymer forming T state to the non-polymer forming R state (Nnamani et al. Chemistry & Biodiversity Vol. 5, 2008 pp. 1762-1769) by acting as allosteric modulators to stabilize the R state through formation of a Schiff base with an amino group on hemoglobin.

U.S. Pat. No. 7,160,910 discloses 2-furfuraldehydes and related compounds that are also allosteric modulators of hemoglobin. One particular compound 5-hydroxymethyl-2-furfuraldehyde (5HMF) was found to be a potent hemoglobin modulator both in vitro and in vivo. Transgenic mice producing human HbS that were treated with 5HMF were found to have significantly improved survival times when exposed to extreme hypoxia (5% oxygen). Under these hypoxic conditions, the 5HMF treated mice were also found to have reduced amounts of hypoxia-induced sickled red blood cells as compared to the non-treated mice.

A need exists for therapeutics that can shift the equilibrium between the deoxygenated and oxygenated states of Hb to treat disorders that are mediated by Hb or by abnormal Hb such as HbS. A need also exists for therapeutics to treat disorders that would benefit from having Hb in the R state with an increased affinity for oxygen. Such therapeutics would have applications ranging, for example, from sensitizing hypoxic tumor cells that are resistant to standard radiotherapy or chemotherapy due to the low levels of oxygen in the cell, to treating pulmonary and hypertensive disorders, and to promoting wound healing.

BRIEF SUMMARY OF THE INVENTION

The present invention provides, in one aspect, allosteric modulators of hemoglobin. In another aspect, provided are pharmaceutical compositions containing the allosteric modulators disclosed herein. In other aspects, provided are methods for treating disorders mediated by hemoglobin and methods for increasing tissue oxygenation for treating disorders that would benefit from increased oxygenation, such methods including administering the allosteric modulators disclosed herein to a subject in need thereof. In still other aspects, provided are methods for preparing the allosteric modulators disclosed herein. These and other embodiments of the invention are more fully described in the description that follows.

DETAILED DESCRIPTION OF THE INVENTION

I. Definitions

As used herein, the below terms have the following meanings unless specified otherwise.

The abbreviations used herein are conventional, unless otherwise defined: aq=aqueous; Boc=t-butylcarboxy, (Boc)$_2$O=di-tert-butyl dicarbonate, ° C.=degrees celcius, mCPBA=m-chloroperoxybenzoic acid, DIAD=diisopropylazodicarboxylate, DCM=dichloromethane (CH$_2$Cl$_2$), DIBAL=diisobutylaluminum hydride, DMF=dimethyl formamide, EtOAc=ethyl acetate, g=gram, H$_2$=hydrogen; H$_2$O=water; HBr=hydrogen bromide; HCl=hydrogen chloride, HPLC=high pressure liquid chromatography, h=hour, LAH=lithium aluminum hydride (LiAlH$_4$); MeCN=acetonitrile; MS=Mass Spectrum, m/z=mass to charge ratio, MHz=Mega Hertz, MeOH=methanol, μM=micromolar, μL=microliter, mg=milligram, mM=millimolar, mmol=millimole, mL=milliliter, min=minute, M=molar, Na$_2$CO$_3$=sodium carbonate, ng=nanogram, N=Normal, NMR=nuclear magnetic resonance, Pd/C=palladium on carbon, rp=reverse phase, sat=saturated, rt=room temperature, TEA=triethylamine, THF=tetrahydrofuran, TFA=trifluoroacetic acid, TLC=thin layer chromatography, and TMS=trimethylsilyl.

It is noted here that as used in this specification and the appended claims, the singular forms "a," "an," and "the" include plural reference unless the context clearly dictates otherwise.

"Alkoxy" refers to —O(alkyl) where alkyl as defined herein. Representative examples of alkoxy groups include methoxy, ethoxy, t-butoxy, and the like.

"Alkyl," by itself or as part of another substituent, means, unless otherwise stated, a straight or branched chain, fully saturated aliphatic hydrocarbon radical having the number of carbon atoms designated. For example, "C$_{1-8}$alkyl" refers to a hydrocarbon radical straight or branched, containing from 1 to 8 carbon atoms that is derived by the removal of one hydrogen atom from a single carbon atom of a parent alkane. Alkyl includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkenyl" refers to a linear monovalent hydrocarbon radical or a branched monovalent hydrocarbon radical having the number of carbon atoms indicated in the prefix and containing at least one double bond, but no more than three double bonds. For example, $C_{2-8}$alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, $C_{2-8}$alkynyl is meant to include ethynyl, propynyl and the like.

The term "allosteric modulators" refers to compounds that bind to hemoglobin to modulate its affinity for oxygen. In one group of embodiments, the allosteric modulators act to stabilize or destabilize a particular hemoglobin conformation. In one group of embodiments, the modulators stabilize the relaxed R state. In other embodiments, the modulators destabilize the tense T state. In one group of embodiments, the allosteric modulators can destabilize one conformation while stabilizing another. In some such embodiments, the modulators stabilize a relaxed R state and destabilize the tense T state. The modulators, in addition to modulating the affinity of hemoglobin for oxygen, may also confer additional properties to hemoglobin such as increasing its solubility. The present disclosure is not intended to be limited to the mechanism by which the allosteric modulators interact with and regulate hemoglobin. In one group of embodiments, the allosteric modulators inhibit the polymerization of HbS and the sickling of red blood cells. In one group of embodiments, the binding of the allosteric modulators provided herein to hemoglobin can occur through covalent or non-covalent interactions. In one embodiment, the allosteric modulators react through its aldehyde substituent with an amine group on a hemoglobin amino acid side chain to form a Schiff base.

"Amino" refers to a monovalent radical —$NH_2$.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of aryl groups include phenyl, 1-naphthyl, 2-naphthyl and 4-biphenyl.

"Bond" when used as an element in a Markush group means that the corresponding group does not exist, and the groups of both sides are directly linked.

"Cycloalkyl" refers to a saturated or partially saturated cyclic group of from 3 to 14 carbon atoms and no ring heteroatoms and having a single ring or multiple rings including fused, bridged, and Spiro ring systems. The term "cycloalkyl" includes cycloalkenyl groups, i.e., partially saturated cycloalkyl rings having at least one site of >C=C< ring unsaturation. Examples of cycloalkyl groups include, for instance, adamantyl, cyclopropyl, cyclobutyl, cyclopentyl, cyclooctyl, and cyclohexenyl. "$C_{u'\text{-}v'}$cycloalkyl" refers to cycloalkyl groups having u' to v' carbon atoms as ring members. "$C_{u'\text{-}v'}$cycloalkenyl" refers to cycloalkenyl groups having u' to v' carbon atoms as ring members. Cycloalkyl and cycloalkenyl groups can have, for example, 5-8 carbon atoms as ring members, or 5-6 carbon atoms as ring members.

The term "hemoglobin" as used herein refers to any hemoglobin protein, including normal hemoglobin (Hb) and sickle hemoglobin (HbS).

"Heteroaryl" refers to a cyclic or polycyclic radical having at least one aromatic ring and from one to five ring heteroatom selected from N, O, and S, and optionally one or more oxo (=O) substituents attached to one or more carbon ring atoms, and wherein the nitrogen and sulfur ring atoms are optionally oxidized. A heteroaryl group can be attached to the remainder of the molecule through a heteroatom or through a carbon atom and can contain 5 to 10 carbon atoms. Heteroaryl groups include polycyclic aromatic ring(s) fused to non-aromatic cycloalkyl or heterocycloalkyl groups, and where the point of attachment to the remainder of the molecule can be through any suitable ring atom of any ring. In a polycyclic heteroaryl group, the ring heteroatom(s) can be in either an aromatic or non-aromatic ring or both. The term "aromatic ring" include any ring having at least one planar resonance structure where 2n+2 pi electrons are delocalized about the ring. Examples of heteroaryl groups include, but are not limited to, imidazopyridinyl groups, pyrrolopyridinyl groups, pyrazolopyridinyl groups, triazolopyridinyl groups, pyrazolopyrazinyl groups, pyridinyl groups, pyrazinyl groups, oxazolyl groups, imidazolyl groups, triazolyl groups, tetrazolyl groups, pyrazolyl groups, quinolinyl groups, isoquinolinyl groups, indazolyl groups, benzooxazolyl groups, naphthyridinyl groups, and quinoxalinyl groups. Other non-limiting examples of heteroaryl groups include xanthine, hypoxanthine, 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl, 6-quinolyl1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. "Bicyclic heteroaryl" refers to a heteroaryl radical that contains two rings.

The term "heterocycloalkyl" refers to a cycloalkyl group containing at least one ring heteroatom and optionally one or more oxo substituents. As used herein, the term "heteroatom" is meant to include oxygen (O), nitrogen (N), and sulfur (S), wherein the heteroatoms are optionally oxidized, and the nitrogen atom(s) are optionally quaternized. Each heterocycle can be attached at any available ring carbon or heteroatom. Each heterocycle may have one or more rings. When multiple rings are present, they can be fused together. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, piperidine, morpholine, piperazine, isoxazoline, pyrazoline, imidazoline, pyrrolidine, and the like.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "haloC1-8alkyl" is meant to include difluoromethyl, trifluoromethyl, 2,2,2-trifluoroethyl, 4-chlorobutyl, 3-bromopropyl, and the like. The term "haloalkenyl", and "haloalkynyl" refers to alkenyl and alkynyl radicals having one or more halogen atoms. Additionally, term "haloalkoxy" refers to an alkoxy radical substituted with one or more halogen atoms. In one group of embodiments, the haloalkyl, haloalkenyl, haloalkynyl, and haloalkoxy groups have from one to 5 or from one to 3 halo atoms. Examples of haloalkoxy groups include difluoromethoxy and trifluoromethoxy. In one group of embodiments, the halo atoms of the haloalkenyl and haloalkynyl groups are attached to the aliphatic portions of these groups.

The terms "optional" or "optionally" as used throughout the specification means that the subsequently described event or circumstance may but need not occur, and that the description includes instances where the event or circumstance occurs and instances in which it does not. For example, "heteroaryl group optionally substituted with an alkyl group means that the alkyl may but need not be present, and the description includes situations where the heteroaryl group is substituted with an alkyl group and situations where the heteroaryl group is not substituted with the alkyl group.

"Oxo" refers to the divalent atom =O.

In each of the above embodiments designating a number of atoms e.g. "$C_{1-8}$" is meant to include all possible embodiments that have one fewer atom. Non-limiting examples include $C_{1-4}$, $C_{1-5}$, $C_{1-6}$, $C_{1-7}$, $C_{2-8}$, $C_{2-7}$, $C_{3-8}$, $C_{3-7}$ and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, $3^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "aldehyde protecting group" refers to any known protecting group used to mask the aldehyde functionality. Aldehyde protecting groups include acetals and hemiacetals. The acetals and hemiacetals can be prepared from $C_{1-8}$ alcohols or $C_{2-8}$ diols. In one group of embodiments, the aldehyde protecting group is a five or six membered cyclic acetal formed from condensation of the aldehyde with ethylene or propylene glycol. In another group of embodiments the aldehyde protecting group is an imine or hydroxyimine. The aldehyde protecting groups of the present disclosure also include prodrug groups that convert the aldehyde to a prodrug, where the aldehyde is formed in vivo as the active agent under physiological conditions upon administration of the prodrug. The prodrug group can also serve to increase the bioavailability of the aldehyde. In one group of embodiments, the prodrug group is hydrolyzed in vivo to the aldehyde. In one group of embodiments, the aldehyde protecting group is a thiazolidine or N-acetylthiazolidine prodrug group. In one group of embodiments, the aldehyde protecting group is a thiazolidine prodrug group disclosed in U.S. Pat. No. 6,355,661. In one group of embodiments the modulators provided herein are condensed with L-cysteine or a L-cysteine derivative to form the corresponding thiazolidine protected aldehyde prodrug. In one group of embodiments, the thiazolidine has the formula

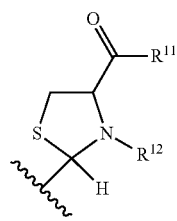

wherein $R^{11}$ is selected from OH, alkoxy, substituted alkoxy, cycloalkoxy, substituted cycloalkoxy, aryloxy, substituted aryloxy, heteroaryloxy, substituted heteroaryloxy, $N(R^{13})_2$ where $R^{13}$ is independently H, alkyl, substituted alkyl, alkenyl, substituted alkenyl, aryl, substituted aryl, heteroaryl, and substituted heteroaryl; $R^{12}$ is H or -L-$R^{14}$, where L is carbonyl or sulfonyl; $R^{14}$ is selected from alkyl, substituted alkyl, aryl, substituted aryl, heteroaryl, and substituted heteroaryl; the wavy line signifies the point of attachment to the phenyl ring of the allosteric modulators disclosed herein; and the term "substituted" refers to substitution by one or more substituents selected from COOH, CHO, oxyacyl, acyloxy, cycloacyloxy, phenol, phenoxy, pyridinyl, pyrrolidinyl, amino, amido, hydroxy, alkoxy, cycloalkoxy, F, Cl, Br, $NO_2$, cyano, sulfuryl, and the like. In one group of embodiments, provided are modulators having a thiazolidine protecting group where $R^{11}$ is alkoxy and $R^{12}$ is H, or where $R^{11}$ is OH and $R^{12}$ is —C(O)alkyl, or where $R^{11}$ is NH(heteroaryl) and $R^{12}$ is —C(O)alkyl.

The term "sickle cell disease" refers to diseases mediated by sickle hemoglobin (HbS) that results from a single point mutation in the hemoglobin (Hb). Sickle cell diseases includes sickle cell anemia, sickle-hemoglobin C disease (HbSC), sickle beta-plus-thalassaemia (HbS/β+) and sickle beta-zero-thalassaemia)(HbS/β⁰).

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

The terms "treat", "treating", "treatment" and grammatical variations thereof as used herein, includes partially or completely delaying, alleviating, mitigating or reducing the intensity, progression, or worsening of one or more attendant symptoms of a disorder or condition and/or alleviating, mitigating or impeding one or more causes of a disorder or condition. Treatments according to the invention may be applied preventively, prophylactically, palliatively or remedially.

The symbol > when used in connection with a substituent signifies that the substituent is a divalent substituent attached to two different atoms through a single atom on the substituent.

The term "wavy line" signifies the point of attachment of the substituent to the remainder of the molecule. When the wavy line is not depicted as being specifically appended to a specific ring atom, the point of attachment can be to any suitable atom of the substituent. For example, the wavy line in the following structure:

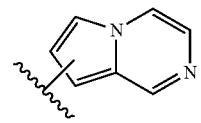

is intended to include, as the point of attachment, any of the six substitutable carbon atoms.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

The compounds of the present invention may also contain unnatural proportions of atomic isotopes at one or more of the atoms that constitute such compounds. For example, the compounds may be radiolabeled with isotopes, such as for example deuterium ($^2$H), tritium ($^3$H), iodine-125 ($^{125}$I) or carbon-14 ($^{14}$C). All isotopic variations of the compounds of the present invention, whether radioactive or not, are intended to be encompassed within the scope of the present invention.

Unless indicated otherwise, the nomenclature of substituents that are not explicitly defined herein are arrived at by naming the terminal portion of the functionality followed by the adjacent functionality toward the point of attachment. For example, the substituent "alkoxyalkyl" refers to an alkyl group that is substituted with alkoxy and "hydoxyalkyl" refers to an alkyl group that is substituted with hydroxy. For both of these substituents, the point of attachment is at the alkyl group.

It is understood that the definitions and formulas provided herein are not intended to include impermissible substitution patterns (e.g., methyl substituted with 5 fluoro groups). Such impermissible substitution patterns are well known to the skilled artisan.

II. Hemoglobin Modulators

Some groups of embodiments provide a compound of Formula (I):

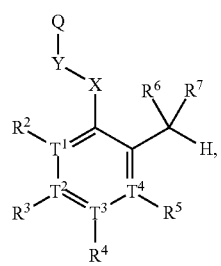

(I)

or a tautomer or pharmaceutically acceptable salt thereof, wherein:

Q is cycloalkyl or cycloalkenyl optionally substituted with one to three $R^a$;

Y is O, S(O)$_q$ or CR$^{1a}$R$^{1b}$, where
  $R^{1a}$ is H or halo, and
  $R^{1b}$ is selected from the group consisting of H, $C_1$-$C_8$alkyl, halo, and OH;

X is selected from the group consisting of O, S(O)$_q$, CH(CH$_2$)$_n$R$^8$, and C(R$^9$)$_2$, where
  q is 0, 1 or 2,
  n is 0 or 1,
  $R^8$ is OH, and
  $R^9$ is independently H or halo;

or Y—X taken together is —NHC(O)— or —C(O)NH—;

$T^1$, $T^2$, $T^3$, and $T^4$ are independently C or N provided that at least one of $T^1$, $T^2$, $T^3$, and $T^4$ is C;

$R^2$, $R^3$, $R^4$, and $R^5$ are independently absent or selected from the group consisting of hydrogen, halo, $R^b$, OR$^d$, —O(CH$_2$)$_z$OR$^d$, —O(CH$_2$)$_z$NR$^d$R$^d$, OC(O)R$^e$, SR$^d$, CN, NO$_2$, CO$_2$R$^d$, CONR$^d$R$^d$, C(O)R$^d$, OC(O)NR$^d$R$^d$, NR$^d$R$^d$, NR$^d$C(O)R$^e$, NR$^d$C(O)$_2$R$^e$, NR$^d$C(O)NR$^d$R$^d$, S(O)R$^e$, S(O)$_2$R$^e$, NR$^d$S(O)$_2$R$^e$, S(O)$_2$NR$^d$R$^d$, and N$_3$, where z is 0, 1, 2, 3, 4, 5, or 6; or $R^5$ is —(CH$_2$)$_p$R$^{5a}$, where p is 0 or 1 and R$^{5a}$ is OH;

$R^6$ and $R^7$ together form oxo or an aldehyde protecting group, or $R^6$ together with $R^{1b}$, $R^8$, or $R^5$ forms a cyclic ether, where one of $R^{1b}$, $R^8$, or $R^{5a}$ is O, $R^6$ is a bond, and $R^7$ is selected from the group consisting of OH, $C_{1-8}$alkoxy, and haloC$_{1-8}$alkoxy;

each $R^a$ is independently selected from the group consisting of of halo, CN, $R^b$, OR$^d$, O(CH$_2$)$_u$OR$^d$, O(CH$_2$)$_u$NR$^d$R$^d$, O(CH$_2$)$_u$NR$^d$C(O)R$^e$, O(CH$_2$)$_u$NR$^d$C(O)$_2$R$^e$, O(CH$_2$)$_u$NR$^d$S(O)$_2$R$^e$, NH$_2$, —(CH$_2$)$_k$OC(O)R$^e$, —(CH$_2$)$_k$SR$^d$, NO$_2$, —(CH$_2$)$_k$CO$_2$(C$_{1-8}$alkyl)OH, —(CH$_2$)$_k$CO$_2$(C$_{1-8}$alkyl)(heteroaryl)C(O)(C$_{1-8}$alkyl), —(CH$_2$)$_k$CO$_2$R$^d$, —(CH$_2$)$_k$CONR$^d$R$^d$, —(CH$_2$)$_k$NR$^d$C(O)R$^e$, —(CH$_2$)$_k$NR$^d$C(O)$_2$R$^e$, —(CH$_2$)$_k$C(O)R$^d$, —(CH$_2$)$_k$OC(O)NR$^d$R$^d$, —NR$^d$(CH$_2$)$_u$OR$^d$, —NR$^d$(CH$_2$)$_u$NR$^d$R$^d$, —NR$^d$(CH$_2$)$_u$NR$^d$C(O)R$^e$, —NR$^d$(CH$_2$)$_u$NR$^d$C(O)$_2$R$^e$, —NR$^d$(CH$_2$)$_u$NR$^d$S(O)$_2$R$^e$, —(CH$_2$)$_k$NR$^d$C(O)R$^e$, —(CH$_2$)$_k$NR$^d$C(O)$_2$R$^d$, —(CH$_2$)$_k$NR$^d$C(O)NR$^d$R$^d$, —(CH$_2$)$_k$S(O)R$^e$, —(CH$_2$)$_k$S(O)$_2$R$^e$, —(CH$_2$)$_k$NR$^d$S(O)$_2$R$^e$, —(CH$_2$)$_k$S(O)$_2$NR$^d$R$^d$, N$_3$, —(CH$_2$)$_k$aryl optionally substituted with one to three $R^c$, —NR$^d$(CH$_2$)$_k$aryl optionally substituted with one to three $R^c$, —(CH$_2$)$_k$heteroaryl optionally substituted with one to three $R^c$, —NR$^d$(CH$_2$)$_k$heteroaryl optionally substituted with one to three $R^c$, —(CH$_2$)$_k$heterocycloalkyl optionally substituted with one to three $R^c$, and —NR$^d$(CH$_2$)$_k$heterocycloalkyl optionally substituted with one to three $R^c$ where k is 0, 1, 2, 3, 4, 5, or 6 and u is 1, 2, 3, 4, 5, or 6;

each $R^b$ is independently selected from the group consisting of $C_{1-8}$alkyl, $C_{2-8}$alkenyl, and $C_{2-8}$ alkynyl, each optionally independently substituted with one to three halo, OR$^d$, or NR$^d$R$^d$;

each $R^c$ is independently selected from the group consisting of halo, $C_{1-8}$alkyl, haloC$_{1-8}$alkyl, $C_{2-8}$alkenyl, haloC$_{2-8}$alkenyl, $C_{2-8}$alkynyl, haloC$_{2-8}$alkynyl, (CH$_2$)$_m$OR$^f$, OC(O)R$^g$, SR$^f$, CN, NO$_2$, CO$_2$R$^f$, CONR$^f$R$^f$, C(O)R$^f$, OC(O)NR$^f$R$^f$, (CH$_2$)$_m$NR$^f$R$^f$, NR$^f$C(O)R$^g$, NR$^f$C(O)$_2$R$^g$, NR$^f$C(O)NR$^f$R$^f$, S(O)R$^g$, S(O)$_2$R$^g$, NR$^f$S(O)$_2$R$^g$, S(O)$_2$NR$^f$R$^f$, N$_3$, heteroaryl optionally substituted with one to three $R^h$, cycloalkyl optionally substituted with one to three $R^h$, and heterocycloalkyl optionally substituted with one to three $R^h$ where m is selected from the group consisting of 0, 1, 2, 3, 4, 5, and 6;

each $R^h$ is independently selected from the group consisting of halo, $C_{1-8}$alkyl, haloC$_{1-8}$alkyl, OR$^j$, OC(O)R, SR$^j$, NO$_2$, CO$_2$R$^j$, CONR$^j$R$^j$, C(O)R$^j$, OC(O)NR$^j$R$^j$, NR$^j$R$^j$, NR$^j$C(O)R$^t$, NR$^j$C(O)$_2$R$^t$, NR$^j$C(O)NR$^j$R$^j$, S(O)R$^t$, S(O)$_2$R$^t$, NR$^j$S(O)$_2$R$^t$, and S(O)$_2$NR$^j$R$^j$;

each $R^d$ is independently selected from the group consisting of hydrogen, $C_{1-8}$ alkyl, haloC$_{1-8}$alkyl, $C_{2-8}$ alkenyl, haloC$_{2-8}$alkenyl, $C_{2-8}$ alkynyl, haloC$_{2-8}$alkynyl, —(CH$_2$)$_k$heterocycloalkyl, and —(CH$_2$)$_u$O—(CH$_2$)$_u$H where k is 0, 1, 2, 3, 4, 5, or 6 and each u is independently 1, 2, 3, 4, 5, or 6;

$R^f$ and $R^j$ are each independently selected from the group consisting of hydrogen, $C_{1-8}$ alkyl, haloC$_{1-8}$alkyl, $C_{2-8}$ alkenyl, haloC$_{2-8}$alkenyl, $C_{2-8}$ alkynyl, and haloC$_{2-8}$alkynyl; and $R^e$, $R^g$, and $R^t$ are each independently selected from the group consisting of $C_{1-8}$ alkyl, haloC$_{1-8}$alkyl, $C_{2-8}$ alkenyl, haloC$_{2-8}$alkenyl, $C_{2-8}$ alkynyl, and haloC$_{2-8}$alkynyl;

provided that X and Y are not both O;

provided that when X is O, $R^{1b}$ is not OH; and provided that when Y is O, and n is 0, $R^8$ is not OH.

In some groups of embodiments, $T^1$, $T^2$, $T^3$, and $T^4$ are C; and $R^2$, $R^3$, $R^4$, and $R^5$ are independently selected from the group consisting of hydrogen, halo, $R^b$, $OR^d$, —$O(CH_2)_zOR^d$, —$O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$, where z is 0, 1, 2, 3, 4, 5, or 6; or $R^5$ is —$(CH_2)_pR^{5a}$ where p is 0 or 1 and $R^{5a}$ is OH.

In some groups of embodiments,

Q is substituted with one to three $R^a$;

$R^2$, and $R^3$ are independently selected from the group consisting of hydrogen, halo, $R^b$, $OR^d$, —$O(CH_2)_zOR^d$, —$O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$, where z is 0, 1, 2, 3, 4, 5, or 6;

$R^4$ and $R^5$ are selected from the group consisting of hydrogen, halo, $R^b$, $OR^d$, and —$(CH_2)_pR^{5a}$, where p is 0 or 1 and $R^{5a}$ is OH; and each $R^a$ is independently selected from the group consisting of halo, —$R^b$, —$OR^d$, —$O(CH_2)_uOR^d$, —$O(CH_2)_uNR^dR^d$, —$O(CH_2)_uNR^dC(O)R^e$, —$O(CH_2)_uNR^dC(O)_2R^e$, —$O(CH_2)_uNR^dS$—$(O)_2R^e$, —$NH_2$, —$(CH_2)_kOC(O)R^e$, —$(CH_2)_kSR^d$, $NO_2$, —$(CH_2)_kCO_2(C_{1-8}$alkyl)OH, —$(CH_2)_kCO_2(C_{1-8}$alkyl)(heteroaryl)C(O)($C_{1-8}$alkyl), —$(CH_2)_kCO_2R^d$, —$(CH_2)_kCONR^dR^d$, —$(CH_2)_kNR^dC(O)R^e$, —$(CH_2)_kNR^dC(O)_2R^e$, —$(CH_2)_kC(O)R^d$, —$(CH_2)_kOC(O)NR^dR^d$, —$NR^d(CH_2)_uOR^d$, —$NR^d(CH_2)_uNR^dR^d$, —$NR^d(CH_2)_uNR^d$-$C(O)R^e$, —$NR^d(CH_2)_uNR^dC(O)_2R^e$, —$NR^d(CH_2)_uNR^dS(O)_2R^e$, —$(CH_2)_kNR^dC(O)R^e$, —$(CH_2)_kNR^dC(O)_2R^d$, —$(CH_2)_kNR^dC(O)NR^dR^d$, —$(CH_2)_kS(O)R^e$, —$(CH_2)_kS$—$(O)_2R^e$, —$(CH_2)_kNR^dS(O)_2R^e$, —$(CH_2)_kS(O)_2NR^dR^d$, $N_3$, —$(CH_2)_k$aryl optionally substituted with one to three $R^c$, $NR^d(CH_2)$karyl optionally substituted with one to three $R^c$, —$(CH_2)_k$heteroaryl optionally substituted with one to three $R^c$, —$NR^d(CH_2)_k$heteroaryl optionally substituted with one to three $R^c$, —$(CH_2)_k$heterocycloalkyl optionally substituted with one to three Rc, and $NR^d(CH_2)_k$heterocycloalkyl optionally substituted with one to three Rc where k is 0, 1, 2, 3, 4, 5, or 6 and u is 1, 2, 3, 4, 5, or 6;

provided that at least one of $R^4$ and $R^5$ is other than hydrogen.

In some groups of embodiments,

Y is O or $CH_2$;

X is O or $CH_2$;

$R^4$ is selected from the group consisting of hydrogen, halo, $R^b$, and $OR^d$;

$R^5$ is selected from the group consisting of halo and $OR^d$; and $R^6$ and $R^7$ together form oxo or an aldehyde protecting group.

In some groups of embodiments, Y is $CH_2$ and X is O.

In some groups of embodiments, $R^2$ and $R^3$ are hydrogen.

In some groups of embodiments, $R^5$ is OH and $R^4$ is hydrogen.

In some groups of embodiments, $R^5$ is OH and $R^4$ is $R^b$.

In some groups of embodiments, $R^4$ is methyl.

In some groups of embodiments, $R^5$ is OH and $R^4$ is halogen.

In some groups of embodiments, $R^5$ is Cl.

In some groups of embodiments, at least one of $T^1$, $T^2$, $T^3$, and $T^4$ is N.

In some groups of embodiments,

Q is substituted with one to three $R^a$;

$T^1$ and $T^3$ are C;

$T^2$ is N and $T^4$ is C, or $T^2$ is C and $T^4$ is N;

$R^2$, and $R^3$ are independently selected from the group consisting of hydrogen, halo, $R^b$, $OR^d$, —$O(CH_2)_zOR^d$, —$O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$, where z is 0, 1, 2, 3, 4, 5, or 6;

$R^4$ and $R^5$ are absent or are independently selected from the group consisting of hydrogen, halo, $R^b$, $OR^d$, and —$(CH_2)_pR^{5a}$, where p is 0 or 1 and $R^{5a}$ is OH; and each $R^a$ is independently selected from the group consisting of halo, —$R^b$, —$OR^d$, —$O(CH_2)_uOR^d$, —$O(CH_2)_uNR^dR^d$, —$O(CH_2)_uNR^dC(O)R^e$, —$O(CH_2)_uNR^dC(O)_2R^e$, —$O(CH_2)_uNR^dS$—$(O)_2R^e$, —$NH_2$, —$(CH_2)_kOC(O)R^e$, —$(CH_2)_kSR^d$, $NO_2$, —$(CH_2)_kCO_2(C_{1-8}$alkyl)OH, —$(CH_2)_kCO_2(C_{1-8}$alkyl)(heteroaryl)C(O)($C_{1-8}$alkyl), —$(CH_2)_kCO_2R^d$, —$(CH_2)_kCONR^dR^d$, —$(CH_2)_kNR^dC(O)R^e$, —$(CH_2)_kNR^dC(O)_2R^e$, —$(CH_2)_kC(O)R^d$, —$(CH_2)_kOC(O)NR^dR^d$, —$NR^d(CH_2)_uOR^d$, —$NR^d(CH_2)_uNR^dR^d$, —$NR^d(CH_2)_uNR^d$-$C(O)R^e$, —$NR^d(CH_2)_uNR^dC(O)_2R^e$, —$NR^d(CH_2)_uNR^dS(O)_2R^e$, —$(CH_2)_kNR^dC(O)R^e$, —$(CH_2)_kNR^dC(O)_2R^d$, —$(CH_2)_kNR^dC(O)NR^dR^d$, —$(CH_2)_kS(O)R^e$, —$(CH_2)_kS$—$(O)_2R^e$, —$(CH_2)_kNR^dS(O)_2R^e$, —$(CH_2)_kS(O)_2NR^dR^d$, $N_3$, —$(CH_2)_k$aryl optionally substituted with one to three $R^c$, $NR^d(CH_2)$karyl optionally substituted with one to three $R^c$, —$(CH_2)_k$heteroaryl optionally substituted with one to three $R^c$, —$NR^d(CH_2)_k$heteroaryl optionally substituted with one to three $R^c$, —$(CH_2)_k$heterocycloalkyl optionally substituted with one to three Rc, and $NR^d(CH_2)_k$heterocycloalkyl optionally substituted with one to three Rc where k is 0, 1, 2, 3, 4, 5, or 6 and u is 1, 2, 3, 4, 5, or 6.

In some groups of embodiments, $T^2$ is C and $T^4$ is N; and $R^2$, $R^3$, $R^4$, and $R^5$ are hydrogen.

In some groups of embodiments, $T^2$ is C and $T^4$ is N;

$R^2$, $R^3$, and $R^5$ are hydrogen; and $R^4$ is $R^b$.

In some groups of embodiments, $T^2$ is N and $T^4$ is C;

$R^2$, $R^3$, $R^4$, are hydrogen; and $R^5$ is halo.

In some groups of embodiments, $T^2$ is N and $T^4$ is C;

$R^2$, $R^3$, $R^4$, are hydrogen; and $R^5$ is $R^b$.

In some groups of embodiments, $T^2$ is N and $T^4$ is C;

$R^2$, $R^3$, $R^4$, are hydrogen; and $R^5$ is $OR^d$.

In some groups of embodiments,
$T^2$ is N and $T^4$ is C;
$R^2$, $R^3$, $R^5$, are hydrogen; and
$R^4$ is $OR^d$.

In some groups of embodiments, $R^d$ is hydrogen.

In some groups of embodiments, $R^d$ is $C_{1-8}$ alkyl.

In some groups of embodiments, $R^d$ is —$(CH_2)_k$heterocycloalkyl, and where k is 1, 2, or 3.

In some groups of embodiments, $R^d$ is —$(CH_2)_uO$—$(CH_2)_uH$, and where each u is independently 1, 2, or 3.

In some groups of embodiments, Q is $C_3$-$C_8$ cycloalkyl.

In some groups of embodiments, Q is $C_3$-$C_6$ cycloalkyl.

In some groups of embodiments, Q is $C_3$-$C_8$ cycloalkenyl.

In some groups of embodiments, Q is $C_3$-$C_6$ cycloalkenyl.

In some groups of embodiments, Q is cyclopentyl.

In some groups of embodiments, Q is cyclohexyl.

In some groups of embodiments, Q is cyclopentenyl.

In some groups of embodiments, Q is cyclohexenyl.

In some groups of embodiments, each $R^a$ is independently selected from the group consisting of $R^b$, $OR^d$, —$(CH_2)_k CO_2R^d$, —$(CH_2)_k$aryl optionally substituted with one to three $R^c$, —$(CH_2)_k$heteroaryl optionally substituted with one to three $R^c$, and —$(CH_2)_k$heterocycloalkyl optionally substituted with one to three $R^c$, where k is 0, 1, 2, 3, 4, 5, or 6.

In some groups of embodiments, Q is substituted with one $R^a$ which is —$(CH_2)_k CO_2R^d$ k is 0, 1, 2, 3, 4, 5, or 6.

In some groups of embodiments, Q is substituted with one $R^a$ which is $R^b$.

In some groups of embodiments, $R^b$ is $C_{1-8}$alkyl optionally substituted with one to three $OR^d$.

In some groups of embodiments, $R^b$ is selected from the group consisting of 2-hydroxybutan-2-yl, 2-hydroxypentan-2-yl, and 2-hydroxypropan-2-yl.

In some groups of embodiments, Q is substituted with one $R^a$ which is aryl optionally substituted with one to three $R^c$.

In some groups of embodiments, $R^a$ is phenyl optionally substituted with one to three $R^c$, and wherein each $R^c$ is independently selected from the group consisting of halo and $OR^f$.

In some groups of embodiments, $R^a$ is selected from the group consisting of phenyl, 2-chlorophenyl, 2-fluorophenyl, and 2-methoxyphenyl.

In some groups of embodiments, Q is substituted with one $R^a$ which is heteroaryl optionally substituted with one to three $R^c$.

In some groups of embodiments, $R^a$ is selected from the group consisting of pyridinyl, pyrazolyl, and imadazolyl, and wherein each $R^c$ is independently selected from the group consisting of halo, $OR^f$, $C_{1-8}$alkyl, halo$C_{1-8}$alkyl, cycloalkyl, and heterocycloalkyl.

In some groups of embodiments, $R^a$ is selected from the group consisting of 2-chloropyridin-3-yl, 2-methoxypyridin-3-yl, 2-cyclobutylpyrazol-3-yl, 2-cyclopentylpyrazol-3-yl, 2-cyclopropylpyrazol-3-yl, 2-ethylpyrazol-3-yl, 2-propan-2-ylpyrazol-3-yl, 2-propylpyrazol-3-yl, 2-(2,2,2-trifluoroethyl)pyrazol-3-yl, 2-(2,2-difluoroethyl)pyrazol-3-yl, 2-(3,3,3-trifluoropropyl)pyrazol-3-yl, 2-(oxetan-3-yl)pyrazol-3-yl, 2-propan-2-ylpyrazol-3-yl, 2-propylpyrazol-3-yl, and (3-propan-2-ylimidazol-4-yl).

In some groups of embodiments,
Q is cyclohexyl substituted with one $R^c$;
Y is $CH_2$ and X is O;
$R^2$, $R^3$, and $R^4$ are hydrogen;
$R^5$ is OH; and
$R^6$ and $R^7$ together form oxo.

In some groups of embodiments,
Q is cyclohexyl substituted with one $R^c$. In some groups of embodiments
Y is $CH_2$ and X is O;
$R^6$ and $R^7$ together form oxo.

In some groups of embodiments,
$R^a$ is pyrazolyl substituted with one $R^c$;
Y is $CH_2$ and X is O;
$R^2$, $R^3$, and $R^4$ are hydrogen;
$R^5$ is OH; and
$R^6$ and $R^7$ together form oxo.

In some groups of embodiments,
$R^a$ is pyrazolyl substituted with one $R^c$;
Y is $CH_2$ and X is O; and
$R^6$ and $R^7$ together form oxo.

In some groups of embodiments, $R^a$ is pyrazol-3-yl substituted with one $R^c$.

In some groups of embodiments, the compound is selected from those listed in Table 1, or tautomers or pharmaceutically acceptable salts thereof.

TABLE 1

| Compound | Structure | Name |
|---|---|---|
| 1 | 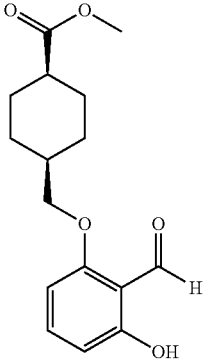 [SMILES: COC(=O)[C@H]1CC[C@@H](COc2cccc(O)c2C=O)CC1] | cis-methyl 4-((2-formyl-3-hydroxyphenoxy)methyl)cyclohexanecarboxylate |

TABLE 1-continued

| Compound | Structure | Name |
|---|---|---|
| 2 | 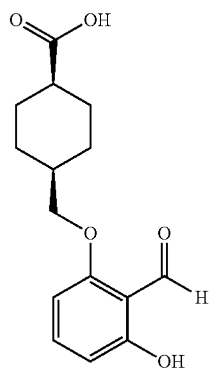 [SMILES: O=Cc1c(O)cccc1OC[C@H]1CC[C@@H](C(=O)O)CC1] | cis-4-((2-formyl-3-hydroxyphenoxy)methyl)cyclohexanecarboxylic acid |
| 3 | 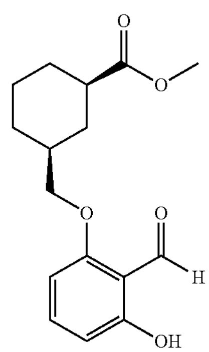 [SMILES: COC(=O)[C@@H]1CCC[C@H](COc2cccc(O)c2C=O)C1] | cis-3-((2-formyl-3-hydroxyphenoxy)methyl)cyclohexanecarboxylic acid |
| 4 | 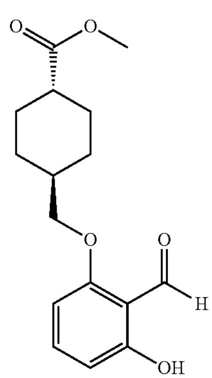 [SMILES: COC(=O)[C@H]1CC[C@H](COc2cccc(O)c2C=O)CC1] | trans-methyl 4-((2-formyl-3-hydroxyphenoxy)methyl)cyclohexanecarboxylate |
| 5 | 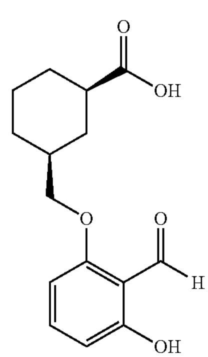 [SMILES: O=Cc1c(O)cccc1OC[C@H]1CCC[C@@H](C(=O)O)C1] | cis-3-((2-formyl-3-hydroxyphenoxy)methyl)cyclohexanecarboxylic acid |

TABLE 1-continued
| Compound | Structure | Name |
|---|---|---|
| 6 | 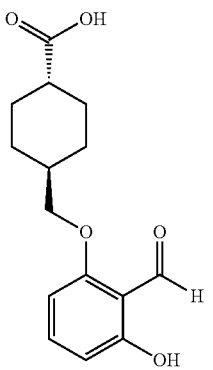 [SMILES: O=Cc1c(O)cccc1OC[C@H]1CC[C@H](C(=O)O)CC1] | trans-4-((2-formyl-3-hydroxyphenoxy)methyl)cyclohexanecarboxylic acid |
| 7 | 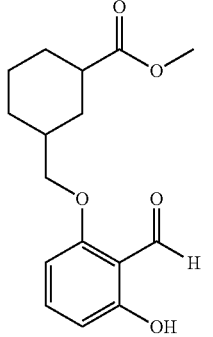 [SMILES: COC(=O)C1CCCC(COc2cccc(O)c2C=O)C1] | methyl 3-((2-formyl-3-hydroxyphenoxy)methyl)cyclohexanecarboxylate |
| 8 | 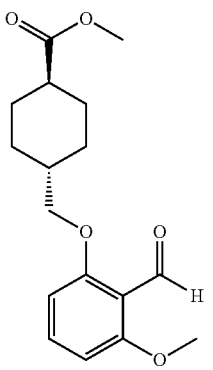 [SMILES: COc1cccc(OC[C@H]2CC[C@H](C(=O)OC)CC2)c1C=O] | trans-methyl 4-((2-formyl-3-methoxyphenoxy)methyl)cyclohexanecarboxylate |
| 9 | 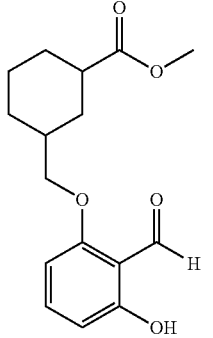 [SMILES: COC(=O)C1CCCC(COc2cccc(O)c2C=O)C1] | methyl 3-((2-formyl-3-hydroxyphenoxy)methyl)cyclohexanecarboxylate |

TABLE 1-continued

| Compound | Structure | Name |
|---|---|---|
| 10 | 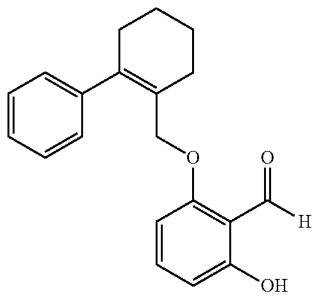 [SMILES: O=Cc1c(O)cccc1OCC1=C(c2ccccc2)CCCC1] | 2-hydroxy-6-((3,4,5,6-tetrahydro-[1,1'-biphenyl]-2-yl)methoxy)benzaldehyde |
| 11 | 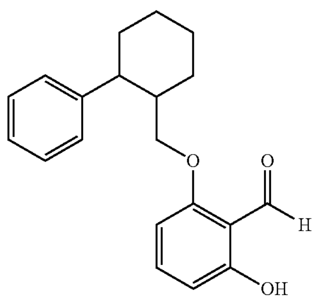 [SMILES: O=Cc1c(O)cccc1OCC1CCCCC1c1ccccc1] | 2-hydroxy-6-((2-phenylcyclohexyl)methoxy)benzaldehyde |
| 12 | 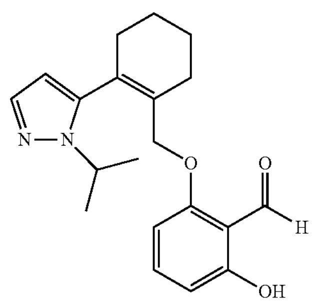 [SMILES: CC(C)n1nccc1C1=C(COc2cccc(O)c2C=O)CCCC1] | 2-hydroxy-6-((2-(1-isopropyl-1H-pyrazol-5-yl)cyclohex-1-en-1-yl)methoxy)benzaldehyde |
| 13 | 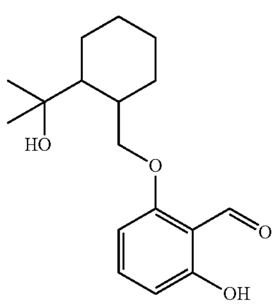 [SMILES: CC(C)(O)C1CCCCC1COc1cccc(O)c1C=O] | 2-hydroxy-6-[[2-(2-hydroxypropan-2-yl)cyclohexyl]methoxy]benzaldehyde |
| 14 | 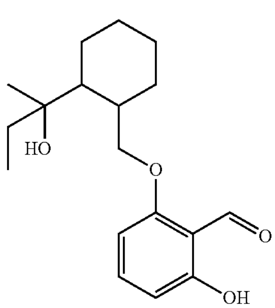 [SMILES: CCC(C)(O)C1CCCCC1COc1cccc(O)c1C=O] | 2-hydroxy-6-[[2-(2-hydroxybutan-2-yl)cyclohexyl]methoxy]benzaldehyde |

TABLE 1-continued

| Compound | Structure | Name |
| --- | --- | --- |
| 15 | 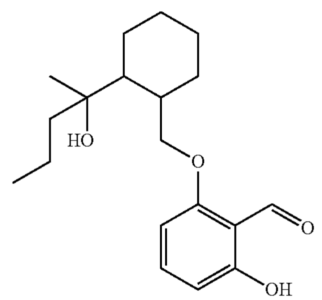 [SMILES: CCCC(C)(O)C1CCCCC1COc1cccc(O)c1C=O] | 2-hydroxy-6-[[2-(2-hydroxypentan-2-yl)cyclohexyl]methoxy]benzaldehyde |
| 16 | 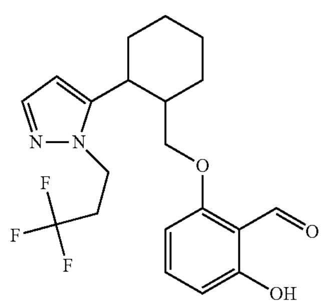 [SMILES: O=Cc1c(O)cccc1OCC1CCCCC1c1ccnn1CCC(F)(F)F] | 2-hydroxy-6-[[2-[2-(3,3,3-trifluoropropyl)pyrazol-3-yl]cyclohexyl]methoxy]benzaldehyde |
| 17 | 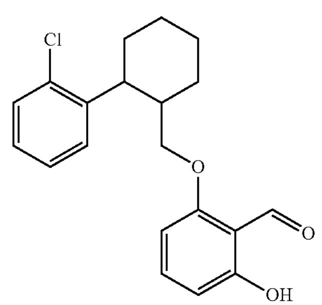 | 2-[[2-(2-chlorophenyl)cyclohexyl]methoxy]-6-hydroxybenzaldehyde |
| 18 | 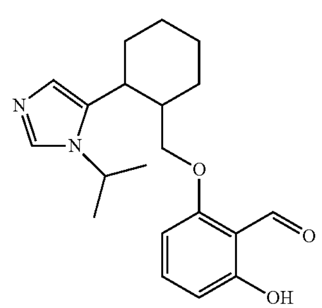 [SMILES: CC(C)n1cncc1C1CCCCC1COc1cccc(O)c1C=O] | 2-hydroxy-6-[[2-(3-propan-2-ylimidazol-4-yl)cyclohexyl]methoxy]benzaldehyde |
| 19 | 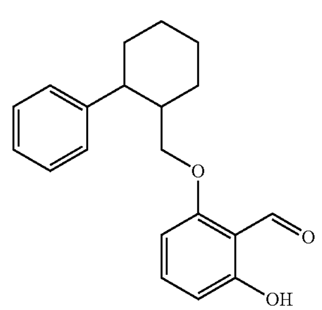 [SMILES: O=Cc1c(O)cccc1OCC1CCCCC1c1ccccc1] | 2-hydroxy-6-[(2-phenylcyclohexyl)methoxy]benzaldehyde |

TABLE 1-continued

| Compound | Structure | Name |
|---|---|---|
| 20 | 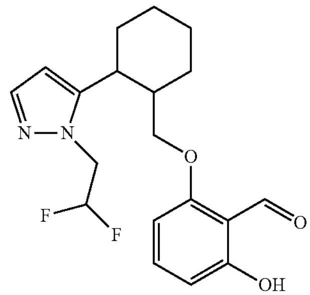 [SMILES: O=Cc1c(O)cccc1OCC1CCCCC1c1ccnn1CC(F)F] | 2-[[2-[2-(2,2-difluoroethyl)pyrazol-3-yl]cyclohexyl]methoxy]-6-hydroxybenzaldehyde |
| 21 | 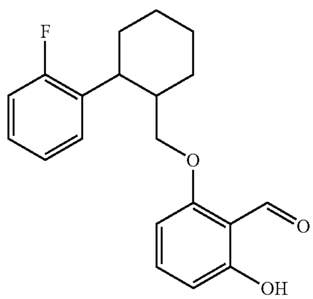 [SMILES: O=Cc1c(O)cccc1OCC1CCCCC1c1ccccc1F] | 2-[[2-(2-fluorophenyl)cyclohexyl]methoxy]-6-hydroxybenzaldehyde |
| 22 | 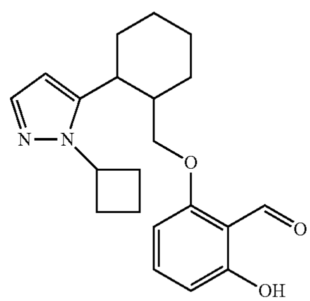 [SMILES: O=Cc1c(O)cccc1OCC1CCCCC1c1ccnn1C1CCC1] | 2-[[2-(2-cyclobutylpyrazol-3-yl)cyclohexyl]methoxy]-6-hydroxybenzaldehyde |
| 23 | 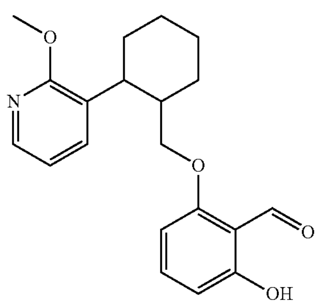 [SMILES: COc1ncccc1C1CCCCC1COc1cccc(O)c1C=O] | 2-hydroxy-6-[[2-(2-methoxypyridin-3-yl)cyclohexyl]methoxy]benzaldehyde |
| 24 | 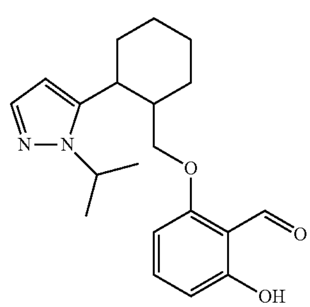 [SMILES: CC(C)n1nccc1C1CCCCC1COc1cccc(O)c1C=O] | 2-hydroxy-6-[[2-(2-propan-2-ylpyrazol-3-yl)cyclohexyl]methoxy]benzaldehyde |

TABLE 1-continued

| Compound | Structure | Name |
|---|---|---|
| 25 | 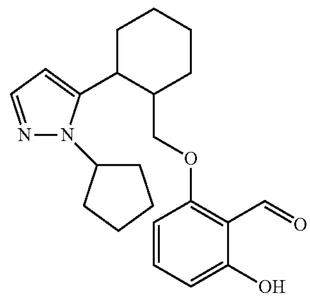 [SMILES: O=Cc1c(O)cccc1OCC1CCCCC1c1ccnn1C1CCCC1] | 2-[[2-(2-cyclopentylpyrazol-3-yl)cyclohexyl]methoxy]-6-hydroxybenzaldehyde |
| 26 | 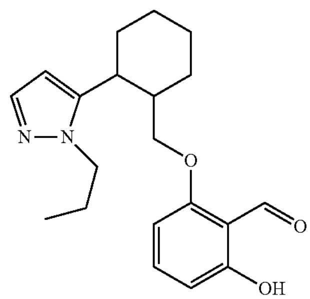 | 2-hydroxy-6-[[2-(2-propylpyrazol-3-yl)cyclohexyl]methoxy]benzaldehyde |
| 27 | 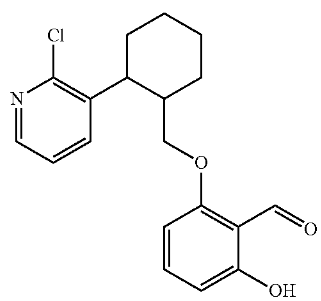 [SMILES: O=Cc1c(O)cccc1OCC1CCCCC1c1cccnc1Cl] | 2-[[2-(2-chloropyridin-3-yl)cyclohexyl]methoxy]-6-hydroxybenzaldehyde |
| 28 | 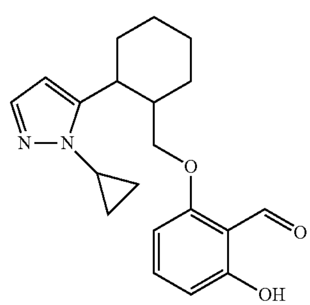 [SMILES: O=Cc1c(O)cccc1OCC1CCCCC1c1ccnn1C1CC1] | 2-[[2-(2-cyclopropylpyrazol-3-yl)cyclohexyl]methoxy]-6-hydroxybenzaldehyde |
| 29 | 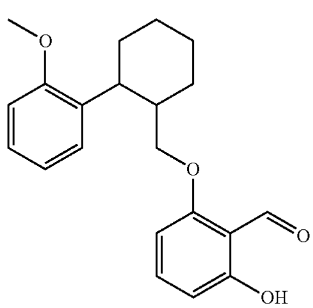 [SMILES: COc1ccccc1C1CCCCC1COc1cccc(O)c1C=O] | 2-hydroxy-6-[[2-(2-methoxyphenyl)cyclohexyl]methoxy]benzaldehyde |

TABLE 1-continued

| Compound | Structure | Name |
| --- | --- | --- |
| 30 | 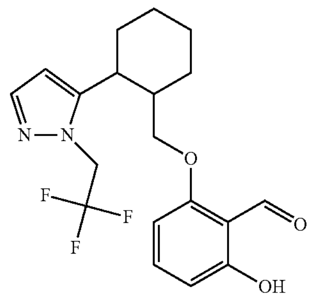 | 2-hydroxy-6-[[2-[2-(2,2,2-trifluoroethyl)pyrazol-3-yl]cyclohexyl]methoxy]benzaldehyde |
| 31 | 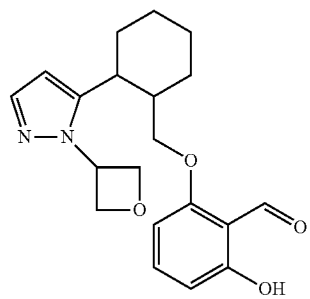 | 2-hydroxy-6-[[2-[2-(oxetan-3-yl)pyrazol-3-yl]cyclohexyl]methoxy]benzaldehyde |
| 32 | 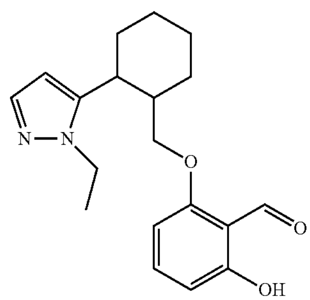 [SMILES: CCn1nccc1C1CCCCC1COc1cccc(O)c1C=O] | 2-[[2-(2-ethylpyrazol-3-yl)cyclohexyl]methoxy]-6-hydroxybenzaldehyde |
| 33 | 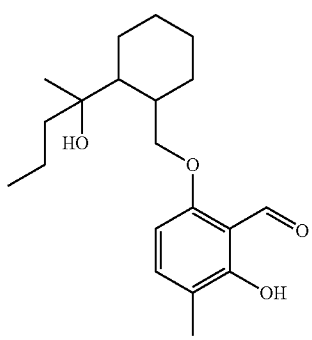 [SMILES: CCCC(C)(O)C1CCCCC1COc1ccc(C)c(O)c1C=O] | 2-hydroxy-6-[[2-(2-hydroxypentan-2-yl)cyclohexyl]methoxy]-3-methylbenzaldehyde |
| 34 | 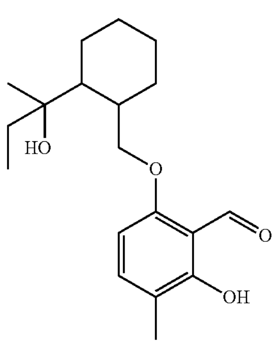 | 2-hydroxy-6-[[2-(2-hydroxybutan-2-yl)cyclohexyl]methoxy]-3-methylbenzaldehyde |

TABLE 1-continued

| Compound | Structure | Name |
| --- | --- | --- |
| 35 | 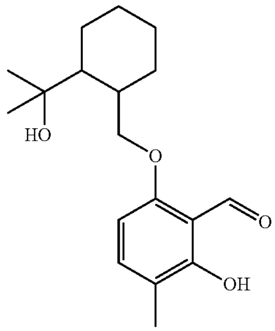 [SMILES: Cc1ccc(OCC2CCCCC2C(C)(C)O)c(C=O)c1O] | 2-hydroxy-6-[[2-(2-hydroxypropan-2-yl)cyclohexyl]methoxy]-3-methylbenzaldehyde |
| 36 | 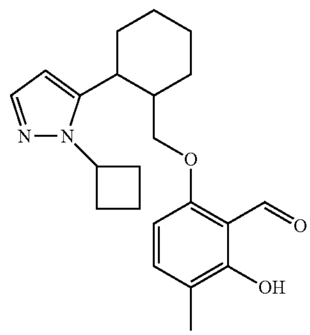 | 6-[[2-(2-cyclobutylpyrazol-3-yl)cyclohexyl]methoxy]-2-hydroxy-3-methylbenzaldehyde |
| 37 | 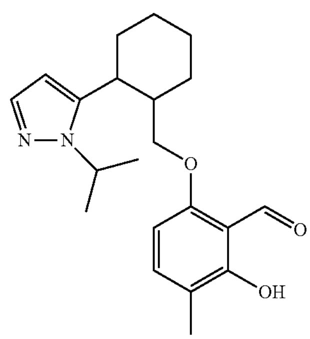 | 2-hydroxy-3-methyl-6-[[2-(2-propan-2-ylpyrazol-3-yl)cyclohexyl]methoxy]benzaldehyde |
| 38 | 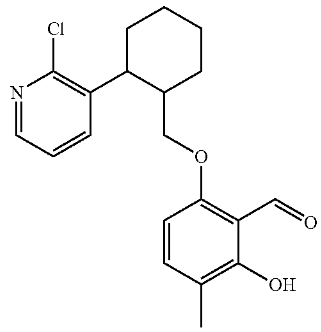 [SMILES: Cc1ccc(OCC2CCCCC2c2cccnc2Cl)c(C=O)c1O] | 6-[[2-(2-chloropyridin-3-yl)cyclohexyl]methoxy]-2-hydroxy-3-methylbenzaldehyde |

TABLE 1-continued

| Compound | Structure | Name |
|---|---|---|
| 39 | 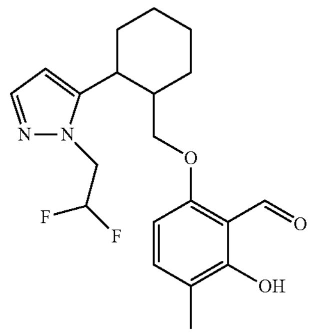 | 6-[[2-[2-(2,2-difluoroethyl)pyrazol-3-yl]cyclohexyl]methoxy]-2-hydroxy-3-methylbenzaldehyde |
| 40 | 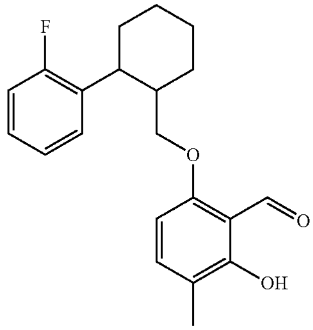 [SMILES: Cc1ccc(OCC2CCCCC2c2ccccc2F)c(C=O)c1O] | 6-[[2-(2-fluorophenyl)cyclohexyl]methoxy]-2-hydroxy-3-methylbenzaldehyde |
| 41 | 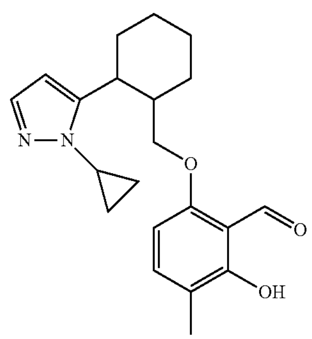 [SMILES: Cc1ccc(OCC2CCCCC2c2ccnn2C2CC2)c(C=O)c1O] | 6-[[2-(2-cyclopropylpyrazol-3-yl)cyclohexyl]methoxy]-2-hydroxy-3-methylbenzaldehyde |
| 42 | 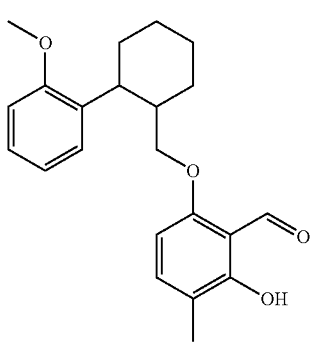 [SMILES: COc1ccccc1C1CCCCC1COc1ccc(C)c(O)c1C=O] | 2-hydroxy-6-[[2-(2-methoxyphenyl)cyclohexyl]methoxy]-3-methylbenzaldehyde |

TABLE 1-continued

| Compound | Structure | Name |
|---|---|---|
| 43 | 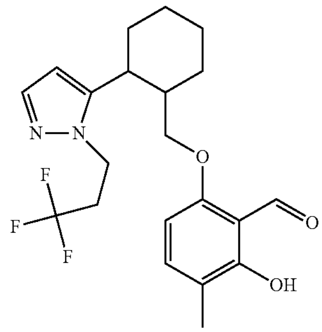 [SMILES: Cc1ccc(OCC2CCCCC2c2ccnn2CCC(F)(F)F)c(C=O)c1O] | 2-hydroxy-3-methyl-6-[[2-[2-(3,3,3-trifluoropropyl)pyrazol-3-yl]cyclohexyl]methoxy]benzaldehyde |
| 44 | 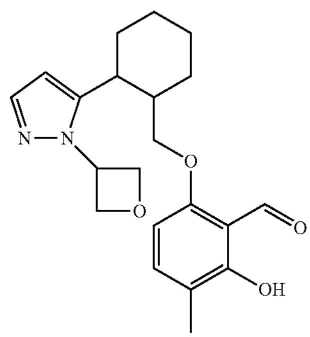 | 2-hydroxy-3-methyl-6-[[2-[2-(oxetan-3-yl)pyrazol-3-yl]cyclohexyl]methoxy]benzaldehyde |
| 45 | 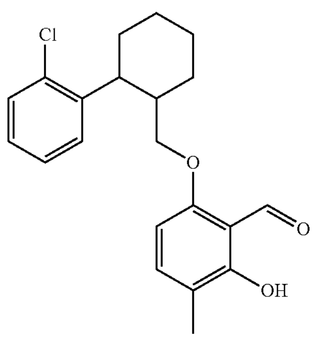 [SMILES: Cc1ccc(OCC2CCCCC2c2ccccc2Cl)c(C=O)c1O] | 6-[[2-(2-chlorophenyl)cyclohexyl]methoxy]-2-hydroxy-3-methylbenzaldehyde |
| 46 | 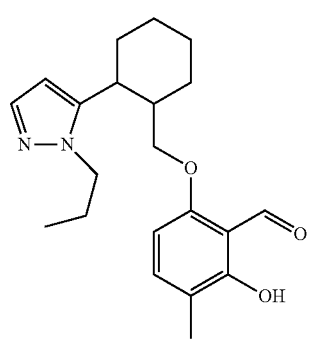 [SMILES: CCCn1nccc1C1CCCCC1COc1ccc(C)c(O)c1C=O] | 2-hydroxy-3-methyl-6-[[2-(2-propylpyrazol-3-yl)cyclohexyl]methoxy]benzaldehyde |

TABLE 1-continued

| Compound | Structure | Name |
|---|---|---|
| 47 | 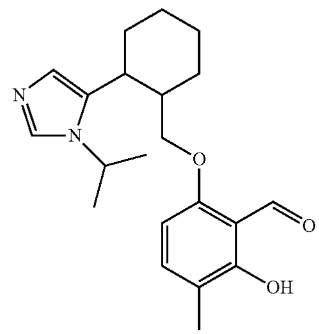 [SMILES: Cc1ccc(OCC2CCCCC2c2cncn2C(C)C)c(C=O)c1O] | 2-hydroxy-3-methyl-6-[[2-(3-propan-2-ylimidazol-4-yl)cyclohexyl]methoxy]benzaldehyde |
| 48 | 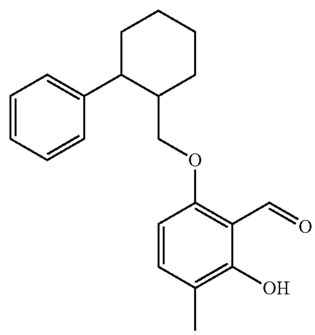 [SMILES: Cc1ccc(OCC2CCCCC2c2ccccc2)c(C=O)c1O] | 2-hydroxy-3-methyl-6-[(2-phenylcyclohexyl)methoxy]benzaldehyde |
| 49 | 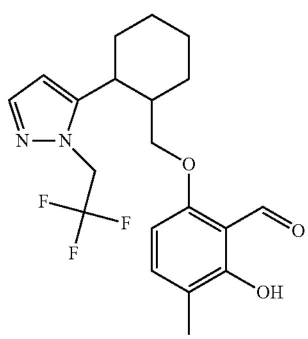 [SMILES: Cc1ccc(OCC2CCCCC2c2ccnn2CC(F)(F)F)c(C=O)c1O] | 2-hydroxy-3-methyl-6-[[2-[2-(2,2,2-trifluoroethyl)pyrazol-3-yl]cyclohexyl]methoxy]benzaldehyde |
| 50 | 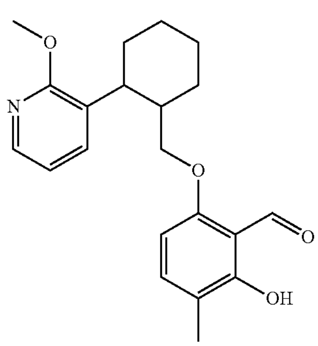 [SMILES: COc1ncccc1C1CCCCC1COc1ccc(C)c(O)c1C=O] | 2-hydroxy-6-[[2-(2-methoxypyridin-3-yl)cyclohexyl]methoxy]-3-methylbenzaldehyde |

TABLE 1-continued

| Compound | Structure | Name |
|---|---|---|
| 51 | 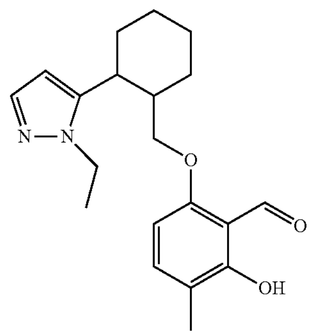 [SMILES: CCn1nccc1C1CCCCC1COc1ccc(C)c(O)c1C=O] | 6-[[2-(2-ethylpyrazol-3-yl)cyclohexyl]methoxy]-2-hydroxy-3-methylbenzaldehyde |
| 52 | 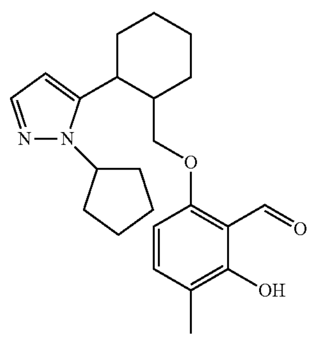 [SMILES: Cc1ccc(OCC2CCCCC2c2ccnn2C2CCCC2)c(C=O)c1O] | 6-[[2-(2-cyclopentylpyrazol-3-yl)cyclohexyl]methoxy]-2-hydroxy-3-methylbenzaldehyde |
| 53 | 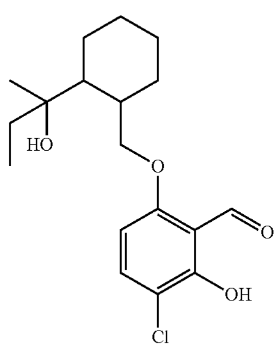 [SMILES: CCC(C)(O)C1CCCCC1COc1ccc(Cl)c(O)c1C=O] | 3-chloro-2-hydroxy-6-[[2-(2-hydroxybutan-2-yl)cyclohexyl]methoxy]benzaldehyde |
| 54 | 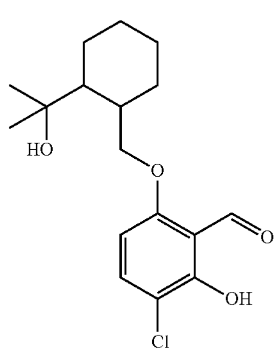 | 3-chloro-2-hydroxy-6-[[2-(2-hydroxypropan-2-yl)cyclohexyl]methoxy]benzaldehyde |

TABLE 1-continued

| Compound | Structure | Name |
|---|---|---|
| 55 | 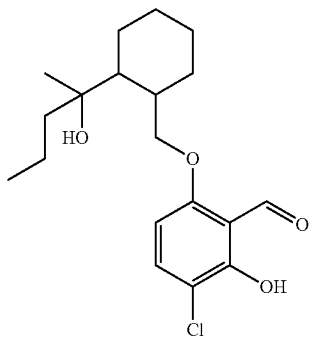 [SMILES: CCCC(C)(O)C1CCCCC1COc1ccc(Cl)c(O)c1C=O] | 3-chloro-2-hydroxy-6-[[2-(2-hydroxypentan-2-yl)cyclohexyl]methoxy]benzaldehyde |
| 56 | 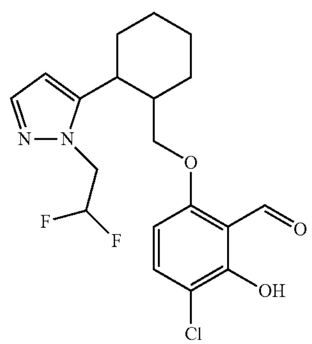 [SMILES: O=Cc1c(OCC2CCCCC2c2ccnn2CC(F)F)ccc(Cl)c1O] | 3-chloro-6-[[2-[2-(2,2-difluoroethyl)pyrazol-3-yl]cyclohexyl]methoxy]-2-hydroxybenzaldehyde |
| 57 | 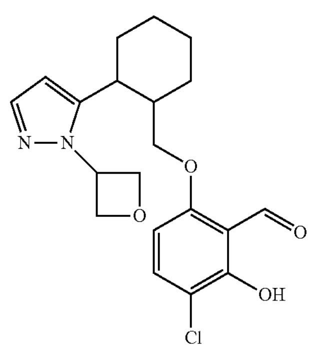 [SMILES: O=Cc1c(OCC2CCCCC2c2ccnn2C2COC2)ccc(Cl)c1O] | 3-chloro-2-hydroxy-6-[[2-[2-(oxetan-3-yl)pyrazol-3-yl]cyclohexyl]methoxy]benzaldehyde |
| 58 | 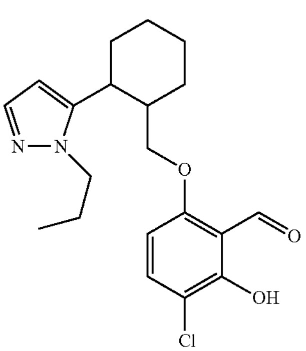 [SMILES: CCCn1nccc1C1CCCCC1COc1ccc(Cl)c(O)c1C=O] | 3-chloro-2-hydroxy-6-[[2-(2-propylpyrazol-3-yl)cyclohexyl]methoxy]benzaldehyde |

TABLE 1-continued

| Compound | Structure | Name |
|---|---|---|
| 59 | 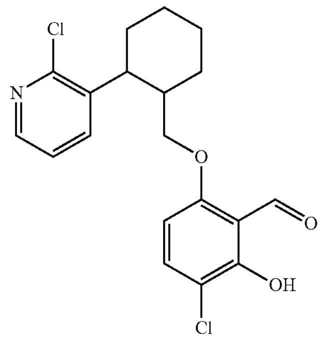 [SMILES: O=Cc1c(OCC2CCCCC2c2cccnc2Cl)ccc(Cl)c1O] | 3-chloro-6-[[2-(2-chloropyridin-3-yl)cyclohexyl]methoxy]-2-hydroxybenzaldehyde |
| 60 | 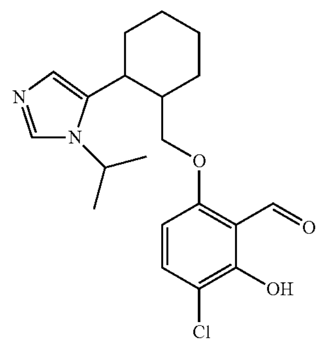 [SMILES: CC(C)n1cncc1C1CCCCC1COc1ccc(Cl)c(O)c1C=O] | 3-chloro-2-hydroxy-6-[[2-(3-propan-2-ylimidazol-4-yl)cyclohexyl]methoxy]benzaldehyde |
| 61 | 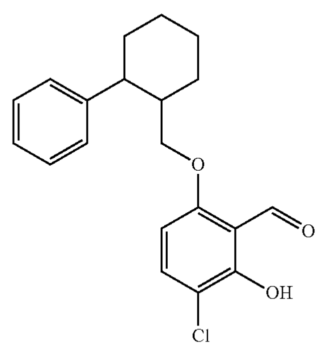 [SMILES: O=Cc1c(OCC2CCCCC2c2ccccc2)ccc(Cl)c1O] | 3-chloro-2-hydroxy-6-[(2-phenylcyclohexyl)methoxy]benzaldehyde |
| 62 | 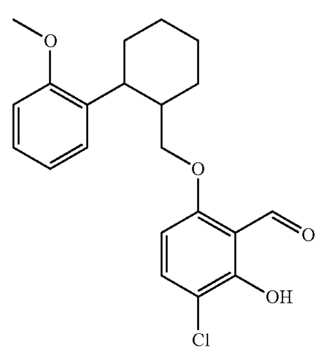 [SMILES: COc1ccccc1C1CCCCC1COc1ccc(Cl)c(O)c1C=O] | 3-chloro-2-hydroxy-6-[[2-(2-methoxyphenyl)cyclohexyl]methoxy]benzaldehyde |

TABLE 1-continued

| Compound | Structure | Name |
|---|---|---|
| 63 | 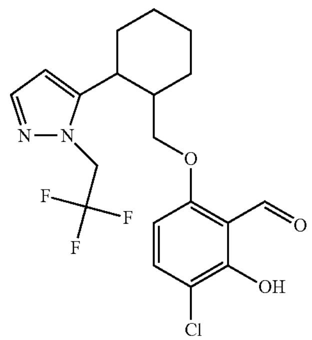 [SMILES: O=Cc1c(OCC2CCCCC2c2ccnn2CC(F)(F)F)ccc(Cl)c1O] | 3-chloro-2-hydroxy-6-[[2-[2-(2,2,2-trifluoroethyl)pyrazol-3-yl]cyclohexyl]methoxy]benzaldehyde |
| 64 | 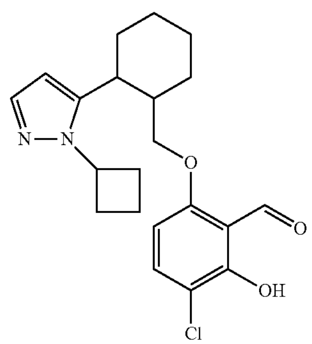 [SMILES: O=Cc1c(OCC2CCCCC2c2ccnn2C2CCC2)ccc(Cl)c1O] | 3-chloro-6-[[2-(2-cyclobutylpyrazol-3-yl)cyclohexyl]methoxy]-2-hydroxybenzaldehyde |
| 65 | 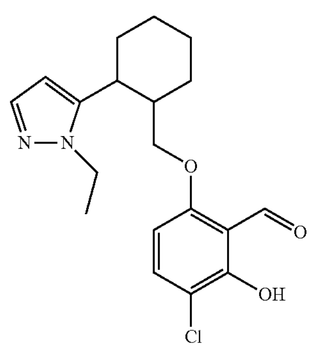 [SMILES: CCn1nccc1C1CCCCC1COc1ccc(Cl)c(O)c1C=O] | 3-chloro-6-[[2-(2-ethylpyrazol-3-yl)cyclohexyl]methoxy]-2-hydroxybenzaldehyde |
| 66 | 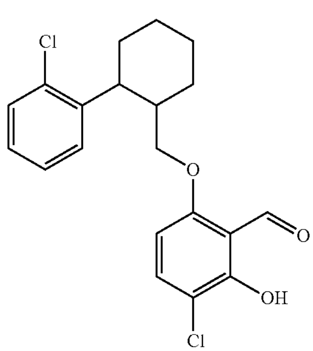 [SMILES: O=Cc1c(OCC2CCCCC2c2ccccc2Cl)ccc(Cl)c1O] | 3-chloro-6-[[2-(2-chlorophenyl)cyclohexyl]methoxy]-2-hydroxybenzaldehyde |

TABLE 1-continued

| Compound | Structure | Name |
|---|---|---|
| 67 | 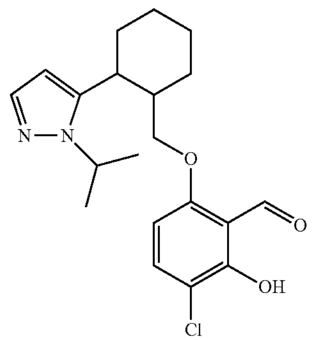 [SMILES: CC(C)n1nccc1C1CCCCC1COc1ccc(Cl)c(O)c1C=O] | 3-chloro-2-hydroxy-6-[[2-(2-propan-2-ylpyrazol-3-yl)cyclohexyl]methoxy]benzaldehyde |
| 68 | 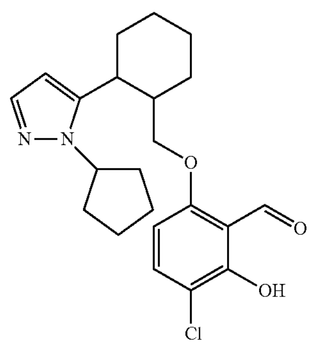 [SMILES: O=Cc1c(OCC2CCCCC2c2ccnn2C2CCCC2)ccc(Cl)c1O] | 3-chloro-6-[[2-(2-cyclopentylpyrazol-3-yl)cyclohexyl]methoxy]-2-hydroxybenzaldehyde |
| 69 | 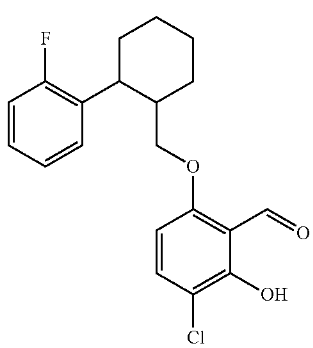 [SMILES: O=Cc1c(OCC2CCCCC2c2ccccc2F)ccc(Cl)c1O] | 3-chloro-6-[[2-(2-fluorophenyl)cyclohexyl]methoxy]-2-hydroxybenzaldehyde |
| 70 | 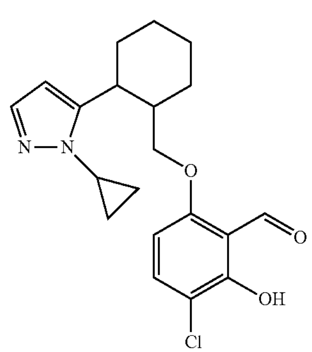 [SMILES: O=Cc1c(OCC2CCCCC2c2ccnn2C2CC2)ccc(Cl)c1O] | 3-chloro-6-[[2-(2-cyclopropylpyrazol-3-yl)cyclohexyl]methoxy]-2-hydroxybenzaldehyde |

TABLE 1-continued

| Compound | Structure | Name |
|---|---|---|
| 71 | 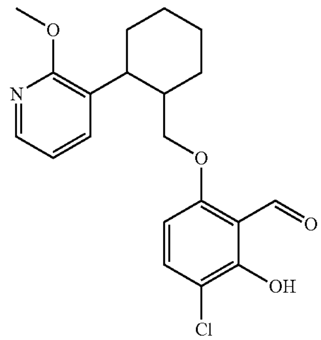 [SMILES: COc1ncccc1C1CCCCC1COc1ccc(Cl)c(O)c1C=O] | 3-chloro-2-hydroxy-6-[[2-(2-methoxypyridin-3-yl)cyclohexyl]methoxy]benzaldehyde |
| 72 | 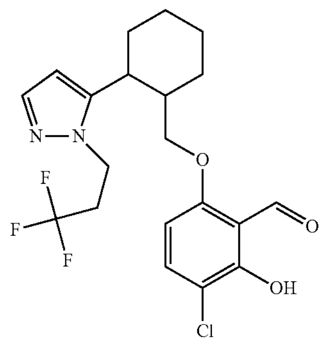 [SMILES: O=Cc1c(OCC2CCCCC2c2ccnn2CCC(F)(F)F)ccc(Cl)c1O] | 3-chloro-2-hydroxy-6-[[2-[2-(3,3,3-trifluoropropyl)pyrazol-3-yl]cyclohexyl]methoxy]benzaldehyde |
| 73 | 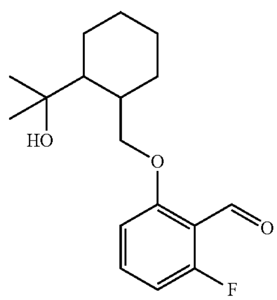 | 2-fluoro-6-[[2-(2-hydroxypropan-2-yl)cyclohexyl]methoxy]benzaldehyde |
| 74 | 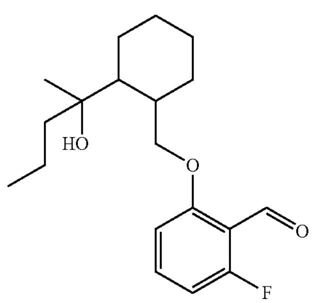 [SMILES: CCCC(C)(O)C1CCCCC1COc1cccc(F)c1C=O] | 2-fluoro-6-[[2-(2-hydroxypentan-2-yl)cyclohexyl]methoxy]benzaldehyde |
| 75 | 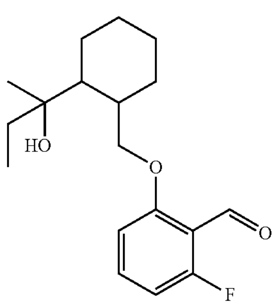 [SMILES: CCC(C)(O)C1CCCCC1COc1cccc(F)c1C=O] | 2-fluoro-6-[[2-(2-hydroxybutan-2-yl)cyclohexyl]methoxy]benzaldehyde |

TABLE 1-continued

| Compound | Structure | Name |
|---|---|---|
| 76 | 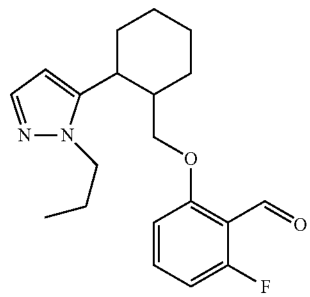 [SMILES: CCCn1nccc1C1CCCCC1COc1cccc(F)c1C=O] | 2-fluoro-6-[[2-(2-propylpyrazol-3-yl)cyclohexyl]methoxy]benzaldehyde |
| 77 | 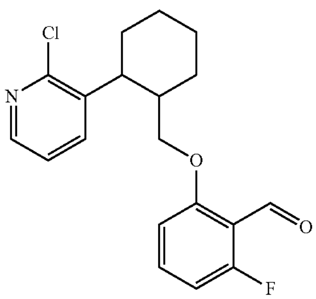 [SMILES: O=Cc1c(F)cccc1OCC1CCCCC1c1cccnc1Cl] | 2-[[2-(2-chloropyridin-3-yl)cyclohexyl]methoxy]-6-fluorobenzaldehyde |
| 78 | 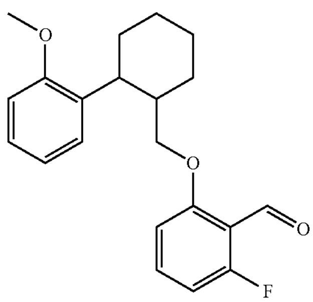 [SMILES: COc1ccccc1C1CCCCC1COc1cccc(F)c1C=O] | 2-fluoro-6-[[2-(2-methoxyphenyl)cyclohexyl]methoxy]benzaldehyde |
| 79 | 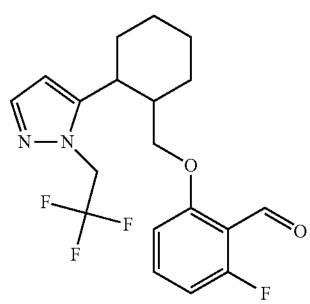 [SMILES: O=Cc1c(F)cccc1OCC1CCCCC1c1ccnn1CC(F)(F)F] | 2-fluoro-6-[[2-[2-(2,2,2-trifluoroethyl)pyrazol-3-yl]cyclohexyl]methoxy]benzaldehyde |
| 80 | 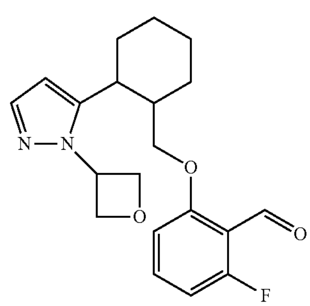 [SMILES: O=Cc1c(F)cccc1OCC1CCCCC1c1ccnn1C1COC1] | 2-fluoro-6-[[2-[2-(oxetan-3-yl)pyrazol-3-yl]cyclohexyl]methoxy]benzaldehyde |

TABLE 1-continued

| Compound | Structure | Name |
|---|---|---|
| 81 | 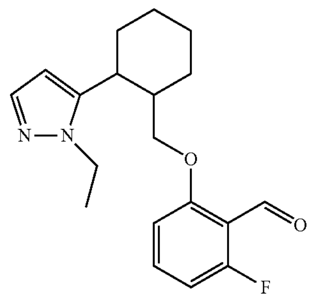 [SMILES: CCn1nccc1C1CCCCC1COc1cccc(F)c1C=O] | 2-[[2-(2-ethylpyrazol-3-yl)cyclohexyl]methoxy]-6-fluorobenzaldehyde |
| 82 | 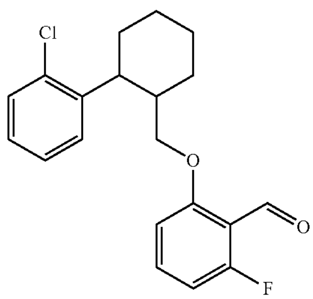 [SMILES: O=Cc1c(F)cccc1OCC1CCCCC1c1ccccc1Cl] | 2-[[2-(2-chlorophenyl)cyclohexyl]methoxy]-6-fluorobenzaldehyde |
| 83 | 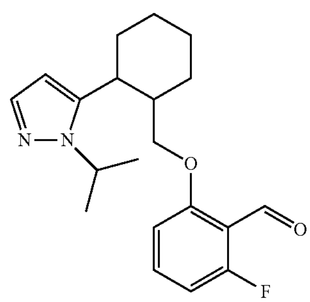 [SMILES: CC(C)n1nccc1C1CCCCC1COc1cccc(F)c1C=O] | 2-fluoro-6-[[2-(2-propan-2-ylpyrazol-3-yl)cyclohexyl]methoxy]benzaldehyde |
| 84 | 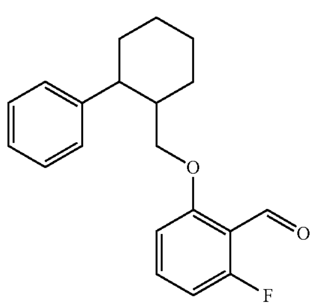 [SMILES: O=Cc1c(F)cccc1OCC1CCCCC1c1ccccc1] | 2-fluoro-6-[(2-phenylcyclohexyl)methoxy]benzaldehyde |
| 85 | 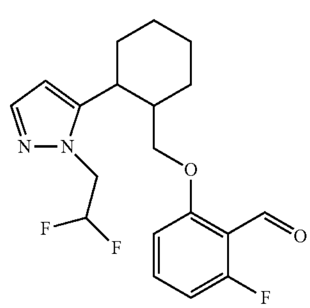 [SMILES: O=Cc1c(F)cccc1OCC1CCCCC1c1ccnn1CC(F)F] | 2-[[2-[2-(2,2-difluoroethyl)pyrazol-3-yl]cyclohexyl]methoxy]-6-fluorobenzaldehyde |

TABLE 1-continued

| Compound | Structure | Name |
|---|---|---|
| 86 | 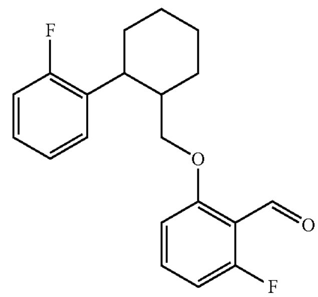 [SMILES: O=Cc1c(F)cccc1OCC1CCCCC1c1ccccc1F] | 2-fluoro-6-[[2-(2-fluorophenyl)cyclohexyl]methoxy]benzaldehyde |
| 87 | 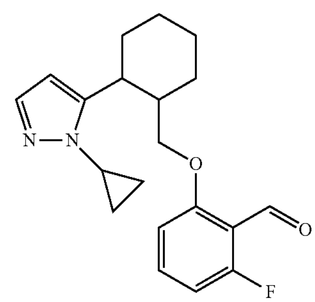 [SMILES: O=Cc1c(F)cccc1OCC1CCCCC1c1ccnn1C1CC1] | 2-[[2-(2-cyclopropylpyrazol-3-yl)cyclohexyl]methoxy]-6-fluorobenzaldehyde |
| 88 | 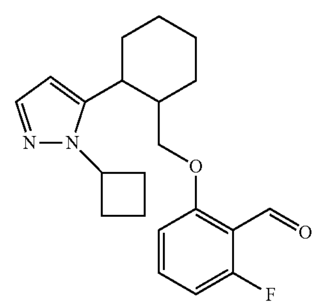 | 2-[[2-(2-cyclobutylpyrazol-3-yl)cyclohexyl]methoxy]-6-fluorobenzaldehyde |
| 89 | 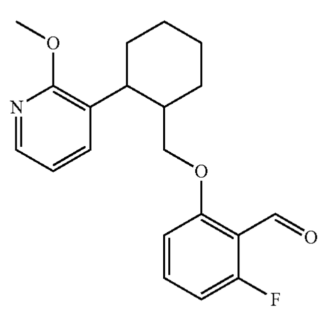 [SMILES: COc1ncccc1C1CCCCC1COc1cccc(F)c1C=O] | 2-fluoro-6-[[2-(2-methoxypyridin-3-yl)cyclohexyl]methoxy]benzaldehyde |
| 90 | 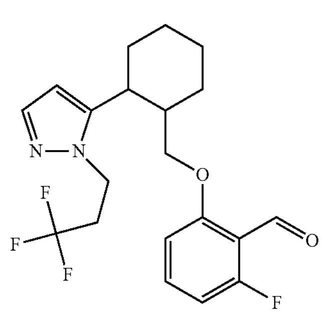 [SMILES: O=Cc1c(F)cccc1OCC1CCCCC1c1ccnn1CCC(F)(F)F] | 2-fluoro-6-[[2-[2-(3,3,3-trifluoropropyl)pyrazol-3-yl]cyclohexyl]methoxy]benzaldehyde |

TABLE 1-continued

| Compound | Structure | Name |
|---|---|---|
| 91 | 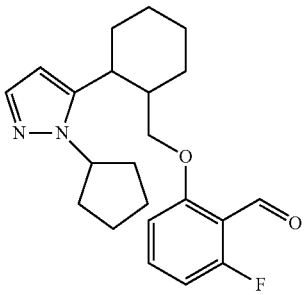 [SMILES: O=Cc1c(F)cccc1OCC1CCCCC1c1ccnn1C1CCCC1] | 2-[[2-(2-cyclopentylpyrazol-3-yl)cyclohexyl]methoxy]-6-fluorobenzaldehyde |
| 92 | 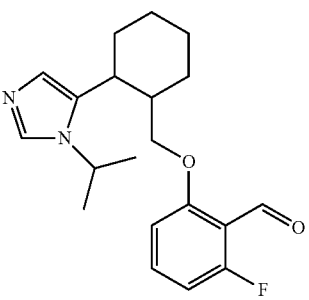 [SMILES: CC(C)n1cncc1C1CCCCC1COc1cccc(F)c1C=O] | 2-fluoro-6-[[2-(3-propan-2-ylimidazol-4-yl)cyclohexyl]methoxy]benzaldehyde |
| 93 | 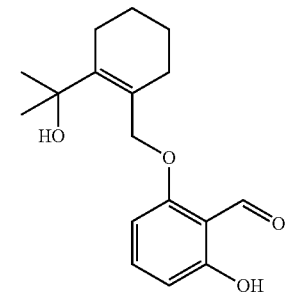 | 2-hydroxy-6-[[2-(2-hydroxypropan-2-yl)cyclohexen-1-yl]methoxy]benzaldehyde |
| 94 | 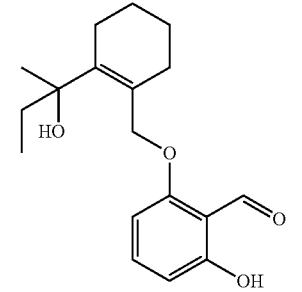 [SMILES: CC(C)(O)C1=C(COc2cccc(O)c2C=O)CCCC1] | 2-hydroxy-6-[[2-(2-hydroxybutan-2-yl)cyclohexen-1-yl]methoxy]benzaldehyde |
| 95 | 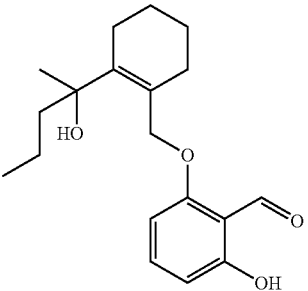 [SMILES: CCCC(C)(O)C1=C(COc2cccc(O)c2C=O)CCCC1] | 2-hydroxy-6-[[2-(2-hydroxypentan-2-yl)cyclohexen-1-yl]methoxy]benzaldehyde |

TABLE 1-continued

| Compound | Structure | Name |
|---|---|---|
| 96 | 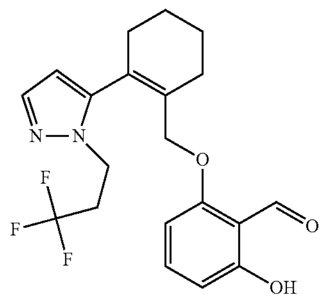 [SMILES: O=Cc1c(O)cccc1OCC1=C(c2ccnn2CCC(F)(F)F)CCCC1] | 2-hydroxy-6-[[2-[2-(3,3,3-trifluoropropyl)pyrazol-3-yl]cyclohexen-1-yl]methoxy]benzaldehyde |
| 97 | 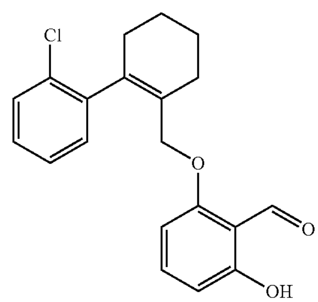 | 2-[[2-(2-chlorophenyl)cyclohexen-1-yl]methoxy]-6-hydroxybenzaldehyde |
| 98 | 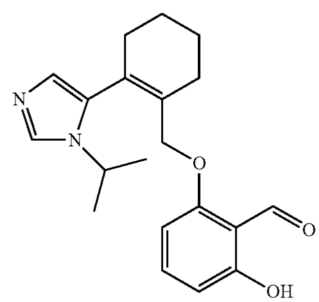 | 2-hydroxy-6-[[2-(3-propan-2-ylimidazol-4-yl)cyclohexen-1-yl]methoxy]benzaldehyde |
| 99 | 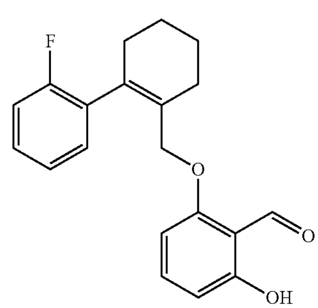 [SMILES: O=Cc1c(O)cccc1OCC1=C(c2ccccc2F)CCCC1] | 2-[[2-(2-fluorophenyl)cyclohexen-1-yl]methoxy]-6-hydroxybenzaldehyde |
| 100 | 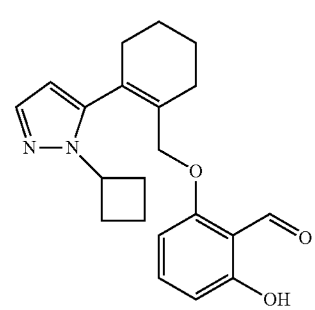 | 2-[[2-(2-cyclobutylpyrazol-3-yl)cyclohexen-1-yl]methoxy]-6-hydroxybenzaldehyde |

TABLE 1-continued

| Compound | Structure | Name |
|---|---|---|
| 101 | 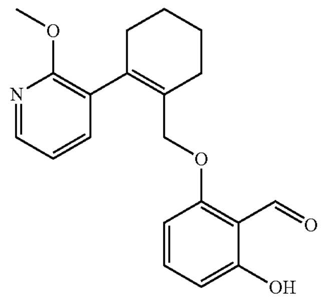 [SMILES: COc1ncccc1C1=C(COc2cccc(O)c2C=O)CCCC1] | 2-hydroxy-6-[[2-(2-methoxypyridin-3-yl)cyclohexen-1-yl]methoxy]benzaldehyde |
| 102 | 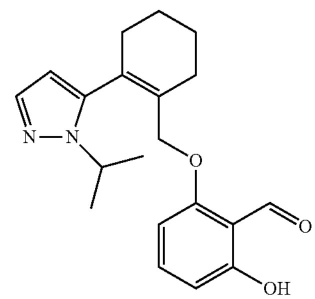 | 2-hydroxy-6-[[2-(2-propan-2-ylpyrazol-3-yl)cyclohexen-1-yl]methoxy]benzaldehyde |
| 103 | 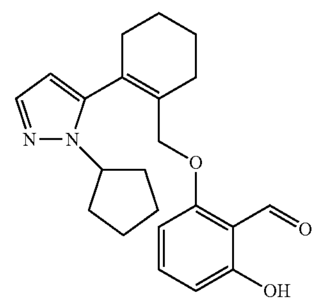 [SMILES: O=Cc1c(O)cccc1OCC1=C(c2ccnn2C2CCCC2)CCCC1] | 2-[[2-(2-cyclopentylpyrazol-3-yl)cyclohexen-1-yl]methoxy]-6-hydroxybenzaldehyde |
| 104 | 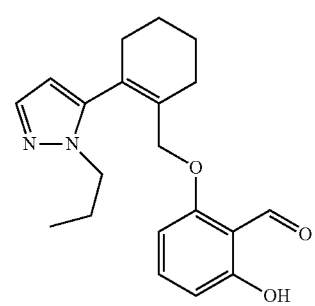 [SMILES: CCCn1nccc1C1=C(COc2cccc(O)c2C=O)CCCC1] | 2-hydroxy-6-[[2-(2-propylpyrazol-3-yl)cyclohexen-1-yl]methoxy]benzaldehyde |
| 105 | 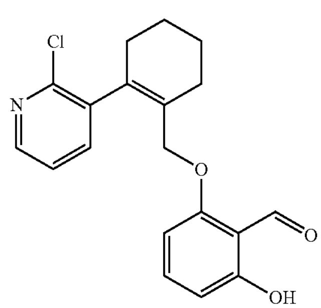 [SMILES: O=Cc1c(O)cccc1OCC1=C(c2cccnc2Cl)CCCC1] | 2-[[2-(2-chloropyridin-3-yl)cyclohexen-1-yl]methoxy]-6-hydroxybenzaldehyde |

TABLE 1-continued

| Compound | Structure | Name |
|---|---|---|
| 106 | 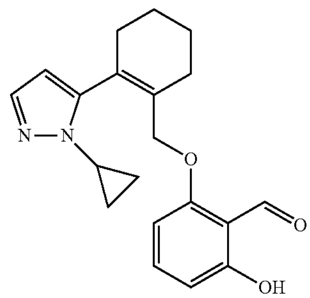 [SMILES: O=Cc1c(O)cccc1OCC1=C(c2ccnn2C2CC2)CCCC1] | 2-[[2-(2-cyclopropylpyrazol-3-yl)cyclohexen-1-yl]methoxy]-6-hydroxybenzaldehyde |
| 107 | 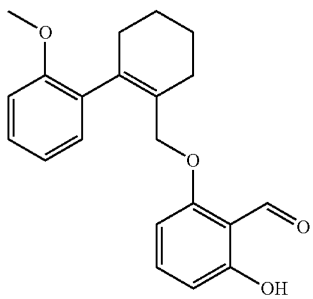 [SMILES: COc1ccccc1C1=C(COc2cccc(O)c2C=O)CCCC1] | 2-hydroxy-6-[[2-(2-methoxyphenyl)cyclohexen-1-yl]methoxy]benzaldehyde |
| 108 | 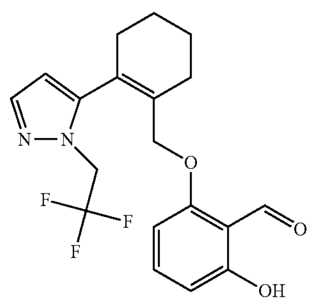 [SMILES: O=Cc1c(O)cccc1OCC1=C(c2ccnn2CC(F)(F)F)CCCC1] | 2-hydroxy-6-[[2-[2-(2,2,2-trifluoroethyl)pyrazol-3-yl]cyclohexen-1-yl]methoxy]benzaldehyde |
| 109 | 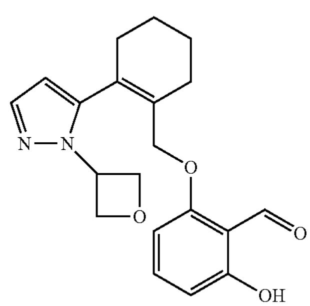 | 2-hydroxy-6-[[2-[2-(oxetan-3-yl)pyrazol-3-yl]cyclohexen-1-yl]methoxy]benzaldehyde |
| 110 | 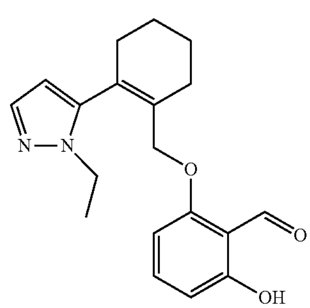 [SMILES: CCn1nccc1C1=C(COc2cccc(O)c2C=O)CCCC1] | 2-[[2-(2-ethylpyrazol-3-yl)cyclohexen-1-yl]methoxy]-6-hydroxybenzaldehyde |

TABLE 1-continued

| Compound | Structure | Name |
|---|---|---|
| 111 | 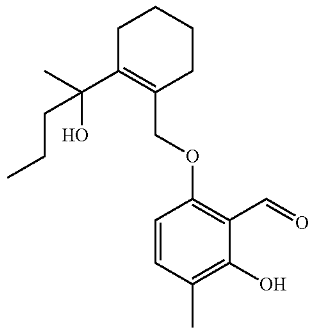 [SMILES: CCCC(C)(O)C1=C(COc2ccc(C)c(O)c2C=O)CCCC1] | 2-hydroxy-6-[[2-(2-hydroxypentan-2-yl)cyclohexen-1-yl]methoxy]-3-methylbenzaldehyde |
| 112 | 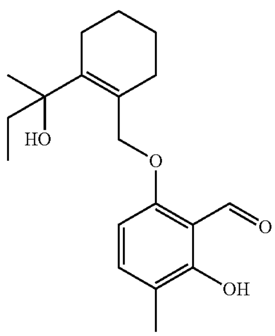 [SMILES: CCC(C)(O)C1=C(COc2ccc(C)c(O)c2C=O)CCCC1] | 2-hydroxy-6-[[2-(2-hydroxybutan-2-yl)cyclohexen-1-yl]methoxy]-3-methylbenzaldehyde |
| 113 | 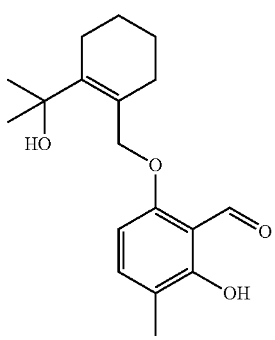 [SMILES: Cc1ccc(OCC2=C(C(C)(C)O)CCCC2)c(C=O)c1O] | 2-hydroxy-6-[[2-(2-hydroxypropan-2-yl)cyclohexen-1-yl]methoxy]-3-methylbenzaldehyde |
| 114 | 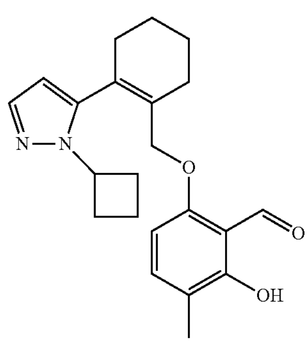 | 6-[[2-(2-cyclobutylpyrazol-3-yl)cyclohexen-1-yl]methoxy]-2-hydroxy-3-methylbenzaldehyde |

TABLE 1-continued

| Compound | Structure | Name |
|---|---|---|
| 115 | 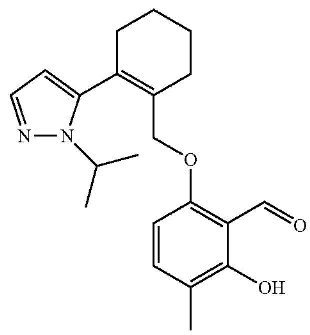 | 2-hydroxy-3-methyl-6-[[2-(2-propan-2-ylpyrazol-3-yl)cyclohexen-1-yl]methoxy]benzaldehyde |
| 116 | 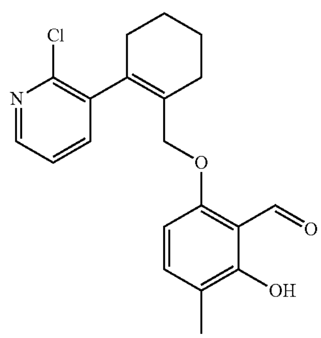 [SMILES: Cc1ccc(OCC2=C(c3cccnc3Cl)CCCC2)c(C=O)c1O] | 6-[[2-(2-chloropyridin-3-yl)cyclohexen-1-yl]methoxy]-2-hydroxy-3-methylbenzaldehyde |
| 117 | 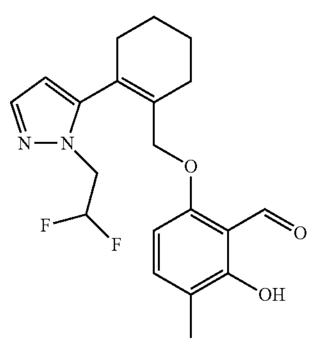 [SMILES: Cc1ccc(OCC2=C(c3ccnn3CC(F)F)CCCC2)c(C=O)c1O] | 6-[[2-[2-(2,2-difluoroethyl)pyrazol-3-yl]cyclohexen-1-yl]methoxy]-2-hydroxy-3-methylbenzaldehyde |
| 118 | 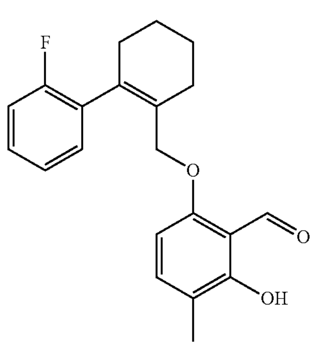 [SMILES: Cc1ccc(OCC2=C(c3ccccc3F)CCCC2)c(C=O)c1O] | 6-[[2-(2-fluorophenyl)cyclohexen-1-yl]methoxy]-2-hydroxy-3-methylbenzaldehyde |

TABLE 1-continued

| Compound | Structure | Name |
|---|---|---|
| 119 | 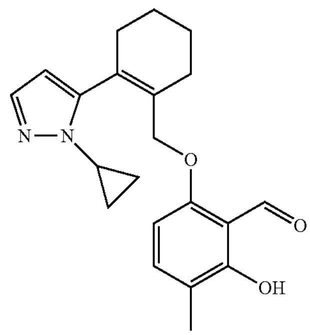 | 6-[[2-(2-cyclopropylpyrazol-3-yl)cyclohexen-1-yl]methoxy]-2-hydroxy-3-methylbenzaldehyde |
| 120 | 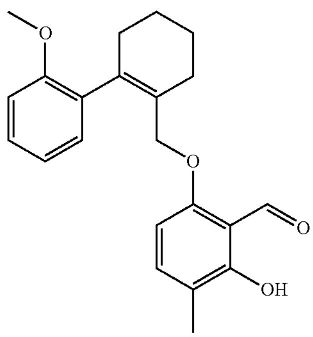 [SMILES: COc1ccccc1C1=C(COc2ccc(C)c(O)c2C=O)CCCC1] | 2-hydroxy-6-[[2-(2-methoxyphenyl)cyclohexen-1-yl]methoxy]-3-methylbenzaldehyde |
| 121 | 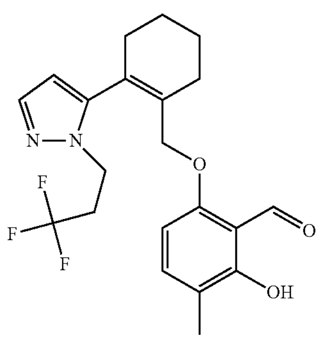 [SMILES: Cc1ccc(OCC2=C(c3ccnn3CCC(F)(F)F)CCCC2)c(C=O)c1O] | 2-hydroxy-3-methyl-6-[[2-[2-(3,3,3-trifluoropropyl)pyrazol-3-yl]cyclohexen-1-yl]methoxy]benzaldehyde |
| 122 | 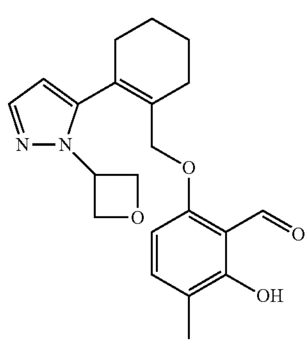 [SMILES: Cc1ccc(OCC2=C(c3ccnn3C3COC3)CCCC2)c(C=O)c1O] | 2-hydroxy-3-methyl-6-[[2-[2-(oxetan-3-yl)pyrazol-3-yl]cyclohexen-1-yl]methoxy]benzaldehyde |

TABLE 1-continued

| Compound | Structure | Name |
|---|---|---|
| 123 | 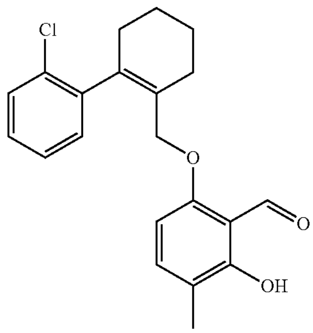 [SMILES: Cc1ccc(OCC2=C(c3ccccc3Cl)CCCC2)c(C=O)c1O] | 6-[[2-(2-chlorophenyl)cyclohexen-1-yl]methoxy]-2-hydroxy-3-methylbenzaldehyde |
| 124 | 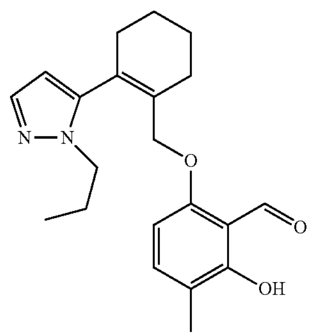 [SMILES: CCCn1nccc1C1=C(COc2ccc(C)c(O)c2C=O)CCCC1] | 2-hydroxy-3-methyl-6-[[2-(2-propylpyrazol-3-yl)cyclohexen-1-yl]methoxy]benzaldehyde |
| 125 | 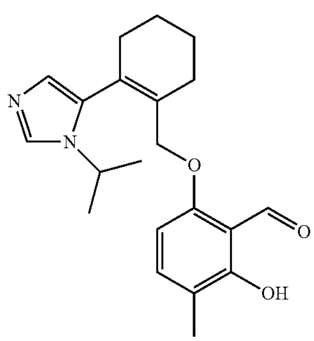 [SMILES: Cc1ccc(OCC2=C(c3cncn3C(C)C)CCCC2)c(C=O)c1O] | 2-hydroxy-3-methyl-6-[[2-(3-propan-2-ylimidazol-4-yl)cyclohexen-1-yl]methoxy]benzaldehyde |
| 126 | 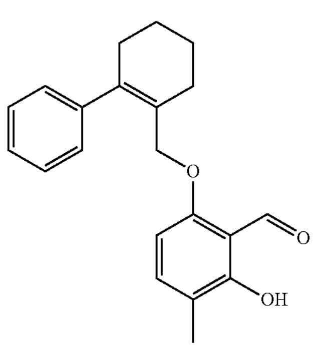 [SMILES: Cc1ccc(OCC2=C(c3ccccc3)CCCC2)c(C=O)c1O] | 2-hydroxy-3-methyl-6-[(2-phenylcyclohexen-1-yl)methoxy]benzaldehyde |

TABLE 1-continued

| Compound | Structure | Name |
|---|---|---|
| 127 | 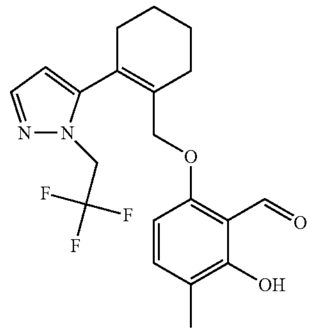 [SMILES: Cc1ccc(OCC2=C(c3ccnn3CC(F)(F)F)CCCC2)c(C=O)c1O] | 2-hydroxy-3-methyl-6-[[2-[2-(2,2,2-trifluoroethyl)pyrazol-3-yl]cyclohexen-1-yl]methoxy]benzaldehyde |
| 128 | 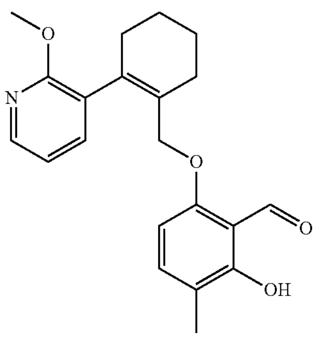 [SMILES: COc1ncccc1C1=C(COc2ccc(C)c(O)c2C=O)CCCC1] | 2-hydroxy-6-[[2-(2-methoxypyridin-3-yl)cyclohexen-1-yl]methoxy]-3-methylbenzaldehyde |
| 129 | 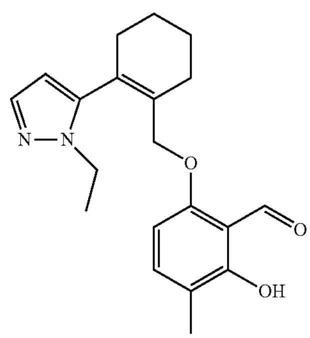 [SMILES: CCn1nccc1C1=C(COc2ccc(C)c(O)c2C=O)CCCC1] | 6-[[2-(2-ethylpyrazol-3-yl)cyclohexen-1-yl]methoxy]-2-hydroxy-3-methylbenzaldehyde |
| 130 | 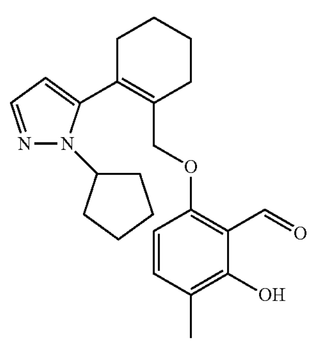 [SMILES: Cc1ccc(OCC2=C(c3ccnn3C3CCCC3)CCCC2)c(C=O)c1O] | 6-[[2-(2-cyclopentylpyrazol-3-yl)cyclohexen-1-yl]methoxy]-2-hydroxy-3-methylbenzaldehyde |

TABLE 1-continued

| Compound | Structure | Name |
|---|---|---|
| 131 | 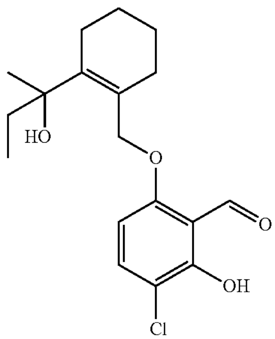 [SMILES: CCC(C)(O)C1=C(COc2ccc(Cl)c(O)c2C=O)CCCC1] | 3-chloro-2-hydroxy-6-[[2-(2-hydroxybutan-2-yl)cyclohexen-1-yl]methoxy]benzaldehyde |
| 132 | 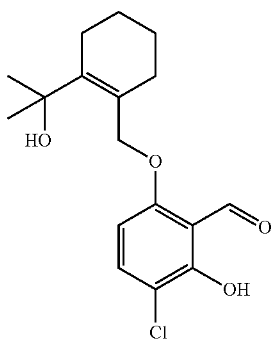 [SMILES: CC(C)(O)C1=C(COc2ccc(Cl)c(O)c2C=O)CCCC1] | 3-chloro-2-hydroxy-6-[[2-(2-hydroxypropan-2-yl)cyclohexen-1-yl]methoxy]benzaldehyde |
| 133 | 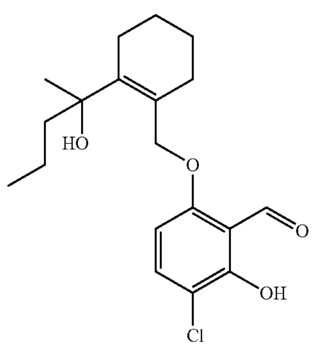 [SMILES: CCCC(C)(O)C1=C(COc2ccc(Cl)c(O)c2C=O)CCCC1] | 3-chloro-2-hydroxy-6-[[2-(2-hydroxypentan-2-yl)cyclohexen-1-yl]methoxy]benzaldehyde |
| 134 | 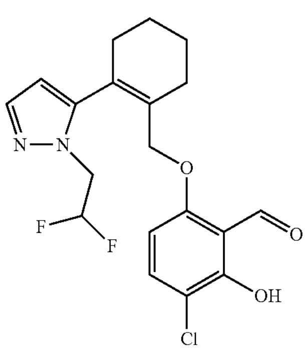 [SMILES: O=Cc1c(OCC2=C(c3ccnn3CC(F)F)CCCC2)ccc(Cl)c1O] | 3-chloro-6-[[2-[2-(2,2-difluoroethyl)pyrazol-3-yl]cyclohexen-1-yl]methoxy]-2-hydroxybenzaldehyde |

TABLE 1-continued

| Compound | Structure | Name |
|---|---|---|
| 135 | 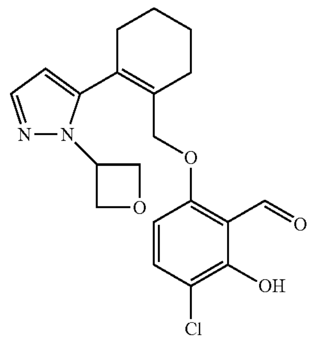 [SMILES: O=Cc1c(OCC2=C(c3ccnn3C3COC3)CCCC2)ccc(Cl)c1O] | 3-chloro-2-hydroxy-6-[[2-[2-(oxetan-3-yl)pyrazol-3-yl]cyclohexen-1-yl]methoxy]benzaldehyde |
| 136 | 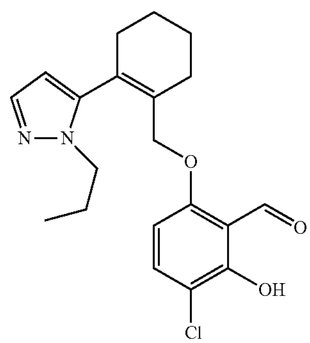 [SMILES: CCCn1nccc1C1=C(COc2ccc(Cl)c(O)c2C=O)CCCC1] | 3-chloro-2-hydroxy-6-[[2-(2-propylpyrazol-3-yl)cyclohexen-1-yl]methoxy]benzaldehyde |
| 137 | 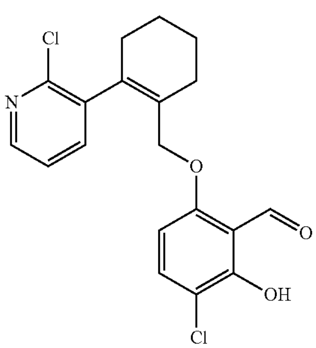 [SMILES: O=Cc1c(OCC2=C(c3cccnc3Cl)CCCC2)ccc(Cl)c1O] | 3-chloro-6-[[2-(2-chloropyridin-3-yl)cyclohexen-1-yl]methoxy]-2-hydroxybenzaldehyde |
| 138 | 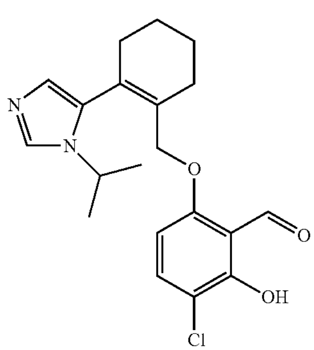 [SMILES: CC(C)n1cncc1C1=C(COc2ccc(Cl)c(O)c2C=O)CCCC1] | 3-chloro-2-hydroxy-6-[[2-(3-propan-2-ylimidazol-4-yl)cyclohexen-1-yl]methoxy]benzaldehyde |

TABLE 1-continued
| Compound | Structure | Name |
|---|---|---|
| 139 | 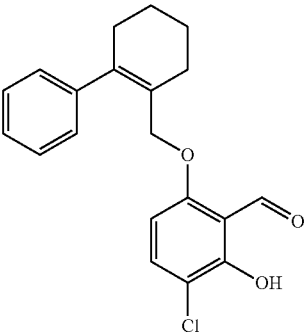 [SMILES: O=Cc1c(OCC2=C(c3ccccc3)CCCC2)ccc(Cl)c1O] | 3-chloro-2-hydroxy-6-[(2-phenylcyclohexen-1-yl)methoxy]benzaldehyde |
| 140 | 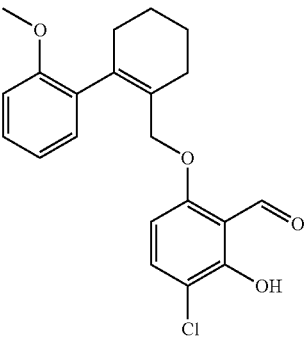 [SMILES: COc1ccccc1C1=C(COc2ccc(Cl)c(O)c2C=O)CCCC1] | 3-chloro-2-hydroxy-6-[[2-(2-methoxyphenyl)cyclohexen-1-yl]methoxy]benzaldehyde |
| 141 | 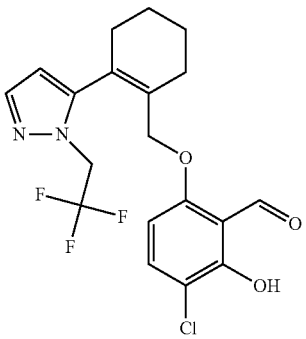 [SMILES: O=Cc1c(OCC2=C(c3ccnn3CC(F)(F)F)CCCC2)ccc(Cl)c1O] | 3-chloro-2-hydroxy-6-[[2-[2-(2,2,2-trifluoroethyl)pyrazol-3-yl]cyclohexen-1-yl]methoxy]benzaldehyde |
| 142 | 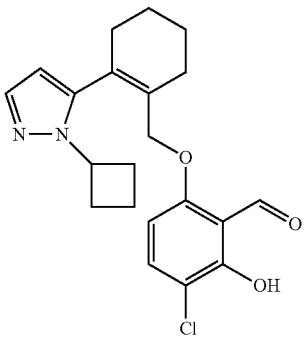 | 3-chloro-6-[[2-(2-cyclobutylpyrazol-3-yl)cyclohexen-1-yl]methoxy]-2-hydroxybenzaldehyde |

TABLE 1-continued

| Compound | Structure | Name |
|---|---|---|
| 143 | 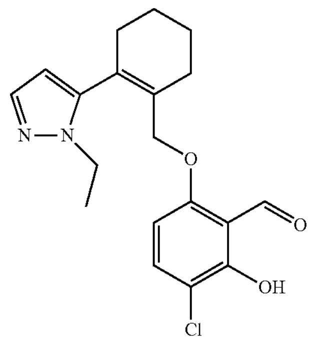 [SMILES: CCn1nccc1C1=C(COc2ccc(Cl)c(O)c2C=O)CCCC1] | 3-chloro-6-[[2-(2-ethylpyrazol-3-yl)cyclohexen-1-yl]methoxy]-2-hydroxybenzaldehyde |
| 144 | 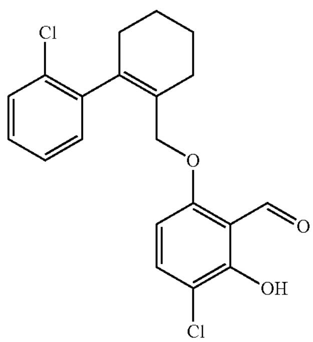 [SMILES: O=Cc1c(OCC2=C(c3ccccc3Cl)CCCC2)ccc(Cl)c1O] | 3-chloro-6-[[2-(2-chlorophenyl)cyclohexen-1-yl]methoxy]-2-hydroxybenzaldehyde |
| 145 | 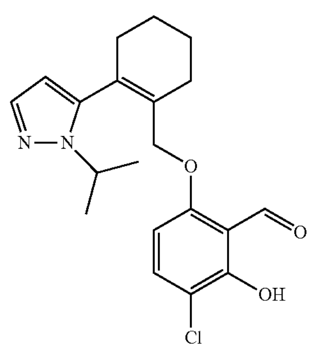 [SMILES: CC(C)n1nccc1C1=C(COc2ccc(Cl)c(O)c2C=O)CCCC1] | 3-chloro-2-hydroxy-6-[[2-(2-propan-2-ylpyrazol-3-yl)cyclohexen-1-yl]methoxy]benzaldehyde |
| 146 | 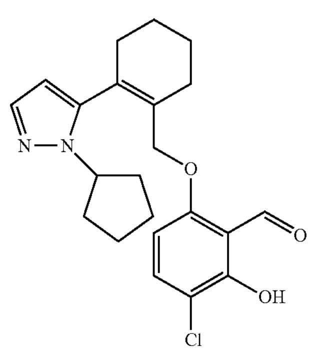 [SMILES: O=Cc1c(OCC2=C(c3ccnn3C3CCCC3)CCCC2)ccc(Cl)c1O] | 3-chloro-6-[[2-(2-cyclopentylpyrazol-3-yl)cyclohexen-1-yl]methoxy]-2-hydroxybenzaldehyde |

TABLE 1-continued
| Compound | Structure | Name |
|---|---|---|
| 147 | 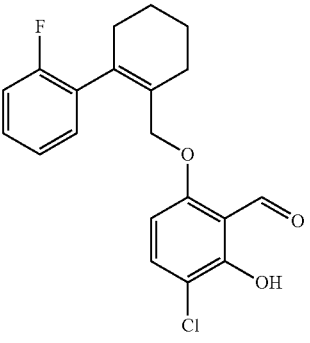 [SMILES: O=Cc1c(OCC2=C(c3ccccc3F)CCCC2)ccc(Cl)c1O] | 3-chloro-6-[[2-(2-fluorophenyl)cyclohexen-1-yl]methoxy]-2-hydroxybenzaldehyde |
| 148 | 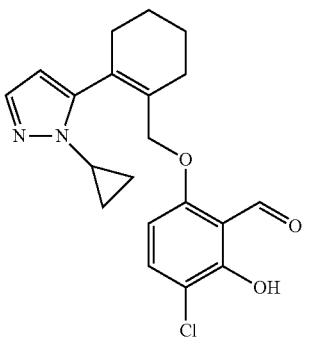 [SMILES: O=Cc1c(OCC2=C(c3ccnn3C3CC3)CCCC2)ccc(Cl)c1O] | 3-chloro-6-[[2-(2-cyclopropylpyrazol-3-yl)cyclohexen-1-yl]methoxy]-2-hydroxybenzaldehyde |
| 149 | 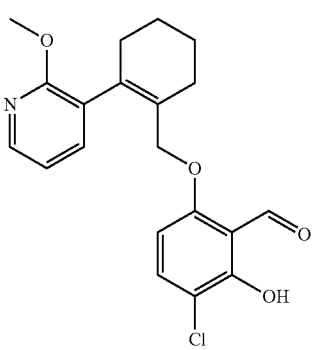 [SMILES: COc1ncccc1C1=C(COc2ccc(Cl)c(O)c2C=O)CCCC1] | 3-chloro-2-hydroxy-6-[[2-(2-methoxypyridin-3-yl)cyclohexen-1-yl]methoxy]benzaldehyde |
| 150 | 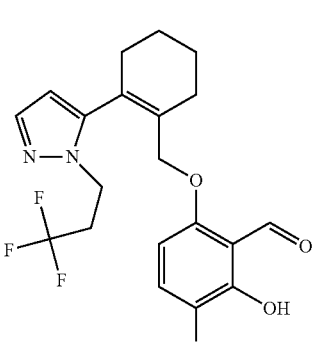 | 3-chloro-2-hydroxy-6-[[2-[2-(3,3,3-trifluoropropyl)pyrazol-3-yl]cyclohexen-1-yl]methoxy]benzaldehyde |

TABLE 1-continued

| Compound | Structure | Name |
|---|---|---|
| 151 | 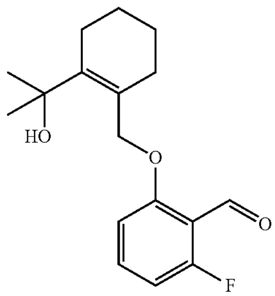 [SMILES: CC(C)(O)C1=C(COc2cccc(F)c2C=O)CCCC1] | 2-fluoro-6-[[2-(2-hydroxypropan-2-yl)cyclohexen-1-yl]methoxy]benzaldehyde |
| 152 | 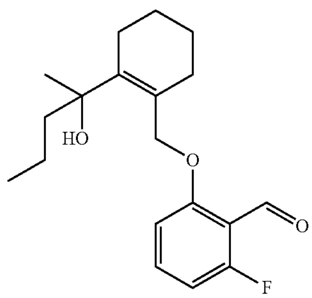 [SMILES: CCCC(C)(O)C1=C(COc2cccc(F)c2C=O)CCCC1] | 2-fluoro-6-[[2-(2-hydroxypentan-2-yl)cyclohexen-1-yl]methoxy]benzaldehyde |
| 153 | 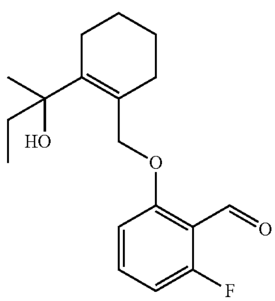 [SMILES: CCC(C)(O)C1=C(COc2cccc(F)c2C=O)CCCC1] | 2-fluoro-6-[[2-(2-hydroxybutan-2-yl)cyclohexen-1-yl]methoxy]benzaldehyde |
| 154 | 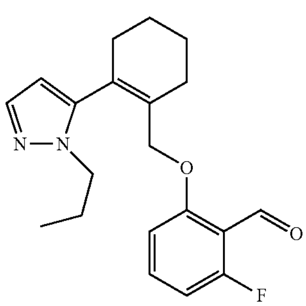 [SMILES: CCCn1nccc1C1=C(COc2cccc(F)c2C=O)CCCC1] | 2-fluoro-6-[[2-(2-propylpyrazol-3-yl)cyclohexen-1-yl]methoxy]benzaldehyde |
| 155 | 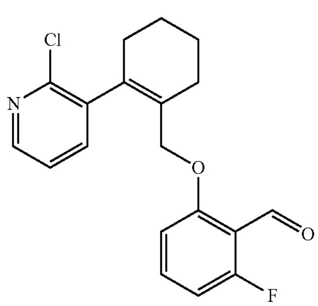 [SMILES: O=Cc1c(F)cccc1OCC1=C(c2cccnc2Cl)CCCC1] | 2-[[2-(2-chloropyridin-3-yl)cyclohexen-1-yl]methoxy]-6-fluorobenzaldehyde |

TABLE 1-continued

| Compound | Structure | Name |
|---|---|---|
| 156 | 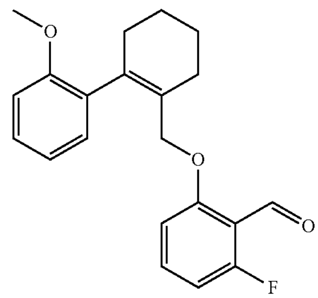 [SMILES: COc1ccccc1C1=C(COc2cccc(F)c2C=O)CCCC1] | 2-fluoro-6-[[2-(2-methoxyphenyl)cyclohexen-1-yl]methoxy]benzaldehyde |
| 157 | 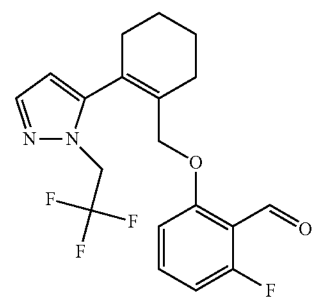 [SMILES: O=Cc1c(F)cccc1OCC1=C(c2ccnn2CC(F)(F)F)CCCC1] | 2-fluoro-6-[[2-[2-(2,2,2-trifluoroethyl)pyrazol-3-yl]cyclohexen-1-yl]methoxy]benzaldehyde |
| 158 | 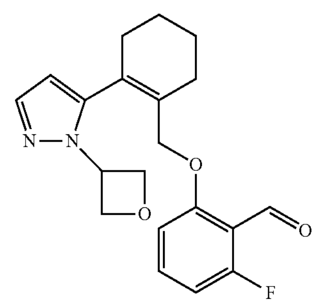 [SMILES: O=Cc1c(F)cccc1OCC1=C(c2ccnn2C2COC2)CCCC1] | 2-fluoro-6-[[2-[2-(oxetan-3-yl)pyrazol-3-yl]cyclohexen-1-yl]methoxy]benzaldehyde |
| 159 | 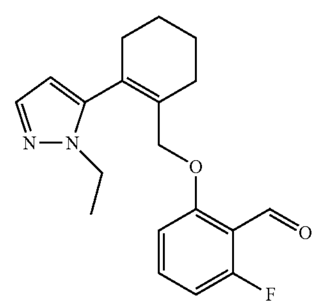 [SMILES: CCn1nccc1C1=C(COc2cccc(F)c2C=O)CCCC1] | 2-[[2-(2-ethylpyrazol-3-yl)cyclohexen-1-yl]methoxy]-6-fluorobenzaldehyde |
| 160 | 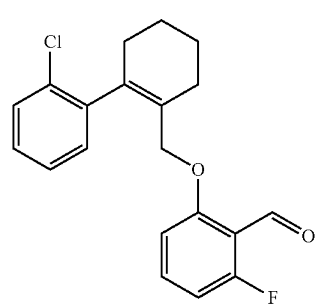 [SMILES: O=Cc1c(F)cccc1OCC1=C(c2ccccc2Cl)CCCC1] | 2-[[2-(2-chlorophenyl)cyclohexen-1-yl]methoxy]-6-fluorobenzaldehyde |

TABLE 1-continued

| Compound | Structure | Name |
| --- | --- | --- |
| 161 | 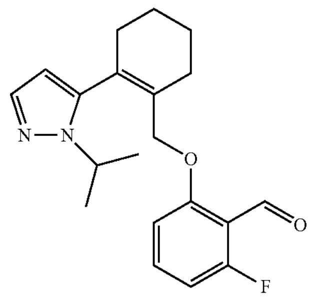 [SMILES: CC(C)n1nccc1C1=C(COc2cccc(F)c2C=O)CCCC1] | 2-fluoro-6-[[2-(2-propan-2-ylpyrazol-3-yl)cyclohexen-1-yl]methoxy]benzaldehyde |
| 162 | 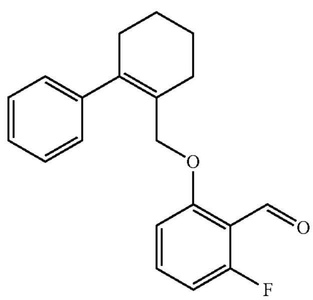 [SMILES: O=Cc1c(F)cccc1OCC1=C(c2ccccc2)CCCC1] | 2-fluoro-6-[(2-phenylcyclohexen-1-yl)methoxy]benzaldehyde |
| 163 | 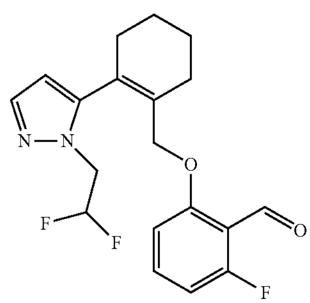 [SMILES: O=Cc1c(F)cccc1OCC1=C(c2ccnn2CC(F)F)CCCC1] | 2-[[2-[2-(2,2-difluoroethyl)pyrazol-3-yl]cyclohexen-1-yl]methoxy]-6-fluorobenzaldehyde |
| 164 | 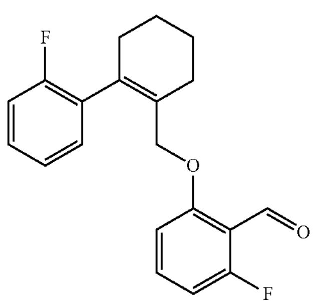 [SMILES: O=Cc1c(F)cccc1OCC1=C(c2ccccc2F)CCCC1] | 2-fluoro-6-[[2-(2-fluorophenyl)cyclohexen-1-yl]methoxy]benzaldehyde |
| 165 | 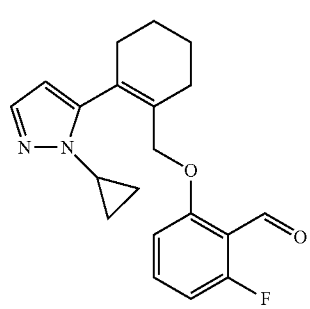 [SMILES: O=Cc1c(F)cccc1OCC1=C(c2ccnn2C2CC2)CCCC1] | 2-[[2-(2-cyclopropylpyrazol-3-yl)cyclohexen-1-yl]methoxy]-6-fluorobenzaldehyde |

TABLE 1-continued

| Compound | Structure | Name |
|---|---|---|
| 166 | 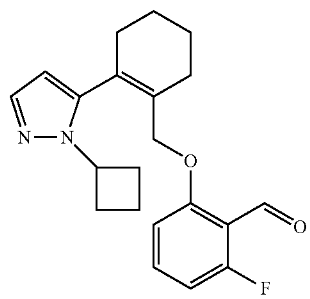 [SMILES: O=Cc1c(F)cccc1OCC1=C(c2ccnn2C2CCC2)CCCC1] | 2-[[2-(2-cyclobutylpyrazol-3-yl)cyclohexen-1-yl]methoxy]-6-fluorobenzaldehyde |
| 167 | 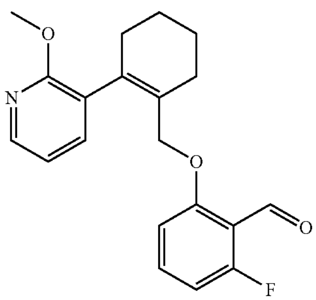 [SMILES: COc1ncccc1C1=C(COc2cccc(F)c2C=O)CCCC1] | 2-fluoro-6-[[2-(2-methoxypyridin-3-yl)cyclohexen-1-yl]methoxy]benzaldehyde |
| 168 | 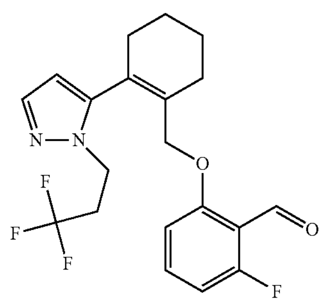 [SMILES: O=Cc1c(F)cccc1OCC1=C(c2ccnn2CCC(F)(F)F)CCCC1] | 2-fluoro-6-[[2-[2-(3,3,3-trifluoropropyl)pyrazol-3-yl]cyclohexen-1-yl]methoxy]benzaldehyde |
| 169 | 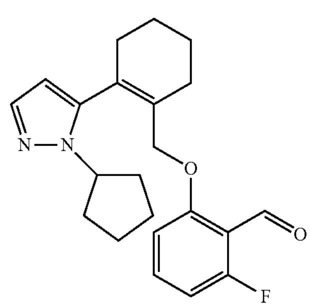 [SMILES: O=Cc1c(F)cccc1OCC1=C(c2ccnn2C2CCCC2)CCCC1] | 2-[[2-(2-cyclopentylpyrazol-3-yl)cyclohexen-1-yl]methoxy]-6-fluorobenzaldehyde |
| 170 | 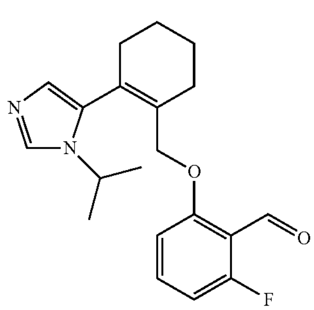 [SMILES: CC(C)n1cncc1C1=C(COc2cccc(F)c2C=O)CCCC1] | 2-fluoro-6-[[2-(3-propan-2-ylimidazol-4-yl)cyclohexen-1-yl]methoxy]benzaldehyde |

TABLE 1-continued

| Compound | Structure | Name |
|---|---|---|
| 171 | 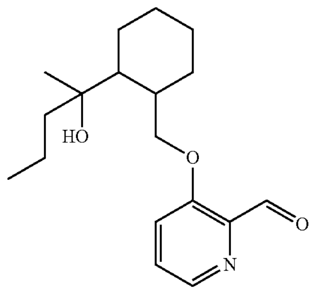 [SMILES: CCCC(C)(O)C1CCCCC1COc1cccnc1C=O] | 3-[[2-(2-hydroxypentan-2-yl)cyclohexyl]methoxy]pyridine-2-carbaldehyde |
| 172 | 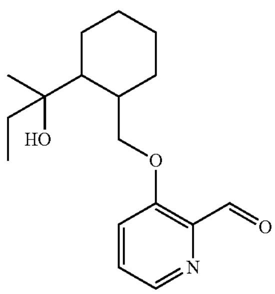 [SMILES: CCC(C)(O)C1CCCCC1COc1cccnc1C=O] | 3-[[2-(2-hydroxybutan-2-yl)cyclohexyl]methoxy]pyridine-2-carbaldehyde |
| 173 | 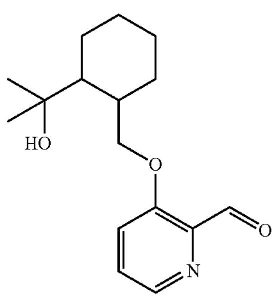 | 3-[[2-(2-hydroxypropan-2-yl)cyclohexyl]methoxy]pyridine-2-carbaldehyde |
| 174 | 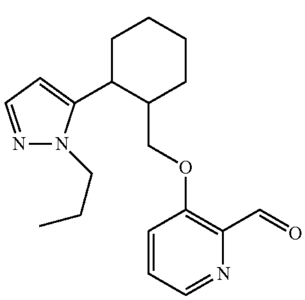 [SMILES: CCCn1nccc1C1CCCCC1COc1cccnc1C=O] | 3-[[2-(2-propylpyrazol-3-yl)cyclohexyl]methoxy]pyridine-2-carbaldehyde |
| 175 | 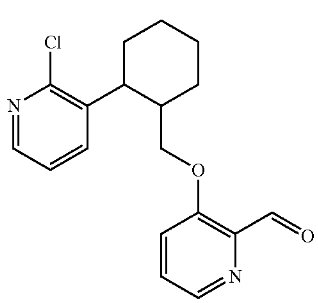 [SMILES: O=Cc1ncccc1OCC1CCCCC1c1cccnc1Cl] | 3-[[2-(2-chloropyridin-3-yl)cyclohexyl]methoxy]pyridine-2-carbaldehyde |

TABLE 1-continued

| Compound | Structure | Name |
|---|---|---|
| 176 | 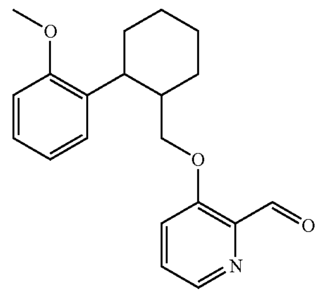 [SMILES: COc1ccccc1C1CCCCC1COc1cccnc1C=O] | 3-[[2-(2-methoxyphenyl)cyclohexyl]methoxy]pyridine-2-carbaldehyde |
| 177 | 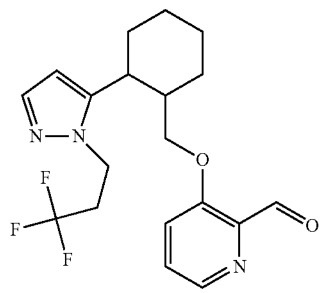 [SMILES: O=Cc1ncccc1OCC1CCCCC1c1ccnn1CCC(F)(F)F] | 3-[[2-[2-(3,3,3-trifluoropropyl)pyrazol-3-yl]cyclohexyl]methoxy]pyridine-2-carbaldehyde |
| 178 | 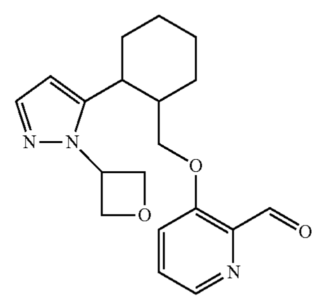 [SMILES: O=Cc1ncccc1OCC1CCCCC1c1ccnn1C1COC1] | 3-[[2-[2-(oxetan-3-yl)pyrazol-3-yl]cyclohexyl]methoxy]pyridine-2-carbaldehyde |
| 179 | 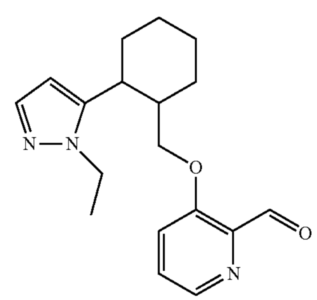 [SMILES: CCn1nccc1C1CCCCC1COc1cccnc1C=O] | 3-[[2-(2-ethylpyrazol-3-yl)cyclohexyl]methoxy]pyridine-2-carbaldehyde |
| 180 | 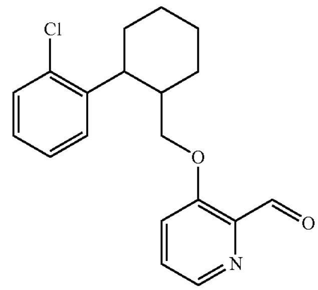 [SMILES: O=Cc1ncccc1OCC1CCCCC1c1ccccc1Cl] | 3-[[2-(2-chlorophenyl)cyclohexyl]methoxy]pyridine-2-carbaldehyde |

TABLE 1-continued

| Compound | Structure | Name |
|---|---|---|
| 181 | 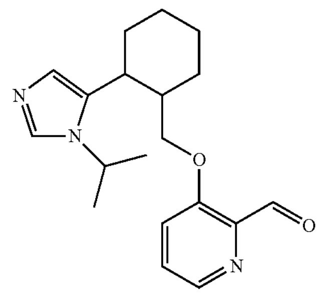 [SMILES: CC(C)n1cncc1C1CCCCC1COc1cccnc1C=O] | 3-[[2-(3-propan-2-ylimidazol-4-yl)cyclohexyl]methoxy]pyridine-2-carbaldehyde |
| 182 | 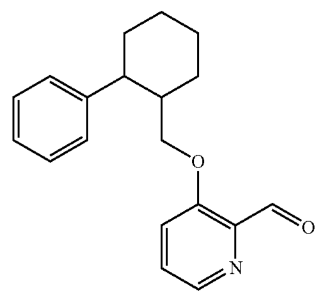 [SMILES: O=Cc1ncccc1OCC1CCCCC1c1ccccc1] | 3-[(2-phenylcyclohexyl)methoxy]pyridine-2-carbaldehyde |
| 183 | 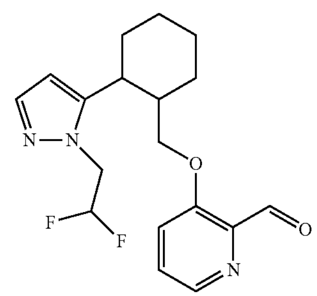 [SMILES: O=Cc1ncccc1OCC1CCCCC1c1ccnn1CC(F)F] | 3-[[2-[2-(2,2-difluoroethyl)pyrazol-3-yl]cyclohexyl]methoxy]pyridine-2-carbaldehyde |
| 184 | 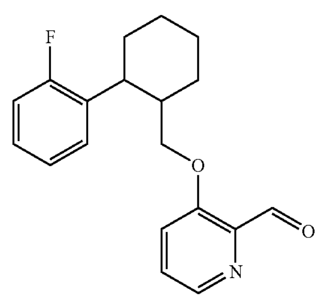 [SMILES: O=Cc1ncccc1OCC1CCCCC1c1ccccc1F] | 3-[[2-(2-fluorophenyl)cyclohexyl]methoxy]pyridine-2-carbaldehyde |
| 185 | 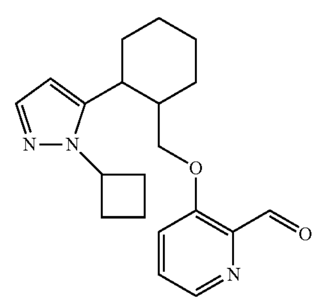 [SMILES: O=Cc1ncccc1OCC1CCCCC1c1ccnn1C1CCC1] | 3-[[2-(2-cyclobutylpyrazol-3-yl)cyclohexyl]methoxy]pyridine-2-carbaldehyde |

TABLE 1-continued

| Compound | Structure | Name |
|---|---|---|
| 186 | 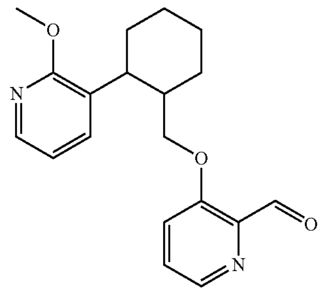 [SMILES: COc1ncccc1C1CCCCC1COc1cccnc1C=O] | 3-[[2-(2-methoxypyridin-3-yl)cyclohexyl]methoxy]pyridine-2-carbaldehyde |
| 187 | 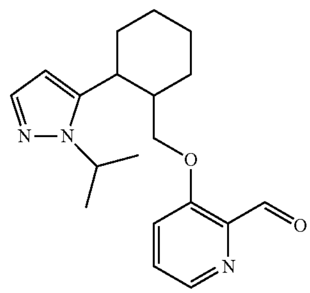 [SMILES: CC(C)n1nccc1C1CCCCC1COc1cccnc1C=O] | 3-[[2-(2-propan-2-ylpyrazol-3-yl)cyclohexyl]methoxy]pyridine-2-carbaldehyde |
| 188 | 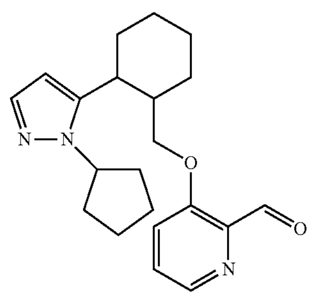 [SMILES: O=Cc1ncccc1OCC1CCCCC1c1ccnn1C1CCCC1] | 3-[[2-(2-cyclopentylpyrazol-3-yl)cyclohexyl]methoxy]pyridine-2-carbaldehyde |
| 189 | 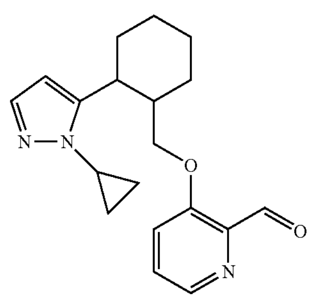 [SMILES: O=Cc1ncccc1OCC1CCCCC1c1ccnn1C1CC1] | 3-[[2-(2-cyclopropylpyrazol-3-yl)cyclohexyl]methoxy]pyridine-2-carbaldehyde |
| 190 | 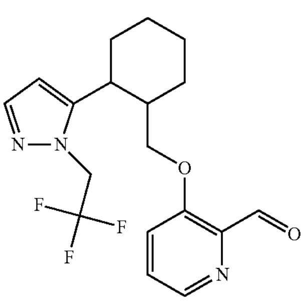 [SMILES: O=Cc1ncccc1OCC1CCCCC1c1ccnn1CC(F)(F)F] | 3-[[2-[2-(2,2,2-trifluoroethyl)pyrazol-3-yl]cyclohexyl]methoxy]pyridine-2-carbaldehyde |

TABLE 1-continued

| Compound | Structure | Name |
|---|---|---|
| 191 | 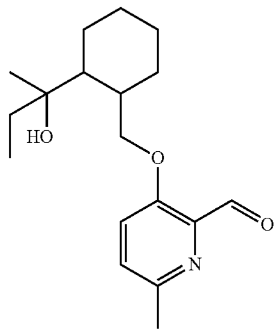 [SMILES: CCC(C)(O)C1CCCCC1COc1ccc(C)nc1C=O] | 3-[[2-(2-hydroxybutan-2-yl)cyclohexyl]methoxy]-6-methylpyridine-2-carbaldehyde |
| 192 | 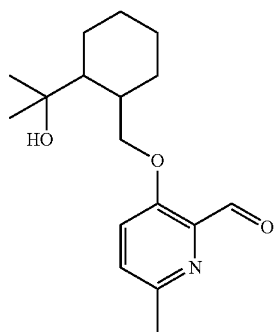 [SMILES: Cc1ccc(OCC2CCCCC2C(C)(C)O)c(C=O)n1] | 3-[[2-(2-hydroxypropan-2-yl)cyclohexyl]methoxy]-6-methylpyridine-2-carbaldehyde |
| 193 | 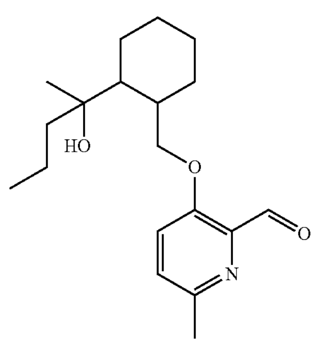 [SMILES: CCCC(C)(O)C1CCCCC1COc1ccc(C)nc1C=O] | 3-[[2-(2-hydroxypentan-2-yl)cyclohexyl]methoxy]-6-methylpyridine-2-carbaldehyde |
| 194 | 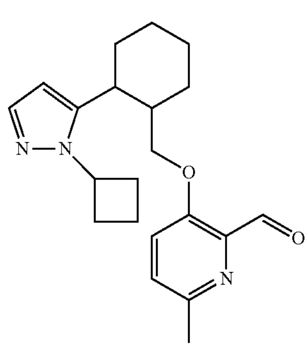 | 3-[[2-(2-cyclobutylpyrazol-3-yl)cyclohexyl]methoxy]-6-methylpyridine-2-carbaldehyde |

TABLE 1-continued

| Compound | Structure | Name |
|---|---|---|
| 195 | 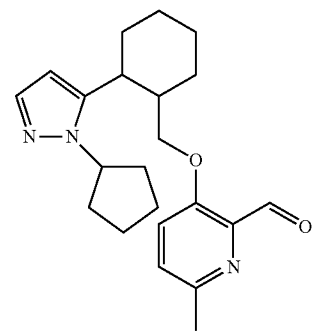 [SMILES: Cc1ccc(OCC2CCCCC2c2ccnn2C2CCCC2)c(C=O)n1] | 3-[[2-(2-cyclopentylpyrazol-3-yl)cyclohexyl]methoxy]-6-methylpyridine-2-carbaldehyde |
| 196 | 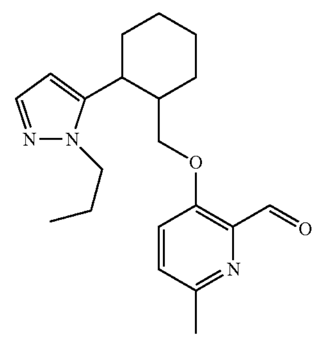 [SMILES: CCCn1nccc1C1CCCCC1COc1ccc(C)nc1C=O] | 6-methyl-3-[[2-(2-propylpyrazol-3-yl)cyclohexyl]methoxy]pyridine-2-carbaldehyde |
| 197 | 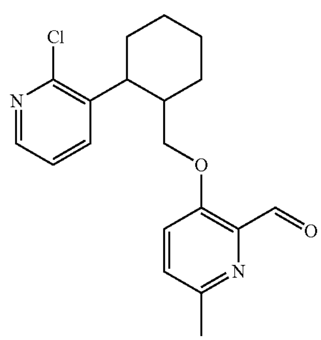 [SMILES: Cc1ccc(OCC2CCCCC2c2cccnc2Cl)c(C=O)n1] | 3-[[2-(2-chloropyridin-3-yl)cyclohexyl]methoxy]-6-methylpyridine-2-carbaldehyde |
| 198 | 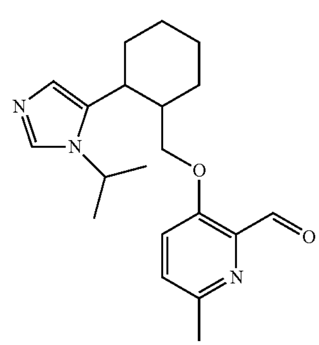 [SMILES: Cc1ccc(OCC2CCCCC2c2cncn2C(C)C)c(C=O)n1] | 6-methyl-3-[[2-(3-propan-2-ylimidazol-4-yl)cyclohexyl]methoxy]pyridine-2-carbaldehyde |

TABLE 1-continued

| Compound | Structure | Name |
|---|---|---|
| 199 | 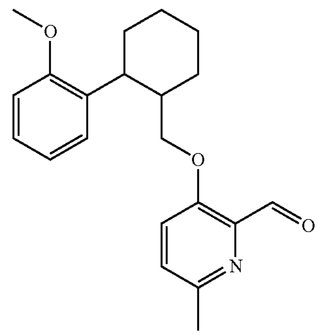 [SMILES: COc1ccccc1C1CCCCC1COc1ccc(C)nc1C=O] | 3-[[2-(2-methoxyphenyl)cyclohexyl]methoxy]-6-methylpyridine-2-carbaldehyde |
| 200 | 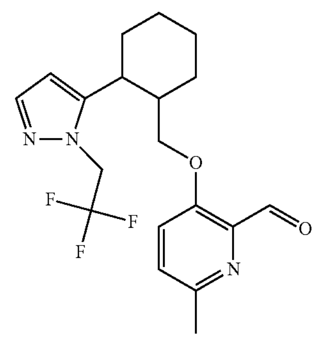 [SMILES: Cc1ccc(OCC2CCCCC2c2ccnn2CC(F)(F)F)c(C=O)n1] | 6-methyl-3-[[2-[2-(2,2,2-trifluoroethyl)pyrazol-3-yl]cyclohexyl]methoxy]pyridine-2-carbaldehyde |
| 201 | 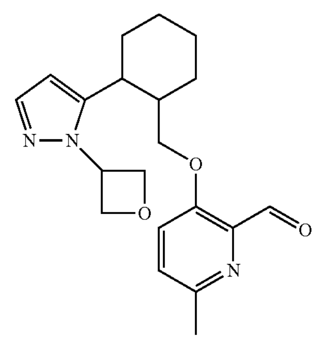 [SMILES: Cc1ccc(OCC2CCCCC2c2ccnn2C2COC2)c(C=O)n1] | 6-methyl-3-[[2-[2-(oxetan-3-yl)pyrazol-3-yl]cyclohexyl]methoxy]pyridine-2-carbaldehyde |
| 202 | 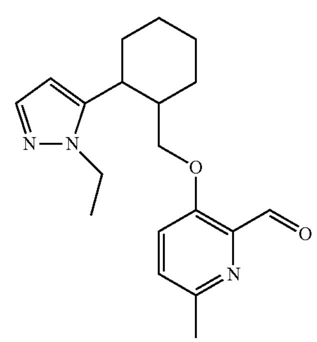 [SMILES: CCn1nccc1C1CCCCC1COc1ccc(C)nc1C=O] | 3-[[2-(2-ethylpyrazol-3-yl)cyclohexyl]methoxy]-6-methylpyridine-2-carbaldehyde |

TABLE 1-continued
| Compound | Structure | Name |
|---|---|---|
| 203 | 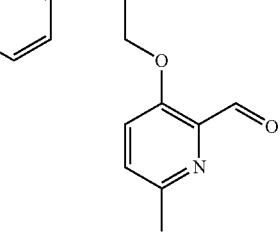 | 3-[[2-(2-chlorophenyl)cyclohexyl]methoxy]-6-methylpyridine-2-carbaldehyde |
| 204 | 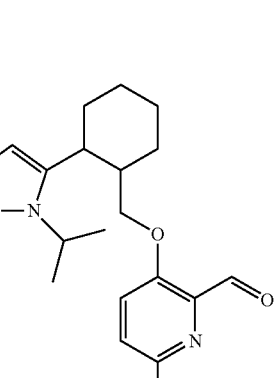 | 6-methyl-3-[[2-(2-propan-2-ylpyrazol-3-yl)cyclohexyl]methoxy]pyridine-2-carbaldehyde |
| 205 | 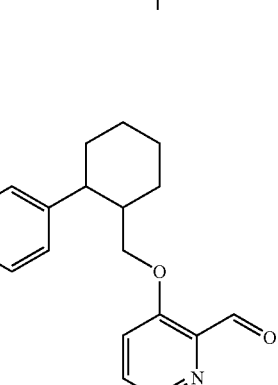 | 6-methyl-3-[(2-phenylcyclohexyl)methoxy]pyridine-2-carbaldehyde |
| 206 | 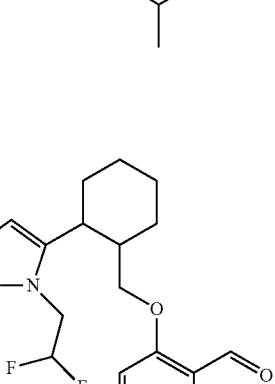 | 3-[[2-[2-(2,2-difluoroethyl)pyrazol-3-yl]cyclohexyl]methoxy]-6-methylpyridine-2-carbaldehyde |

TABLE 1-continued

| Compound | Structure | Name |
|---|---|---|
| 207 | 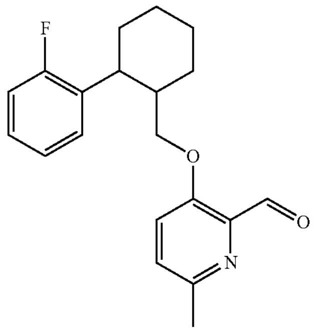 [SMILES: Cc1ccc(OCC2CCCCC2c2ccccc2F)c(C=O)n1] | 3-[[2-(2-fluorophenyl)cyclohexyl]methoxy]-6-methylpyridine-2-carbaldehyde |
| 208 | 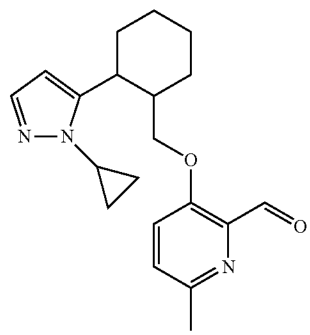 [SMILES: Cc1ccc(OCC2CCCCC2c2ccnn2C2CC2)c(C=O)n1] | 3-[[2-(2-cyclopropylpyrazol-3-yl)cyclohexyl]methoxy]-6-methylpyridine-2-carbaldehyde |
| 209 | 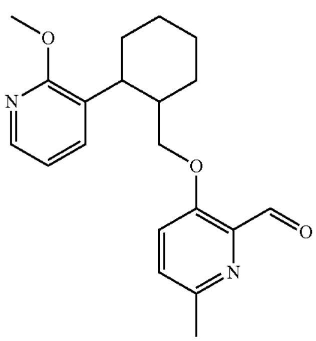 [SMILES: COc1ncccc1C1CCCCC1COc1ccc(C)nc1C=O] | 3-[[2-(2-methoxypyridin-3-yl)cyclohexyl]methoxy]-6-methylpyridine-2-carbaldehyde |
| 210 | 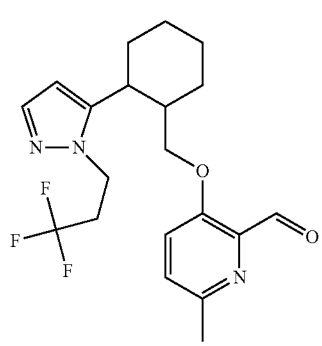 [SMILES: Cc1ccc(OCC2CCCCC2c2ccnn2CCC(F)(F)F)c(C=O)n1] | 6-methyl-3-[[2-[2-(3,3,3-trifluoropropyl)pyrazol-3-yl]cyclohexyl]methoxy]pyridine-2-carbaldehyde |

TABLE 1-continued

| Compound | Structure | Name |
|---|---|---|
| 211 | 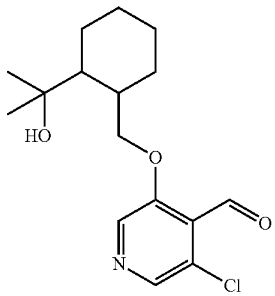 [SMILES: CC(C)(O)C1CCCCC1COc1cncc(Cl)c1C=O] | 3-chloro-5-[[2-(2-hydroxypropan-2-yl)cyclohexyl]methoxy]pyridine-4-carbaldehyde |
| 212 | 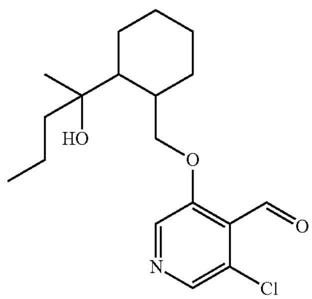 [SMILES: CCCC(C)(O)C1CCCCC1COc1cncc(Cl)c1C=O] | 3-chloro-5-[[2-(2-hydroxypentan-2-yl)cyclohexyl]methoxy]pyridine-4-carbaldehyde |
| 213 | 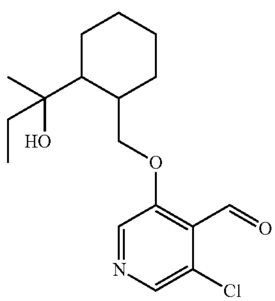 [SMILES: CCC(C)(O)C1CCCCC1COc1cncc(Cl)c1C=O] | 3-chloro-5-[[2-(2-hydroxybutan-2-yl)cyclohexyl]methoxy]pyridine-4-carbaldehyde |
| 214 | 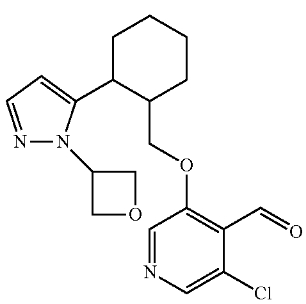 [SMILES: O=Cc1c(Cl)cncc1OCC1CCCCC1c1ccnn1C1COC1] | 3-chloro-5-[[2-[2-(oxetan-3-yl)pyrazol-3-yl]cyclohexyl]methoxy]pyridine-4-carbaldehyde |
| 215 | 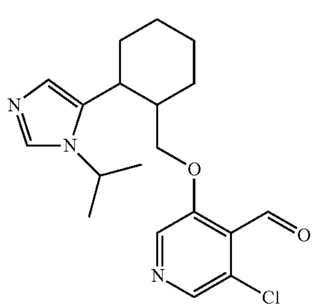 [SMILES: CC(C)n1cncc1C1CCCCC1COc1cncc(Cl)c1C=O] | 3-chloro-5-[[2-(3-propan-2-ylimidazol-4-yl)cyclohexyl]methoxy]pyridine-4-carbaldehyde |

TABLE 1-continued

| Compound | Structure | Name |
| --- | --- | --- |
| 216 | 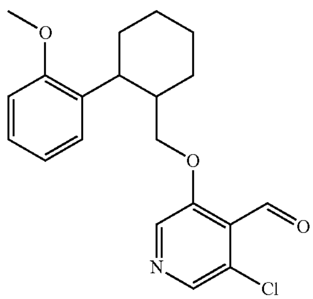 [SMILES: COc1ccccc1C1CCCCC1COc1cncc(Cl)c1C=O] | 3-chloro-5-[[2-(2-methoxyphenyl)cyclohexyl]methoxy]pyridine-4-carbaldehyde |
| 217 | 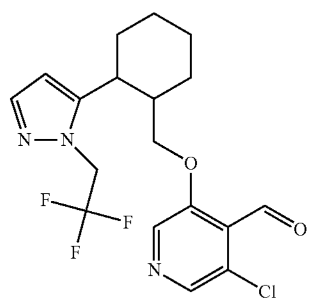 [SMILES: O=Cc1c(Cl)cncc1OCC1CCCCC1c1ccnn1CC(F)(F)F] | 3-chloro-5-[[2-[2-(2,2,2-trifluoroethyl)pyrazol-3-yl]cyclohexyl]methoxy]pyridine-4-carbaldehyde |
| 218 | 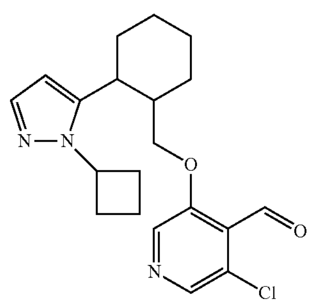 [SMILES: O=Cc1c(Cl)cncc1OCC1CCCCC1c1ccnn1C1CCC1] | 3-chloro-5-[[2-(2-cyclobutylpyrazol-3-yl)cyclohexyl]methoxy]pyridine-4-carbaldehyde |
| 219 | 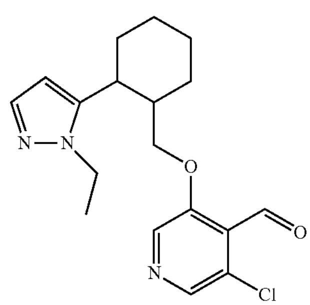 [SMILES: CCn1nccc1C1CCCCC1COc1cncc(Cl)c1C=O] | 3-chloro-5-[[2-(2-ethylpyrazol-3-yl)cyclohexyl]methoxy]pyridine-4-carbaldehyde |
| 220 | 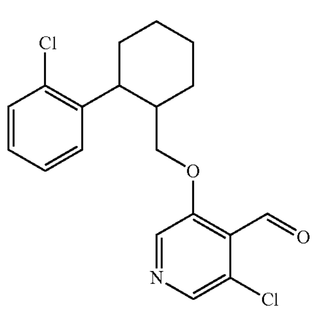 [SMILES: O=Cc1c(Cl)cncc1OCC1CCCCC1c1ccccc1Cl] | 3-chloro-5-[[2-(2-chlorophenyl)cyclohexyl]methoxy]pyridine-4-carbaldehyde |

TABLE 1-continued

| Compound | Structure | Name |
|---|---|---|
| 221 | 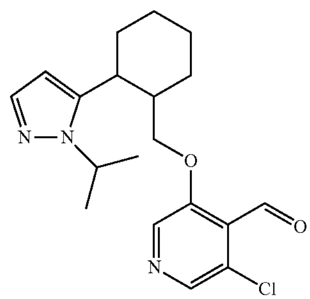 [SMILES: CC(C)n1nccc1C1CCCCC1COc1cncc(Cl)c1C=O] | 3-chloro-5-[[2-(2-propan-2-ylpyrazol-3-yl)cyclohexyl]methoxy]pyridine-4-carbaldehyde |
| 222 | 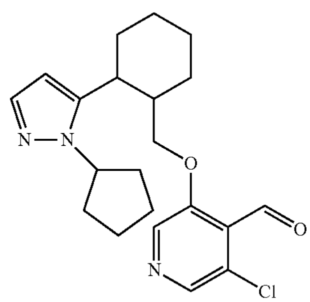 [SMILES: O=Cc1c(Cl)cncc1OCC1CCCCC1c1ccnn1C1CCCC1] | 3-chloro-5-[[2-(2-cyclopentylpyrazol-3-yl)cyclohexyl]methoxy]pyridine-4-carbaldehyde |
| 223 | 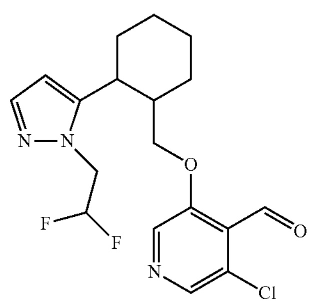 [SMILES: O=Cc1c(Cl)cncc1OCC1CCCCC1c1ccnn1CC(F)F] | 3-chloro-5-[[2-[2-(2,2-difluoroethyl)pyrazol-3-yl]cyclohexyl]methoxy]pyridine-4-carbaldehyde |
| 224 | 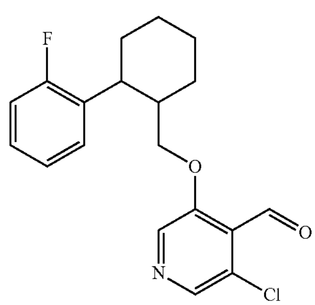 [SMILES: O=Cc1c(Cl)cncc1OCC1CCCCC1c1ccccc1F] | 3-chloro-5-[[2-(2-fluorophenyl)cyclohexyl]methoxy]pyridine-4-carbaldehyde |
| 225 | 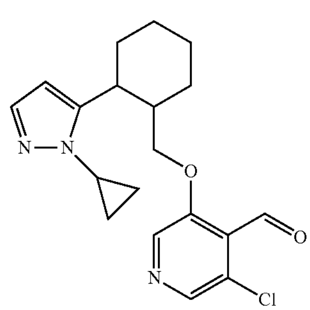 [SMILES: O=Cc1c(Cl)cncc1OCC1CCCCC1c1ccnn1C1CC1] | 3-chloro-5-[[2-(2-cyclopropylpyrazol-3-yl)cyclohexyl]methoxy]pyridine-4-carbaldehyde |

TABLE 1-continued

| Compound | Structure | Name |
|---|---|---|
| 226 | 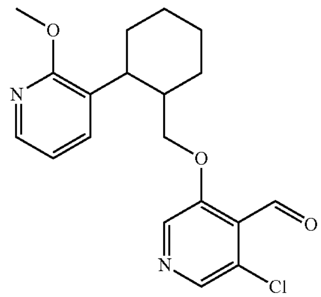 [SMILES: COc1ncccc1C1CCCCC1COc1cncc(Cl)c1C=O] | 3-chloro-5-[[2-(2-methoxypyridin-3-yl)cyclohexyl]methoxy]pyridine-4-carbaldehyde |
| 227 | 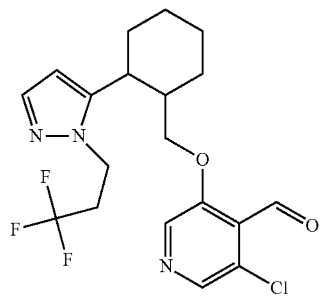 [SMILES: O=Cc1c(Cl)cncc1OCC1CCCCC1c1ccnn1CCC(F)(F)F] | 3-chloro-5-[[2-[2-(3,3,3-trifluoropropyl)pyrazol-3-yl]cyclohexyl]methoxy]pyridine-4-carbaldehyde |
| 228 | 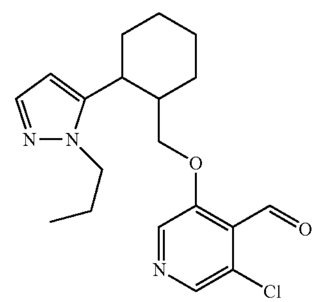 [SMILES: CCCn1nccc1C1CCCCC1COc1cncc(Cl)c1C=O] | 3-chloro-5-[[2-(2-propylpyrazol-3-yl)cyclohexyl]methoxy]pyridine-4-carbaldehyde |
| 229 | 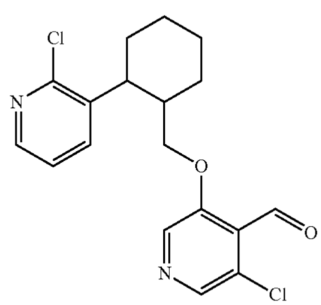 [SMILES: O=Cc1c(Cl)cncc1OCC1CCCCC1c1cccnc1Cl] | 3-chloro-5-[[2-(2-chloropyridin-3-yl)cyclohexyl]methoxy]pyridine-4-carbaldehyde |
| 230 | 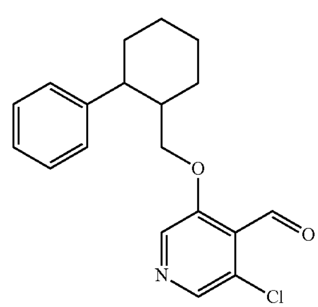 [SMILES: O=Cc1c(Cl)cncc1OCC1CCCCC1c1ccccc1] | 3-chloro-5-[(2-phenylcyclohexyl)methoxy]pyridine-4-carbaldehyde |

TABLE 1-continued

| Compound | Structure | Name |
|---|---|---|
| 231 | 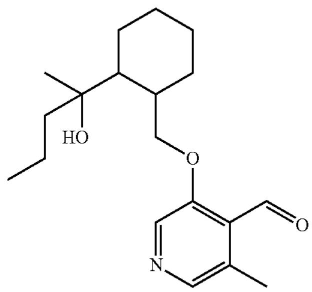 [SMILES: CCCC(C)(O)C1CCCCC1COc1cncc(C)c1C=O] | 3-[[2-(2-hydroxypentan-2-yl)cyclohexyl]methoxy]-5-methylpyridine-4-carbaldehyde |
| 232 | 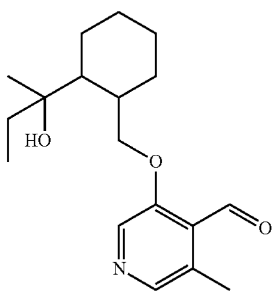 [SMILES: CCC(C)(O)C1CCCCC1COc1cncc(C)c1C=O] | 3-[[2-(2-hydroxybutan-2-yl)cyclohexyl]methoxy]-5-methylpyridine-4-carbaldehyde |
| 233 | 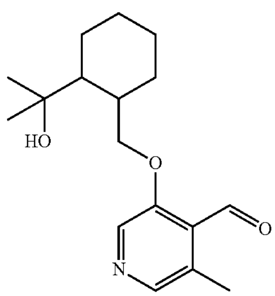 [SMILES: Cc1cncc(OCC2CCCCC2C(C)(C)O)c1C=O] | 3-[[2-(2-hydroxypropan-2-yl)cyclohexyl]methoxy]-5-methylpyridine-4-carbaldehyde |
| 234 | 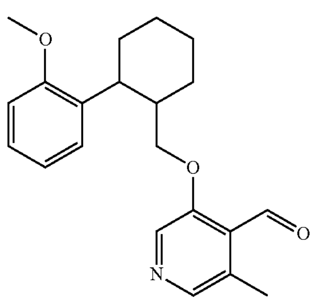 [SMILES: COc1ccccc1C1CCCCC1COc1cncc(C)c1C=O] | 3-[[2-(2-methoxyphenyl)cyclohexyl]methoxy]-5-methylpyridine-4-carbaldehyde |
| 235 | 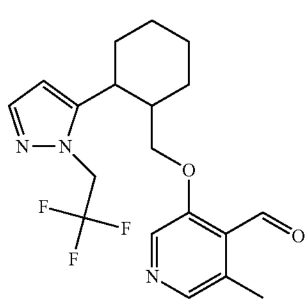 [SMILES: Cc1cncc(OCC2CCCCC2c2ccnn2CC(F)(F)F)c1C=O] | 3-methyl-5-[[2-[2-(2,2,2-trifluoroethyl)pyrazol-3-yl]cyclohexyl]methoxy]pyridine-4-carbaldehyde |

TABLE 1-continued

| Compound | Structure | Name |
|---|---|---|
| 236 | 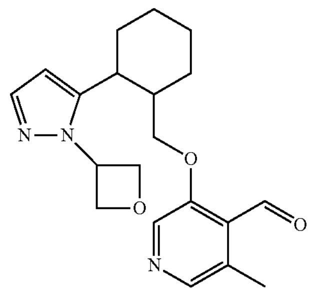 [SMILES: Cc1cncc(OCC2CCCCC2c2ccnn2C2COC2)c1C=O] | 3-methyl-5-[[2-[2-(oxetan-3-yl)pyrazol-3-yl]cyclohexyl]methoxy]pyridine-4-carbaldehyde |
| 237 | 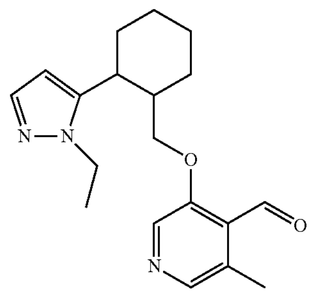 [SMILES: CCn1nccc1C1CCCCC1COc1cncc(C)c1C=O] | 3-[[2-(2-ethylpyrazol-3-yl)cyclohexyl]methoxy]-5-methylpyridine-4-carbaldehyde |
| 238 | 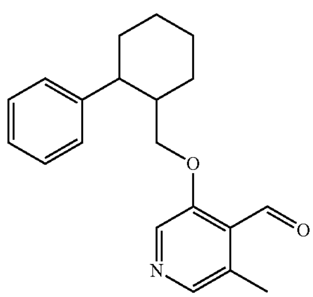 [SMILES: Cc1cncc(OCC2CCCCC2c2ccccc2)c1C=O] | 3-methyl-5-[(2-phenylcyclohexyl)methoxy]pyridine-4-carbaldehyde |
| 239 | 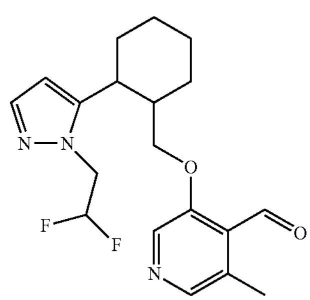 [SMILES: Cc1cncc(OCC2CCCCC2c2ccnn2CC(F)F)c1C=O] | 3-[[2-[2-(2,2-difluoroethyl)pyrazol-3-yl]cyclohexyl]methoxy]-5-methylpyridine-4-carbaldehyde |
| 240 | 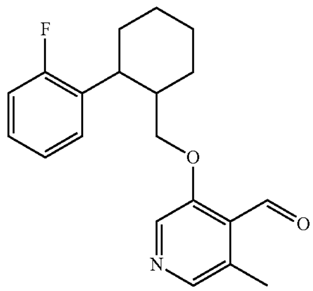 [SMILES: Cc1cncc(OCC2CCCCC2c2ccccc2F)c1C=O] | 3-[[2-(2-fluorophenyl)cyclohexyl]methoxy]-5-methylpyridine-4-carbaldehyde |

TABLE 1-continued

| Compound | Structure | Name |
|---|---|---|
| 241 | 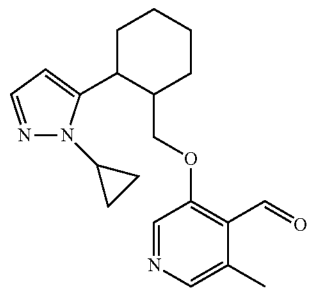 [SMILES: Cc1cncc(OCC2CCCCC2c2ccnn2C2CC2)c1C=O] | 3-[[2-(2-cyclopropylpyrazol-3-yl)cyclohexyl]methoxy]-5-methylpyridine-4-carbaldehyde |
| 242 | 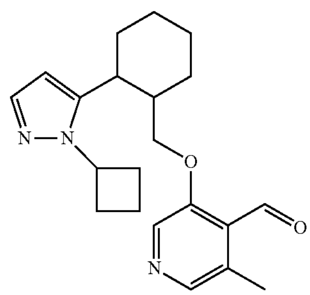 [SMILES: Cc1cncc(OCC2CCCCC2c2ccnn2C2CCC2)c1C=O] | 3-[[2-(2-cyclobutylpyrazol-3-yl)cyclohexyl]methoxy]-5-methylpyridine-4-carbaldehyde |
| 243 | 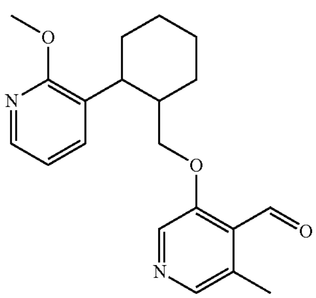 [SMILES: COc1ncccc1C1CCCCC1COc1cncc(C)c1C=O] | 3-[[2-(2-methoxypyridin-3-yl)cyclohexyl]methoxy]-5-methylpyridine-4-carbaldehyde |
| 244 | 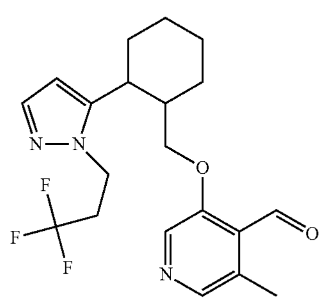 [SMILES: Cc1cncc(OCC2CCCCC2c2ccnn2CCC(F)(F)F)c1C=O] | 3-methyl-5-[[2-[2-(3,3,3-trifluoropropyl)pyrazol-3-yl]cyclohexyl]methoxy]pyridine-4-carbaldehyde |
| 245 | 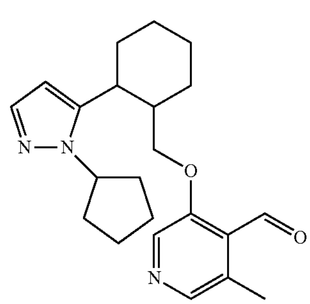 [SMILES: Cc1cncc(OCC2CCCCC2c2ccnn2C2CCCC2)c1C=O] | 3-[[2-(2-cyclopentylpyrazol-3-yl)cyclohexyl]methoxy]-5-methylpyridine-4-carbaldehyde |

TABLE 1-continued

| Compound | Structure | Name |
|---|---|---|
| 246 | 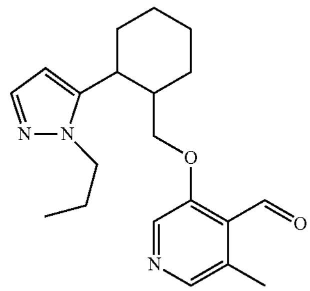 [SMILES: CCCn1nccc1C1CCCCC1COc1cncc(C)c1C=O] | 3-methyl-5-[[2-(2-propylpyrazol-3-yl)cyclohexyl]methoxy]pyridine-4-carbaldehyde |
| 247 | 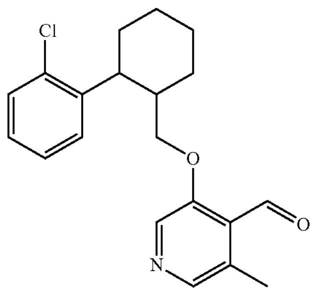 [SMILES: Cc1cncc(OCC2CCCCC2c2ccccc2Cl)c1C=O] | 3-[[2-(2-chloropyridin-3-yl)cyclohexyl]methoxy]-5-methylpyridine-4-carbaldehyde |
| 248 | 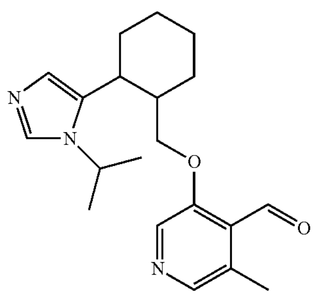 [SMILES: Cc1cncc(OCC2CCCCC2c2cncn2C(C)C)c1C=O] | 3-methyl-5-[[2-(3-propan-2-ylimidazol-4-yl)cyclohexyl]methoxy]pyridine-4-carbaldehyde |
| 249 | 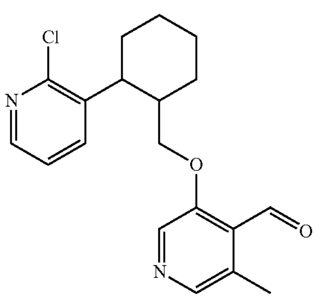 [SMILES: Cc1cncc(OCC2CCCCC2c2cccnc2Cl)c1C=O] | 3-[[2-(2-chlorophenyl)cyclohexyl]methoxy]-5-methylpyridine-4-carbaldehyde |
| 250 | 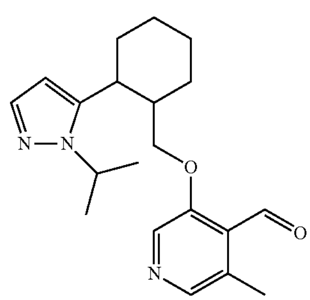 [SMILES: Cc1cncc(OCC2CCCCC2c2ccnn2C(C)C)c1C=O] | 3-methyl-5-[[2-(2-propan-2-ylpyrazol-3-yl)cyclohexyl]methoxy]pyridine-4-carbaldehyde |

TABLE 1-continued

| Compound | Structure | Name |
|---|---|---|
| 251 | 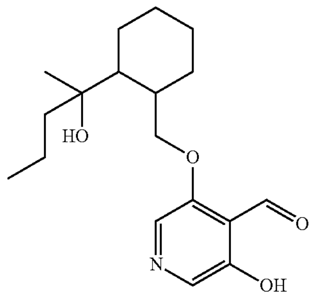 | 3-hydroxy-5-[[2-(2-hydroxypentan-2-yl)cyclohexyl]methoxy]pyridine-4-carbaldehyde |
| 252 | 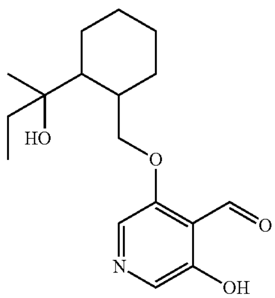 [SMILES: CCC(C)(O)C1CCCCC1COc1cncc(O)c1C=O] | 3-hydroxy-5-[[2-(2-hydroxybutan-2-yl)cyclohexyl]methoxy]pyridine-4-carbaldehyde |
| 253 | 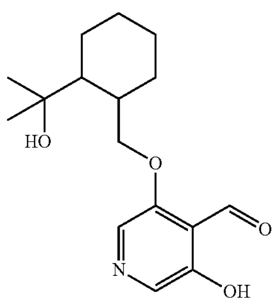 [SMILES: CC(C)(O)C1CCCCC1COc1cncc(O)c1C=O] | 3-hydroxy-5-[[2-(2-hydroxypropan-2-yl)cyclohexyl]methoxy]pyridine-4-carbaldehyde |
| 254 | 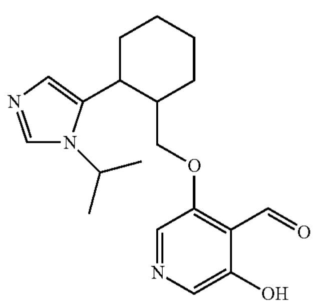 | 3-hydroxy-5-[[2-(3-propan-2-ylimidazol-4-yl)cyclohexyl]methoxy]pyridine-4-carbaldehyde |
| 255 | 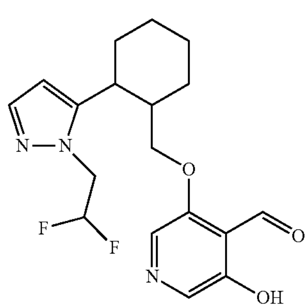 [SMILES: O=Cc1c(O)cncc1OCC1CCCCC1c1ccnn1CC(F)F] | 3-[[2-[2-(2,2-difluoroethyl)pyrazol-3-yl]cyclohexyl]methoxy]-5-hydroxypyridine-4-carbaldehyde |

TABLE 1-continued

| Compound | Structure | Name |
|---|---|---|
| 256 | 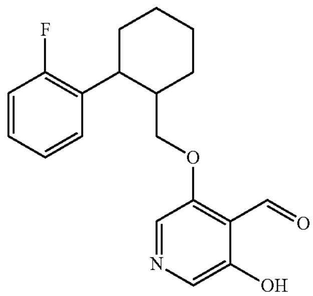 [SMILES: O=Cc1c(O)cncc1OCC1CCCCC1c1ccccc1F] | 3-[[2-(2-fluorophenyl)cyclohexyl]methoxy]-5-hydroxypyridine-4-carbaldehyde |
| 257 | 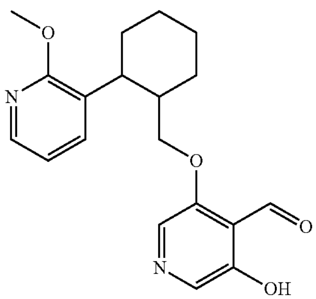 [SMILES: COc1ncccc1C1CCCCC1COc1cncc(O)c1C=O] | 3-hydroxy-5-[[2-(2-methoxypyridin-3-yl)cyclohexyl]methoxy]pyridine-4-carbaldehyde |
| 258 | 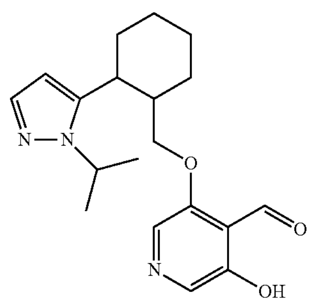 [SMILES: CC(C)n1nccc1C1CCCCC1COc1cncc(O)c1C=O] | 3-hydroxy-5-[[2-(2-propan-2-ylpyrazol-3-yl)cyclohexyl]methoxy]pyridine-4-carbaldehyde |
| 259 | 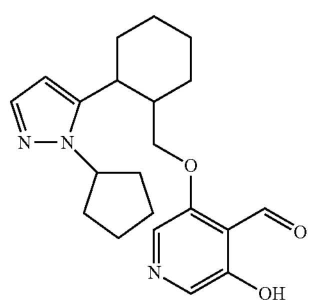 | 3-[[2-(2-cyclopentylpyrazol-3-yl)cyclohexyl]methoxy]-5-hydroxypyridine-4-carbaldehyde |
| 260 | 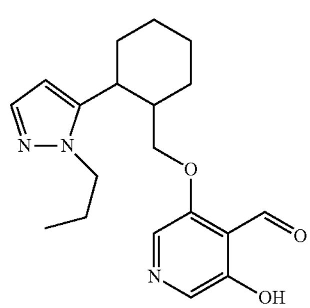 [SMILES: CCCn1nccc1C1CCCCC1COc1cncc(O)c1C=O] | 3-hydroxy-5-[[2-(2-propylpyrazol-3-yl)cyclohexyl]methoxy]pyridine-4-carbaldehyde |

TABLE 1-continued

| Compound | Structure | Name |
|---|---|---|
| 261 | 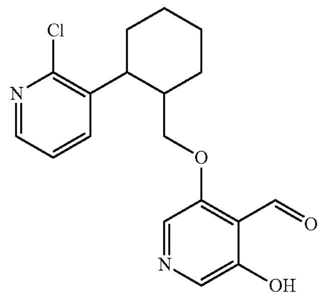 [SMILES: O=Cc1c(O)cncc1OCC1CCCCC1c1cccnc1Cl] | 3-[[2-(2-chloropyridin-3-yl)cyclohexyl]methoxy]-5-hydroxypyridine-4-carbaldehyde |
| 262 | 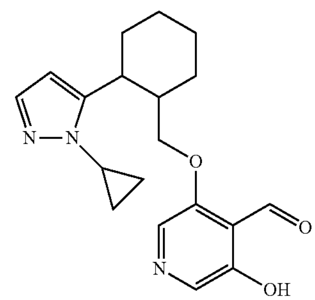 [SMILES: O=Cc1c(O)cncc1OCC1CCCCC1c1ccnn1C1CC1] | 3-[[2-(2-cyclopropylpyrazol-3-yl)cyclohexyl]methoxy]-5-hydroxypyridine-4-carbaldehyde |
| 263 | 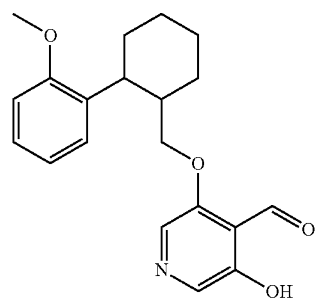 [SMILES: COc1ccccc1C1CCCCC1COc1cncc(O)c1C=O] | 3-hydroxy-5-[[2-(2-methoxyphenyl)cyclohexyl]methoxy]pyridine-4-carbaldehyde |
| 264 | 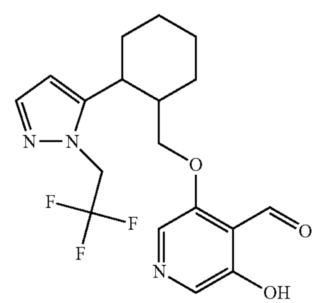 | 3-hydroxy-5-[[2-[2-(2,2,2-trifluoroethyl)pyrazol-3-yl]cyclohexyl]methoxy]pyridine-4-carbaldehyde |
| 265 | 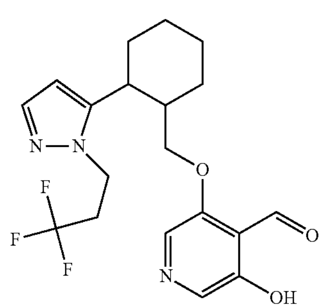 [SMILES: O=Cc1c(O)cncc1OCC1CCCCC1c1ccnn1CCC(F)(F)F] | 3-hydroxy-5-[[2-[2-(3,3,3-trifluoropropyl)pyrazol-3-yl]cyclohexyl]methoxy]pyridine-4-carbaldehyde |

TABLE 1-continued

| Compound | Structure | Name |
|---|---|---|
| 266 | 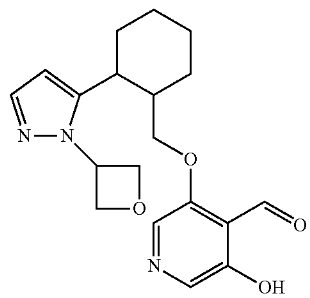 [SMILES: O=Cc1c(O)cncc1OCC1CCCCC1c1ccnn1C1COC1] | 3-hydroxy-5-[[2-[2-(oxetan-3-yl)pyrazol-3-yl]cyclohexyl]methoxy]pyridine-4-carbaldehyde |
| 267 | 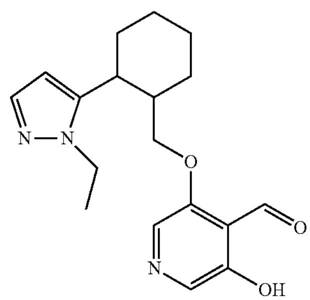 [SMILES: CCn1nccc1C1CCCCC1COc1cncc(O)c1C=O] | 3-[[2-(2-ethylpyrazol-3-yl)cyclohexyl]methoxy]-5-hydroxypyridine-4-carbaldehyde |
| 268 | 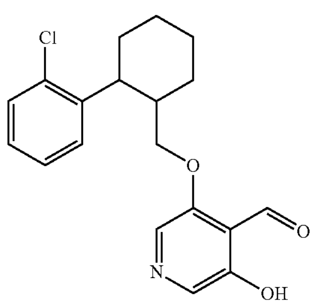 [SMILES: O=Cc1c(O)cncc1OCC1CCCCC1c1ccccc1Cl] | 3-[[2-(2-chlorophenyl)cyclohexyl]methoxy]-5-hydroxypyridine-4-carbaldehyde |
| 269 | 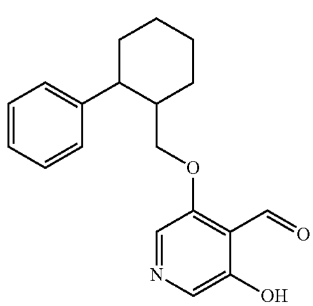 [SMILES: O=Cc1c(O)cncc1OCC1CCCCC1c1ccccc1] | 3-hydroxy-5-[(2-phenylcyclohexyl)methoxy]pyridine-4-carbaldehyde |
| 270 | 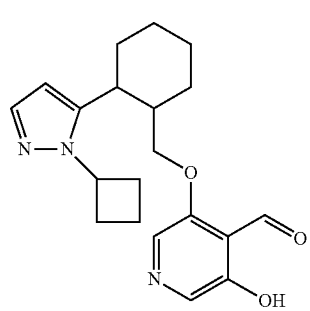 [SMILES: O=Cc1c(O)cncc1OCC1CCCCC1c1ccnn1C1CCC1] | 3-[[2-(2-cyclobutylpyrazol-3-yl)cyclohexyl]methoxy]-5-hydroxypyridine-4-carbaldehyde |

TABLE 1-continued

| Compound | Structure | Name |
| --- | --- | --- |
| 271 | 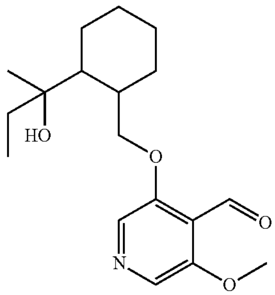 [SMILES: CCC(C)(O)C1CCCCC1COc1cncc(OC)c1C=O] | 3-[[2-(2-hydroxybutan-2-yl)cyclohexyl]methoxy]-5-methoxypyridine-4-carbaldehyde |
| 272 | 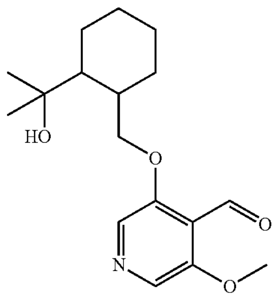 [SMILES: COc1cncc(OCC2CCCCC2C(C)(C)O)c1C=O] | 3-[[2-(2-hydroxypropan-2-yl)cyclohexyl]methoxy]-5-methoxypyridine-4-carbaldehyde |
| 273 | 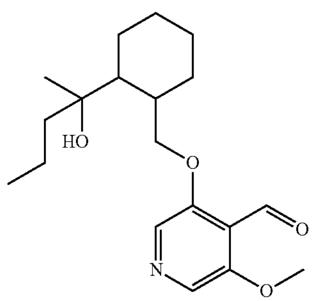 [SMILES: CCCC(C)(O)C1CCCCC1COc1cncc(OC)c1C=O] | 3-[[2-(2-hydroxypentan-2-yl)cyclohexyl]methoxy]-5-methoxypyridine-4-carbaldehyde |
| 274 | 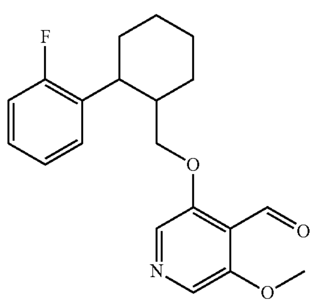 [SMILES: COc1cncc(OCC2CCCCC2c2ccccc2F)c1C=O] | 3-[[2-(2-fluorophenyl)cyclohexyl]methoxy]-5-methoxypyridine-4-carbaldehyde |
| 275 | 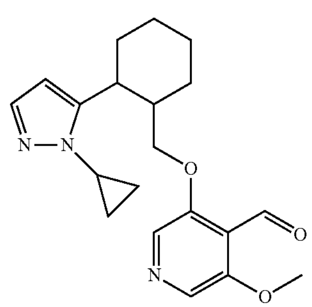 [SMILES: COc1cncc(OCC2CCCCC2c2ccnn2C2CC2)c1C=O] | 3-[[2-(2-cyclopropylpyrazol-3-yl)cyclohexyl]methoxy]-5-methoxypyridine-4-carbaldehyde |

TABLE 1-continued

| Compound | Structure | Name |
| --- | --- | --- |
| 276 | 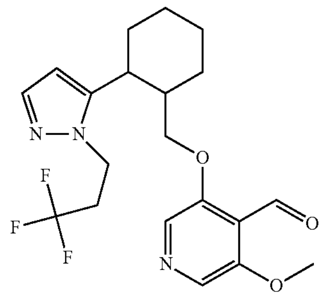 [SMILES: COc1cncc(OCC2CCCCC2c2ccnn2CCC(F)(F)F)c1C=O] | 3-methoxy-5-[[2-[2-(3,3,3-trifluoropropyl)pyrazol-3-yl]cyclohexyl]methoxy]pyridine-4-carbaldehyde |
| 277 | 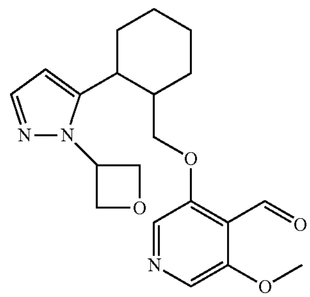 [SMILES: COc1cncc(OCC2CCCCC2c2ccnn2C2COC2)c1C=O] | 3-methoxy-5-[[2-[2-(oxetan-3-yl)pyrazol-3-yl]cyclohexyl]methoxy]pyridine-4-carbaldehyde |
| 278 | 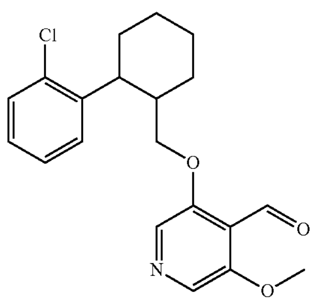 [SMILES: COc1cncc(OCC2CCCCC2c2ccccc2Cl)c1C=O] | 3-[[2-(2-chlorophenyl)cyclohexyl]methoxy]-5-methoxypyridine-4-carbaldehyde |
| 279 | 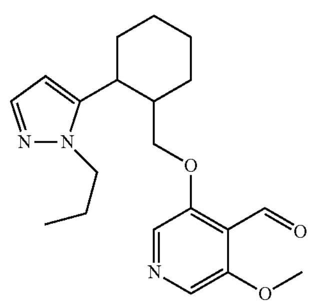 [SMILES: CCCn1nccc1C1CCCCC1COc1cncc(OC)c1C=O] | 3-methoxy-5-[[2-(2-propylpyrazol-3-yl)cyclohexyl]methoxy]pyridine-4-carbaldehyde |
| 280 | 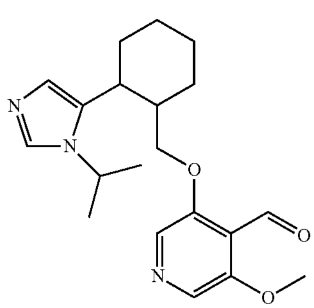 [SMILES: COc1cncc(OCC2CCCCC2c2cncn2C(C)C)c1C=O] | 3-methoxy-5-[[2-(3-propan-2-ylimidazol-4-yl)cyclohexyl]methoxy]pyridine-4-carbaldehyde |

TABLE 1-continued

| Compound | Structure | Name |
|---|---|---|
| 281 | 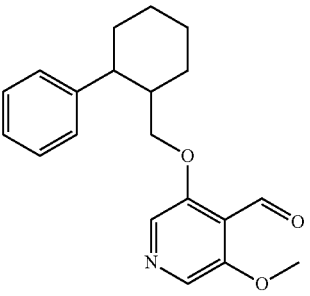 [SMILES: COc1cncc(OCC2CCCCC2c2ccccc2)c1C=O] | 3-methoxy-5-[(2-phenylcyclohexyl)methoxy]pyridine-4-carbaldehyde |
| 282 | 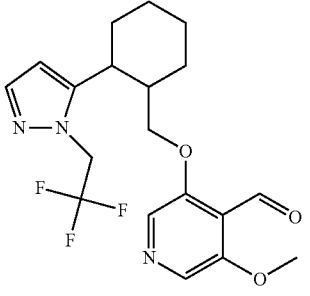 [SMILES: COc1cncc(OCC2CCCCC2c2ccnn2CC(F)(F)F)c1C=O] | 3-methoxy-5-[[2-[2-(2,2,2-trifluoroethyl)pyrazol-3-yl]cyclohexyl]methoxy]pyridine-4-carbaldehyde |
| 283 | 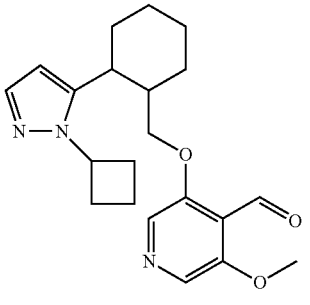 [SMILES: COc1cncc(OCC2CCCCC2c2ccnn2C2CCC2)c1C=O] | 3-[[2-(2-cyclobutylpyrazol-3-yl)cyclohexyl]methoxy]-5-methoxypyridine-4-carbaldehyde |
| 284 | 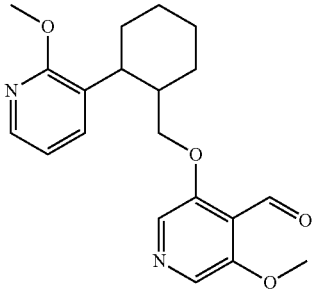 [SMILES: COc1cncc(OCC2CCCCC2c2cccnc2OC)c1C=O] | 3-methoxy-5-[[2-(2-methoxypyridin-3-yl)cyclohexyl]methoxy]pyridine-4-carbaldehyde |
| 285 | 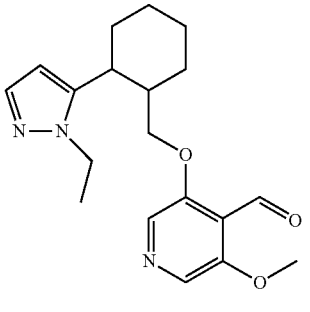 [SMILES: CCn1nccc1C1CCCCC1COc1cncc(OC)c1C=O] | 3-[[2-(2-ethylpyrazol-3-yl)cyclohexyl]methoxy]-5-methoxypyridine-4-carbaldehyde |

TABLE 1-continued

| Compound | Structure | Name |
|---|---|---|
| 286 | 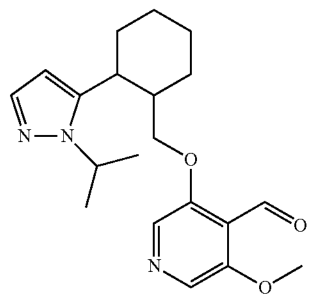 [SMILES: COc1cncc(OCC2CCCCC2c2ccnn2C(C)C)c1C=O] | 3-methoxy-5-[[2-(2-propan-2-ylpyrazol-3-yl)cyclohexyl]methoxy]pyridine-4-carbaldehyde |
| 287 | 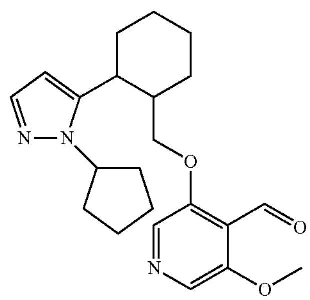 [SMILES: COc1cncc(OCC2CCCCC2c2ccnn2C2CCCC2)c1C=O] | 3-[[2-(2-cyclopentylpyrazol-3-yl)cyclohexyl]methoxy]-5-methoxypyridine-4-carbaldehyde |
| 288 | 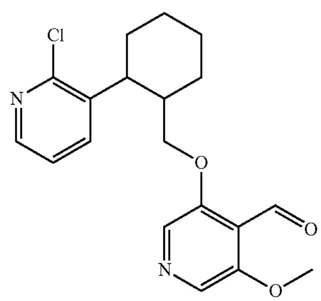 [SMILES: COc1cncc(OCC2CCCCC2c2cccnc2Cl)c1C=O] | 3-[[2-(2-chloropyridin-3-yl)cyclohexyl]methoxy]-5-methoxypyridine-4-carbaldehyde |
| 289 | 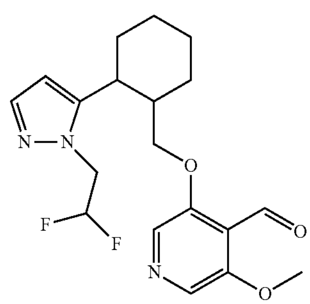 [SMILES: COc1cncc(OCC2CCCCC2c2ccnn2CC(F)F)c1C=O] | 3-[[2-[2-(2,2-difluoroethyl)pyrazol-3-yl]cyclohexyl]methoxy]-5-methoxypyridine-4-carbaldehyde |
| 290 | 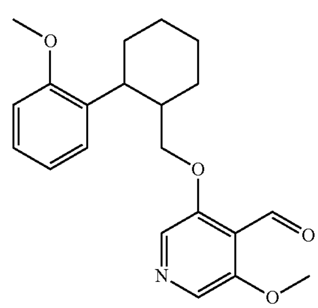 [SMILES: COc1ccccc1C1CCCCC1COc1cncc(OC)c1C=O] | 3-methoxy-5-[[2-(2-methoxyphenyl)cyclohexyl]methoxy]pyridine-4-carbaldehyde |

TABLE 1-continued

| Compound | Structure | Name |
|---|---|---|
| 291 | 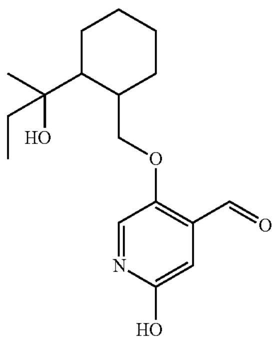 [SMILES: CCC(C)(O)C1CCCCC1COc1cnc(O)cc1C=O] | 2-hydroxy-5-[[2-(2-hydroxybutan-2-yl)cyclohexyl]methoxy]pyridine-4-carbaldehyde |
| 292 | 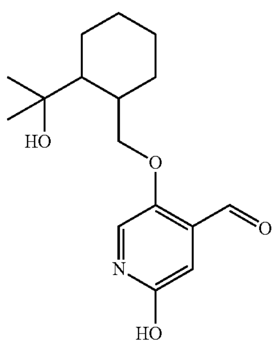 [SMILES: CC(C)(O)C1CCCCC1COc1cnc(O)cc1C=O] | 2-hydroxy-5-[[2-(2-hydroxypropan-2-yl)cyclohexyl]methoxy]pyridine-4-carbaldehyde |
| 293 | 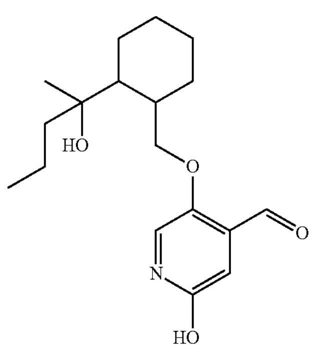 [SMILES: CCCC(C)(O)C1CCCCC1COc1cnc(O)cc1C=O] | 2-hydroxy-5-[[2-(2-hydroxypentan-2-yl)cyclohexyl]methoxy]pyridine-4-carbaldehyde |
| 294 | 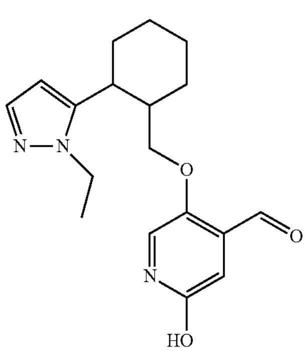 [SMILES: CCn1nccc1C1CCCCC1COc1cnc(O)cc1C=O] | 5-[[2-(2-ethylpyrazol-3-yl)cyclohexyl]methoxy]-2-hydroxypyridine-4-carbaldehyde |

TABLE 1-continued

| Compound | Structure | Name |
|---|---|---|
| 295 | 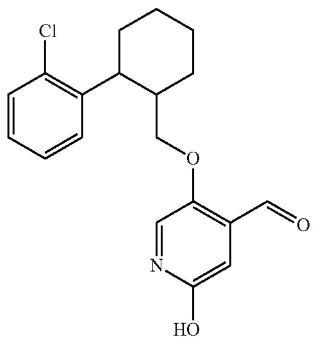 [SMILES: O=Cc1cc(O)ncc1OCC1CCCCC1c1ccccc1Cl] | 5-[[2-(2-chlorophenyl)cyclohexyl]methoxy]-2-hydroxypyridine-4-carbaldehyde |
| 296 | 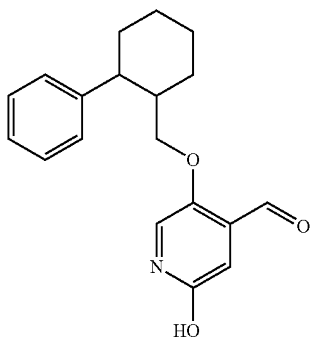 [SMILES: O=Cc1cc(O)ncc1OCC1CCCCC1c1ccccc1] | 2-hydroxy-5-[(2-phenylcyclohexyl)methoxy]pyridine-4-carbaldehyde |
| 297 | 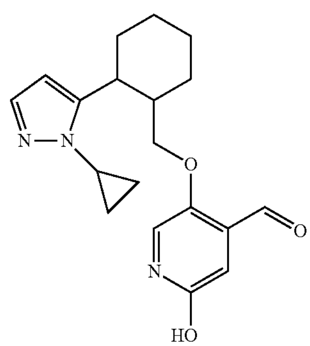 [SMILES: O=Cc1cc(O)ncc1OCC1CCCCC1c1ccnn1C1CC1] | 5-[[2-(2-cyclopropylpyrazol-3-yl)cyclohexyl]methoxy]-2-hydroxypyridine-4-carbaldehyde |
| 298 | 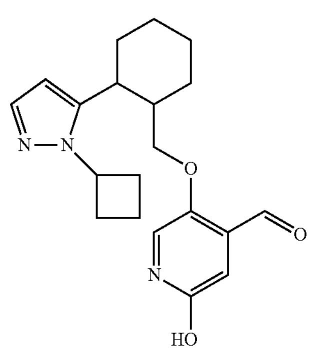 [SMILES: O=Cc1cc(O)ncc1OCC1CCCCC1c1ccnn1C1CCC1] | 5-[[2-(2-cyclobutylpyrazol-3-yl)cyclohexyl]methoxy]-2-hydroxypyridine-4-carbaldehyde |

TABLE 1-continued

| Compound | Structure | Name |
|---|---|---|
| 299 | 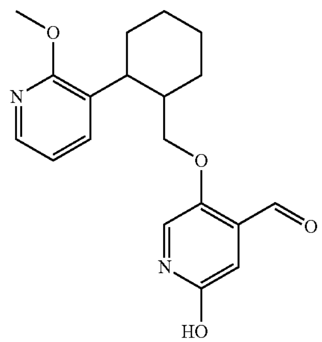 [SMILES: COc1ncccc1C1CCCCC1COc1cnc(O)cc1C=O] | 2-hydroxy-5-[[2-(2-methoxypyridin-3-yl)cyclohexyl]methoxy]pyridine-4-carbaldehyde |
| 300 | 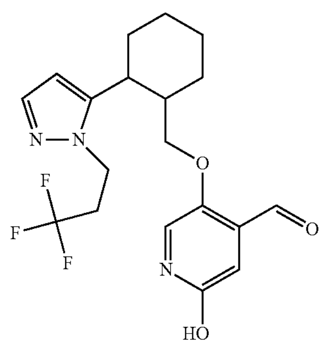 [SMILES: O=Cc1cc(O)ncc1OCC1CCCCC1c1ccnn1CCC(F)(F)F] | 2-hydroxy-5-[[2-[2-(3,3,3-trifluoropropyl)pyrazol-3-yl]cyclohexyl]methoxy]pyridine-4-carbaldehyde |
| 301 | 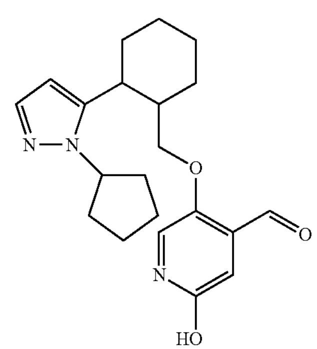 [SMILES: O=Cc1cc(O)ncc1OCC1CCCCC1c1ccnn1C1CCCC1] | 5-[[2-(2-cyclopentylpyrazol-3-yl)cyclohexyl]methoxy]-2-hydroxypyridine-4-carbaldehyde |
| 302 | 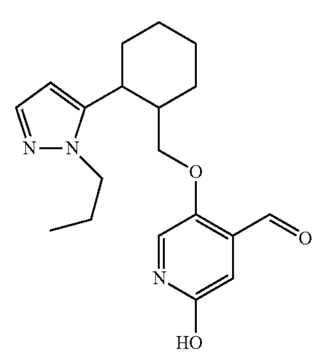 [SMILES: CCCn1nccc1C1CCCCC1COc1cnc(O)cc1C=O] | 2-hydroxy-5-[[2-(2-propylpyrazol-3-yl)cyclohexyl]methoxy]pyridine-4-carbaldehyde |

TABLE 1-continued

| Compound | Structure | Name |
|---|---|---|
| 303 | 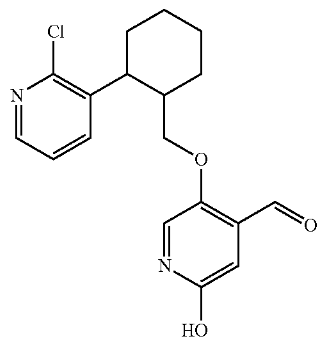 [SMILES: O=Cc1cc(O)ncc1OCC1CCCCC1c1cccnc1Cl] | 5-[[2-(2-chloropyridin-3-yl)cyclohexyl]methoxy]-2-hydroxypyridine-4-carbaldehyde |
| 304 | 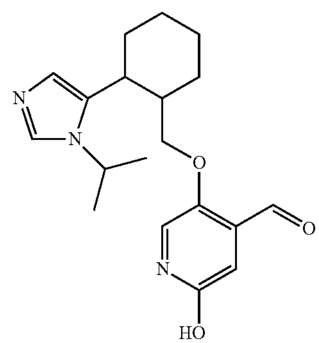 [SMILES: CC(C)n1cncc1C1CCCCC1COc1cnc(O)cc1C=O] | 2-hydroxy-5-[[2-(3-propan-2-ylimidazol-4-yl)cyclohexyl]methoxy]pyridine-4-carbaldehyde |
| 305 | 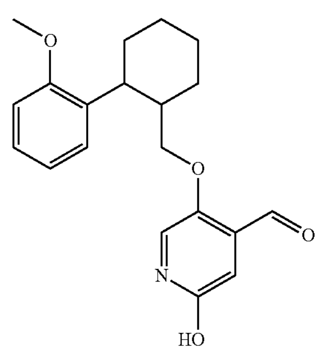 [SMILES: COc1ccccc1C1CCCCC1COc1cnc(O)cc1C=O] | 2-hydroxy-5-[[2-(2-methoxyphenyl)cyclohexyl]methoxy]pyridine-4-carbaldehyde |
| 306 | 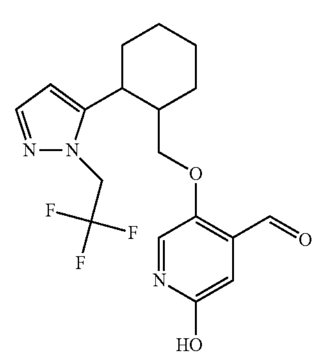 [SMILES: O=Cc1cc(O)ncc1OCC1CCCCC1c1ccnn1CC(F)(F)F] | 2-hydroxy-5-[[2-[2-(2,2,2-trifluoroethyl)pyrazol-3-yl]cyclohexyl]methoxy]pyridine-4-carbaldehyde |

TABLE 1-continued

| Compound | Structure | Name |
|---|---|---|
| 307 | 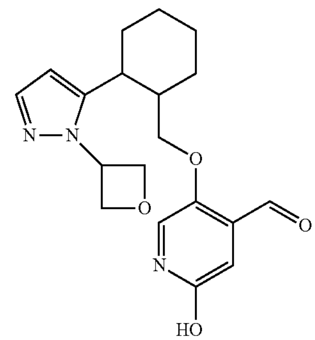 | 2-hydroxy-5-[[2-[2-(oxetan-3-yl)pyrazol-3-yl]cyclohexyl]methoxy]pyridine-4-carbaldehyde |
| 308 | 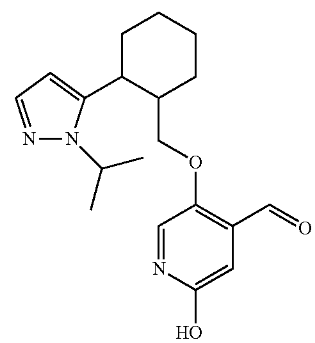 [SMILES: CC(C)n1nccc1C1CCCCC1COc1cnc(O)cc1C=O] | 2-hydroxy-5-[[2-(2-propan-2-ylpyrazol-3-yl)cyclohexyl]methoxy]pyridine-4-carbaldehyde |
| 309 | 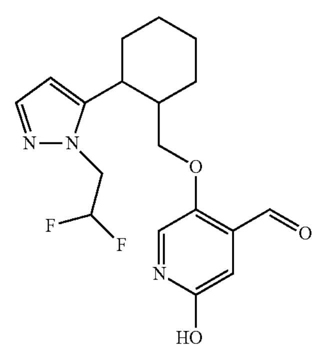 [SMILES: O=Cc1cc(O)ncc1OCC1CCCCC1c1ccnn1CC(F)F] | 5-[[2-[2-(2,2-difluoroethyl)pyrazol-3-yl]cyclohexyl]methoxy]-2-hydroxypyridine-4-carbaldehyde |
| 310 | 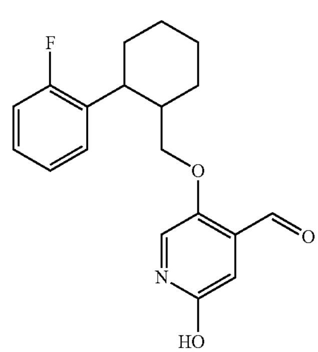 [SMILES: O=Cc1cc(O)ncc1OCC1CCCCC1c1ccccc1F] | 5-[[2-(2-fluorophenyl)cyclohexyl]methoxy]-2-hydroxypyridine-4-carbaldehyde |

TABLE 1-continued

| Compound | Structure | Name |
|---|---|---|
| 311 | 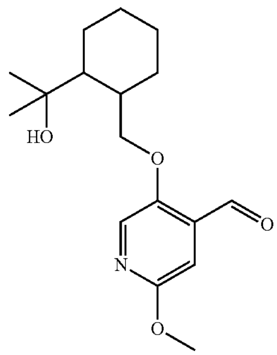 | 5-[[2-(2-hydroxypropan-2-yl)cyclohexyl]methoxy]-2-methoxypyridine-4-carbaldehyde |
| 312 | 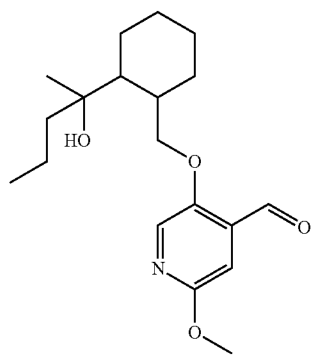 [SMILES: CCCC(C)(O)C1CCCCC1COc1cnc(OC)cc1C=O] | 5-[[2-(2-hydroxypentan-2-yl)cyclohexyl]methoxy]-2-methoxypyridine-4-carbaldehyde |
| 313 | 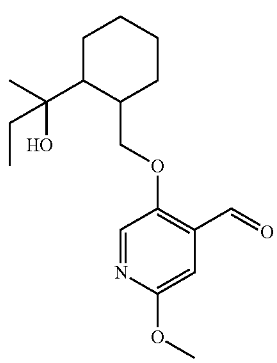 [SMILES: CCC(C)(O)C1CCCCC1COc1cnc(OC)cc1C=O] | 5-[[2-(2-hydroxybutan-2-yl)cyclohexyl]methoxy]-2-methoxypyridine-4-carbaldehyde |
| 314 | 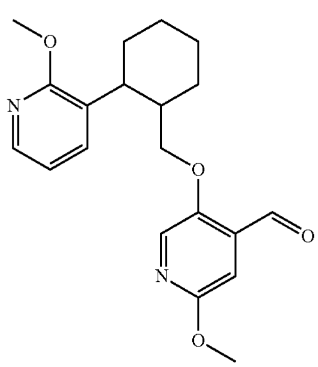 [SMILES: COc1cc(C=O)c(OCC2CCCCC2c2cccnc2OC)cn1] | 2-methoxy-5-[[2-(2-methoxypyridin-3-yl)cyclohexyl]methoxy]pyridine-4-carbaldehyde |

TABLE 1-continued

| Compound | Structure | Name |
|---|---|---|
| 315 | 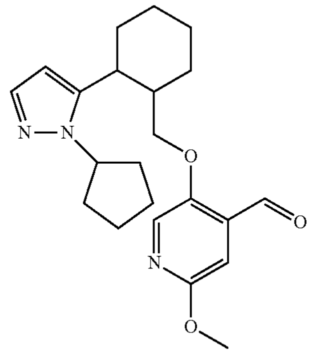 [SMILES: COc1cc(C=O)c(OCC2CCCCC2c2ccnn2C2CCCC2)cn1] | 5-[[2-(2-cyclopentylpyrazol-3-yl)cyclohexyl]methoxy]-2-methoxypyridine-4-carbaldehyde |
| 316 | 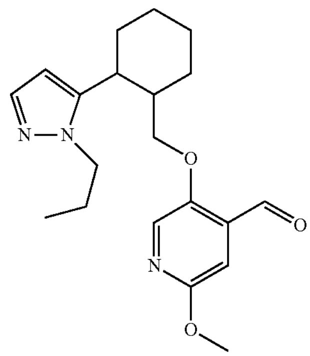 [SMILES: CCCn1nccc1C1CCCCC1COc1cnc(OC)cc1C=O] | 2-methoxy-5-[[2-(2-propylpyrazol-3-yl)cyclohexyl]methoxy]pyridine-4-carbaldehyde |
| 317 | 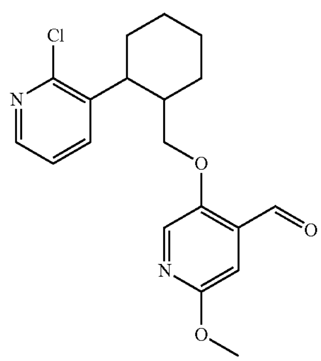 [SMILES: COc1cc(C=O)c(OCC2CCCCC2c2cccnc2Cl)cn1] | 5-[[2-(2-chloropyridin-3-yl)cyclohexyl]methoxy]-2-methoxypyridine-4-carbaldehyde |
| 318 | 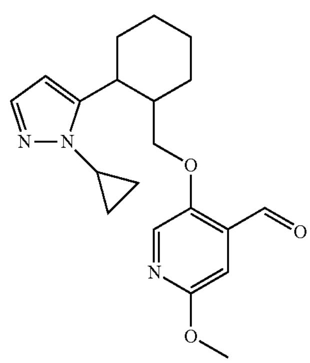 [SMILES: COc1cc(C=O)c(OCC2CCCCC2c2ccnn2C2CC2)cn1] | 5-[[2-(2-cyclopropylpyrazol-3-yl)cyclohexyl]methoxy]-2-methoxypyridine-4-carbaldehyde |

TABLE 1-continued

| Compound | Structure | Name |
|---|---|---|
| 319 | 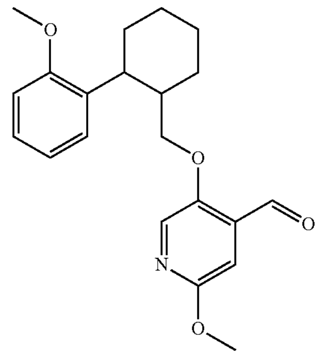 [SMILES: COc1cc(C=O)c(OCC2CCCCC2c2ccccc2OC)cn1] | 2-methoxy-5-[[2-(2-methoxyphenyl)cyclohexyl]methoxy]pyridine-4-carbaldehyde |
| 320 | 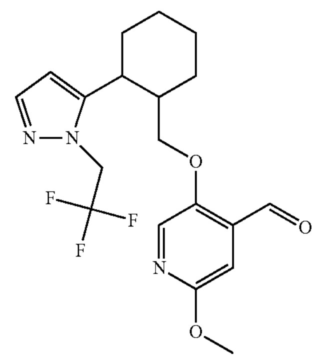 [SMILES: COc1cc(C=O)c(OCC2CCCCC2c2ccnn2CC(F)(F)F)cn1] | 2-methoxy-5-[[2-[2-(2,2,2-trifluoroethyl)pyrazol-3-yl]cyclohexyl]methoxy]pyridine-4-carbaldehyde |
| 321 | 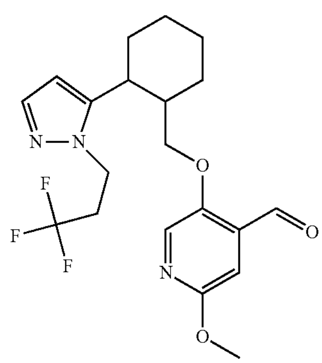 [SMILES: COc1cc(C=O)c(OCC2CCCCC2c2ccnn2CCC(F)(F)F)cn1] | 2-methoxy-5-[[2-[2-(3,3,3-trifluoropropyl)pyrazol-3-yl]cyclohexyl]methoxy]pyridine-4-carbaldehyde |
| 322 | 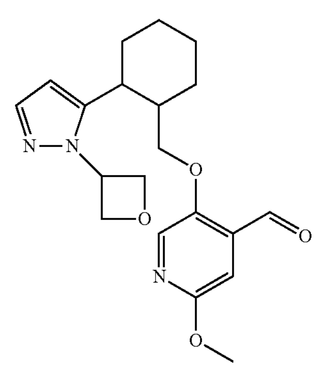 [SMILES: COc1cc(C=O)c(OCC2CCCCC2c2ccnn2C2COC2)cn1] | 2-methoxy-5-[[2-[2-(oxetan-3-yl)pyrazol-3-yl]cyclohexyl]methoxy]pyridine-4-carbaldehyde |

TABLE 1-continued

| Compound | Structure | Name |
|---|---|---|
| 323 | 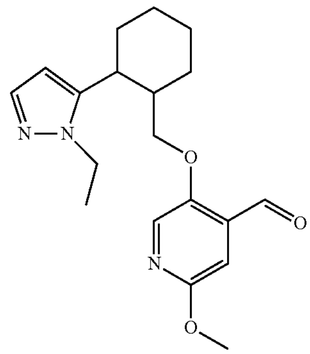 [SMILES: CCn1nccc1C1CCCCC1COc1cnc(OC)cc1C=O] | 5-[[2-(2-ethylpyrazol-3-yl)cyclohexyl]methoxy]-2-methoxypyridine-4-carbaldehyde |
| 324 | 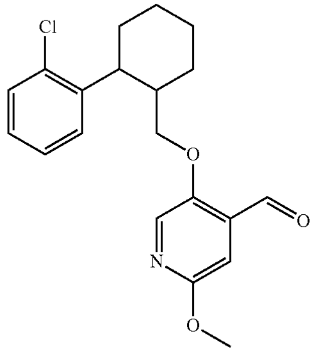 [SMILES: COc1cc(C=O)c(OCC2CCCCC2c2ccccc2Cl)cn1] | 5-[[2-(2-chlorophenyl)cyclohexyl]methoxy]-2-methoxypyridine-4-carbaldehyde |
| 325 | 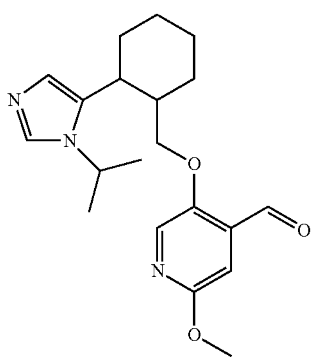 [SMILES: COc1cc(C=O)c(OCC2CCCCC2c2cncn2C(C)C)cn1] | 2-methoxy-5-[[2-(3-propan-2-ylimidazol-4-yl)cyclohexyl]methoxy]pyridine-4-carbaldehyde |
| 326 | 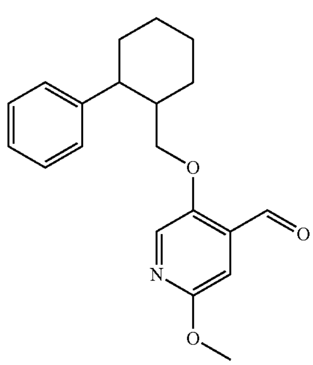 [SMILES: COc1cc(C=O)c(OCC2CCCCC2c2ccccc2)cn1] | 2-methoxy-5-[(2-phenylcyclohexyl)methoxy]pyridine-4-carbaldehyde |

TABLE 1-continued

| Compound | Structure | Name |
|---|---|---|
| 327 | 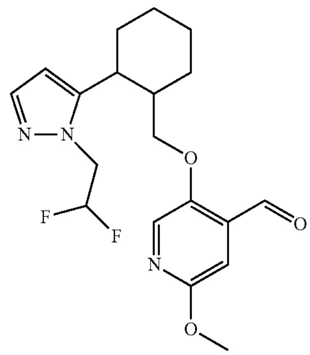 [SMILES: COc1cc(C=O)c(OCC2CCCCC2c2ccnn2CC(F)F)cn1] | 5-[[2-[2-(2,2-difluoroethyl)pyrazol-3-yl]cyclohexyl]methoxy]-2-methoxypyridine-4-carbaldehyde |
| 328 | 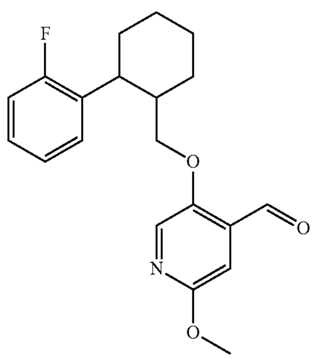 [SMILES: COc1cc(C=O)c(OCC2CCCCC2c2ccccc2F)cn1] | 5-[[2-(2-fluorophenyl)cyclohexyl]methoxy]-2-methoxypyridine-4-carbaldehyde |
| 329 | 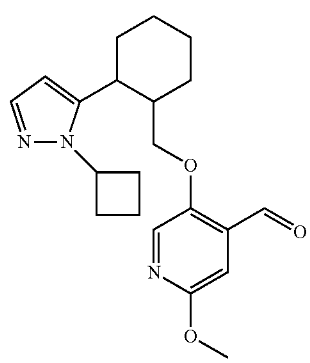 [SMILES: COc1cc(C=O)c(OCC2CCCCC2c2ccnn2C2CCC2)cn1] | 5-[[2-(2-cyclobutylpyrazol-3-yl)cyclohexyl]methoxy]-2-methoxypyridine-4-carbaldehyde |
| 330 | 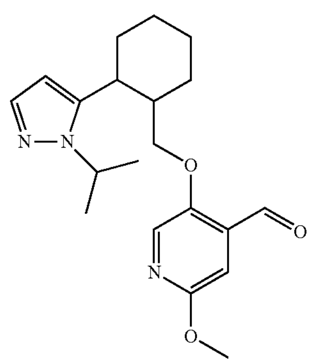 [SMILES: COc1cc(C=O)c(OCC2CCCCC2c2ccnn2C(C)C)cn1] | 2-methoxy-5-[[2-(2-propan-2-ylpyrazol-3-yl)cyclohexyl]methoxy]pyridine-4-carbaldehyde |

TABLE 1-continued

| Compound | Structure | Name |
|---|---|---|
| 331 | 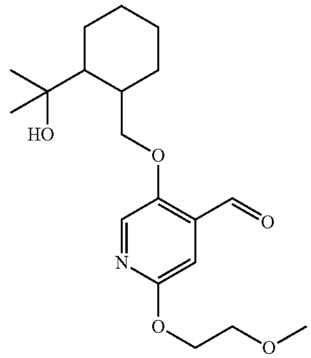 | 5-[[2-(2-hydroxypropan-2-yl)cyclohexyl]methoxy]-2-(2-methoxyethoxy)pyridine-4-carbaldehyde |
| 332 | 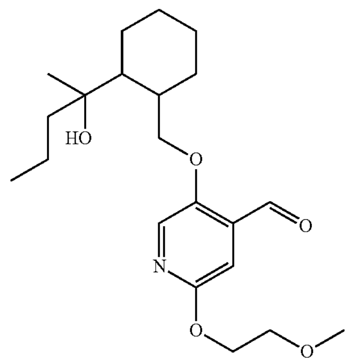 [SMILES: CCCC(C)(O)C1CCCCC1COc1cnc(OCCOC)cc1C=O] | 5-[[2-(2-hydroxypentan-2-yl)cyclohexyl]methoxy]-2-(2-methoxyethoxy)pyridine-4-carbaldehyde |
| 333 | 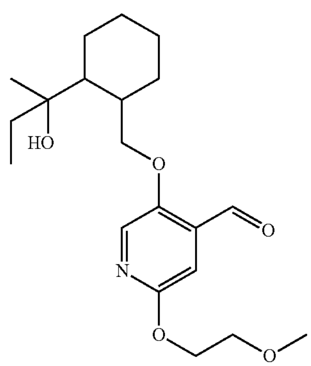 [SMILES: CCC(C)(O)C1CCCCC1COc1cnc(OCCOC)cc1C=O] | 5-[[2-(2-hydroxybutan-2-yl)cyclohexyl]methoxy]-2-(2-methoxyethoxy)pyridine-4-carbaldehyde |
| 334 | 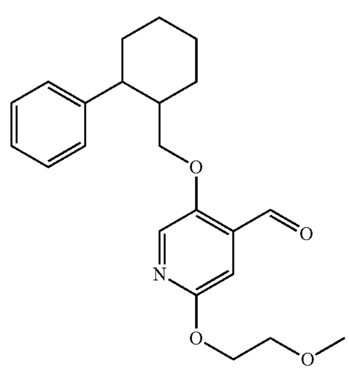 [SMILES: COCCOc1cc(C=O)c(OCC2CCCCC2c2ccccc2)cn1] | 2-(2-methoxyethoxy)-5-[(2-phenylcyclohexyl)methoxy]pyridine-4-carbaldehyde |

TABLE 1-continued

| Compound | Structure | Name |
| --- | --- | --- |
| 335 | 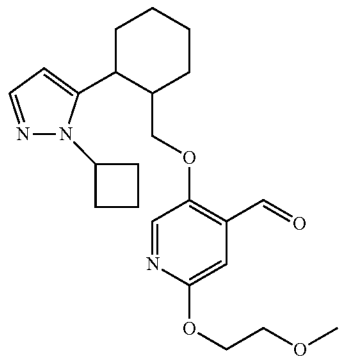 [SMILES: COCCOc1cc(C=O)c(OCC2CCCCC2c2ccnn2C2CCC2)cn1] | 5-[[2-(2-cyclobutylpyrazol-3-yl)cyclohexyl]methoxy]-2-(2-methoxyethoxy)pyridine-4-carbaldehyde |
| 336 | 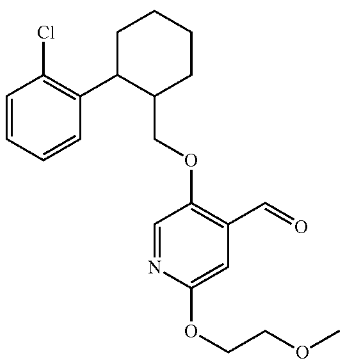 [SMILES: COCCOc1cc(C=O)c(OCC2CCCCC2c2ccccc2Cl)cn1] | 5-[[2-(2-chlorophenyl)cyclohexyl]methoxy]-2-(2-methoxyethoxy)pyridine-4-carbaldehyde |
| 337 | 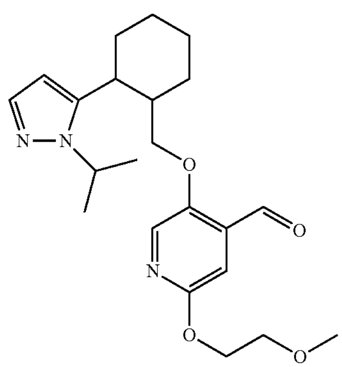 [SMILES: COCCOc1cc(C=O)c(OCC2CCCCC2c2ccnn2C(C)C)cn1] | 2-(2-methoxyethoxy)-5-[[2-(2-propan-2-ylpyrazol-3-yl)cyclohexyl]methoxy]pyridine-4-carbaldehyde |
| 338 | 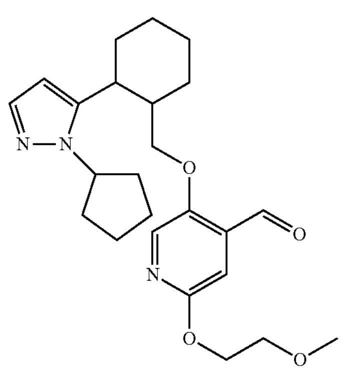 [SMILES: COCCOc1cc(C=O)c(OCC2CCCCC2c2ccnn2C2CCCC2)cn1] | 5-[[2-(2-cyclopentylpyrazol-3-yl)cyclohexyl]methoxy]-2-(2-methoxyethoxy)pyridine-4-carbaldehyde |

TABLE 1-continued

| Compound | Structure | Name |
|---|---|---|
| 339 | 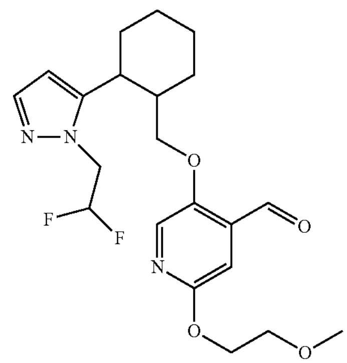 [SMILES: COCCOc1cc(C=O)c(OCC2CCCCC2c2ccnn2CC(F)F)cn1] | 5-[[2-[2-(2,2-difluoroethyl)pyrazol-3-yl]cyclohexyl]methoxy]-2-(2-methoxyethoxy)pyridine-4-carbaldehyde |
| 340 | 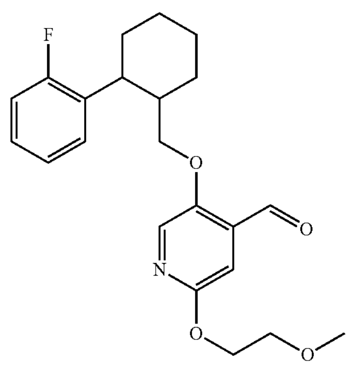 [SMILES: COCCOc1cc(C=O)c(OCC2CCCCC2c2ccccc2F)cn1] | 5-[[2-(2-fluorophenyl)cyclohexyl]methoxy]-2-(2-methoxyethoxy)pyridine-4-carbaldehyde |
| 341 | 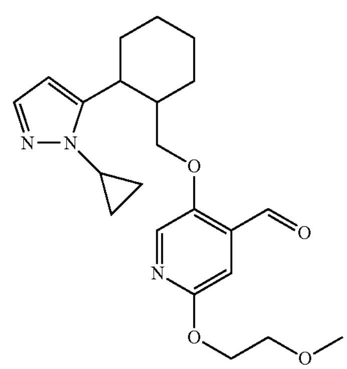 [SMILES: COCCOc1cc(C=O)c(OCC2CCCCC2c2ccnn2C2CC2)cn1] | 5-[[2-(2-cyclopropylpyrazol-3-yl)cyclohexyl]methoxy]-2-(2-methoxyethoxy)pyridine-4-carbaldehyde |
| 342 | 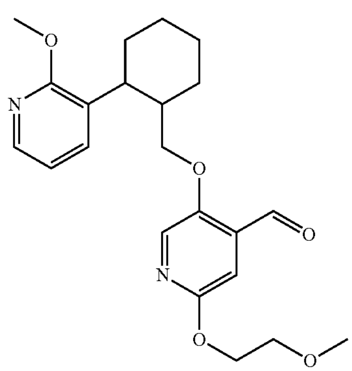 [SMILES: COCCOc1cc(C=O)c(OCC2CCCCC2c2cccnc2OC)cn1] | 2-(2-methoxyethoxy)-5-[[2-(2-methoxypyridin-3-yl)cyclohexyl]methoxy]pyridine-4-carbaldehyde |

TABLE 1-continued

| Compound | Structure | Name |
|---|---|---|
| 343 | 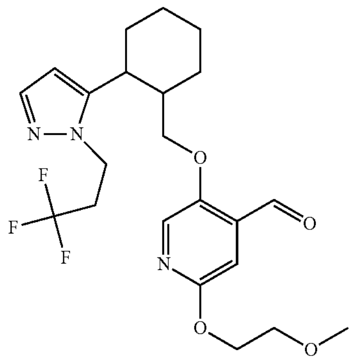 [SMILES: COCCOc1cc(C=O)c(OCC2CCCCC2c2ccnn2CCC(F)(F)F)cn1] | 2-(2-methoxyethoxy)-5-[[2-[2-(3,3,3-trifluoropropyl)pyrazol-3-yl]cyclohexyl]methoxy]pyridine-4-carbaldehyde |
| 344 | 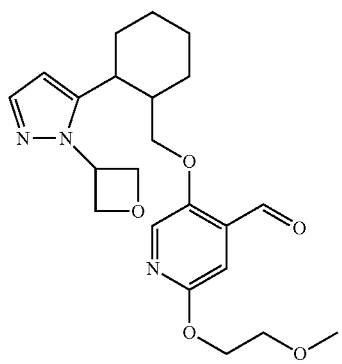 [SMILES: COCCOc1cc(C=O)c(OCC2CCCCC2c2ccnn2C2COC2)cn1] | 2-(2-methoxyethoxy)-5-[[2-[2-(oxetan-3-yl)pyrazol-3-yl]cyclohexyl]methoxy]pyridine-4-carbaldehyde |
| 345 | 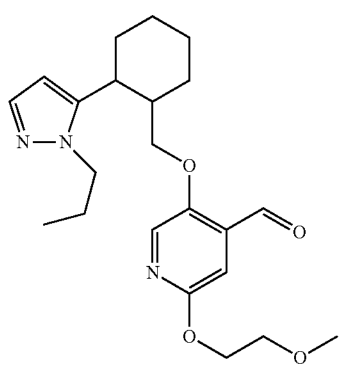 [SMILES: CCCn1nccc1C1CCCCC1COc1cnc(OCCOC)cc1C=O] | 2-(2-methoxyethoxy)-5-[[2-(2-propylpyrazol-3-yl)cyclohexyl]methoxy]pyridine-4-carbaldehyde |
| 346 | 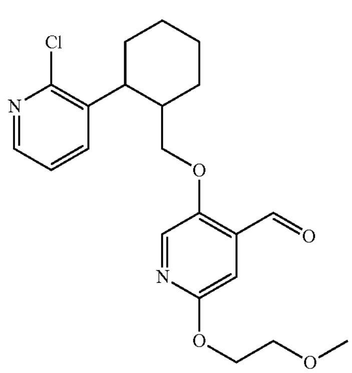 [SMILES: COCCOc1cc(C=O)c(OCC2CCCCC2c2cccnc2Cl)cn1] | 5-[[2-(2-chloropyridin-3-yl)cyclohexyl]methoxy]-2-(2-methoxyethoxy)pyridine-4-carbaldehyde |

TABLE 1-continued

| Compound | Structure | Name |
|---|---|---|
| 347 | 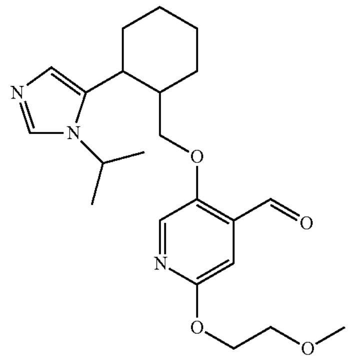 [SMILES: COCCOc1cc(C=O)c(OCC2CCCCC2c2cncn2C(C)C)cn1] | 2-(2-methoxyethoxy)-5-[[2-(3-propan-2-ylimidazol-4-yl)cyclohexyl]methoxy]pyridine-4-carbaldehyde |
| 348 | 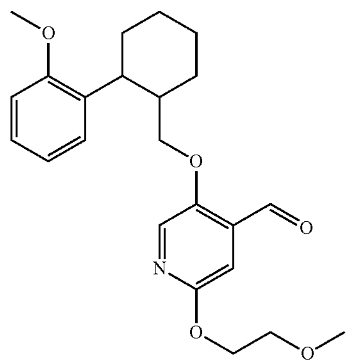 [SMILES: COCCOc1cc(C=O)c(OCC2CCCCC2c2ccccc2OC)cn1] | 2-(2-methoxyethoxy)-5-[[2-(2-methoxyphenyl)cyclohexyl]methoxy]pyridine-4-carbaldehyde |
| 349 | 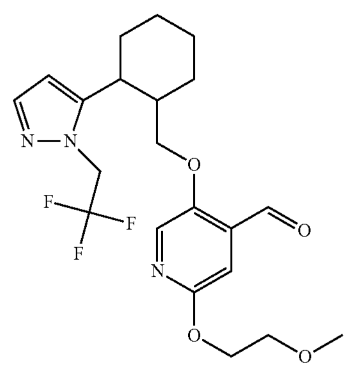 [SMILES: COCCOc1cc(C=O)c(OCC2CCCCC2c2ccnn2CC(F)(F)F)cn1] | 2-(2-methoxyethoxy)-5-[[2-[2-(2,2,2-trifluoroethyl)pyrazol-3-yl]cyclohexyl]methoxy]pyridine-4-carbaldehyde |
| 350 | 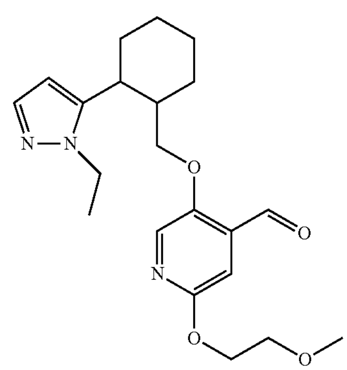 [SMILES: CCn1nccc1C1CCCCC1COc1cnc(OCCOC)cc1C=O] | 5-[[2-(2-ethylpyrazol-3-yl)cyclohexyl]methoxy]-2-(2-methoxyethoxy)pyridine-4-carbaldehyde |

TABLE 1-continued

| Compound | Structure | Name |
|---|---|---|
| 351 | 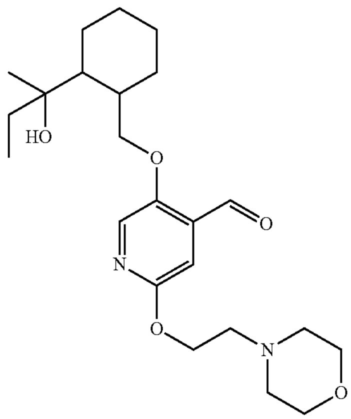 | 5-[[2-(2-hydroxybutan-2-yl)cyclohexyl]methoxy]-2-(2-morpholin-4-ylethoxy)pyridine-4-carbaldehyde |
| 352 | 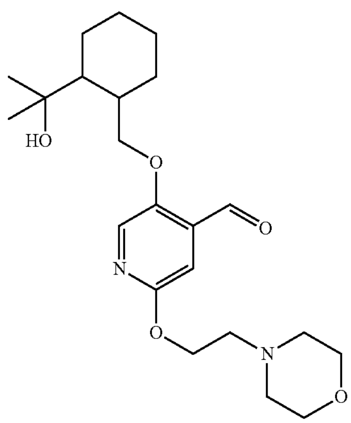 [SMILES: CC(C)(O)C1CCCCC1COc1cnc(OCCN2CCOCC2)cc1C=O] | 5-[[2-(2-hydroxypropan-2-yl)cyclohexyl]methoxy]-2-(2-morpholin-4-ylethoxy)pyridine-4-carbaldehyde |
| 353 | 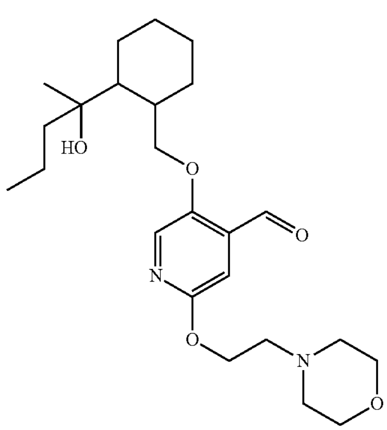 | 5-[[2-(2-hydroxypentan-2-yl)cyclohexyl]methoxy]-2-(2-morpholin-4-ylethoxy)pyridine-4-carbaldehyde |

TABLE 1-continued

| Compound | Structure | Name |
|---|---|---|
| 354 | 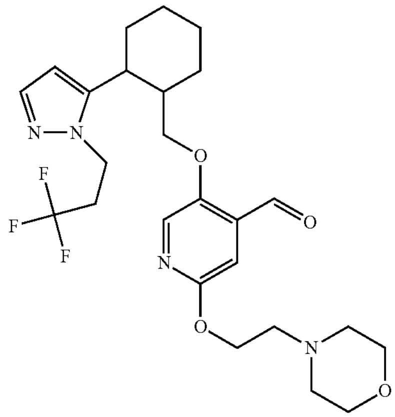 [SMILES: O=Cc1cc(OCCN2CCOCC2)ncc1OCC1CCCCC1c1ccnn1CCC(F)(F)F] | 2-(2-morpholin-4-ylethoxy)-5-[[2-[2-(3,3,3-trifluoropropyl)pyrazol-3-yl]cyclohexyl]methoxy]pyridine-4-carbaldehyde |
| 355 | 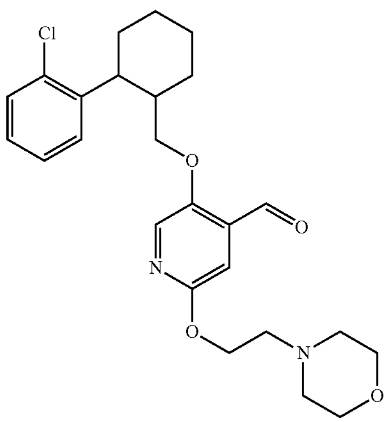 | 5-[[2-(2-chlorophenyl)cyclohexyl]methoxy]-2-(2-morpholin-4-ylethoxy)pyridine-4-carbaldehyde |
| 356 | 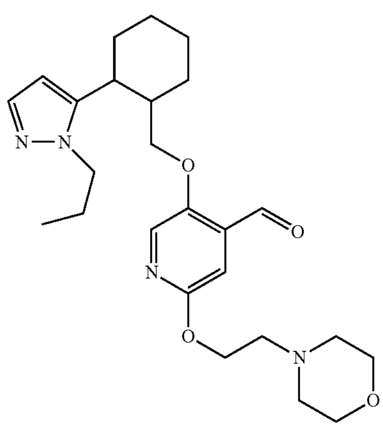 [SMILES: CCCn1nccc1C1CCCCC1COc1cnc(OCCN2CCOCC2)cc1C=O] | 2-(2-morpholin-4-ylethoxy)-5-[[2-(2-propylpyrazol-3-yl)cyclohexyl]methoxy]pyridine-4-carbaldehyde |

TABLE 1-continued

| Compound | Structure | Name |
|---|---|---|
| 357 | 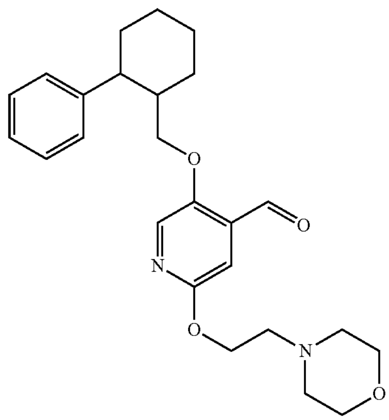 [SMILES: O=Cc1cc(OCCN2CCOCC2)ncc1OCC1CCCCC1c1ccccc1] | 2-(2-morpholin-4-ylethoxy)-5-[(2-phenylcyclohexyl)methoxy]pyridine-4-carbaldehyde |
| 358 | 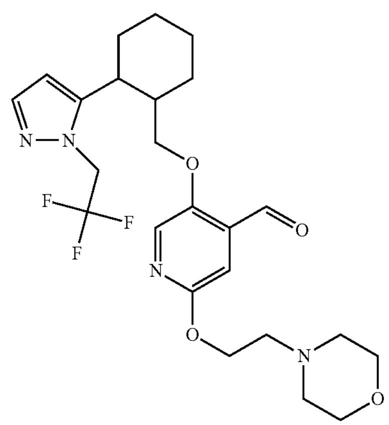 [SMILES: O=Cc1cc(OCCN2CCOCC2)ncc1OCC1CCCCC1c1ccnn1CC(F)(F)F] | 2-(2-morpholin-4-ylethoxy)-5-[[2-[2-(2,2,2-trifluoroethyl)pyrazol-3-yl]cyclohexyl]methoxy]pyridine-4-carbaldehyde |
| 359 | 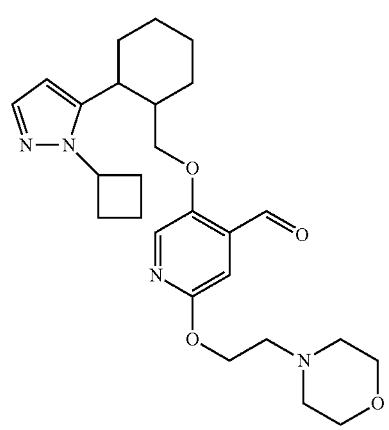 [SMILES: O=Cc1cc(OCCN2CCOCC2)ncc1OCC1CCCCC1c1ccnn1C1CCC1] | 5-[[2-(2-cyclobutylpyrazol-3-yl)cyclohexyl]methoxy]-2-(2-morpholin-4-ylethoxy)pyridine-4-carbaldehyde |

TABLE 1-continued

| Compound | Structure | Name |
|---|---|---|
| 360 | 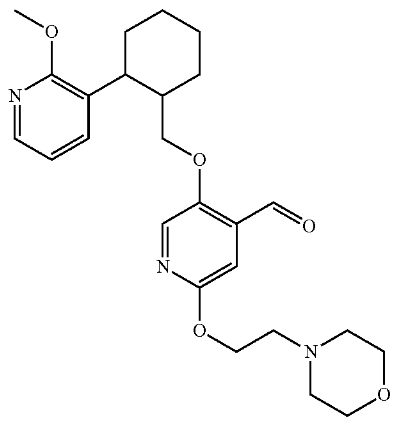 [SMILES: COc1ncccc1C1CCCCC1COc1cnc(OCCN2CCOCC2)cc1C=O] | 5-[[2-(2-methoxypyridin-3-yl)cyclohexyl]methoxy]-2-(2-morpholin-4-ylethoxy)pyridine-4-carbaldehyde |
| 361 | 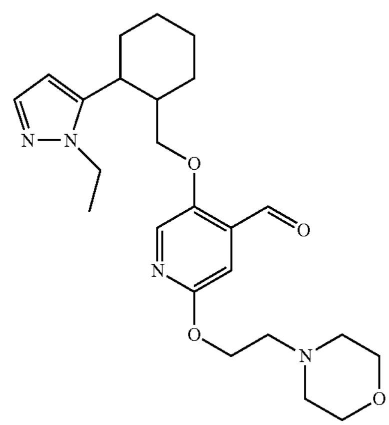 [SMILES: CCn1nccc1C1CCCCC1COc1cnc(OCCN2CCOCC2)cc1C=O] | 5-[[2-(2-ethylpyrazol-3-yl)cyclohexyl]methoxy]-2-(2-morpholin-4-ylethoxy)pyridine-4-carbaldehyde |
| 362 | 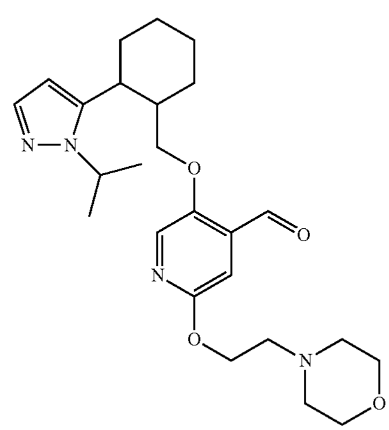 [SMILES: CC(C)n1nccc1C1CCCCC1COc1cnc(OCCN2CCOCC2)cc1C=O] | 2-(2-morpholin-4-ylethoxy)-5-[[2-(2-propan-2-ylpyrazol-3-yl)cyclohexyl]methoxy]pyridine-4-carbaldehyde |

TABLE 1-continued

| Compound | Structure | Name |
|---|---|---|
| 363 | 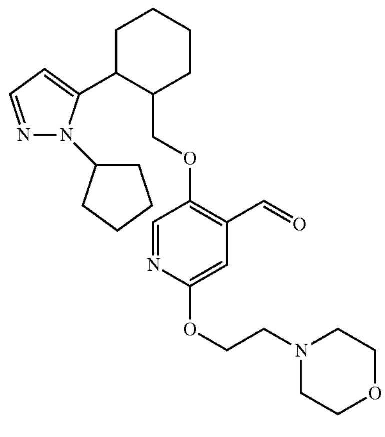 [SMILES: O=Cc1cc(OCCN2CCOCC2)ncc1OCC1CCCCC1c1ccnn1C1CCCC1] | 5-[[2-(2-cyclopentylpyrazol-3-yl)cyclohexyl]methoxy]-2-(2-morpholin-4-ylethoxy)pyridine-4-carbaldehyde |
| 364 | 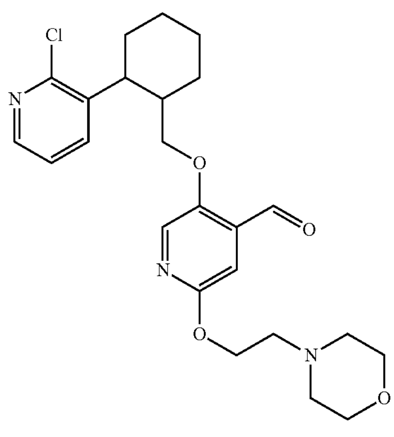 [SMILES: O=Cc1cc(OCCN2CCOCC2)ncc1OCC1CCCCC1c1cccnc1Cl] | 5-[[2-(2-chloropyridin-3-yl)cyclohexyl]methoxy]-2-(2-morpholin-4-ylethoxy)pyridine-4-carbaldehyde |
| 365 | 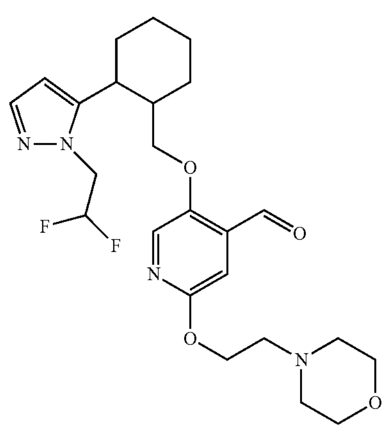 [SMILES: O=Cc1cc(OCCN2CCOCC2)ncc1OCC1CCCCC1c1ccnn1CC(F)F] | 5-[[2-[2-(2,2-difluoroethyl)pyrazol-3-yl]cyclohexyl]methoxy]-2-(2-morpholin-4-ylethoxy)pyridine-4-carbaldehyde |

TABLE 1-continued

| Compound | Structure | Name |
|---|---|---|
| 366 | 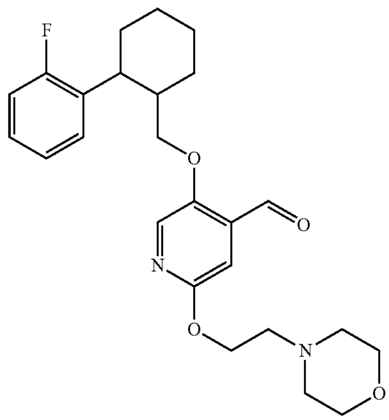 [SMILES: O=Cc1cc(OCCN2CCOCC2)ncc1OCC1CCCCC1c1ccccc1F] | 5-[[2-(2-fluorophenyl)cyclohexyl]methoxy]-2-(2-morpholin-4-ylethoxy)pyridine-4-carbaldehyde |
| 367 | 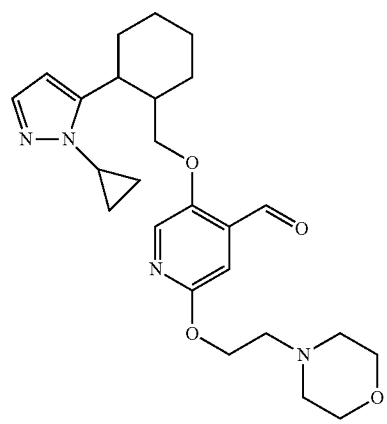 [SMILES: O=Cc1cc(OCCN2CCOCC2)ncc1OCC1CCCCC1c1ccnn1C1CC1] | 5-[[2-(2-cyclopropylpyrazol-3-yl)cyclohexyl]methoxy]-2-(2-morpholin-4-ylethoxy)pyridine-4-carbaldehyde |
| 368 | 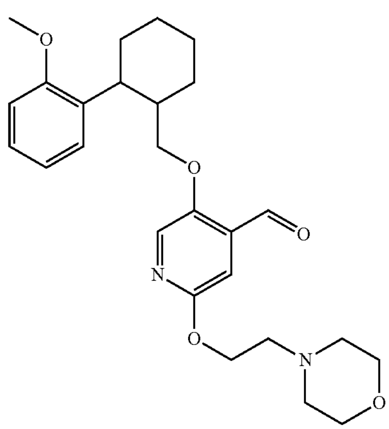 [SMILES: COc1ccccc1C1CCCCC1COc1cnc(OCCN2CCOCC2)cc1C=O] | 5-[[2-(2-methoxyphenyl)cyclohexyl]methoxy]-2-(2-morpholin-4-ylethoxy)pyridine-4-carbaldehyde |

TABLE 1-continued

| Compound | Structure | Name |
|---|---|---|
| 369 | 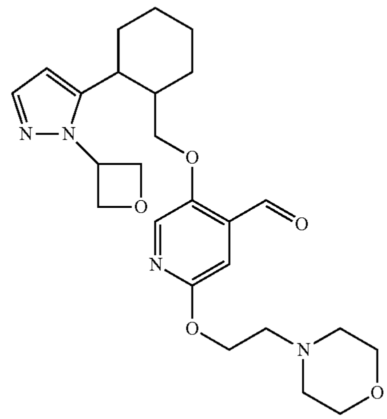 [SMILES: O=Cc1cc(OCCN2CCOCC2)ncc1OCC1CCCCC1c1ccnn1C1COC1] | 2-(2-morpholin-4-ylethoxy)-5-[[2-[2-(oxetan-3-yl)pyrazol-3-yl]cyclohexyl]methoxy]pyridine-4-carbaldehyde |
| 370 | 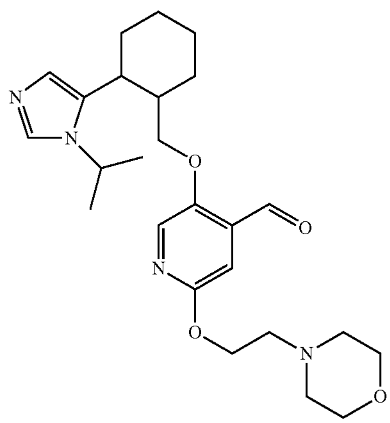 [SMILES: CC(C)n1cncc1C1CCCCC1COc1cnc(OCCN2CCOCC2)cc1C=O] | 2-(2-morpholin-4-ylethoxy)-5-[[2-(3-propan-2-ylimidazol-4-yl)cyclohexyl]methoxy]pyridine-4-carbaldehyde |
| 371 | 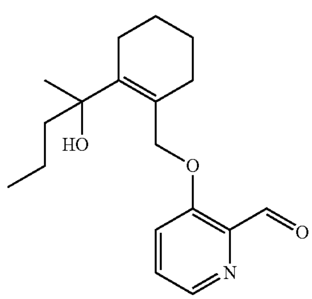 [SMILES: CCCC(C)(O)C1=C(COc2cccnc2C=O)CCCC1] | 3-[[2-(2-hydroxypentan-2-yl)cyclohexen-1-yl]methoxy]pyridine-2-carbaldehyde |
| 372 | 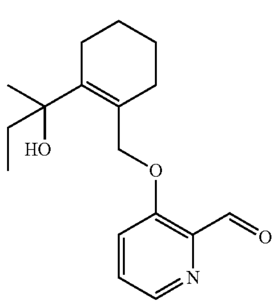 [SMILES: CCC(C)(O)C1=C(COc2cccnc2C=O)CCCC1] | 3-[[2-(2-hydroxybutan-2-yl)cyclohexen-1-yl]methoxy]pyridine-2-carbaldehyde |

TABLE 1-continued

| Compound | Structure | Name |
|---|---|---|
| 373 | 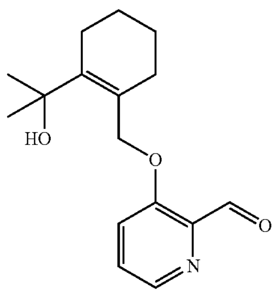 [SMILES: CC(C)(O)C1=C(COc2cccnc2C=O)CCCC1] | 3-[[2-(2-hydroxypropan-2-yl)cyclohexen-1-yl]methoxy]pyridine-2-carbaldehyde |
| 374 | 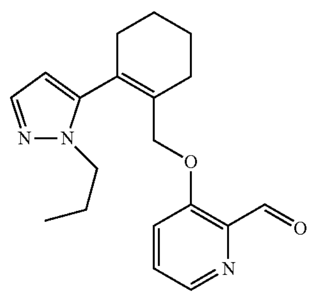 [SMILES: CCCn1nccc1C1=C(COc2cccnc2C=O)CCCC1] | 3-[[2-(2-propylpyrazol-3-yl)cyclohexen-1-yl]methoxy]pyridine-2-carbaldehyde |
| 375 | 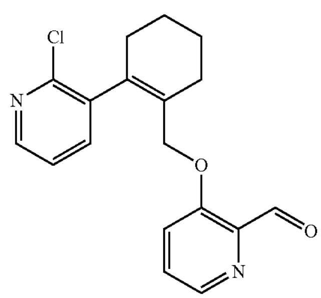 [SMILES: O=Cc1ncccc1OCC1=C(c2cccnc2Cl)CCCC1] | 3-[[2-(2-chloropyridin-3-yl)cyclohexen-1-yl]methoxy]pyridine-2-carbaldehyde |
| 376 | 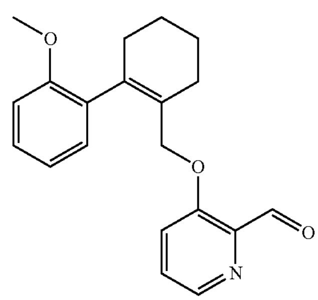 [SMILES: COc1ccccc1C1=C(COc2cccnc2C=O)CCCC1] | 3-[[2-(2-methoxyphenyl)cyclohexen-1-yl]methoxy]pyridine-2-carbaldehyde |
| 377 | 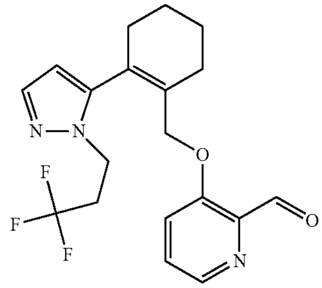 [SMILES: O=Cc1ncccc1OCC1=C(c2ccnn2CCC(F)(F)F)CCCC1] | 3-[[2-[2-(3,3,3-trifluoropropyl)pyrazol-3-yl]cyclohexen-1-yl]methoxy]pyridine-2-carbaldehyde |

TABLE 1-continued

| Compound | Structure | Name |
|---|---|---|
| 378 | 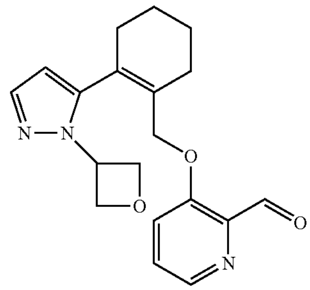 [SMILES: O=Cc1ncccc1OCC1=C(c2ccnn2C2COC2)CCCC1] | 3-[[2-[2-(oxetan-3-yl)pyrazol-3-yl]cyclohexen-1-yl]methoxy]pyridine-2-carbaldehyde |
| 379 | 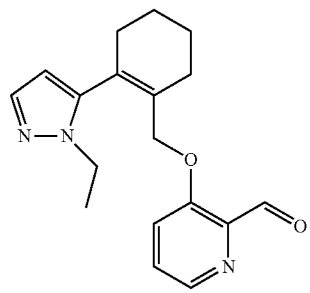 [SMILES: CCn1nccc1C1=C(COc2cccnc2C=O)CCCC1] | 3-[[2-(2-ethylpyrazol-3-yl)cyclohexen-1-yl]methoxy]pyridine-2-carbaldehyde |
| 380 | 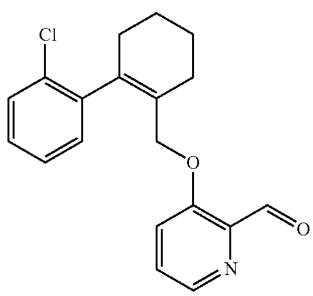 [SMILES: O=Cc1ncccc1OCC1=C(c2ccccc2Cl)CCCC1] | 3-[[2-(2-chlorophenyl)cyclohexen-1-yl]methoxy]pyridine-2-carbaldehyde |
| 381 | 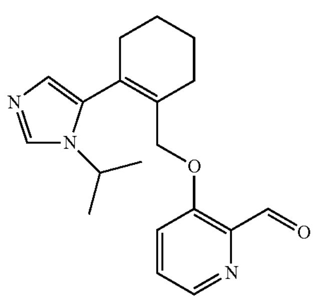 [SMILES: CC(C)n1cncc1C1=C(COc2cccnc2C=O)CCCC1] | 3-[[2-(3-propan-2-ylimidazol-4-yl)cyclohexen-1-yl]methoxy]pyridine-2-carbaldehyde |
| 382 | 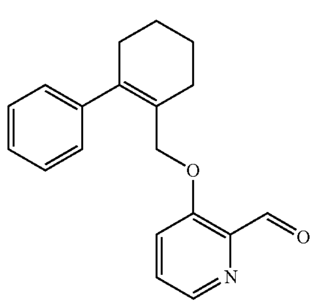 [SMILES: O=Cc1ncccc1OCC1=C(c2ccccc2)CCCC1] | 3-[(2-phenylcyclohexen-1-yl)methoxy]pyridine-2-carbaldehyde |

TABLE 1-continued

| Compound | Structure | Name |
|---|---|---|
| 383 | 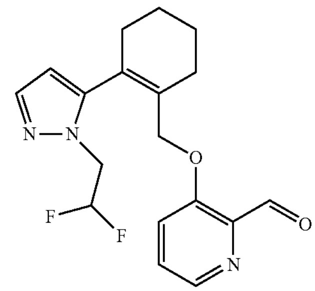 [SMILES: O=Cc1ncccc1OCC1=C(c2ccnn2CC(F)F)CCCC1] | 3-[[2-[2-(2,2-difluoroethyl)pyrazol-3-yl]cyclohexen-1-yl]methoxy]pyridine-2-carbaldehyde |
| 384 | 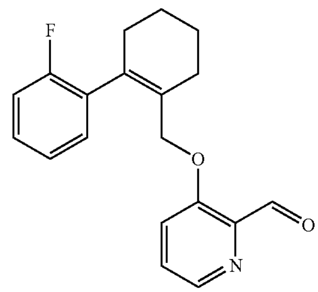 [SMILES: O=Cc1ncccc1OCC1=C(c2ccccc2F)CCCC1] | 3-[[2-(2-fluorophenyl)cyclohexen-1-yl]methoxy]pyridine-2-carbaldehyde |
| 385 | 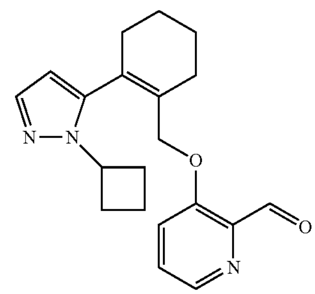 [SMILES: O=Cc1ncccc1OCC1=C(c2ccnn2C2CCC2)CCCC1] | 3-[[2-(2-cyclobutylpyrazol-3-yl)cyclohexen-1-yl]methoxy]pyridine-2-carbaldehyde |
| 386 | 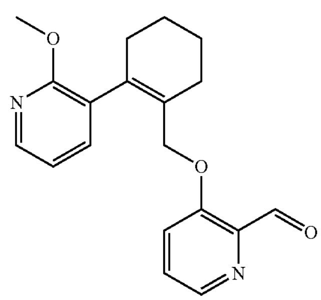 [SMILES: COc1ncccc1C1=C(COc2cccnc2C=O)CCCC1] | 3-[[2-(2-methoxypyridin-3-yl)cyclohexen-1-yl]methoxy]pyridine-2-carbaldehyde |
| 387 | 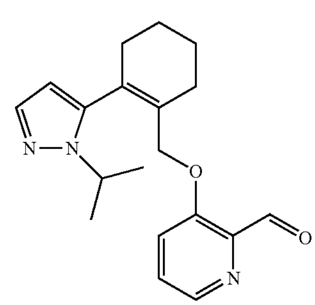 [SMILES: CC(C)n1nccc1C1=C(COc2cccnc2C=O)CCCC1] | 3-[[2-(2-propan-2-ylpyrazol-3-yl)cyclohexen-1-yl]methoxy]pyridine-2-carbaldehyde |

TABLE 1-continued

| Compound | Structure | Name |
|---|---|---|
| 388 | 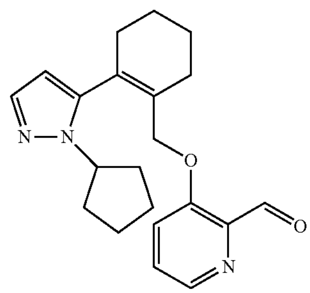 [SMILES: O=Cc1ncccc1OCC1=C(c2ccnn2C2CCCC2)CCCC1] | 3-[[2-(2-cyclopentylpyrazol-3-yl)cyclohexen-1-yl]methoxy]pyridine-2-carbaldehyde |
| 389 | 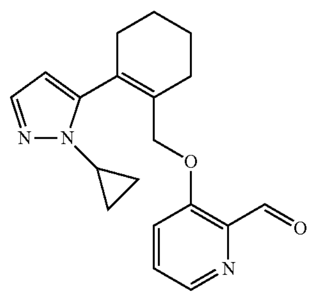 [SMILES: O=Cc1ncccc1OCC1=C(c2ccnn2C2CC2)CCCC1] | 3-[[2-(2-cyclopropylpyrazol-3-yl)cyclohexen-1-yl]methoxy]pyridine-2-carbaldehyde |
| 390 | 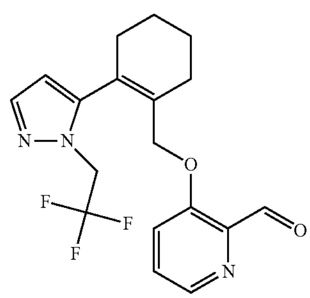 [SMILES: O=Cc1ncccc1OCC1=C(c2ccnn2CC(F)(F)F)CCCC1] | 3-[[2-[2-(2,2,2-trifluoroethyl)pyrazol-3-yl]cyclohexen-1-yl]methoxy]pyridine-2-carbaldehyde |
| 391 | 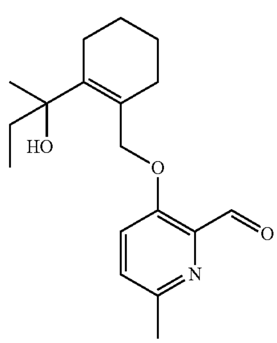 [SMILES: CCC(C)(O)C1=C(COc2ccc(C)nc2C=O)CCCC1] | 3-[[2-(2-hydroxybutan-2-yl)cyclohexen-1-yl]methoxy]-6-methylpyridine-2-carbaldehyde |
| 392 | 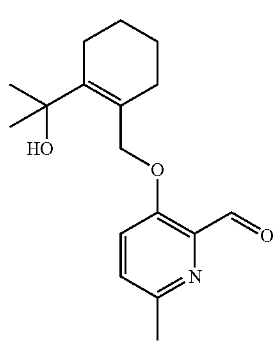 [SMILES: Cc1ccc(OCC2=C(C(C)(C)O)CCCC2)c(C=O)n1] | 3-[[2-(2-hydroxypropan-2-yl)cyclohexen-1-yl]methoxy]-6-methylpyridine-2-carbaldehyde |

TABLE 1-continued

| Compound | Structure | Name |
| --- | --- | --- |
| 393 | 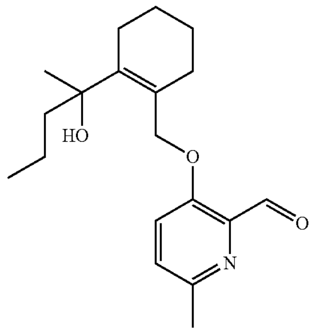 [SMILES: CCCC(C)(O)C1=C(COc2ccc(C)nc2C=O)CCCC1] | 3-[[2-(2-hydroxypentan-2-yl)cyclohexen-1-yl]methoxy]-6-methylpyridine-2-carbaldehyde |
| 394 | 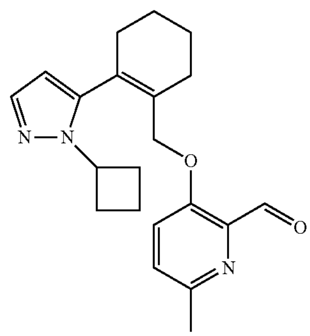 | 3-[[2-(2-cyclobutylpyrazol-3-yl)cyclohexen-1-yl]methoxy]-6-methylpyridine-2-carbaldehyde |
| 395 | 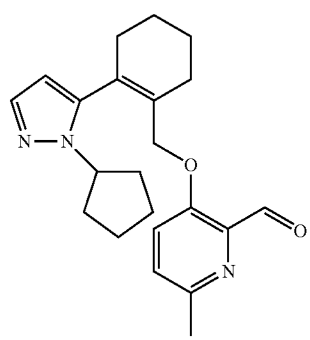 [SMILES: Cc1ccc(OCC2=C(c3ccnn3C3CCCC3)CCCC2)c(C=O)n1] | 3-[[2-(2-cyclopentylpyrazol-3-yl)cyclohexen-1-yl]methoxy]-6-methylpyridine-2-carbaldehyde |
| 396 | 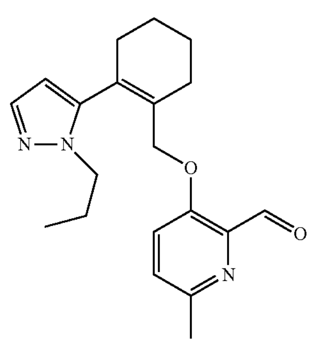 [SMILES: CCCn1nccc1C1=C(COc2ccc(C)nc2C=O)CCCC1] | 6-methyl-3-[[2-(2-propylpyrazol-3-yl)cyclohexen-1-yl]methoxy]pyridine-2-carbaldehyde |

TABLE 1-continued

| Compound | Structure | Name |
| --- | --- | --- |
| 397 | 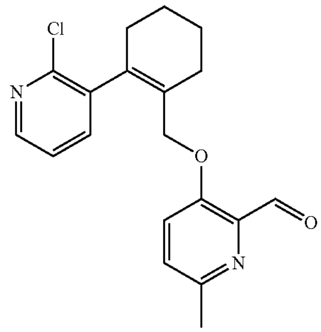 [SMILES: Cc1ccc(OCC2=C(c3cccnc3Cl)CCCC2)c(C=O)n1] | 3-[[2-(2-chloropyridin-3-yl)cyclohexen-1-yl]methoxy]-6-methylpyridine-2-carbaldehyde |
| 398 | 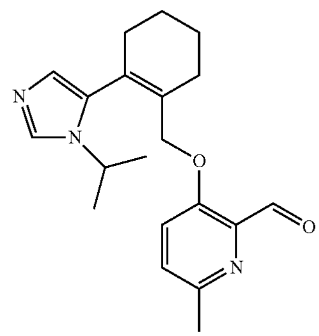 [SMILES: Cc1ccc(OCC2=C(c3cncn3C(C)C)CCCC2)c(C=O)n1] | 6-methyl-3-[[2-(3-propan-2-ylimidazol-4-yl)cyclohexen-1-yl]methoxy]pyridine-2-carbaldehyde |
| 399 | 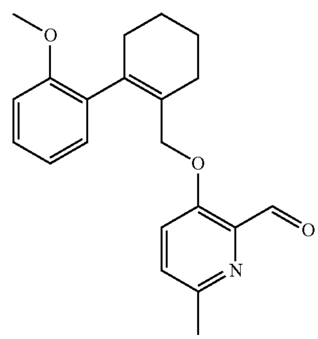 [SMILES: COc1ccccc1C1=C(COc2ccc(C)nc2C=O)CCCC1] | 3-[[2-(2-methoxyphenyl)cyclohexen-1-yl]methoxy]-6-methylpyridine-2-carbaldehyde |
| 400 | 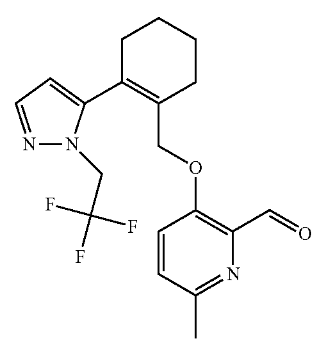 [SMILES: Cc1ccc(OCC2=C(c3ccnn3CC(F)(F)F)CCCC2)c(C=O)n1] | 6-methyl-3-[[2-[2-(2,2,2-trifluoroethyl)pyrazol-3-yl]cyclohexen-1-yl]methoxy]pyridine-2-carbaldehyde |

TABLE 1-continued

| Compound | Structure | Name |
|---|---|---|
| 401 | 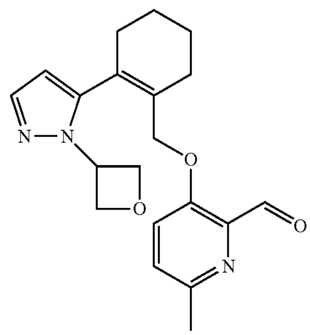 [SMILES: Cc1ccc(OCC2=C(c3ccnn3C3COC3)CCCC2)c(C=O)n1] | 6-methyl-3-[[2-[2-(oxetan-3-yl)pyrazol-3-yl]cyclohexen-1-yl]methoxy]pyridine-2-carbaldehyde |
| 402 | 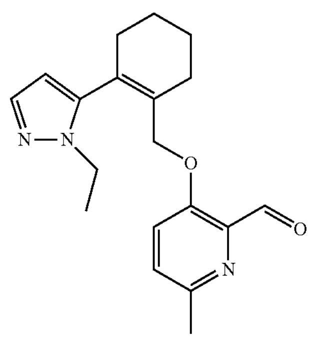 [SMILES: CCn1nccc1C1=C(COc2ccc(C)nc2C=O)CCCC1] | 3-[[2-(2-ethylpyrazol-3-yl)cyclohexen-1-yl]methoxy]-6-methylpyridine-2-carbaldehyde |
| 403 | 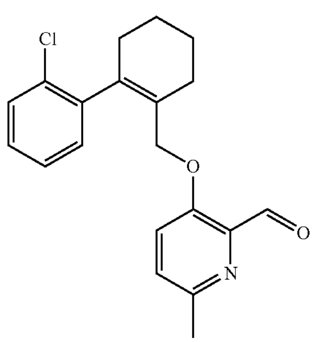 [SMILES: Cc1ccc(OCC2=C(c3ccccc3Cl)CCCC2)c(C=O)n1] | 3-[[2-(2-chlorophenyl)cyclohexen-1-yl]methoxy]-6-methylpyridine-2-carbaldehyde |
| 404 | 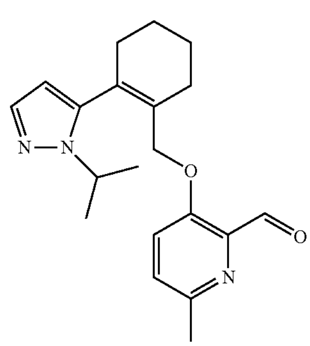 [SMILES: Cc1ccc(OCC2=C(c3ccnn3C(C)C)CCCC2)c(C=O)n1] | 6-methyl-3-[[2-(2-propan-2-ylpyrazol-3-yl)cyclohexen-1-yl]methoxy]pyridine-2-carbaldehyde |

TABLE 1-continued

| Compound | Structure | Name |
|---|---|---|
| 405 | 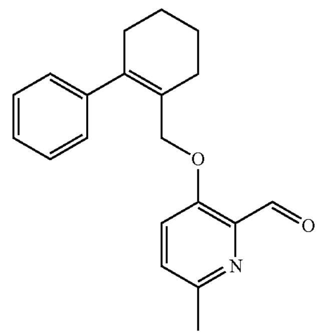 [SMILES: Cc1ccc(OCC2=C(c3ccccc3)CCCC2)c(C=O)n1] | 6-methyl-3-[(2-phenylcyclohexen-1-yl)methoxy]pyridine-2-carbaldehyde |
| 406 | 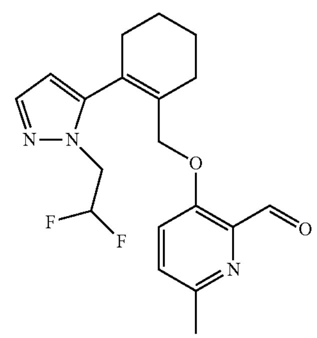 [SMILES: Cc1ccc(OCC2=C(c3ccnn3CC(F)F)CCCC2)c(C=O)n1] | 3-[[2-[2-(2,2-difluoroethyl)pyrazol-3-yl]cyclohexen-1-yl]methoxy]-6-methylpyridine-2-carbaldehyde |
| 407 | 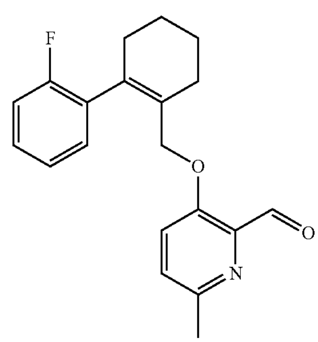 [SMILES: Cc1ccc(OCC2=C(c3ccccc3F)CCCC2)c(C=O)n1] | 3-[[2-(2-fluorophenyl)cyclohexen-1-yl]methoxy]-6-methylpyridine-2-carbaldehyde |
| 408 | 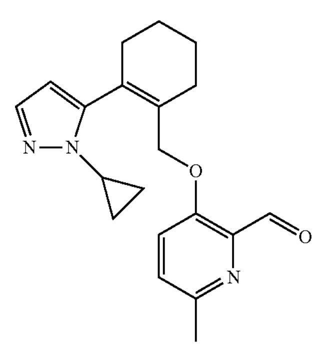 [SMILES: Cc1ccc(OCC2=C(c3ccnn3C3CC3)CCCC2)c(C=O)n1] | 3-[[2-(2-cyclopropylpyrazol-3-yl)cyclohexen-1-yl]methoxy]-6-methylpyridine-2-carbaldehyde |

TABLE 1-continued

| Compound | Structure | Name |
|---|---|---|
| 409 | 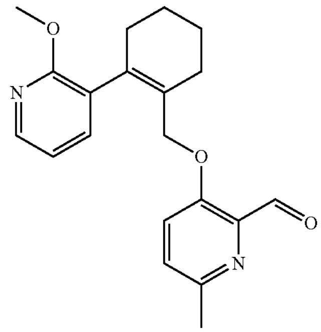 [SMILES: COc1ncccc1C1=C(COc2ccc(C)nc2C=O)CCCC1] | 3-[[2-(2-methoxypyridin-3-yl)cyclohexen-1-yl]methoxy]-6-methylpyridine-2-carbaldehyde |
| 410 | 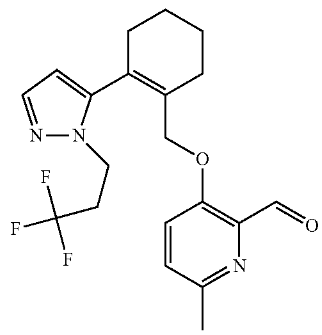 [SMILES: Cc1ccc(OCC2=C(c3ccnn3CCC(F)(F)F)CCCC2)c(C=O)n1] | 6-methyl-3-[[2-[2-(3,3,3-trifluoropropyl)pyrazol-3-yl]cyclohexen-1-yl]methoxy]pyridine-2-carbaldehyde |
| 411 | 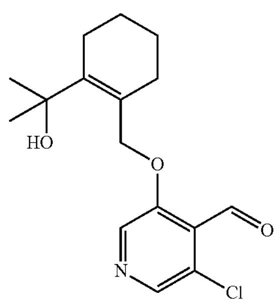 | 3-chloro-5-[[2-(2-hydroxypropan-2-yl)cyclohexen-1-yl]methoxy]pyridine-4-carbaldehyde |
| 412 | 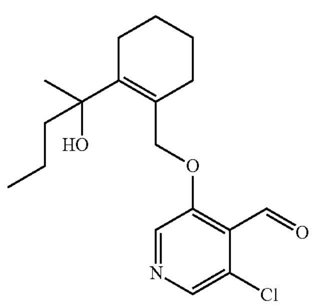 [SMILES: CCCC(C)(O)C1=C(COc2cncc(Cl)c2C=O)CCCC1] | 3-chloro-5-[[2-(2-hydroxypentan-2-yl)cyclohexen-1-yl]methoxy]pyridine-4-carbaldehyde |
| 413 | 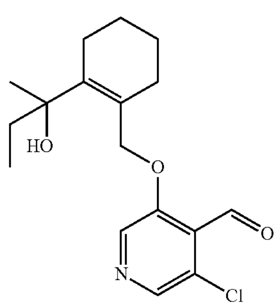 [SMILES: CCC(C)(O)C1=C(COc2cncc(Cl)c2C=O)CCCC1] | 3-chloro-5-[[2-(2-hydroxybutan-2-yl)cyclohexen-1-yl]methoxy]pyridine-4-carbaldehyde |

TABLE 1-continued

| Compound | Structure | Name |
| --- | --- | --- |
| 414 | 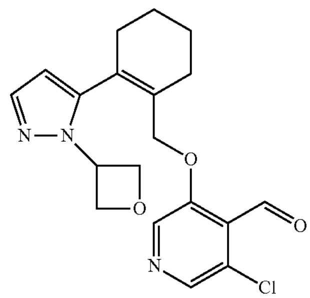 [SMILES: O=Cc1c(Cl)cncc1OCC1=C(c2ccnn2C2COC2)CCCC1] | 3-chloro-5-[[2-[2-(oxetan-3-yl)pyrazol-3-yl]cyclohexen-1-yl]methoxy]pyridine-4-carbaldehyde |
| 415 | 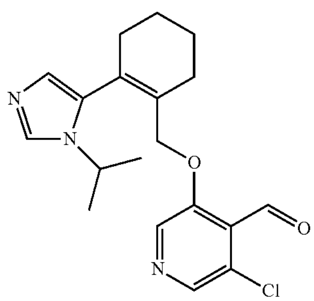 [SMILES: CC(C)n1cncc1C1=C(COc2cncc(Cl)c2C=O)CCCC1] | 3-chloro-5-[[2-(3-propan-2-ylimidazol-4-yl)cyclohexen-1-yl]methoxy]pyridine-4-carbaldehyde |
| 416 | 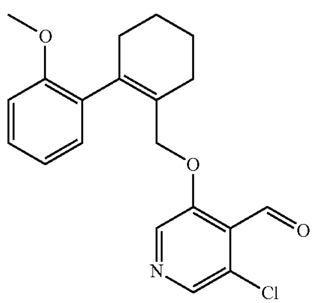 [SMILES: COc1ccccc1C1=C(COc2cncc(Cl)c2C=O)CCCC1] | 3-chloro-5-[[2-(2-methoxyphenyl)cyclohexen-1-yl]methoxy]pyridine-4-carbaldehyde |
| 417 | 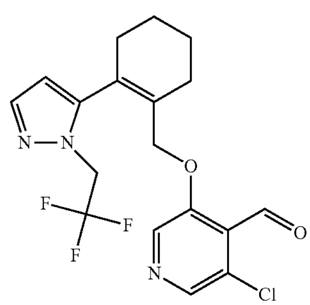 [SMILES: O=Cc1c(Cl)cncc1OCC1=C(c2ccnn2CC(F)(F)F)CCCC1] | 3-chloro-5-[[2-[2-(2,2,2-trifluoroethyl)pyrazol-3-yl]cyclohexen-1-yl]methoxy]pyridine-4-carbaldehyde |
| 418 | 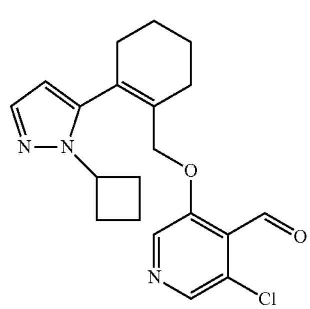 [SMILES: O=Cc1c(Cl)cncc1OCC1=C(c2ccnn2C2CCC2)CCCC1] | 3-chloro-5-[[2-(2-cyclobutylpyrazol-3-yl)cyclohexen-1-yl]methoxy]pyridine-4-carbaldehyde |

TABLE 1-continued

| Compound | Structure | Name |
|---|---|---|
| 419 | 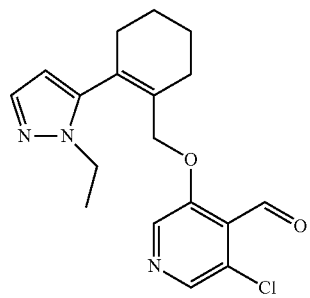 [SMILES: CCn1nccc1C1=C(COc2cncc(Cl)c2C=O)CCCC1] | 3-chloro-5-[[2-(2-ethylpyrazol-3-yl)cyclohexen-1-yl]methoxy]pyridine-4-carbaldehyde |
| 420 | 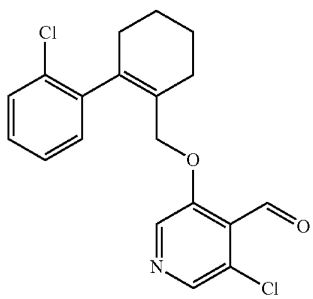 | 3-chloro-5-[[2-(2-chlorophenyl)cyclohexen-1-yl]methoxy]pyridine-4-carbaldehyde |
| 421 | 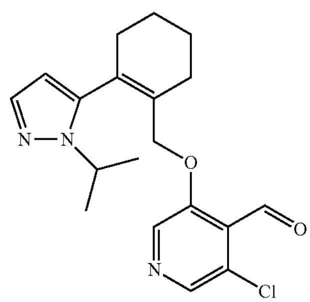 [SMILES: CC(C)n1nccc1C1=C(COc2cncc(Cl)c2C=O)CCCC1] | 3-chloro-5-[[2-(2-propan-2-ylpyrazol-3-yl)cyclohexen-1-yl]methoxy]pyridine-4-carbaldehyde |
| 422 | 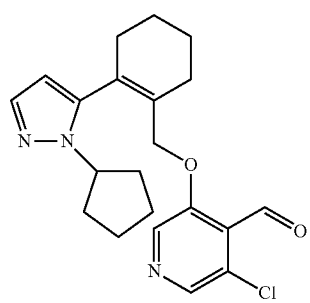 [SMILES: O=Cc1c(Cl)cncc1OCC1=C(c2ccnn2C2CCCC2)CCCC1] | 3-chloro-5-[[2-(2-cyclopentylpyrazol-3-yl)cyclohexen-1-yl]methoxy]pyridine-4-carbaldehyde |
| 423 | 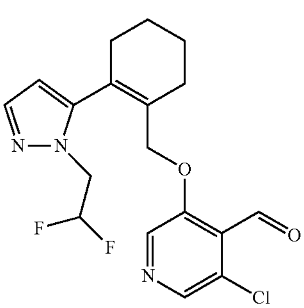 [SMILES: O=Cc1c(Cl)cncc1OCC1=C(c2ccnn2CC(F)F)CCCC1] | 3-chloro-5-[[2-[2-(2,2-difluoroethyl)pyrazol-3-yl]cyclohexen-1-yl]methoxy]pyridine-4-carbaldehyde |

TABLE 1-continued

| Compound | Structure | Name |
|---|---|---|
| 424 | 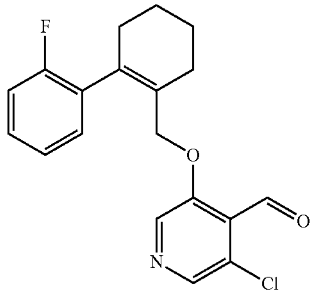 [SMILES: O=Cc1c(Cl)cncc1OCC1=C(c2ccccc2F)CCCC1] | 3-chloro-5-[[2-(2-fluorophenyl)cyclohexen-1-yl]methoxy]pyridine-4-carbaldehyde |
| 425 | 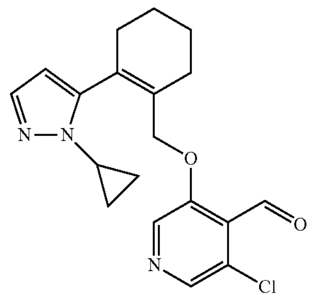 [SMILES: O=Cc1c(Cl)cncc1OCC1=C(c2ccnn2C2CC2)CCCC1] | 3-chloro-5-[[2-(2-cyclopropylpyrazol-3-yl)cyclohexen-1-yl]methoxy]pyridine-4-carbaldehyde |
| 426 | 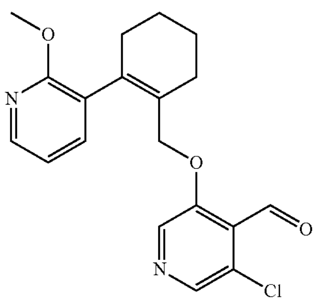 [SMILES: COc1ncccc1C1=C(COc2cncc(Cl)c2C=O)CCCC1] | 3-chloro-5-[[2-(2-methoxypyridin-3-yl)cyclohexen-1-yl]methoxy]pyridine-4-carbaldehyde |
| 427 | 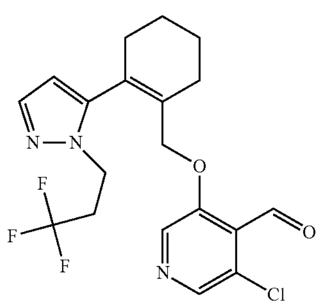 [SMILES: O=Cc1c(Cl)cncc1OCC1=C(c2ccnn2CCC(F)(F)F)CCCC1] | 3-chloro-5-[[2-[2-(3,3,3-trifluoropropyl)pyrazol-3-yl]cyclohexen-1-yl]methoxy]pyridine-4-carbaldehyde |
| 428 | 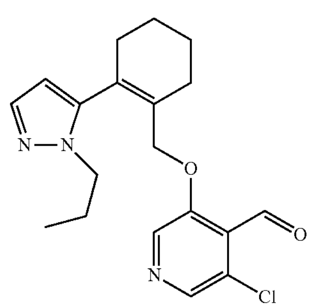 [SMILES: CCCn1nccc1C1=C(COc2cncc(Cl)c2C=O)CCCC1] | 3-chloro-5-[[2-(2-propylpyrazol-3-yl)cyclohexen-1-yl]methoxy]pyridine-4-carbaldehyde |

TABLE 1-continued

| Compound | Structure | Name |
|---|---|---|
| 429 | 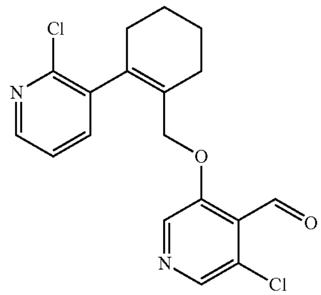 [SMILES: O=Cc1c(Cl)cncc1OCC1=C(c2cccnc2Cl)CCCC1] | 3-chloro-5-[[2-(2-chloropyridin-3-yl)cyclohexen-1-yl]methoxy]pyridine-4-carbaldehyde |
| 430 | 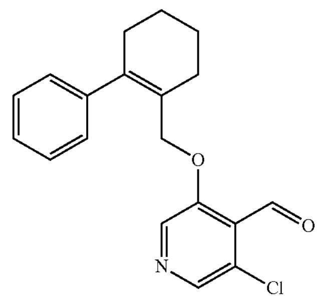 [SMILES: O=Cc1c(Cl)cncc1OCC1=C(c2ccccc2)CCCC1] | 3-chloro-5-[(2-phenylcyclohexen-1-yl)methoxy]pyridine-4-carbaldehyde |
| 431 | 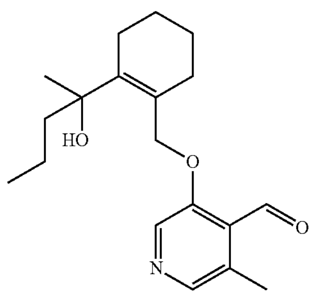 [SMILES: CCCC(C)(O)C1=C(COc2cncc(C)c2C=O)CCCC1] | 3-[[2-(2-hydroxypentan-2-yl)cyclohexen-1-yl]methoxy]-5-methylpyridine-4-carbaldehyde |
| 432 | 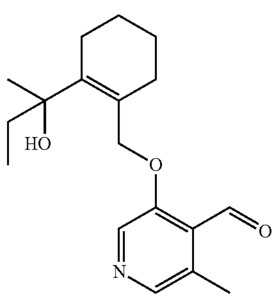 [SMILES: CCC(C)(O)C1=C(COc2cncc(C)c2C=O)CCCC1] | 3-[[2-(2-hydroxybutan-2-yl)cyclohexen-1-yl]methoxy]-5-methylpyridine-4-carbaldehyde |
| 433 | 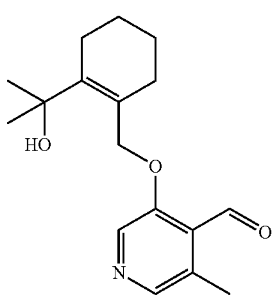 [SMILES: Cc1cncc(OCC2=C(C(C)(C)O)CCCC2)c1C=O] | 3-[[2-(2-hydroxypropan-2-yl)cyclohexen-1-yl]methoxy]-5-methylpyridine-4-carbaldehyde |

TABLE 1-continued

| Compound | Structure | Name |
|---|---|---|
| 434 | 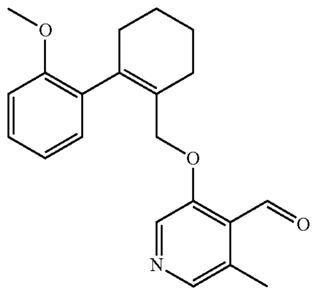 [SMILES: COc1ccccc1C1=C(COc2cncc(C)c2C=O)CCCC1] | 3-[[2-(2-methoxyphenyl)cyclohexen-1-yl]methoxy]-5-methylpyridine-4-carbaldehyde |
| 435 | 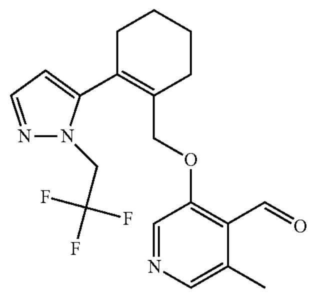 [SMILES: Cc1cncc(OCC2=C(c3ccnn3CC(F)(F)F)CCCC2)c1C=O] | 3-methyl-5-[[2-[2-(2,2,2-trifluoroethyl)pyrazol-3-yl]cyclohexen-1-yl]methoxy]pyridine-4-carbaldehyde |
| 436 | 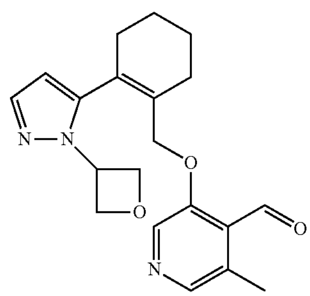 [SMILES: Cc1cncc(OCC2=C(c3ccnn3C3COC3)CCCC2)c1C=O] | 3-methyl-5-[[2-[2-(oxetan-3-yl)pyrazol-3-yl]cyclohexen-1-yl]methoxy]pyridine-4-carbaldehyde |
| 437 | 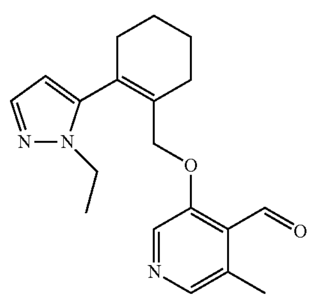 [SMILES: CCn1nccc1C1=C(COc2cncc(C)c2C=O)CCCC1] | 3-[[2-(2-ethylpyrazol-3-yl)cyclohexen-1-yl]methoxy]-5-methylpyridine-4-carbaldehyde |
| 438 | 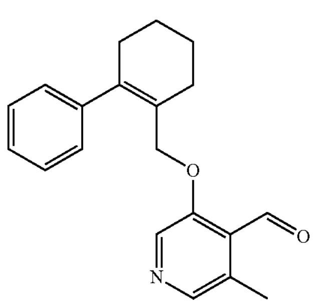 [SMILES: Cc1cncc(OCC2=C(c3ccccc3)CCCC2)c1C=O] | 3-methyl-5-[(2-phenylcyclohexen-1-yl)methoxy]pyridine-4-carbaldehyde |

TABLE 1-continued

| Compound | Structure | Name |
|---|---|---|
| 439 | 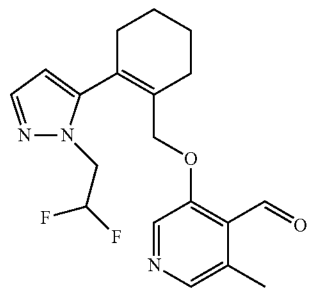 [SMILES: Cc1cncc(OCC2=C(c3ccnn3CC(F)F)CCCC2)c1C=O] | 3-[[2-[2-(2,2-difluoroethyl)pyrazol-3-yl]cyclohexen-1-yl]methoxy]-5-methylpyridine-4-carbaldehyde |
| 440 | 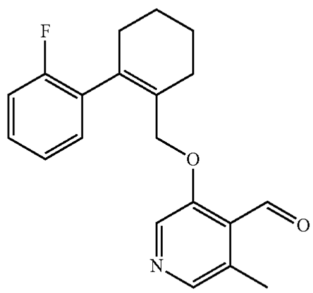 [SMILES: Cc1cncc(OCC2=C(c3ccccc3F)CCCC2)c1C=O] | 3-[[2-(2-fluorophenyl)cyclohexen-1-yl]methoxy]-5-methylpyridine-4-carbaldehyde |
| 441 | 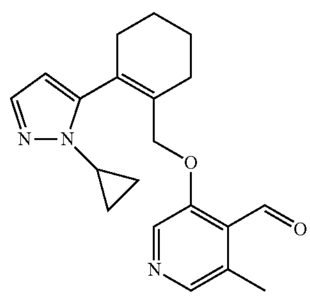 [SMILES: Cc1cncc(OCC2=C(c3ccnn3C3CC3)CCCC2)c1C=O] | 3-[[2-(2-cyclopropylpyrazol-3-yl)cyclohexen-1-yl]methoxy]-5-methylpyridine-4-carbaldehyde |
| 442 | 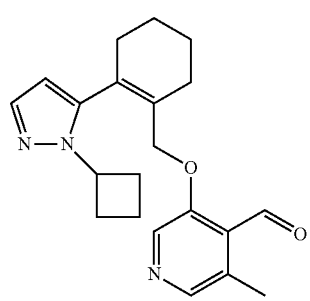 [SMILES: Cc1cncc(OCC2=C(c3ccnn3C3CCC3)CCCC2)c1C=O] | 3-[[2-(2-cyclobutylpyrazol-3-yl)cyclohexen-1-yl]methoxy]-5-methylpyridine-4-carbaldehyde |
| 443 | 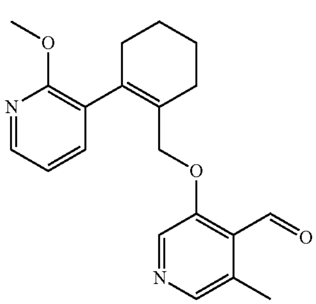 [SMILES: COc1ncccc1C1=C(COc2cncc(C)c2C=O)CCCC1] | 3-[[2-(2-methoxypyridin-3-yl)cyclohexen-1-yl]methoxy]-5-methylpyridine-4-carbaldehyde |

TABLE 1-continued

| Compound | Structure | Name |
|---|---|---|
| 444 | 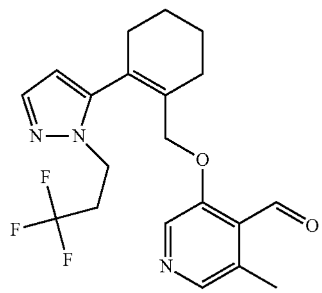 [SMILES: Cc1cncc(OCC2=C(c3ccnn3CCC(F)(F)F)CCCC2)c1C=O] | 3-methyl-5-[[2-[2-(3,3,3-trifluoropropyl)pyrazol-3-yl]cyclohexen-1-yl]methoxy]pyridine-4-carbaldehyde |
| 445 | 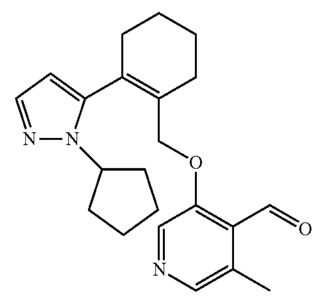 [SMILES: Cc1cncc(OCC2=C(c3ccnn3C3CCCC3)CCCC2)c1C=O] | 3-[[2-(2-cyclopentylpyrazol-3-yl)cyclohexen-1-yl]methoxy]-5-methylpyridine-4-carbaldehyde |
| 446 | 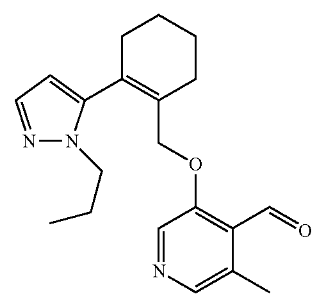 [SMILES: CCCn1nccc1C1=C(COc2cncc(C)c2C=O)CCCC1] | 3-methyl-5-[[2-(2-propylpyrazol-3-yl)cyclohexen-1-yl]methoxy]pyridine-4-carbaldehyde |
| 447 | 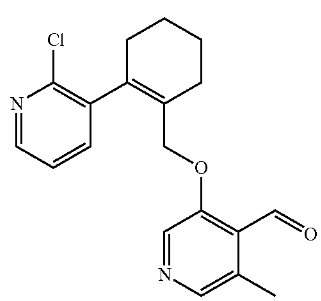 [SMILES: Cc1cncc(OCC2=C(c3cccnc3Cl)CCCC2)c1C=O] | 3-[[2-(2-chloropyridin-3-yl)cyclohexen-1-yl]methoxy]-5-methylpyridine-4-carbaldehyde |
| 448 | 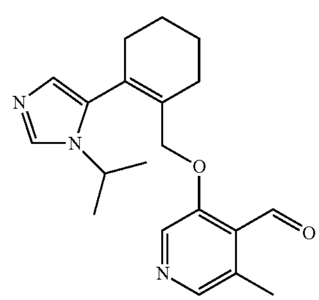 [SMILES: Cc1cncc(OCC2=C(c3cncn3C(C)C)CCCC2)c1C=O] | 3-methyl-5-[[2-(3-propan-2-ylimidazol-4-yl)cyclohexen-1-yl]methoxy]pyridine-4-carbaldehyde |

TABLE 1-continued

| Compound | Structure | Name |
|---|---|---|
| 449 | 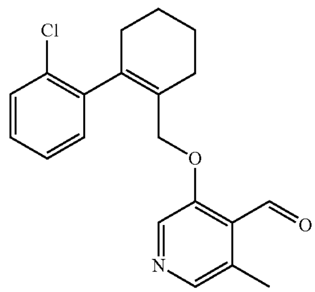 [SMILES: Cc1cncc(OCC2=C(c3ccccc3Cl)CCCC2)c1C=O] | 3-[[2-(2-chlorophenyl)cyclohexen-1-yl]methoxy]-5-methylpyridine-4-carbaldehyde |
| 450 | 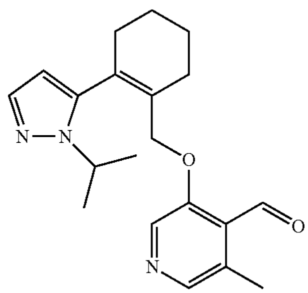 [SMILES: Cc1cncc(OCC2=C(c3ccnn3C(C)C)CCCC2)c1C=O] | 3-methyl-5-[[2-(2-propan-2-ylpyrazol-3-yl)cyclohexen-1-yl]methoxy]pyridine-4-carbaldehyde |
| 451 | 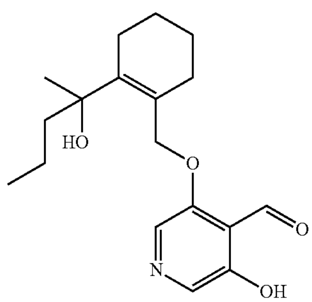 | 3-hydroxy-5-[[2-(2-hydroxypentan-2-yl)cyclohexen-1-yl]methoxy]pyridine-4-carbaldehyde |
| 452 | 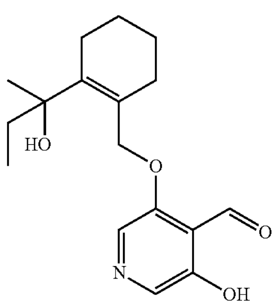 | 3-hydroxy-5-[[2-(2-hydroxybutan-2-yl)cyclohexen-1-yl]methoxy]pyridine-4-carbaldehyde |
| 453 | 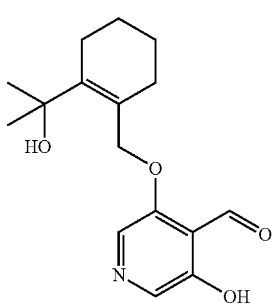 | 3-hydroxy-5-[[2-(2-hydroxypropan-2-yl)cyclohexen-1-yl]methoxy]pyridine-4-carbaldehyde |

TABLE 1-continued

| Compound | Structure | Name |
|---|---|---|
| 454 | 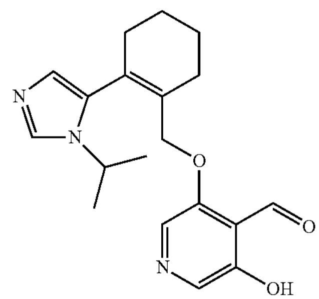 [SMILES: CC(C)n1cncc1C1=C(COc2cncc(O)c2C=O)CCCC1] | 3-hydroxy-5-[[2-(3-propan-2-ylimidazol-4-yl)cyclohexen-1-yl]methoxy]pyridine-4-carbaldehyde |
| 455 | 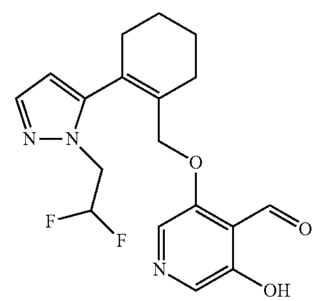 [SMILES: O=Cc1c(O)cncc1OCC1=C(c2ccnn2CC(F)F)CCCC1] | 3-[[2-[2-(2,2-difluoroethyl)pyrazol-3-yl]cyclohexen-1-yl]methoxy]-5-hydroxypyridine-4-carbaldehyde |
| 456 | 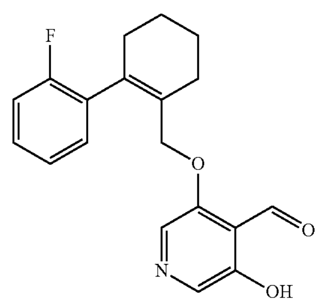 [SMILES: O=Cc1c(O)cncc1OCC1=C(c2ccccc2F)CCCC1] | 3-[[2-(2-fluorophenyl)cyclohexen-1-yl]methoxy]-5-hydroxypyridine-4-carbaldehyde |
| 457 | 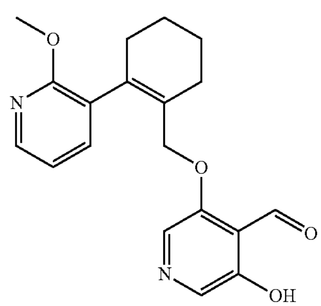 [SMILES: COc1ncccc1C1=C(COc2cncc(O)c2C=O)CCCC1] | 3-hydroxy-5-[[2-(2-methoxypyridin-3-yl)cyclohexen-1-yl]methoxy]pyridine-4-carbaldehyde |
| 458 | 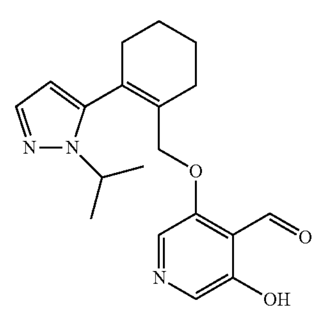 [SMILES: CC(C)n1nccc1C1=C(COc2cncc(O)c2C=O)CCCC1] | 3-hydroxy-5-[[2-(2-propan-2-ylpyrazol-3-yl)cyclohexen-1-yl]methoxy]pyridine-4-carbaldehyde |

TABLE 1-continued

| Compound | Structure | Name |
|---|---|---|
| 459 | 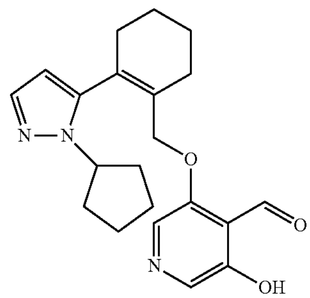 [SMILES: O=Cc1c(O)cncc1OCC1=C(c2ccnn2C2CCCC2)CCCC1] | 3-[[2-(2-cyclopentylpyrazol-3-yl)cyclohexen-1-yl]methoxy]-5-hydroxypyridine-4-carbaldehyde |
| 460 | 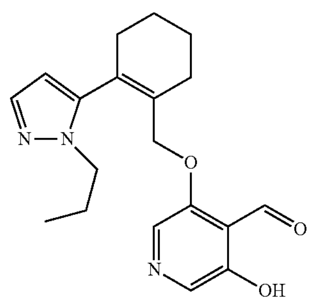 [SMILES: CCCn1nccc1C1=C(COc2cncc(O)c2C=O)CCCC1] | 3-hydroxy-5-[[2-(2-propylpyrazol-3-yl)cyclohexen-1-yl]methoxy]pyridine-4-carbaldehyde |
| 461 | 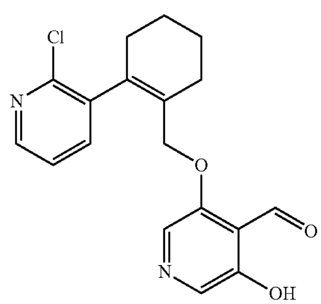 [SMILES: O=Cc1c(O)cncc1OCC1=C(c2cccnc2Cl)CCCC1] | 3-[[2-(2-chloropyridin-3-yl)cyclohexen-1-yl]methoxy]-5-hydroxypyridine-4-carbaldehyde |
| 462 | 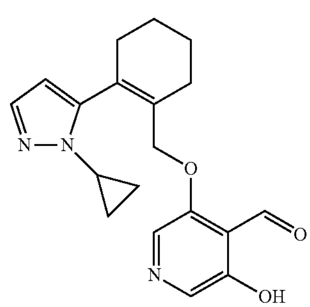 [SMILES: O=Cc1c(O)cncc1OCC1=C(c2ccnn2C2CC2)CCCC1] | 3-[[2-(2-cyclopropylpyrazol-3-yl)cyclohexen-1-yl]methoxy]-5-hydroxypyridine-4-carbaldehyde |
| 463 | 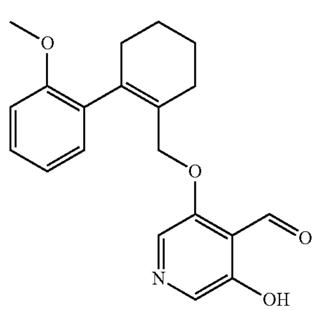 [SMILES: COc1ccccc1C1=C(COc2cncc(O)c2C=O)CCCC1] | 3-hydroxy-5-[[2-(2-methoxyphenyl)cyclohexen-1-yl]methoxy]pyridine-4-carbaldehyde |

TABLE 1-continued

| Compound | Structure | Name |
|---|---|---|
| 464 | 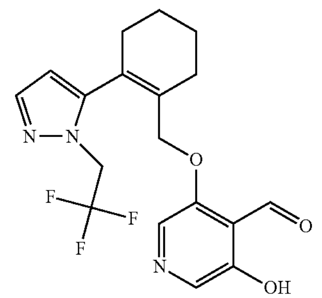 | 3-hydroxy-5-[[2-[2-(2,2,2-trifluoroethyl)pyrazol-3-yl]cyclohexen-1-yl]methoxy]pyridine-4-carbaldehyde |
| 465 | 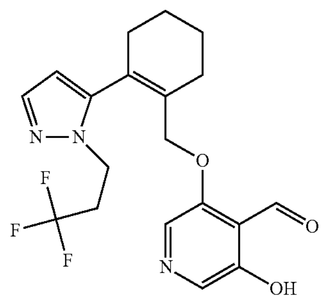 [SMILES: O=Cc1c(O)cncc1OCC1=C(c2ccnn2CCC(F)(F)F)CCCC1] | 3-hydroxy-5-[[2-[2-(3,3,3-trifluoropropyl)pyrazol-3-yl]cyclohexen-1-yl]methoxy]pyridine-4-carbaldehyde |
| 466 | 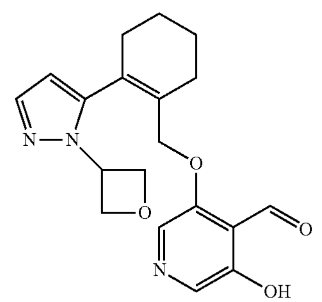 [SMILES: O=Cc1c(O)cncc1OCC1=C(c2ccnn2C2COC2)CCCC1] | 3-hydroxy-5-[[2-[2-(oxetan-3-yl)pyrazol-3-yl]cyclohexen-1-yl]methoxy]pyridine-4-carbaldehyde |
| 467 | 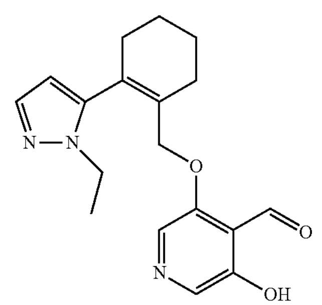 [SMILES: CCn1nccc1C1=C(COc2cncc(O)c2C=O)CCCC1] | 3-[[2-(2-ethylpyrazol-3-yl)cyclohexen-1-yl]methoxy]-5-hydroxypyridine-4-carbaldehyde |
| 468 | 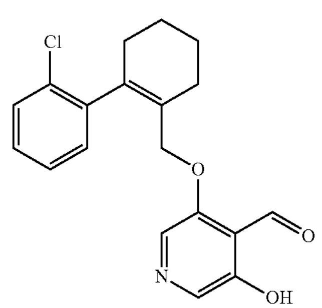 [SMILES: O=Cc1c(O)cncc1OCC1=C(c2ccccc2Cl)CCCC1] | 3-[[2-(2-chlorophenyl)cyclohexen-1-yl]methoxy]-5-hydroxypyridine-4-carbaldehyde |

TABLE 1-continued

| Compound | Structure | Name |
|---|---|---|
| 469 | 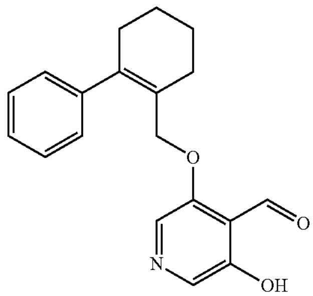 [SMILES: O=Cc1c(O)cncc1OCC1=C(c2ccccc2)CCCC1] | 3-hydroxy-5-[(2-phenylcyclohexen-1-yl)methoxy]pyridine-4-carbaldehyde |
| 470 | 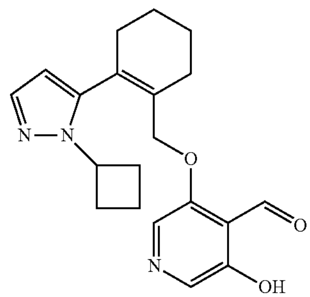 [SMILES: O=Cc1c(O)cncc1OCC1=C(c2ccnn2C2CCC2)CCCC1] | 3-[[2-(2-cyclobutylpyrazol-3-yl)cyclohexen-1-yl]methoxy]-5-hydroxypyridine-4-carbaldehyde |
| 471 | 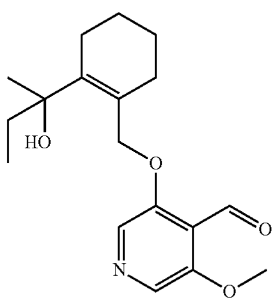 [SMILES: CCC(C)(O)C1=C(COc2cncc(OC)c2C=O)CCCC1] | 3-[[2-(2-hydroxybutan-2-yl)cyclohexen-1-yl]methoxy]-5-methoxypyridine-4-carbaldehyde |
| 472 | 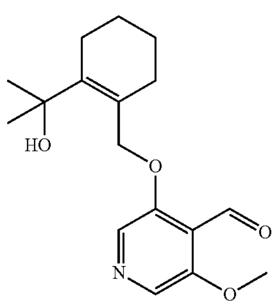 | 3-[[2-(2-hydroxypropan-2-yl)cyclohexen-1-yl]methoxy]-5-methoxypyridine-4-carbaldehyde |
| 473 | 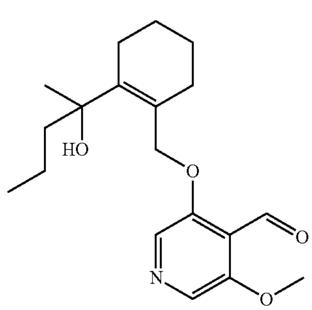 [SMILES: CCCC(C)(O)C1=C(COc2cncc(OC)c2C=O)CCCC1] | 3-[[2-(2-hydroxypentan-2-yl)cyclohexen-1-yl]methoxy]-5-methoxypyridine-4-carbaldehyde |

TABLE 1-continued

| Compound | Structure | Name |
|---|---|---|
| 474 | 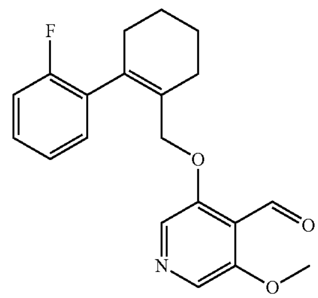 [SMILES: COc1cncc(OCC2=C(c3ccccc3F)CCCC2)c1C=O] | 3-[[2-(2-fluorophenyl)cyclohexen-1-yl]methoxy]-5-methoxypyridine-4-carbaldehyde |
| 475 | 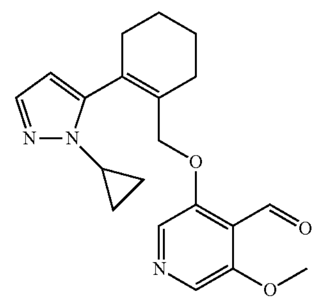 [SMILES: COc1cncc(OCC2=C(c3ccnn3C3CC3)CCCC2)c1C=O] | 3-[[2-(2-cyclopropylpyrazol-3-yl)cyclohexen-1-yl]methoxy]-5-methoxypyridine-4-carbaldehyde |
| 476 | 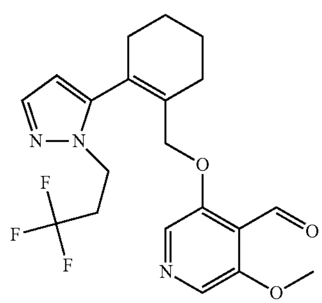 [SMILES: COc1cncc(OCC2=C(c3ccnn3CCC(F)(F)F)CCCC2)c1C=O] | 3-methoxy-5-[[2-[2-(3,3,3-trifluoropropyl)pyrazol-3-yl]cyclohexen-1-yl]methoxy]pyridine-4-carbaldehyde |
| 477 | 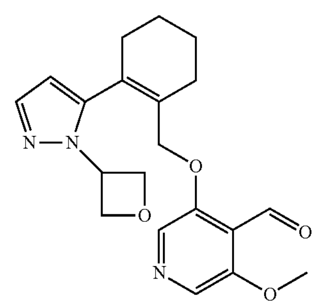 [SMILES: COc1cncc(OCC2=C(c3ccnn3C3COC3)CCCC2)c1C=O] | 3-methoxy-5-[[2-[2-(oxetan-3-yl)pyrazol-3-yl]cyclohexen-1-yl]methoxy]pyridine-4-carbaldehyde |
| 478 | 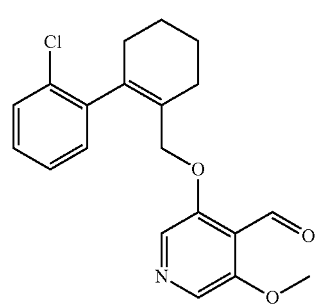 [SMILES: COc1cncc(OCC2=C(c3ccccc3Cl)CCCC2)c1C=O] | 3-[[2-(2-chlorophenyl)cyclohexen-1-yl]methoxy]-5-methoxypyridine-4-carbaldehyde |

TABLE 1-continued

| Compound | Structure | Name |
|---|---|---|
| 479 | 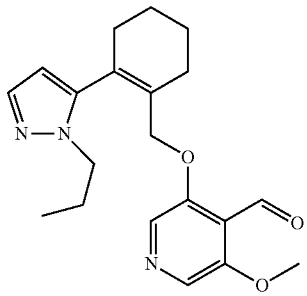 [SMILES: CCCn1nccc1C1=C(COc2cncc(OC)c2C=O)CCCC1] | 3-methoxy-5-[[2-(2-propylpyrazol-3-yl)cyclohexen-1-yl]methoxy]pyridine-4-carbaldehyde |
| 480 | 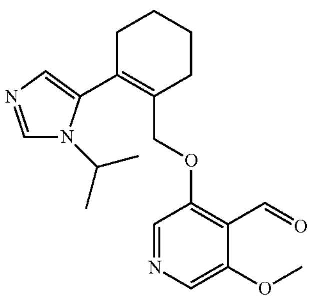 [SMILES: COc1cncc(OCC2=C(c3cncn3C(C)C)CCCC2)c1C=O] | 3-methoxy-5-[[2-(3-propan-2-ylimidazol-4-yl)cyclohexen-1-yl]methoxy]pyridine-4-carbaldehyde |
| 481 | 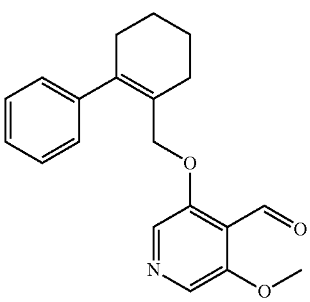 [SMILES: COc1cncc(OCC2=C(c3ccccc3)CCCC2)c1C=O] | 3-methoxy-5-[(2-phenylcyclohexen-1-yl)methoxy]pyridine-4-carbaldehyde |
| 482 | 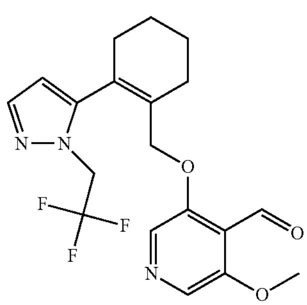 [SMILES: COc1cncc(OCC2=C(c3ccnn3CC(F)(F)F)CCCC2)c1C=O] | 3-methoxy-5-[[2-[2-(2,2,2-trifluoroethyl)pyrazol-3-yl]cyclohexen-1-yl]methoxy]pyridine-4-carbaldehyde |
| 483 | 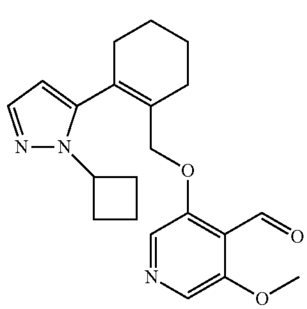 [SMILES: COc1cncc(OCC2=C(c3ccnn3C3CCC3)CCCC2)c1C=O] | 3-[[2-(2-cyclobutylpyrazol-3-yl)cyclohexen-1-yl]methoxy]-5-methoxypyridine-4-carbaldehyde |

TABLE 1-continued

| Compound | Structure | Name |
|---|---|---|
| 484 | 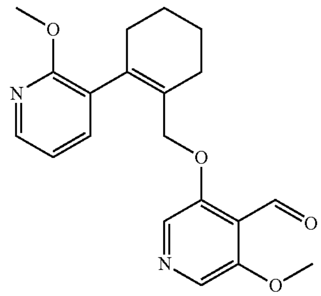 [SMILES: COc1cncc(OCC2=C(c3cccnc3OC)CCCC2)c1C=O] | 3-methoxy-5-[[2-(2-methoxypyridin-3-yl)cyclohexen-1-yl]methoxy]pyridine-4-carbaldehyde |
| 485 | 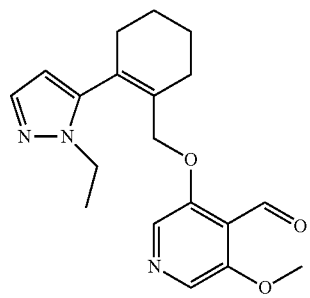 [SMILES: CCn1nccc1C1=C(COc2cncc(OC)c2C=O)CCCC1] | 3-[[2-(2-ethylpyrazol-3-yl)cyclohexen-1-yl]methoxy]-5-methoxypyridine-4-carbaldehyde |
| 486 | 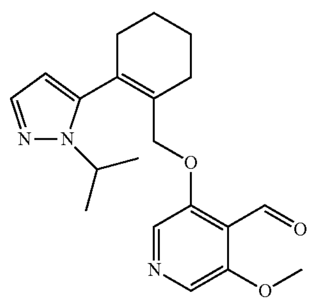 [SMILES: COc1cncc(OCC2=C(c3ccnn3C(C)C)CCCC2)c1C=O] | 3-methoxy-5-[[2-(2-propan-2-ylpyrazol-3-yl)cyclohexen-1-yl]methoxy]pyridine-4-carbaldehyde |
| 487 | 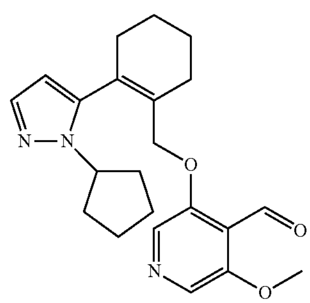 [SMILES: COc1cncc(OCC2=C(c3ccnn3C3CCCC3)CCCC2)c1C=O] | 3-[[2-(2-cyclopentylpyrazol-3-yl)cyclohexen-1-yl]methoxy]-5-methoxypyridine-4-carbaldehyde |
| 488 | 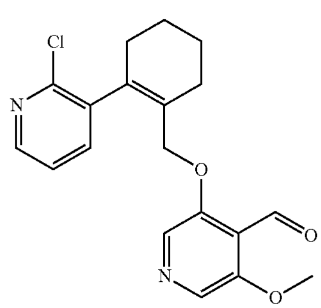 [SMILES: COc1cncc(OCC2=C(c3cccnc3Cl)CCCC2)c1C=O] | 3-[[2-(2-chloropyridin-3-yl)cyclohexen-1-yl]methoxy]-5-methoxypyridine-4-carbaldehyde |

TABLE 1-continued

| Compound | Structure | Name |
|---|---|---|
| 489 | 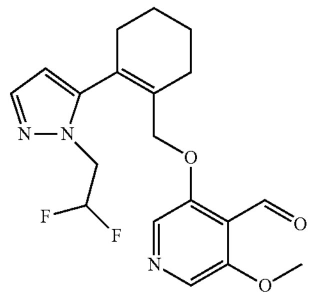 [SMILES: COc1cncc(OCC2=C(c3ccnn3CC(F)F)CCCC2)c1C=O] | 3-[[2-[2-(2,2-difluoroethyl)pyrazol-3-yl]cyclohexen-1-yl]methoxy]-5-methoxypyridine-4-carbaldehyde |
| 490 | 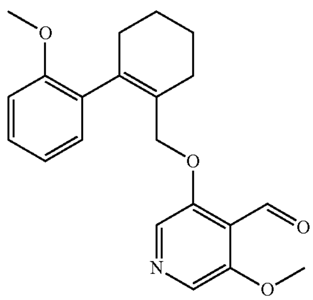 [SMILES: COc1ccccc1C1=C(COc2cncc(OC)c2C=O)CCCC1] | 3-methoxy-5-[[2-(2-methoxyphenyl)cyclohexen-1-yl]methoxy]pyridine-4-carbaldehyde |
| 491 | 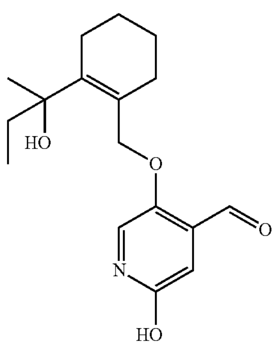 [SMILES: CCC(C)(O)C1=C(COc2cnc(O)cc2C=O)CCCC1] | 2-hydroxy-5-[[2-(2-hydroxybutan-2-yl)cyclohexen-1-yl]methoxy]pyridine-4-carbaldehyde |
| 492 | 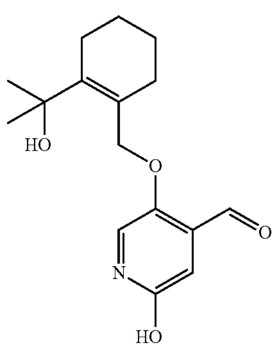 | 2-hydroxy-5-[[2-(2-hydroxypropan-2-yl)cyclohexen-1-yl]methoxy]pyridine-4-carbaldehyde |

TABLE 1-continued

| Compound | Structure | Name |
|---|---|---|
| 493 | 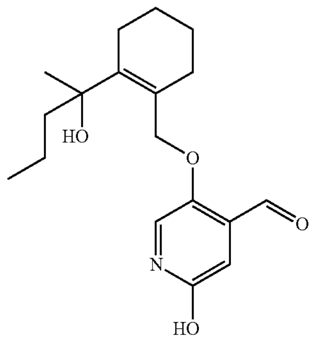 [SMILES: CCCC(C)(O)C1=C(COc2cnc(O)cc2C=O)CCCC1] | 2-hydroxy-5-[[2-(2-hydroxypentan-2-yl)cyclohexen-1-yl]methoxy]pyridine-4-carbaldehyde |
| 494 | 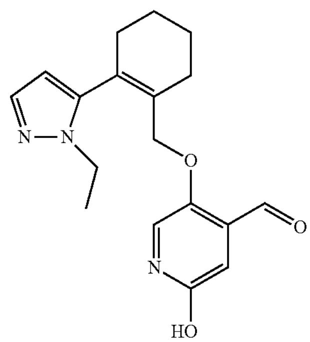 [SMILES: CCn1nccc1C1=C(COc2cnc(O)cc2C=O)CCCC1] | 5-[[2-(2-ethylpyrazol-3-yl)cyclohexen-1-yl]methoxy]-2-hydroxypyridine-4-carbaldehyde |
| 495 | 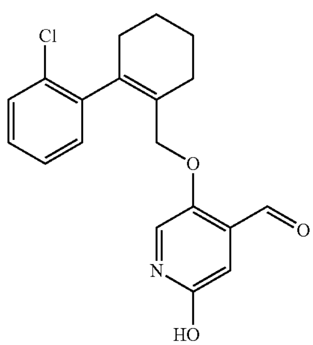 | 5-[[2-(2-chlorophenyl)cyclohexen-1-yl]methoxy]-2-hydroxypyridine-4-carbaldehyde |
| 496 | 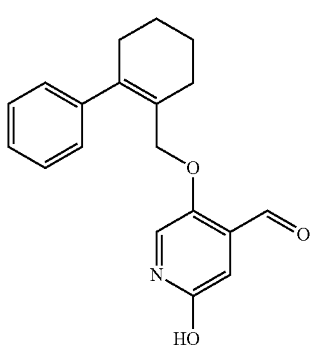 [SMILES: O=Cc1cc(O)ncc1OCC1=C(c2ccccc2)CCCC1] | 2-hydroxy-5-[(2-phenylcyclohexen-1-yl)methoxy]pyridine-4-carbaldehyde |

TABLE 1-continued

| Compound | Structure | Name |
|---|---|---|
| 497 | 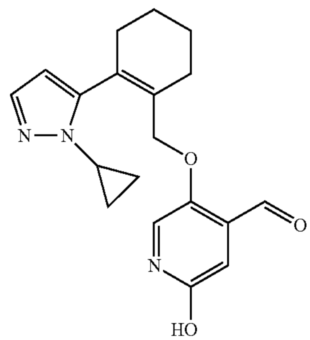 [SMILES: O=Cc1cc(O)ncc1OCC1=C(c2ccnn2C2CC2)CCCC1] | 5-[[2-(2-cyclopropylpyrazol-3-yl)cyclohexen-1-yl]methoxy]-2-hydroxypyridine-4-carbaldehyde |
| 498 | 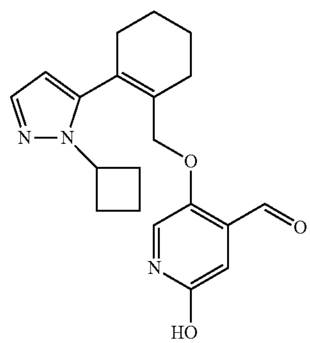 [SMILES: O=Cc1cc(O)ncc1OCC1=C(c2ccnn2C2CCC2)CCCC1] | 5-[[2-(2-cyclobutylpyrazol-3-yl)cyclohexen-1-yl]methoxy]-2-hydroxypyridine-4-carbaldehyde |
| 499 | 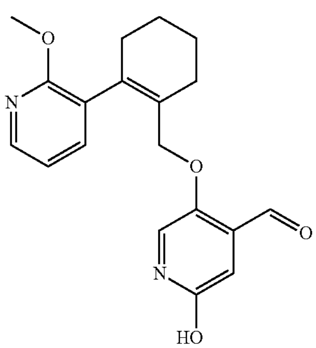 [SMILES: COc1ncccc1C1=C(COc2cnc(O)cc2C=O)CCCC1] | 2-hydroxy-5-[[2-(2-methoxypyridin-3-yl)cyclohexen-1-yl]methoxy]pyridine-4-carbaldehyde |
| 500 | 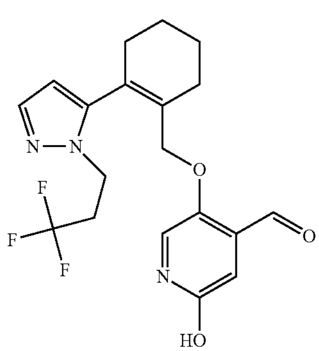 [SMILES: O=Cc1cc(O)ncc1OCC1=C(c2ccnn2CCC(F)(F)F)CCCC1] | 2-hydroxy-5-[[2-[2-(3,3,3-trifluoropropyl)pyrazol-3-yl]cyclohexen-1-yl]methoxy]pyridine-4-carbaldehyde |

TABLE 1-continued

| Compound | Structure | Name |
|---|---|---|
| 501 | 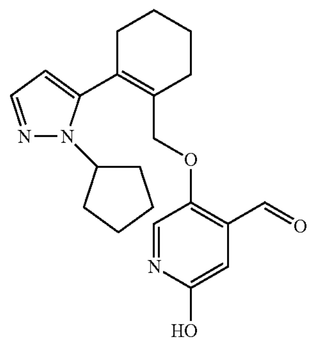 [SMILES: O=Cc1cc(O)ncc1OCC1=C(c2ccnn2C2CCCC2)CCCC1] | 5-[[2-(2-cyclopentylpyrazol-3-yl)cyclohexen-1-yl]methoxy]-2-hydroxypyridine-4-carbaldehyde |
| 502 | 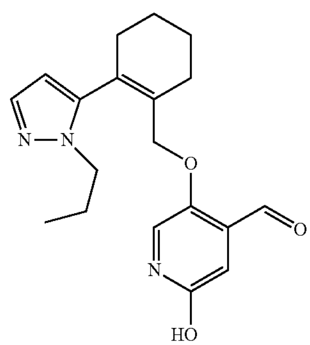 [SMILES: CCCn1nccc1C1=C(COc2cnc(O)cc2C=O)CCCC1] | 2-hydroxy-5-[[2-(2-propylpyrazol-3-yl)cyclohexen-1-yl]methoxy]pyridine-4-carbaldehyde |
| 503 | 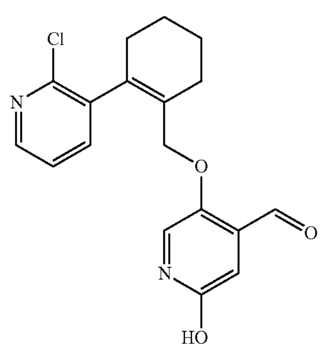 [SMILES: O=Cc1cc(O)ncc1OCC1=C(c2cccnc2Cl)CCCC1] | 5-[[2-(2-chloropyridin-3-yl)cyclohexen-1-yl]methoxy]-2-hydroxypyridine-4-carbaldehyde |
| 504 | 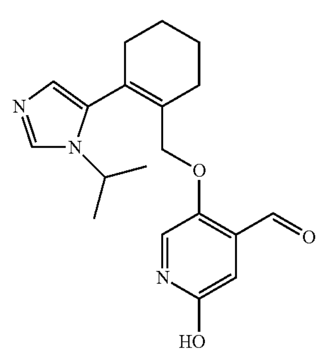 [SMILES: CC(C)n1cncc1C1=C(COc2cnc(O)cc2C=O)CCCC1] | 2-hydroxy-5-[[2-(3-propan-2-ylimidazol-4-yl)cyclohexen-1-yl]methoxy]pyridine-4-carbaldehyde |

TABLE 1-continued

| Compound | Structure | Name |
|---|---|---|
| 505 | 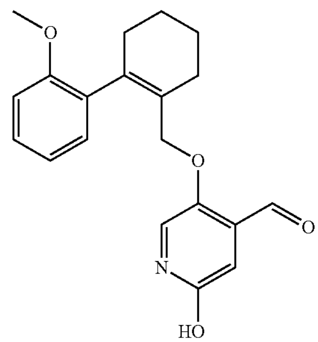 [SMILES: COc1ccccc1C1=C(COc2cnc(O)cc2C=O)CCCC1] | 2-hydroxy-5-[[2-(2-methoxyphenyl)cyclohexen-1-yl]methoxy]pyridine-4-carbaldehyde |
| 506 | 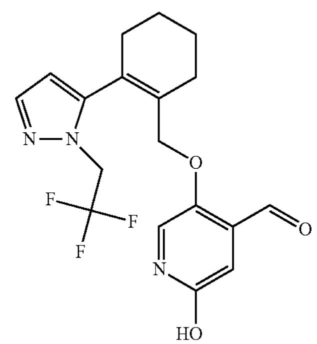 [SMILES: O=Cc1cc(O)ncc1OCC1=C(c2ccnn2CC(F)(F)F)CCCC1] | 2-hydroxy-5-[[2-[2-(2,2,2-trifluoroethyl)pyrazol-3-yl]cyclohexen-1-yl]methoxy]pyridine-4-carbaldehyde |
| 507 | 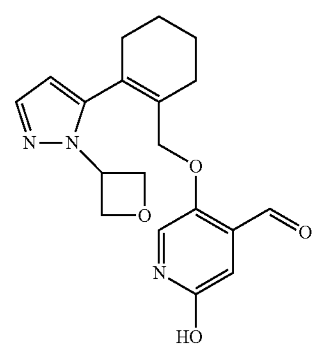 [SMILES: O=Cc1cc(O)ncc1OCC1=C(c2ccnn2C2COC2)CCCC1] | 2-hydroxy-5-[[2-[2-(oxetan-3-yl)pyrazol-3-yl]cyclohexen-1-yl]methoxy]pyridine-4-carbaldehyde |
| 508 | 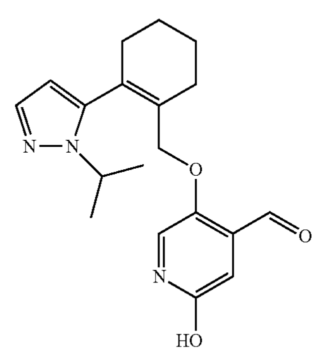 [SMILES: CC(C)n1nccc1C1=C(COc2cnc(O)cc2C=O)CCCC1] | 2-hydroxy-5-[[2-(2-propan-2-ylpyrazol-3-yl)cyclohexen-1-yl]methoxy]pyridine-4-carbaldehyde |

TABLE 1-continued

| Compound | Structure | Name |
|---|---|---|
| 509 | 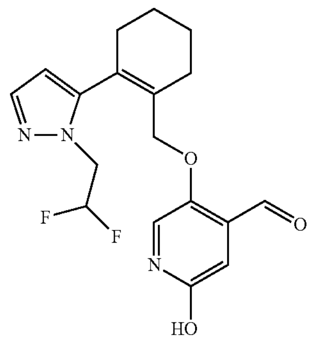 [SMILES: O=Cc1cc(O)ncc1OCC1=C(c2ccnn2CC(F)F)CCCC1] | 5-[[2-[2-(2,2-difluoroethyl)pyrazol-3-yl]cyclohexen-1-yl]methoxy]-2-hydroxypyridine-4-carbaldehyde |
| 510 | 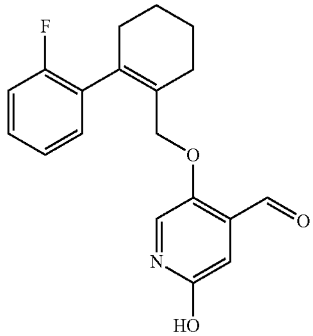 [SMILES: O=Cc1cc(O)ncc1OCC1=C(c2ccccc2F)CCCC1] | 5-[[2-(2-fluorophenyl)cyclohexen-1-yl]methoxy]-2-hydroxypyridine-4-carbaldehyde |
| 511 | 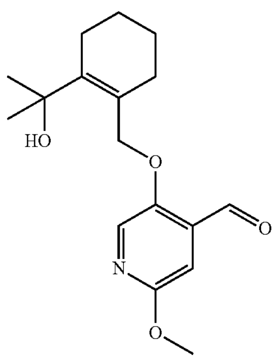 [SMILES: COc1cc(C=O)c(OCC2=C(C(C)(C)O)CCCC2)cn1] | 5-[[2-(2-hydroxypropan-2-yl)cyclohexen-1-yl]methoxy]-2-methoxypyridine-4-carbaldehyde |
| 512 | 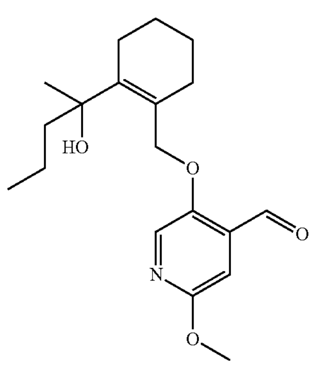 [SMILES: CCCC(C)(O)C1=C(COc2cnc(OC)cc2C=O)CCCC1] | 5-[[2-(2-hydroxypentan-2-yl)cyclohexen-1-yl]methoxy]-2-methoxypyridine-4-carbaldehyde |

TABLE 1-continued

| Compound | Structure | Name |
|---|---|---|
| 513 | 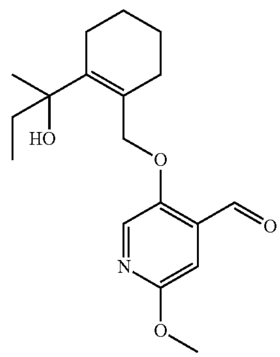 [SMILES: CCC(C)(O)C1=C(COc2cnc(OC)cc2C=O)CCCC1] | 5-[[2-(2-hydroxybutan-2-yl)cyclohexen-1-yl]methoxy]-2-methoxypyridine-4-carbaldehyde |
| 514 | 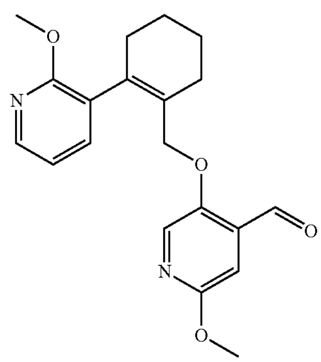 [SMILES: COc1cc(C=O)c(OCC2=C(c3cccnc3OC)CCCC2)cn1] | 2-methoxy-5-[[2-(2-methoxypyridin-3-yl)cyclohexen-1-yl]methoxy]pyridine-4-carbaldehyde |
| 515 | 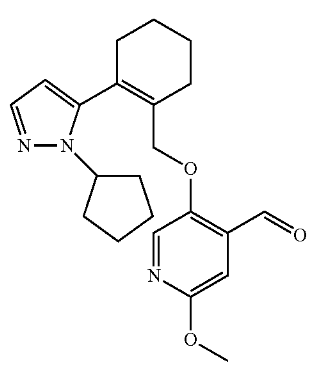 [SMILES: COc1cc(C=O)c(OCC2=C(c3ccnn3C3CCCC3)CCCC2)cn1] | 5-[[2-(2-cyclopentylpyrazol-3-yl)cyclohexen-1-yl]methoxy]-2-methoxypyridine-4-carbaldehyde |
| 516 | 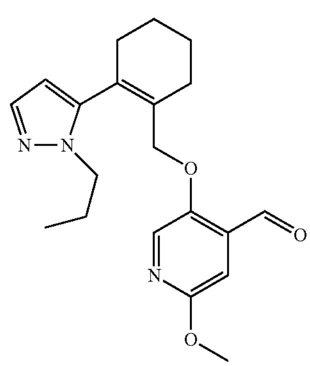 [SMILES: CCCn1nccc1C1=C(COc2cnc(OC)cc2C=O)CCCC1] | 2-methoxy-5-[[2-(2-propylpyrazol-3-yl)cyclohexen-1-yl]methoxy]pyridine-4-carbaldehyde |

TABLE 1-continued

| Compound | Structure | Name |
|---|---|---|
| 517 | 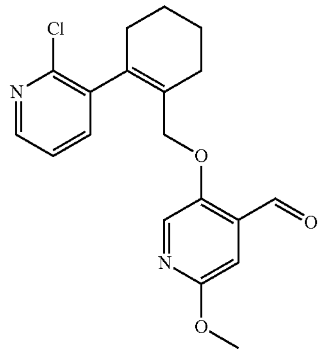 [SMILES: COc1cc(C=O)c(OCC2=C(c3cccnc3Cl)CCCC2)cn1] | 5-[[2-(2-chloropyridin-3-yl)cyclohexen-1-yl]methoxy]-2-methoxypyridine-4-carbaldehyde |
| 518 | 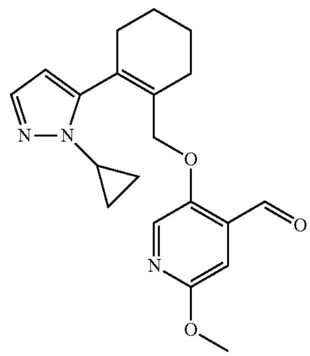 [SMILES: COc1cc(C=O)c(OCC2=C(c3ccnn3C3CC3)CCCC2)cn1] | 5-[[2-(2-cyclopropylpyrazol-3-yl)cyclohexen-1-yl]methoxy]-2-methoxypyridine-4-carbaldehyde |
| 519 | 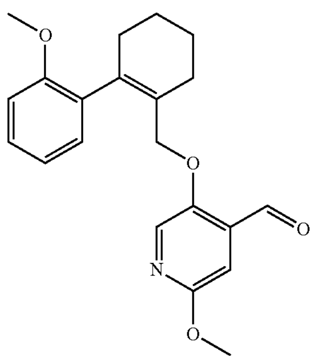 [SMILES: COc1cc(C=O)c(OCC2=C(c3ccccc3OC)CCCC2)cn1] | 2-methoxy-5-[[2-(2-methoxyphenyl)cyclohexen-1-yl]methoxy]pyridine-4-carbaldehyde |
| 520 | 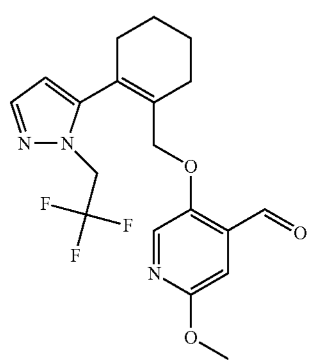 [SMILES: COc1cc(C=O)c(OCC2=C(c3ccnn3CC(F)(F)F)CCCC2)cn1] | 2-methoxy-5-[[2-[2-(2,2,2-trifluoroethyl)pyrazol-3-yl]cyclohexen-1-yl]methoxy]pyridine-4-carbaldehyde |

TABLE 1-continued

| Compound | Structure | Name |
|---|---|---|
| 521 | 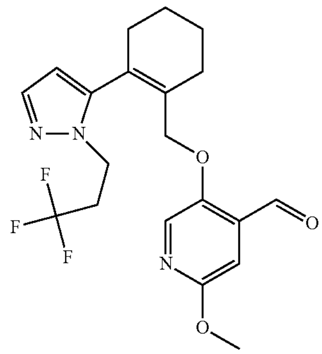 [SMILES: COc1cc(C=O)c(OCC2=C(c3ccnn3CCC(F)(F)F)CCCC2)cn1] | 2-methoxy-5-[[2-[2-(3,3,3-trifluoropropyl)pyrazol-3-yl]cyclohexen-1-yl]methoxy]pyridine-4-carbaldehyde |
| 522 | 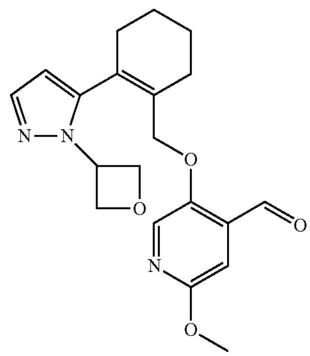 [SMILES: COc1cc(C=O)c(OCC2=C(c3ccnn3C3COC3)CCCC2)cn1] | 2-methoxy-5-[[2-[2-(oxetan-3-yl)pyrazol-3-yl]cyclohexen-1-yl]methoxy]pyridine-4-carbaldehyde |
| 523 | 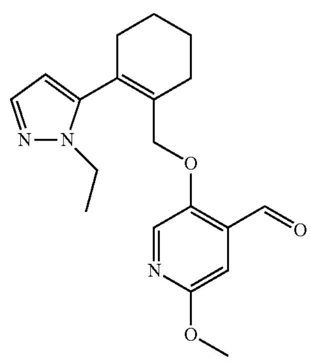 [SMILES: CCn1nccc1C1=C(COc2cnc(OC)cc2C=O)CCCC1] | 5-[[2-(2-ethylpyrazol-3-yl)cyclohexen-1-yl]methoxy]-2-methoxypyridine-4-carbaldehyde |
| 524 | 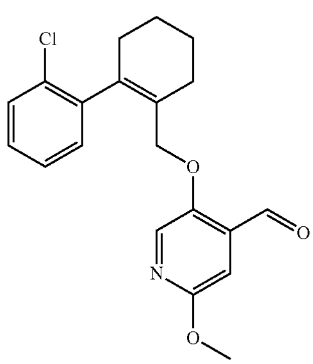 [SMILES: COc1cc(C=O)c(OCC2=C(c3ccccc3Cl)CCCC2)cn1] | 5-[[2-(2-chlorophenyl)cyclohexen-1-yl]methoxy]-2-methoxypyridine-4-carbaldehyde |

TABLE 1-continued

| Compound | Structure | Name |
|---|---|---|
| 525 | 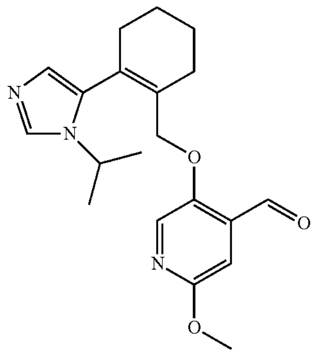 [SMILES: COc1cc(C=O)c(OCC2=C(c3cncn3C(C)C)CCCC2)cn1] | 2-methoxy-5-[[2-(3-propan-2-ylimidazol-4-yl)cyclohexen-1-yl]methoxy]pyridine-4-carbaldehyde |
| 526 | 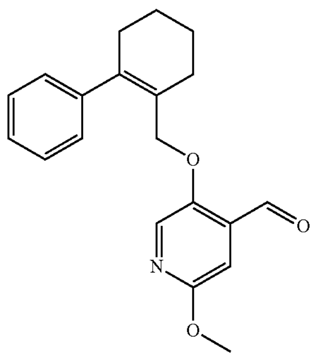 [SMILES: COc1cc(C=O)c(OCC2=C(c3ccccc3)CCCC2)cn1] | 2-methoxy-5-[(2-phenylcyclohexen-1-yl)methoxy]pyridine-4-carbaldehyde |
| 527 | 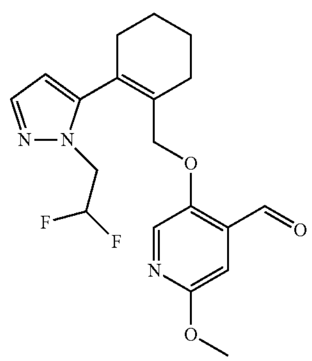 [SMILES: COc1cc(C=O)c(OCC2=C(c3ccnn3CC(F)F)CCCC2)cn1] | 5-[[2-[2-(2,2-difluoroethyl)pyrazol-3-yl]cyclohexen-1-yl]methoxy]-2-methoxypyridine-4-carbaldehyde |
| 528 | 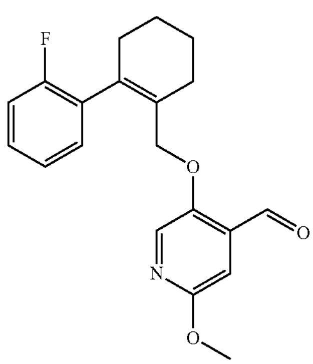 [SMILES: COc1cc(C=O)c(OCC2=C(c3ccccc3F)CCCC2)cn1] | 5-[[2-(2-fluorophenyl)cyclohexen-1-yl]methoxy]-2-methoxypyridine-4-carbaldehyde |

TABLE 1-continued

| Compound | Structure | Name |
| --- | --- | --- |
| 529 | 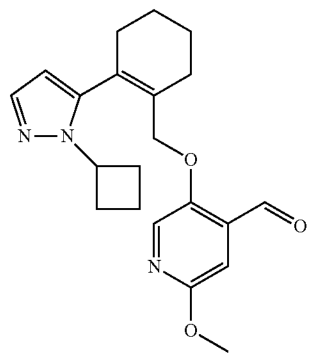 [SMILES: COc1cc(C=O)c(OCC2=C(c3ccnn3C3CCC3)CCCC2)cn1] | 5-[[2-(2-cyclobutylpyrazol-3-yl)cyclohexen-1-yl]methoxy]-2-methoxypyridine-4-carbaldehyde |
| 530 | 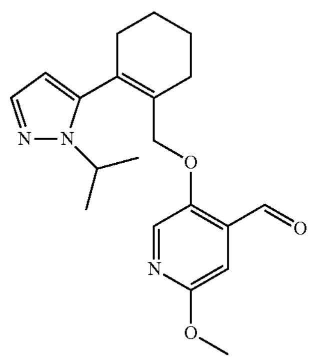 [SMILES: COc1cc(C=O)c(OCC2=C(c3ccnn3C(C)C)CCCC2)cn1] | 2-methoxy-5-[[2-(2-propan-2-ylpyrazol-3-yl)cyclohexen-1-yl]methoxy]pyridine-4-carbaldehyde |
| 531 | 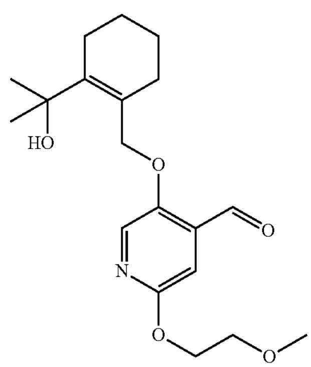 [SMILES: COCCOc1cc(C=O)c(OCC2=C(C(C)(C)O)CCCC2)cn1] | 5-[[2-(2-hydroxypropan-2-yl)cyclohexen-1-yl]methoxy]-2-(2-methoxyethoxy)pyridine-4-carbaldehyde |
| 532 | 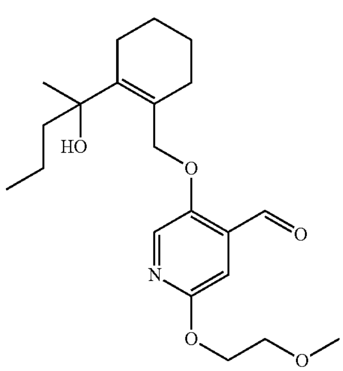 [SMILES: CCCC(C)(O)C1=C(COc2cnc(OCCOC)cc2C=O)CCCC1] | 5-[[2-(2-hydroxypentan-2-yl)cyclohexen-1-yl]methoxy]-2-(2-methoxyethoxy)pyridine-4-carbaldehyde |

TABLE 1-continued

| Compound | Structure | Name |
|---|---|---|
| 533 | 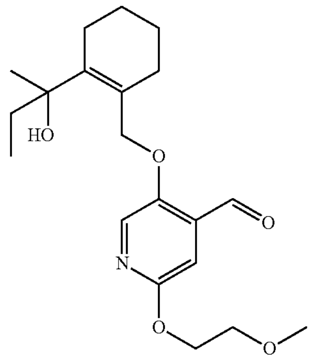 [SMILES: CCC(C)(O)C1=C(COc2cnc(OCCOC)cc2C=O)CCCC1] | 5-[[2-(2-hydroxybutan-2-yl)cyclohexen-1-yl]methoxy]-2-(2-methoxyethoxy)pyridine-4-carbaldehyde |
| 534 | 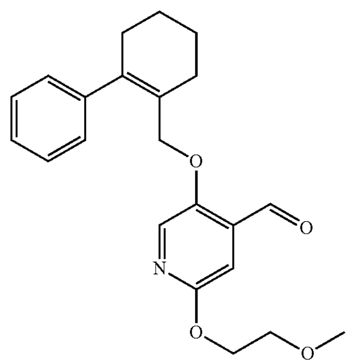 [SMILES: COCCOc1cc(C=O)c(OCC2=C(c3ccccc3)CCCC2)cn1] | 2-(2-methoxyethoxy)-5-[(2-phenylcyclohexen-1-yl)methoxy]pyridine-4-carbaldehyde |
| 535 | 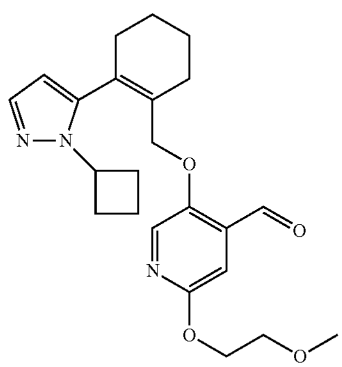 [SMILES: COCCOc1cc(C=O)c(OCC2=C(c3ccnn3C3CCC3)CCCC2)cn1] | 5-[[2-(2-cyclobutylpyrazol-3-yl)cyclohexen-1-yl]methoxy]-2-(2-methoxyethoxy)pyridine-4-carbaldehyde |
| 536 | 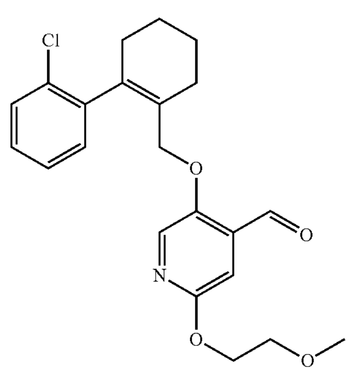 [SMILES: COCCOc1cc(C=O)c(OCC2=C(c3ccccc3Cl)CCCC2)cn1] | 5-[[2-(2-chlorophenyl)cyclohexen-1-yl]methoxy]-2-(2-methoxyethoxy)pyridine-4-carbaldehyde |

TABLE 1-continued

| Compound | Structure | Name |
|---|---|---|
| 537 | 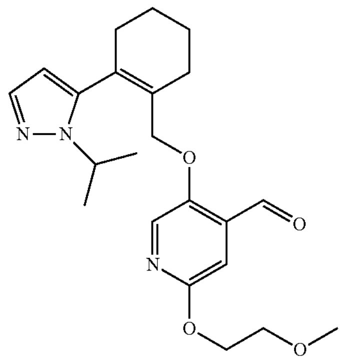 [SMILES: COCCOc1cc(C=O)c(OCC2=C(c3ccnn3C(C)C)CCCC2)cn1] | 2-(2-methoxyethoxy)-5-[[2-(2-propan-2-ylpyrazol-3-yl)cyclohexen-1-yl]methoxy]pyridine-4-carbaldehyde |
| 538 | 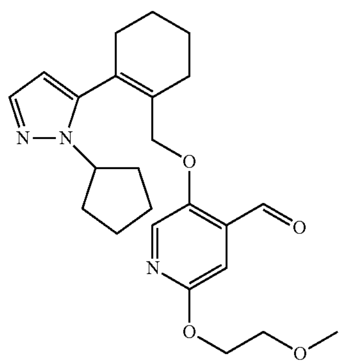 [SMILES: COCCOc1cc(C=O)c(OCC2=C(c3ccnn3C3CCCC3)CCCC2)cn1] | 5-[[2-(2-cyclopentylpyrazol-3-yl)cyclohexen-1-yl]methoxy]-2-(2-methoxyethoxy)pyridine-4-carbaldehyde |
| 539 | 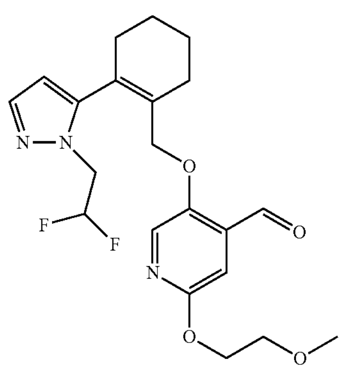 [SMILES: COCCOc1cc(C=O)c(OCC2=C(c3ccnn3CC(F)F)CCCC2)cn1] | 5-[[2-[2-(2,2-difluoroethyl)pyrazol-3-yl]cyclohexen-1-yl]methoxy]-2-(2-methoxyethoxy)pyridine-4-carbaldehyde |
| 540 | 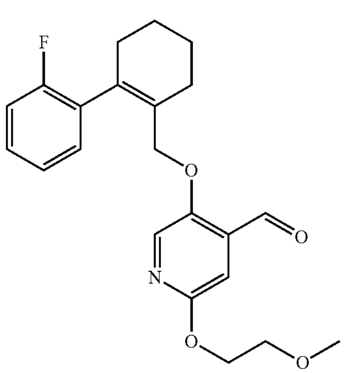 [SMILES: COCCOc1cc(C=O)c(OCC2=C(c3ccccc3F)CCCC2)cn1] | 5-[[2-(2-fluorophenyl)cyclohexen-1-yl]methoxy]-2-(2-methoxyethoxy)pyridine-4-carbaldehyde |

TABLE 1-continued

| Compound | Structure | Name |
|---|---|---|
| 541 | 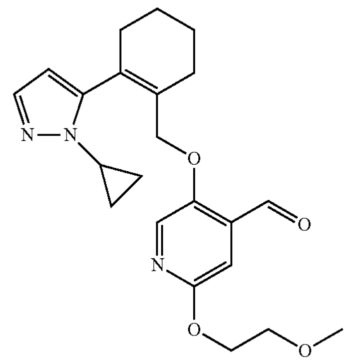 [SMILES: COCCOc1cc(C=O)c(OCC2=C(c3ccnn3C3CC3)CCCC2)cn1] | 5-[[2-(2-cyclopropylpyrazol-3-yl)cyclohexen-1-yl]methoxy]-2-(2-methoxyethoxy)pyridine-4-carbaldehyde |
| 542 | 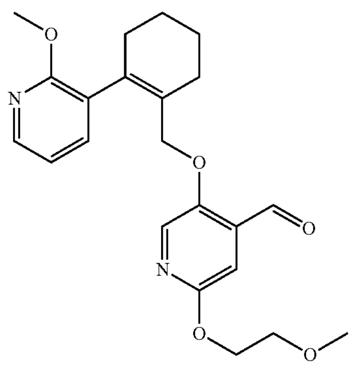 [SMILES: COCCOc1cc(C=O)c(OCC2=C(c3cccnc3OC)CCCC2)cn1] | 2-(2-methoxyethoxy)-5-[[2-(2-methoxypyridin-3-yl)cyclohexen-1-yl]methoxy]pyridine-4-carbaldehyde |
| 543 | 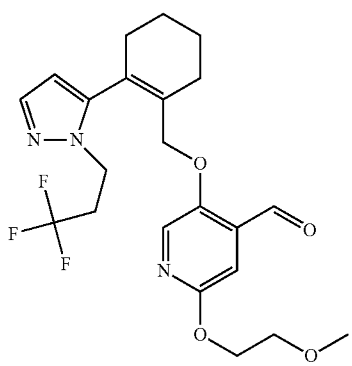 [SMILES: COCCOc1cc(C=O)c(OCC2=C(c3ccnn3CCC(F)(F)F)CCCC2)cn1] | 2-(2-methoxyethoxy)-5-[[2-[2-(3,3,3-trifluoropropyl)pyrazol-3-yl]cyclohexen-1-yl]methoxy]pyridine-4-carbaldehyde |
| 544 | 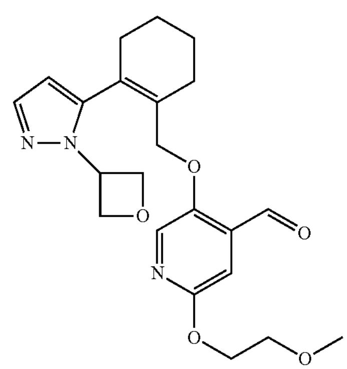 [SMILES: COCCOc1cc(C=O)c(OCC2=C(c3ccnn3C3COC3)CCCC2)cn1] | 2-(2-methoxyethoxy)-5-[[2-[2-(oxetan-3-yl)pyrazol-3-yl]cyclohexen-1-yl]methoxy]pyridine-4-carbaldehyde |

TABLE 1-continued

| Compound | Structure | Name |
| --- | --- | --- |
| 545 | 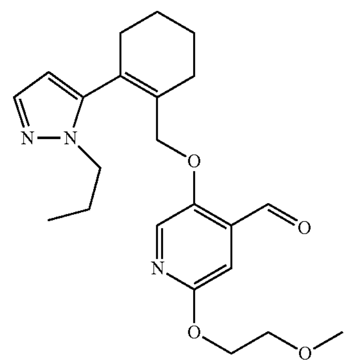 [SMILES: CCCn1nccc1C1=C(COc2cnc(OCCOC)cc2C=O)CCCC1] | 2-(2-methoxyethoxy)-5-[[2-(2-propylpyrazol-3-yl)cyclohexen-1-yl]methoxy]pyridine-4-carbaldehyde |
| 546 | 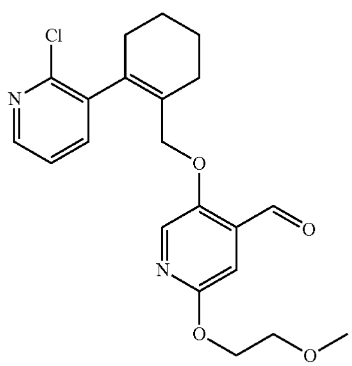 [SMILES: COCCOc1cc(C=O)c(OCC2=C(c3cccnc3Cl)CCCC2)cn1] | 5-[[2-(2-chloropyridin-3-yl)cyclohexen-1-yl]methoxy]-2-(2-methoxyethoxy)pyridine-4-carbaldehyde |
| 547 | 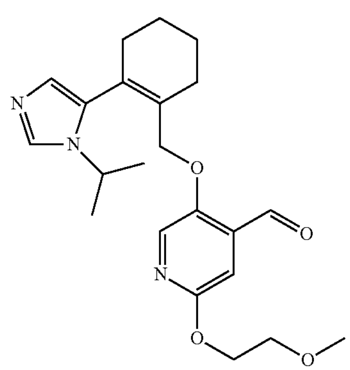 [SMILES: COCCOc1cc(C=O)c(OCC2=C(c3cncn3C(C)C)CCCC2)cn1] | 2-(2-methoxyethoxy)-5-[[2-(3-propan-2-ylimidazol-4-yl)cyclohexen-1-yl]methoxy]pyridine-4-carbaldehyde |
| 548 | 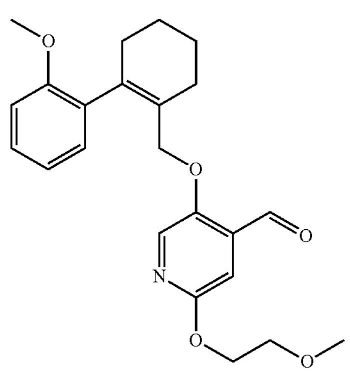 [SMILES: COCCOc1cc(C=O)c(OCC2=C(c3ccccc3OC)CCCC2)cn1] | 2-(2-methoxyethoxy)-5-[[2-(2-methoxyphenyl)cyclohexen-1-yl]methoxy]pyridine-4-carbaldehyde |

TABLE 1-continued

| Compound | Structure | Name |
|---|---|---|
| 549 | 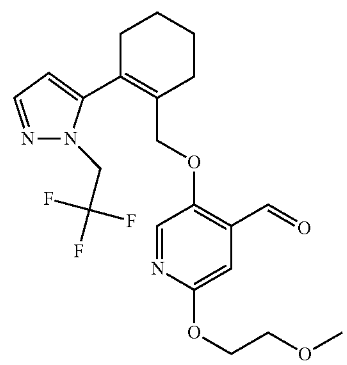 [SMILES: COCCOc1cc(C=O)c(OCC2=C(c3ccnn3CC(F)(F)F)CCCC2)cn1] | 2-(2-methoxyethoxy)-5-[[2-[2-(2,2,2-trifluoroethyl)pyrazol-3-yl]cyclohexen-1-yl]methoxy]pyridine-4-carbaldehyde |
| 550 | 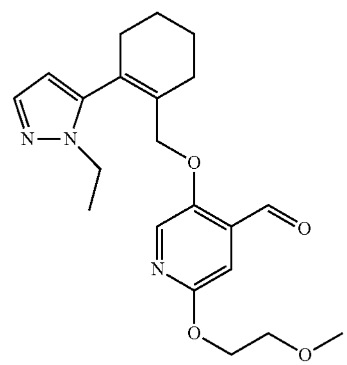 [SMILES: CCn1nccc1C1=C(COc2cnc(OCCOC)cc2C=O)CCCC1] | 5-[[2-(2-ethylpyrazol-3-yl)cyclohexen-1-yl]methoxy]-2-(2-methoxyethoxy)pyridine-4-carbaldehyde |
| 551 | 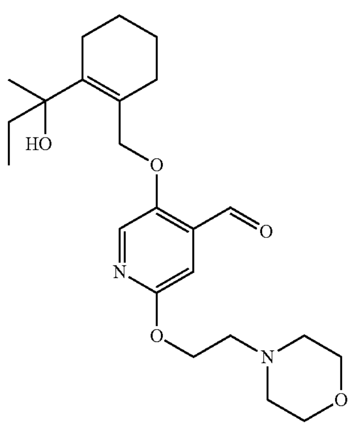 [SMILES: CCC(C)(O)C1=C(COc2cnc(OCCN3CCOCC3)cc2C=O)CCCC1] | 5-[[2-(2-hydroxybutan-2-yl)cyclohexen-1-yl]methoxy]-2-(2-morpholin-4-ylethoxy)pyridine-4-carbaldehyde |
| 552 | 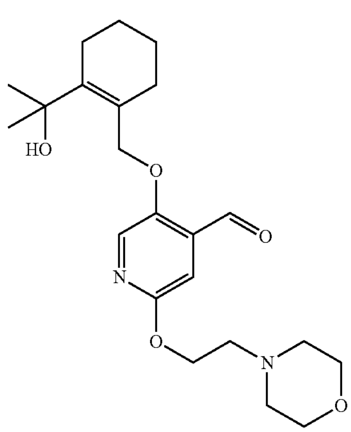 | 5-[[2-(2-hydroxypropan-2-yl)cyclohexen-1-yl]methoxy]-2-(2-morpholin-4-ylethoxy)pyridine-4-carbaldehyde |

TABLE 1-continued

| Compound | Structure | Name |
|---|---|---|
| 553 | 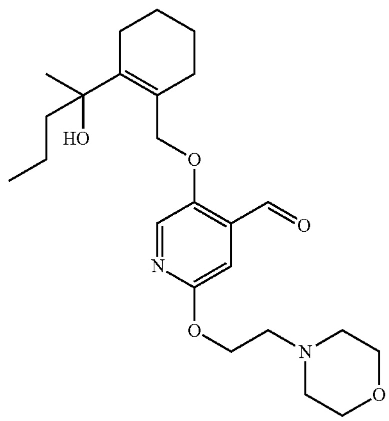 [SMILES: CCCC(C)(O)C1=C(COc2cnc(OCCN3CCOCC3)cc2C=O)CCCC1] | 5-[[2-(2-hydroxypentan-2-yl)cyclohexen-1-yl]methoxy]-2-(2-morpholin-4-ylethoxy)pyridine-4-carbaldehyde |
| 554 | 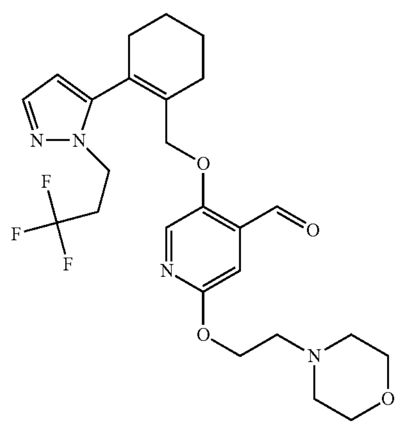 [SMILES: O=Cc1cc(OCCN2CCOCC2)ncc1OCC1=C(c2ccnn2CCC(F)(F)F)CCCC1] | 2-(2-morpholin-4-ylethoxy)-5-[[2-[2-(3,3,3-trifluoropropyl)pyrazol-3-yl]cyclohexen-1-yl]methoxy]pyridine-4-carbaldehyde |
| 555 | 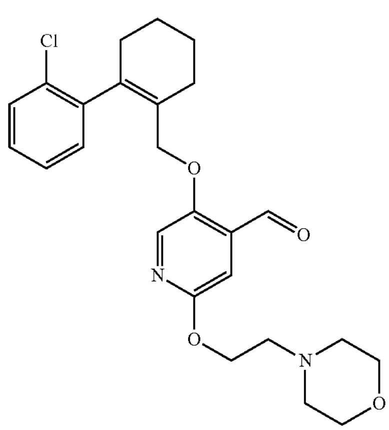 [SMILES: O=Cc1cc(OCCN2CCOCC2)ncc1OCC1=C(c2ccccc2Cl)CCCC1] | 5-[[2-(2-chlorophenyl)cyclohexen-1-yl]methoxy]-2-(2-morpholin-4-ylethoxy)pyridine-4-carbaldehyde |

TABLE 1-continued

| Compound | Structure | Name |
|---|---|---|
| 556 | 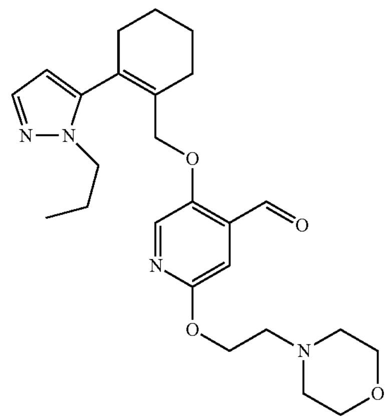 [SMILES: CCCn1nccc1C1=C(COc2cnc(OCCN3CCOCC3)cc2C=O)CCCC1] | 2-(2-morpholin-4-ylethoxy)-5-[[2-(2-propylpyrazol-3-yl)cyclohexen-1-yl]methoxy]pyridine-4-carbaldehyde |
| 557 | 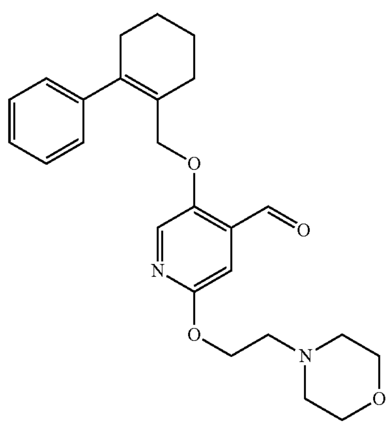 [SMILES: O=Cc1cc(OCCN2CCOCC2)ncc1OCC1=C(c2ccccc2)CCCC1] | 2-(2-morpholin-4-ylethoxy)-5-[(2-phenylcyclohexen-1-yl)methoxy]pyridine-4-carbaldehyde |
| 558 | 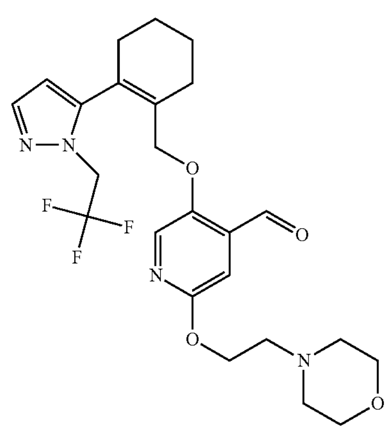 [SMILES: O=Cc1cc(OCCN2CCOCC2)ncc1OCC1=C(c2ccnn2CC(F)(F)F)CCCC1] | 2-(2-morpholin-4-ylethoxy)-5-[[2-[2-(2,2,2-trifluoroethyl)pyrazol-3-yl]cyclohexen-1-yl]methoxy]pyridine-4-carbaldehyde |

TABLE 1-continued

| Compound | Structure | Name |
|---|---|---|
| 559 | 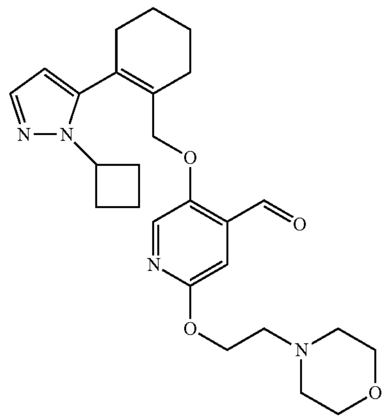 [SMILES: O=Cc1cc(OCCN2CCOCC2)ncc1OCC1=C(c2ccnn2C2CCC2)CCCC1] | 5-[[2-(2-cyclobutylpyrazol-3-yl)cyclohexen-1-yl]methoxy]-2-(2-morpholin-4-ylethoxy)pyridine-4-carbaldehyde |
| 560 | 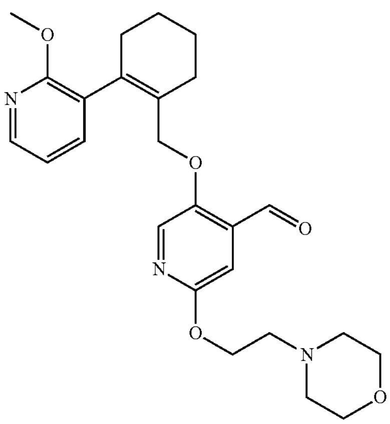 [SMILES: COc1ncccc1C1=C(COc2cnc(OCCN3CCOCC3)cc2C=O)CCCC1] | 5-[[2-(2-methoxypyridin-3-yl)cyclohexen-1-yl]methoxy]-2-(2-morpholin-4-ylethoxy)pyridine-4-carbaldehyde |
| 561 | 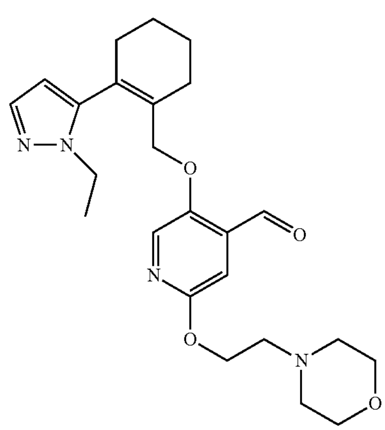 [SMILES: CCn1nccc1C1=C(COc2cnc(OCCN3CCOCC3)cc2C=O)CCCC1] | 5-[[2-(2-ethylpyrazol-3-yl)cyclohexen-1-yl]methoxy]-2-(2-morpholin-4-ylethoxy)pyridine-4-carbaldehyde |

TABLE 1-continued

| Compound | Structure | Name |
|---|---|---|
| 562 | 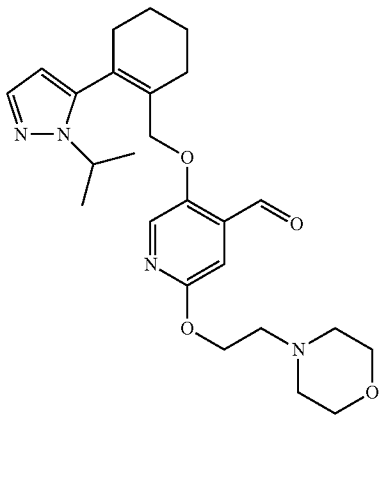 [SMILES: CC(C)n1nccc1C1=C(COc2cnc(OCCN3CCOCC3)cc2C=O)CCCC1] | 2-(2-morpholin-4-ylethoxy)-5-[[2-(2-propan-2-ylpyrazol-3-yl)cyclohexen-1-yl]methoxy]pyridine-4-carbaldehyde |
| 563 | 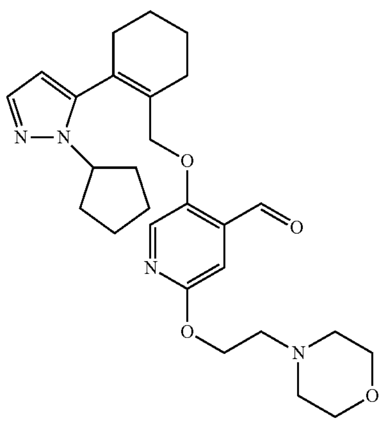 [SMILES: O=Cc1cc(OCCN2CCOCC2)ncc1OCC1=C(c2ccnn2C2CCCC2)CCCC1] | 5-[[2-(2-cyclopentylpyrazol-3-yl)cyclohexen-1-yl]methoxy]-2-(2-morpholin-4-ylethoxy)pyridine-4-carbaldehyde |
| 564 | 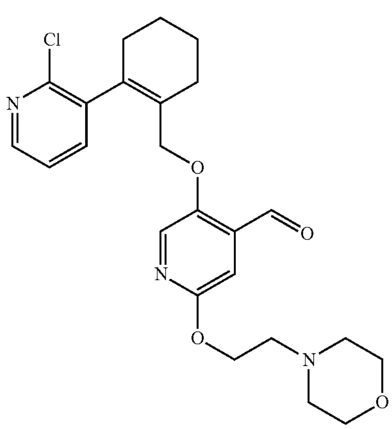 [SMILES: O=Cc1cc(OCCN2CCOCC2)ncc1OCC1=C(c2cccnc2Cl)CCCC1] | 5-[[2-(2-chloropyridin-3-yl)cyclohexen-1-yl]methoxy]-2-(2-morpholin-4-ylethoxy)pyridine-4-carbaldehyde |

TABLE 1-continued

| Compound | Structure | Name |
|---|---|---|
| 565 | 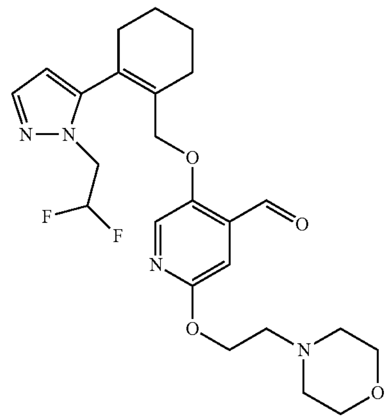 [SMILES: O=Cc1cc(OCCN2CCOCC2)ncc1OCC1=C(c2ccnn2CC(F)F)CCCC1] | 5-[[2-[2-(2,2-difluoroethyl)pyrazol-3-yl]cyclohexen-1-yl]methoxy]-2-(2-morpholin-4-ylethoxy)pyridine-4-carbaldehyde |
| 566 | 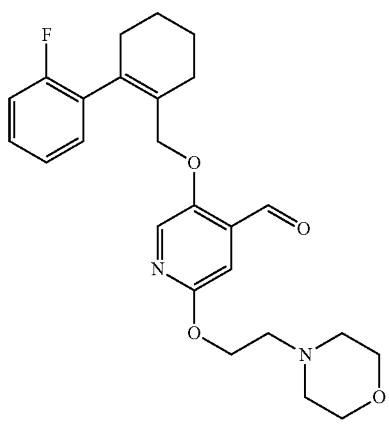 [SMILES: O=Cc1cc(OCCN2CCOCC2)ncc1OCC1=C(c2ccccc2F)CCCC1] | 5-[[2-(2-fluorophenyl)cyclohexen-1-yl]methoxy]-2-(2-morpholin-4-ylethoxy)pyridine-4-carbaldehyde |
| 567 | 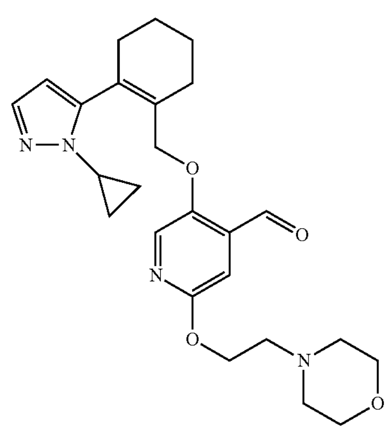 [SMILES: O=Cc1cc(OCCN2CCOCC2)ncc1OCC1=C(c2ccnn2C2CC2)CCCC1] | 5-[[2-(2-cyclopropylpyrazol-3-yl)cyclohexen-1-yl]methoxy]-2-(2-morpholin-4-ylethoxy)pyridine-4-carbaldehyde |

TABLE 1-continued

| Compound | Structure | Name |
|---|---|---|
| 568 | 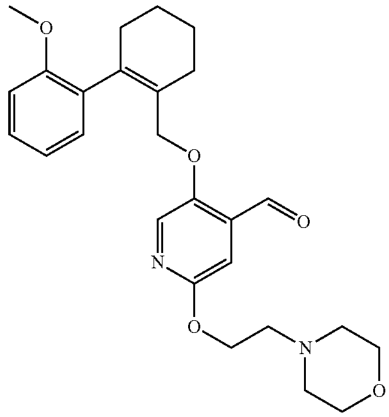 [SMILES: COc1ccccc1C1=C(COc2cnc(OCCN3CCOCC3)cc2C=O)CCCC1] | 5-[[2-(2-methoxyphenyl)cyclohexen-1-yl]methoxy]-2-(2-morpholin-4-ylethoxy)pyridine-4-carbaldehyde |
| 569 | 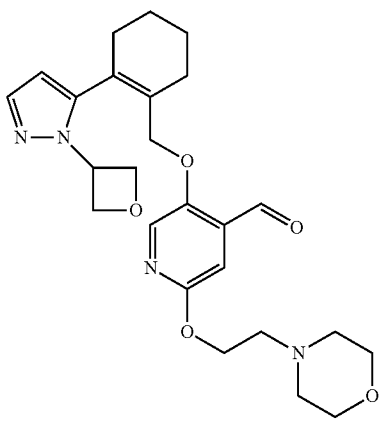 [SMILES: O=Cc1cc(OCCN2CCOCC2)ncc1OCC1=C(c2ccnn2C2COC2)CCCC1] | 2-(2-morpholin-4-ylethoxy)-5-[[2-[2-(oxetan-3-yl)pyrazol-3-yl]cyclohexen-1-yl]methoxy]pyridine-4-carbaldehyde |
| 570 | 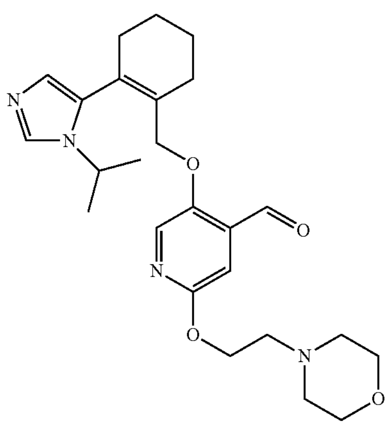 [SMILES: CC(C)n1cncc1C1=C(COc2cnc(OCCN3CCOCC3)cc2C=O)CCCC1] | 2-(2-morpholin-4-ylethoxy)-5-[[2-(3-propan-2-ylimidazol-4-yl)cyclohexen-1-yl]methoxy]pyridine-4-carbaldehyde |

In some groups of embodiments, the invention provides a compound, or a tautomer or pharmaceutically acceptable salt thereof, selected from:

cis-methyl4-((2-formyl-3-hydroxyphenoxy)methyl)cyclohexanecarboxylate;
cis-4-((2-formyl-3-hydroxyphenoxy)methyl)cyclohexanecarboxylic acid;
cis-3-((2-formyl-3-hydroxyphenoxy)methyl)cyclohexanecarboxylic acid;
trans-methyl4-((2-formyl-3-hydroxyphenoxy)methyl)cyclohexanecarboxylate;
cis-3-((2-formyl-3-hydroxyphenoxy)methyl)cyclohexanecarboxylic acid;
trans-4-((2-formyl-3-hydroxyphenoxy)methyl)cyclohexanecarboxylic acid;
methyl3-((2-formyl-3-hydroxyphenoxy)methyl)cyclohexanecarboxylate;
trans-methyl4-((2-formyl-3-methoxyphenoxy)methyl)cyclohexanecarboxylate;
methyl3-((2-formyl-3-hydroxyphenoxy)methyl)cyclohexanecarboxylate;
2-hydroxy-6-((3,4,5,6-tetrahydro-[1,1'-biphenyl]-2-yl)methoxy)benzaldehyde;
2-hydroxy-6-((2-phenylcyclohexyl)methoxy)benzaldehyde; and 2-hydroxy-6-((2-(1-isopropyl-1H-pyrazol-5-yl)cyclohex-1-en-1-yl)methoxy)benzaldehyde.

In some groups of embodiments, the invention provides a compound, or a tautomer or pharmaceutically acceptable salt thereof, selected from:
2-hydroxy-6-((2-(1-isopropyl-1H-pyrazol-5-yl)cyclopent-1-en-1-yl)methoxy)benzaldehyde;
2,6-dihydroxy-3-((2-(1-isopropyl-1H-pyrazol-5-yl)cyclopent-1-en-1-yl)methyl)benzaldehyde;
2-hydroxy-6-((2-(1-isopropyl-1H-pyrazol-5-yl)cyclopentyl)-methoxy)benzaldehyde;
2-hydroxy-6-((2-(2-methoxypyridin-3-yl)cyclopent-1-en-1-yl)methoxy)benzaldehyde;
2-hydroxy-6-((2-(2-methoxypyridin-3-yl)cyclopentyl)methoxy)-benzaldehyde;
2-((2-(8-oxa-3-azabicyclo[3.2.1]octan-3-yl)cyclohexyl)-methoxy)-6-hydroxybenzaldehyde; and
2-hydroxy-6-((2-(1-isopropyl-1H-pyrazol-5-yl)cyclohept-1-en-1-yl)methoxy)-benzaldehyde.

In some groups of embodiments, the invention provides cis-cycloalkyl substituted aldehydes having a cycloalkyl moiety containing two substituents on the same face of the cycloalkyl moiety. In some groups of embodiments, the invention provides trans-cycloalkyl substituted aldehydes having a cycloalkyl moiety containing two substituents on different faces of the cycloalkyl moiety. In some groups of embodiments, the cis and trans isomers of any cycloalkyl substituted aldehyde described herein are provided. As one non-limiting example, 2-hydroxy-6-[[2-(2-hydroxypropan-2-yl)cyclohexyl]methoxy]benzaldehyde (Compound 13) can be provided as cis-2-hydroxy-6-[[2-(2-hydroxypropan-2-yl)cyclohexyl]methoxy]benzaldehyde or trans-2-hydroxy-6-[[2-(2-hydroxypropan-2-yl)cyclohexyl]methoxy]benzaldehyde. As another non-limiting example, 3-[[2-(2-propylpyrazol-3-yl)cyclohexyl]methoxy]pyridine-2-carbaldehyde (Compound 174) can be provided as cis-3-[[2-(2-propylpyrazol-3-yl)cyclohexyl]methoxy]pyridine-2-carbaldehyde or trans-3-[[2-(2-propylpyrazol-3-yl)cyclohexyl]methoxy]pyridine-2-carbaldehyde. In some groups of embodiments, the invention provides the cis isomer of any cyclohexyl-substituted aldehyde listed in Table 1. In some groups of embodiments, the invention provides the trans isomer of any cyclohexyl-substituted aldehyde listed in Table 1.

In one group of embodiments, provided is a compound in any of the Examples or Tables. In another group of embodiments, provided are any combinations of subembodiments as disclosed herein including any combination of elements disclosed herein including the a selection of any single elements.

In one group of embodiments, the invention provides a pharmaceutical composition containing a compound of any of the preceding claims or a tautomer or pharmaceutically acceptable salt thereof.

The compounds of the present invention may be prepared by known organic synthesis techniques, including the methods described in more detail in the Examples.

In one group of embodiments, provided is an intermediate compound used in the preparation of the compounds disclosed herein.

In one group of embodiments, provided are methods for preparing the compounds disclosed herein.

For example, Scheme I shows a synthetic route for the synthesis of the compounds of Formula (I) where X is O and Y is $CH_2$. Phenol 1.1 is contacted with intermediate 1.2 in the presence of base under ether forming conditions to give ether 1.3, where Lg represents a leaving group such as a halogen leaving group or an oxophosphonium leaving group or sulfonate leaving group. Conversely, when X is O and Y is $CH_2$, the compounds of Formula (I) can be prepared using the appropriate starting materials where the OH moiety of intermediate 1.1 is replaced with a leaving group and the Lg group of intermediate 1.2 is replaced with an OH group.

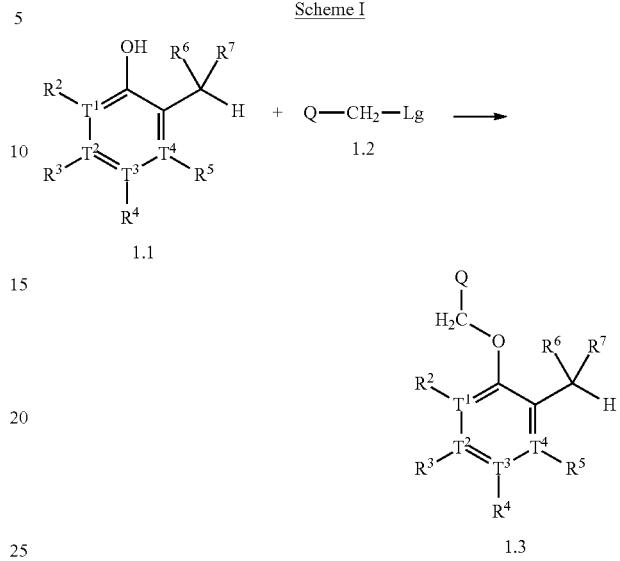

Scheme I

Scheme II shows an example of a synthetic route for the synthesis of the compounds of Formula (I) where X and Y are $CH_2$. Alkene 2.1 is contacted with alkene 2.2 under metathesis forming conditions in the presence of an appropriate transition metal catalyst. Suitable catalysts include ruthenium catalysts such as Grubbs' catalyst. Product 2.3 is then hydrogenated to give compound 2.4.

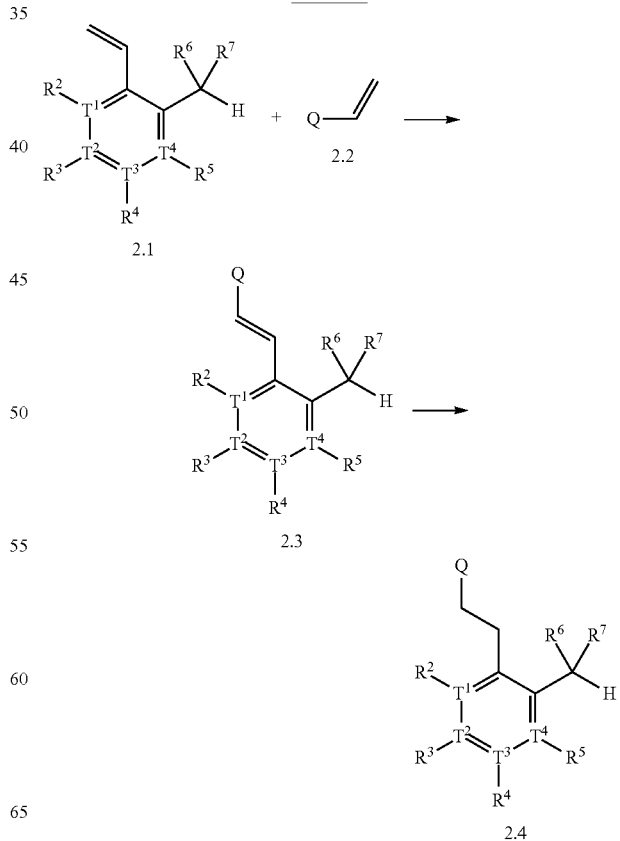

Scheme II

Scheme III shows an example of a synthetic route for the synthesis of the compounds of Formula (I) where $R^6$ together with $R^{1b}$ form a cyclic ether. Compound 3.1, is reacted with diethylphosphite and a base such as sodium methoxide to give intermediate 3.2, that is then condensed with aldehyde 3.3 to give alkene 3.4. Treatment of the alkene with $H_2$ under hydrogenation conditions gives lactone 3.4, which is then reduced with a suitable reducing agent such as $LiBHEt_3$ to give cyclic hemiacetal 3.5.

Scheme III

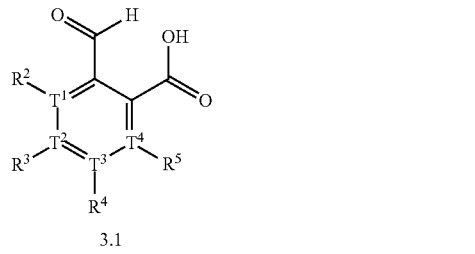

3.1

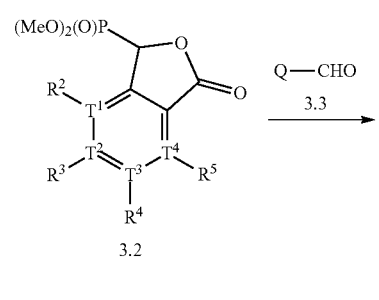

3.2

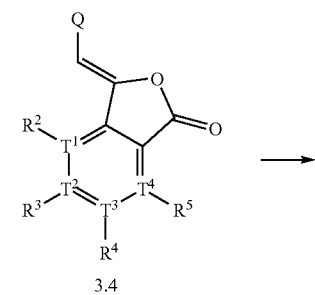

3.4

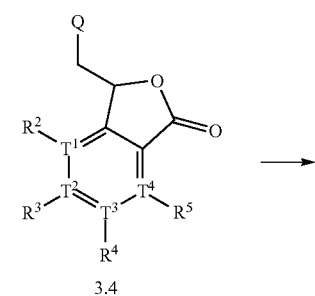

3.4

-continued

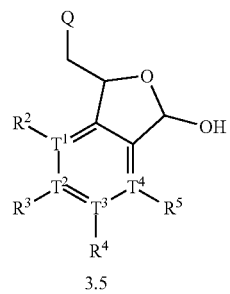

3.5

In some embodiments, cyclohexane- and cyclohexene-substituted aldehydes can be synthesized according to Schemes IV and V. Scheme IV shows a general scheme for the synthesis of a cyclohexane-substituted benzaldehyde 4.4 from hydroxy-aldehyde 4.3 via a Mitsunobu reaction with cyclohexylmethanol 4.1, or via alkylation of cyclohexylmethane 4.2. The cyclohexylmethane 4.2 is substituted with a leaving group X, such as a halogen or a sulfonic ester.

Scheme IV

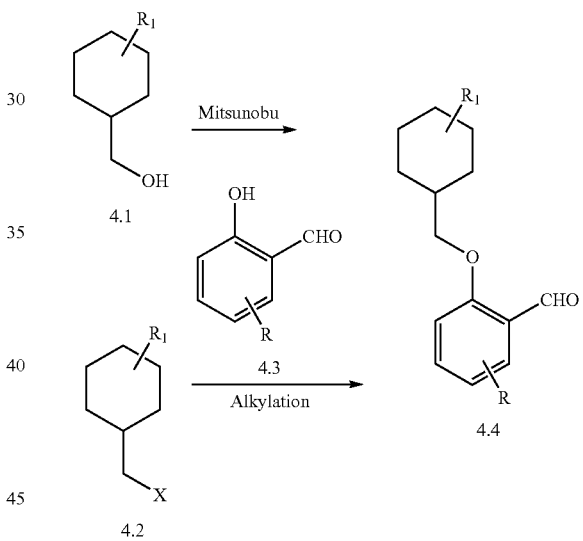

Scheme V shows the synthesis of cyclohexylmethanol 5.7a, cyclohexenylmethanol 5.5a, cyclohexylmethane 5.7b, and cyclohexenylmethane 5.5b. Ketoester 5.1 can be converted to aryl triflate 5.2, which can be elaborated via Suzuki coupling to provide cyclohexenylester 5.4. Cyclohexenylester 5.4 can then be used to access the cyclohexenylmethanol 5.5a and cyclohexenylmethane 5.5b. Cyclohexenylester 5.4 can also be hydrogenated in order to access cyclohexylmethanol 5.7a and cyclohexylmethane 5.7b. One skilled in the art will appreciate that this approach can be used to synthesize cis and trans isomers of cycloalkane-substituted methane and methanol compounds. The substituted methanol and methane compounds can be used for synthesis of substituted benzaldehydes 5.9 as described above. Scheme VI shows that cylopentane- and cyclopentene-substituted aldehydes 6.10 can be synthesized using an analogous approach.

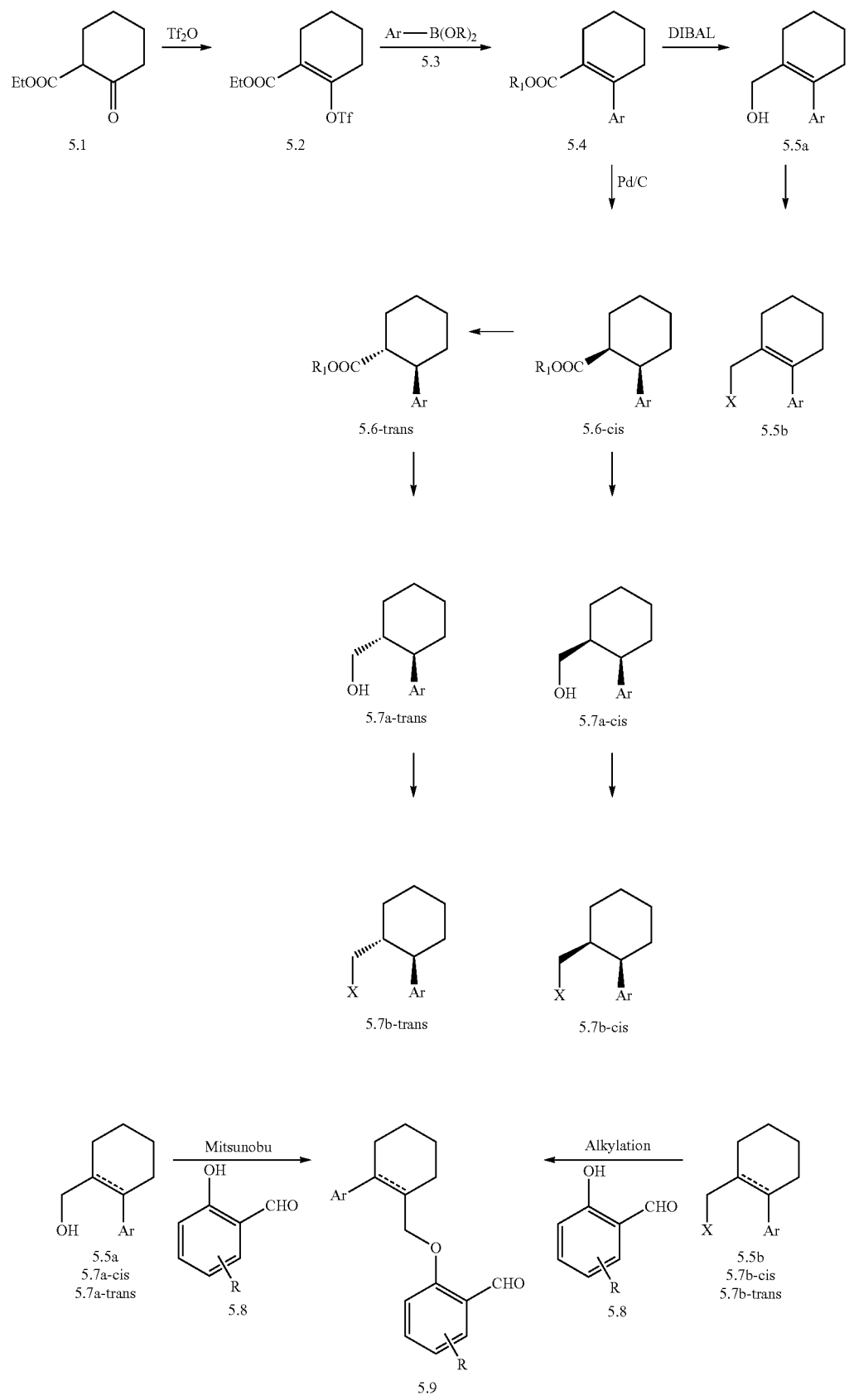

Scheme VI

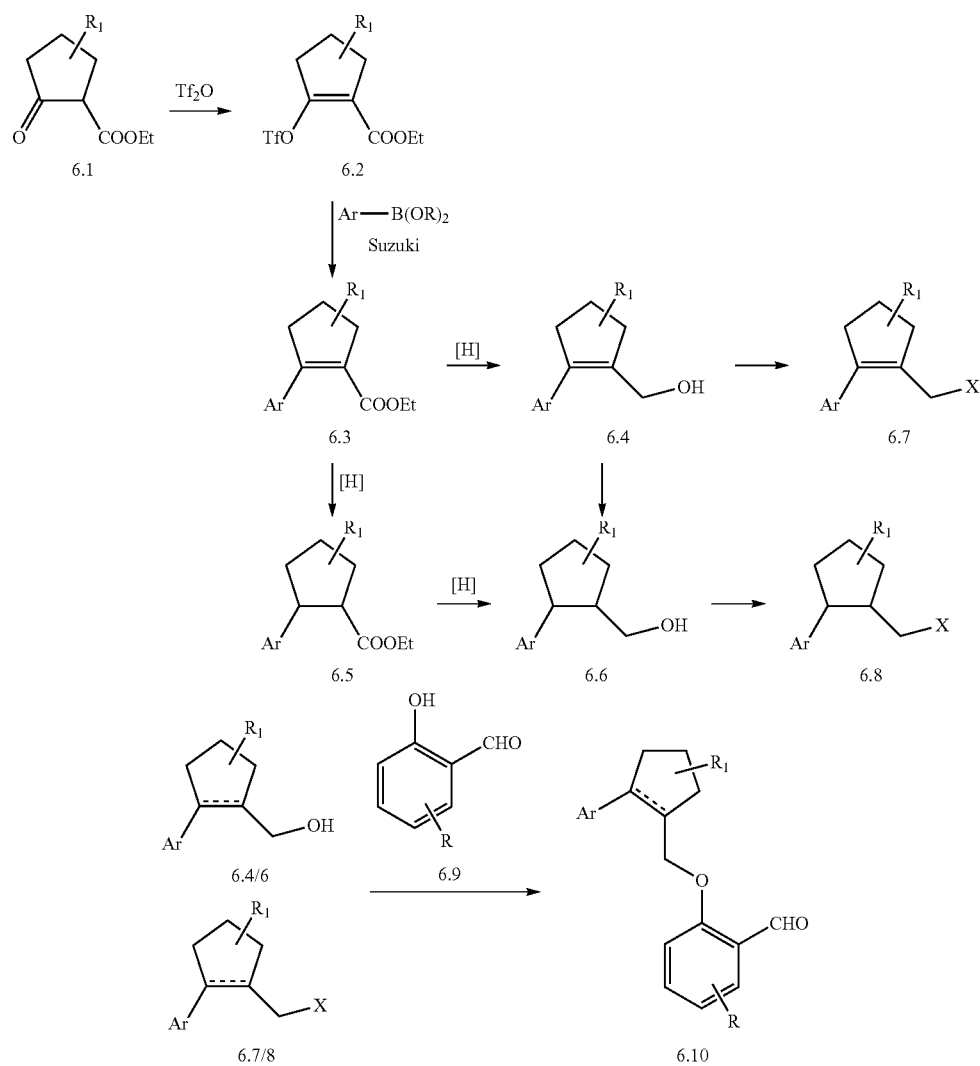

One skilled in the art will recognize that in certain embodiments it may be advantageous to use a protecting group strategy. The protecting group can be removed using methods known to those skilled in the art.

In one group of embodiments, certain of the compounds disclosed herein may generally be utilized as the free base. Alternatively, certain of the compounds may be used in the form of acid addition salts.

It is understood that in another group of embodiments, any of the above embodiments may also be combined with other embodiments listed herein, to form other embodiments of the invention. Similarly, it is understood that in other embodiments, listing of groups includes embodiments wherein one or more of the elements of those groups is not included.

III. Compositions and Methods of Administration

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active compound(s) and which is not toxic or otherwise undesirable to the subject to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The pharmaceutical compositions of this invention may also be formulated in lyophilized form for parenteral administration. Lyophilized formulations may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of the indicated disease.

The pharmaceutical composition may additionally contain one or more other pharmacologically active agents in addition to a compound of this invention.

Dosage forms containing effective amounts of the modulators are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

IV. Methods

In one group of embodiments, the invention provides a method for increasing tissue oxygenation, the method including administering to a subject in need thereof a therapeutically effective amount of a compound according to any of the preceding claims, or a tautomer or pharmaceutically acceptable salt thereof.

In one group of embodiments, the invention provides a method for treating a condition associated with oxygen deficiency, the method including administering to a subject in need thereof a therapeutically effective amount of a compound according to any of the preceding claims, or a tautomer or pharmaceutically acceptable salt thereof.

In one group of embodiments, the invention provides a method for treating a condition associated with oxygen deficiency as described above, wherein the condition is selected from sickle cell disease, cancer, a pulmonary disorder, stroke, high altitude sickness, an ulcer, a pressure sore, Alzheimer's disease, acute respiratory disease syndrome, and a wound V. Examples The following examples are offered to illustrate, but not to limit, the claimed invention.

PREPARATIVE EXAMPLES

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods known in the art.

Example 1

Preparation of cis-methyl4-((2-formyl-3-hydroxyphenoxy)methyl)cyclohexanecarboxylate (Compound 1)

Step 1.

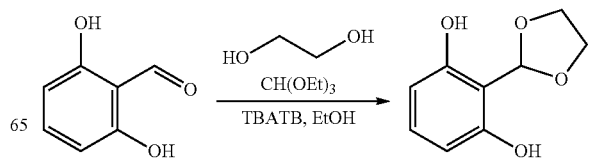

287

To a mixture of 2,6-dihydroxybenzaldehyde (100 mg, 0.73 mmol, 1 eq.) and CH(OEt)$_3$ in EtOH (10.0 mL) were added ethane-1,2-diol (225 mg, 3.62 mmol, 5.0 eq.) and tetrabutylammonium tribromide (TBATB, 3.5 mg, 0.007 mmol, 0.01 eq.). The mixture was stirred at rt for 2 h, diluted with EtOAc (20 mL), washed with water and brine, dried over Na$_2$SO$_4$, concentrated, and purified on silica gel using a mixture of EtOAc and hexanes as eluent to give 2-(1,3-dioxolan-2-yl)benzene-1,3-diol (40 mg, 30%) as a yellow solid. $^1$H NMR (400 MHz, CDCl$_3$) δ 7.96 (s, 2H), 7.07 (t, J=8.2 Hz, 2H), 6.41 (d, J=8.2 Hz, 2H), 6.01 (s, 2H), 3.76-3.66 (m, 4H).

Step 2.

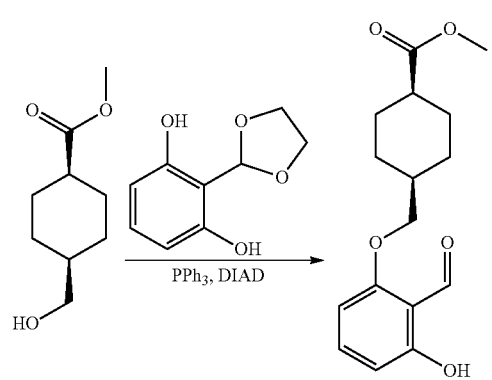

To a mixture of 2-(1,3-dioxolan-2-yl)benzene-1,3-diol (40 mg, 0.22 mmol, 1 eq.), cis-methyl4-(hydroxymethyl) cyclohexanecarboxylate (45 mg, 0.26 mmol, 1.2 eq.), and PPh$_3$ (86 mg, 0.33 mmol, 1.5 eq.) in THF (0.5 mL) was added DIAD (67 mg, 0.33, 1.5 eq.). The mixture was stirred at rt for 1 h and filtered. The filtrate was purified by RP-HPLC (Gemini 21.2×150 mm) using a mixture of CH$_3$CN and water as eluent to give cis-methyl4-((2-formyl-3-hydroxyphenoxy)methyl)cyclohexanecarboxylate (16 mg, 25%) as a colorless oil. $^1$H NMR (400 MHz, CDCl$_3$) δ 11.96 (s, 1H), 10.38 (s, 1H), 7.41 (t, J=8.4 Hz, 1H), 6.53 (d, J=8.4 Hz, 1H), 6.37 (d, J=8.3 Hz, 1H), 3.91 (d, J=6.7 Hz, 2H), 3.72 (s, 3H), 2.66 (quin, J=4.8 Hz, 1H), 2.14-2.05 (m, 2H), 2.04-1.91 (m, 1H), 1.84-1.70 (m, 2H), 1.70-1.57 (m, 2H), 1.52-1.38 (m, 2H). LRMS (M−H$^+$) m/z 291.2.

Example 2

Preparation of cis-4-((2-formyl-3-hydroxyphenoxy)methyl)cyclohexanecarboxylic acid (Compound 2)

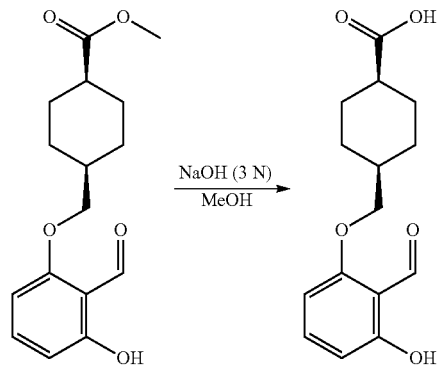 [SMILES: "MeOH" ; COC(=O)[C@H]1CC[C@@H](COc2cccc(O)c2C=O)CC1 ; O=Cc1c(O)cccc1OC[C@H]1CC[C@@H](C(=O)O)CC1]

288

To cis-methyl4-((2-formyl-3-hydroxyphenoxy)methyl) cyclohexanecarboxylate (13 mg, 0.045 mmol, 1 eq.) in MeOH (3.0 mL) was added NaOH (3 N, 1 mL, 4.6 mmol). The mixture was stirred at rt for 2 h, acidified to pH 3, and filtered. The filtrate was purified by RP-HPLC (Gemini 21.2×150 mm) using a mixture of CH$_3$CN and water as eluent to give cis-4-((2-formyl-3-hydroxyphenoxy)methyl) cyclohexanecarboxylic acid (6.0 mg, 49%) as a colorless oil. $^1$H NMR (400 MHz, CDCl$_3$) δ 12.14 (s, 1H), 10.57 (s, 1H), 7.59 (t, J=8.4 Hz, 1H), 6.71 (d, J=8.5 Hz, 1H), 6.55 (d, J=8.4 Hz, 1H), 4.10 (d, J=6.6 Hz, 2H), 2.92 (quin, J=4.5 Hz, 1H), 2.37-2.27 (m, 2H), 2.24-2.14 (m, 1H), 2.03-1.92 (m, 2H), 1.92-1.80 (m, 2H), 1.74-1.60 (m, 2H). LRMS (M−H$^+$) m/z 277.1.

The compounds in Examples 3-7 were prepared according to the procedure described in Examples 1 and 2.

Example 3

Preparation of (1R,3S)-3-((2-formyl-3-hydroxyphenoxy)methyl)cyclohexanecarboxylic acid (Compound 3)

$^1$H NMR (400 MHz, CDCl$_3$) δ 11.95 (s, 1H), 10.39 (s, 1H), 7.40 (t, J=8.4 Hz, 1H), 6.53 (d, J=8.4 Hz, 1H), 6.36 (d, J=8.3 Hz, 1H), 3.95-3.83 (m, 2H), 3.70 (s, 3H), 2.49-2.32 (m, 1H), 2.16 (d, J=12.9 Hz, 1H), 2.10-2.01 (m, 1H), 2.01-1.82 (m, 3H), 1.48-1.22 (m, 3H), 1.22-0.99 (m, 1H).

Example 4

Preparation of trans-methyl4-((2-formyl-3-hydroxyphenoxy)methyl)-cyclohexanecarboxylate (Compound 4)

$^1$H NMR (400 MHz, CDCl$_3$) δ 11.95 (s, 1H), 10.40 (s, 1H), 7.41 (t, J=8.4 Hz, 1H), 6.53 (d, J=8.4 Hz, 1H), 6.36 (d, J=8.3 Hz, 1H), 3.88 (d, J=6.2 Hz, 2H), 2.32 (tt, J=12.3, 3.5 Hz, 1H), 2.10 (dd, J=13.6, 2.7 Hz, 2H), 1.99 (dd, J=13.3, 2.6 Hz, 2H), 1.95-1.77 (m, 1H), 1.53 (ddd, J=25.8, 13.1, 3.3 Hz, 2H), 1.18 (ddd, J=25.4, 13.1, 3.4 Hz, 2H).

Example 5

Preparation of (1R,3S)-3-((2-formyl-3-hydroxyphenoxy)methyl)-cyclohexanecarboxylic acid (Compound 5)

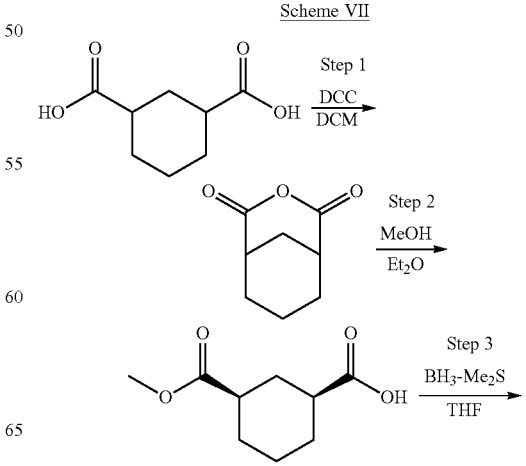

-continued

Step 4

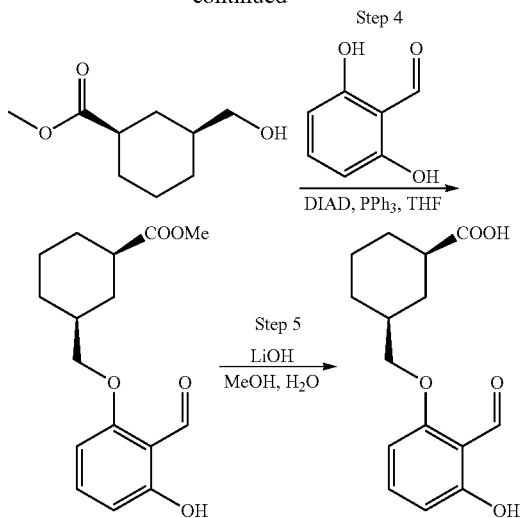

Step 5
LiOH
MeOH, H₂O

Step 1

Into a 150-mL round-bottom flask, which was purged and maintained with an inert atmosphere of nitrogen, was placed a solution of cyclohexane-1,3-dicarboxylic acid (25 g, 145.20 mmol, 1.00 equiv) in dichloromethane (1000 mL). This was followed by the addition of a solution of DCC (29.8 g, 144.43 mmol, 1.00 equiv) in dichloromethane (100 mL) dropwise with stirring in 30 min. The resulting solution was stirred for 4 h at 25° C. The solids were collected by filtration, then dried in an oven under reduced pressure. The crude product was purified by re-crystallization from MTBE. This resulted in 7.2 g (32%) of 3-oxabicyclo[3.3.1]nonane-2,4-dione as a white solid.

Step 2

Into a 150-mL round-bottom flask, which was purged and maintained with an inert atmosphere of nitrogen, was placed a solution of 3-oxabicyclo[3.3.1]nonane-2,4-dione (5.5 g, 35.68 mmol, 1.00 equiv) in ether (100 ml). Methanol (11.4 g, 355.78 mmol, 10.00 equiv) was added to the reaction. The resulting solution was stirred for 24 h at 25° C., and then it was concentrated under vacuum. This resulted in 5.6 g (84%) of cis-3-(methoxycarbonyl)cyclohexane-1-carboxylic acid as a white solid.

Step 3

Into a 150-mL round-bottom flask, which was purged and maintained with an inert atmosphere of nitrogen, was placed a solution of cis-3 (methoxycarbonyl)cyclohexane-1-carboxylic acid (5.5 g, 29.54 mmol, 1.00 equiv) in tetrahydrofuran (200 mL). This was followed by the addition of $BH_3Me_2S(2M)$ (16.5 mL, 1.10 equiv) dropwise with stirring at −78° C. in 30 min. The resulting solution was stirred for 18 h at room temperature, and then it was quenched by the addition of 20 mL of $NH_4Cl$ (sat. aq). The resulting solution was extracted with 3×200 mL of ethyl acetate, and the combined organic layers were dried over anhydrous sodium sulfate and concentrated under vacuum. The residue was applied onto a silica gel column with PE:EA (2:1) as eluent. This resulted in 3.5 g (69%) of methyl cis-3-(hydroxymethyl)cyclohexane-1-carboxylate as a colorless oil.

Step 4

Into a 70-mL round-bottom flask, was placed a solution of methyl cis-3-(hydroxymethyl)cyclohexane-1-carboxylate (598 mg, 3.47 mmol, 1.20 equiv) in tetrahydrofuran (40 mL). 2,6-Dihydroxybenzaldehyde (400 mg, 2.90 mmol, 1.00 equiv), $PPh_3$ (1.14 mg, 1.50 equiv) were added to the reaction mixture. A solution of DIAD (867 mg, 4.29 mmol, 1.50 equiv) in tetrahydrofuran (30 mL) was then added to the reaction mixture dropwise. The resulting solution was stirred for 18 h at 25° C., and then it was concentrated under vacuum. The residue was applied onto a silica gel column with PE:EA (15:1) as eluent. This resulted in 425 mg (50%) of methyl cis-3-(2-formyl-3-hydroxyphenoxymethyl)cyclohexane-1-carboxylate (Compound 3) as a colorless oil.

Step 5

Into a 50-mL round-bottom flask, was placed a solution of methyl cis-3-(2-formyl-3-hydroxyphenoxymethyl)cyclohexane-1-carboxylate (450 mg, 1.54 mmol, 1.00 equiv) in methanol (50 mL). This was followed by the addition of a solution of sodium hydroxide (2.9 g, 72.50 mmol, 50.00 equiv) in water (20 mL) dropwise in 20 min. The resulting solution was stirred overnight at 25° C. The pH value of the solution was adjusted to 4 with HCl (aq.) (3 mol/L). The resulting solution was extracted with 3×50 mL of ethyl acetate, and the combined organic layers were concentrated under vacuum. This resulted in 410 mg (91%) of cis-3-(2-formyl-3-hydroxyphenoxymethyl)cyclohexane-1-carboxylic acid as a light-yellow solid.

$^1$H NMR (300 MHz, CDCl$_3$) δ 11.94 (s, 1H), 11.36 (brs, 1H), 10.35 (s, 1H), 7.42-7.36 (t, J=8.4 Hz, 1H), 6.53-6.5 (d, J=8.4 Hz, 1H), 6.36-6.33 (d, J=8.4 Hz, 1H), 3.93-3.78 (m, 2H), 2.48-2.36 (m, 1H), 2.21-2.06 (m, 2H), 1.95-1.88 (m, 3H), 1.48-1.27 (m, 3H), 1.18-1.08 (m, 1H); MS (ESI) m/z 279 [M+H]$^+$.

Example 6

Synthesis of 2-hydroxy-6-((3,4,5,6-tetrahydro-[1,1'-biphenyl]-2-yl)methoxy)-benzaldehyde (Compound 10)

Scheme VIII

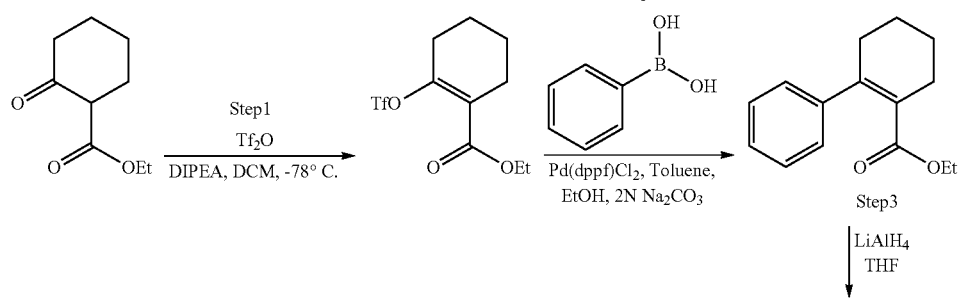

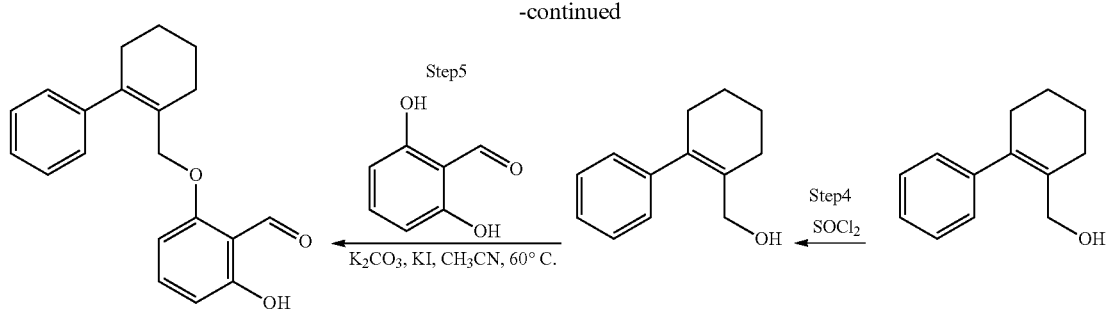

Step 1

Into a 1000-mL 3-necked round-bottom flask, was placed a solution of ethyl2-oxocyclohexane-1-carboxylate (40 g, 235.01 mmol, 1.00 equiv) in dichloromethane (400 mL). This was followed by the addition of DIPEA (92 mL, 2.40 equiv) dropwise with stirring at −78° C. The mixture was stirred for 10 min at −78° C. To this was added Tf$_2$O (44.4 mL, 1.20 equiv) dropwise at −78° C. The resulting solution was stirred overnight at room temperature, and then it was washed with 3×300 mL of brine. The resulting mixture was concentrated under vacuum. The residue was applied onto a silica gel column with ethyl acetate/petroleum ether (1:100-1:10) as eluent. This resulted in 70 g (crude) of ethyl2-[(trifluoromethane)sulfonyloxy]cyclohex-1-ene-1-carboxylate as a yellow oil Step 2

Into a 500-mL round-bottom flask, which was purged and maintained with an inert atmosphere of nitrogen, was placed a solution of ethyl2-[(trifluoromethane)sulfonyloxy]cyclohex-1-ene-1-carboxylate (40 g, 132.33 mmol, 1.10 equiv) in a solvent mixture of toluene and ethanol (150/50 mL). Phenylboronic acid (15 g, 123.02 mmol, 1.00 equiv), sodium carbonate(2M) (50 mL), and Pd(dppf)Cl$_2$ (5 g, 6.83 mmol, 0.05 equiv) were added to the reaction mixture. The resulting solution was stirred for 2 h at 80° C., and then it was diluted with 200 ml of ethyl acetate. The resulting mixture was washed with 2×200 mL of brine, and concentrated under vacuum. The residue was applied onto a silica gel column with EA:PE (1:100-1:10) as eluent to furnish 23 g (81%) of ethyl2-phenylcyclohex-1-ene-1-carboxylate as a yellow oil.

Step 3

Into a 500-mL three neck round-bottom flask, was placed a solution of ethyl2-phenylcyclohex-1-ene-1-carboxylate (22 g, 95.53 mmol, 1.00 equiv) in anhydrous tetrahydrofuran (200 mL). This was followed by the addition of LAH (5.5 g, 144.93 mmol, 1.50 equiv) batchwise at 0° C. The mixture was stirred for 10 min at 0° C., and 3 h at room temperature. The reaction was then quenched with 5 mL of water at 0° C., followed by 15 mL of NaOH (15%), and another 5 mL of water. The mixture was stirred at rt for 1 h. The solids were filtered out. The filtrate was concentrated under vacuum. The residue was applied onto a silica gel column with ethyl acetate/petroleum ether (2:3) as eluent. This resulted in 14 g (78%) of (2-phenylcyclohex-1-en-1-yl)methanol as a colorless oil. $^1$H NMR (300 MHz, CDCl$_3$) δ 7.32 (m, 2H), 7.20 (m, 3H), 4.49 (m, 1H), 3.72 (d, J=5.1 Hz, 2H), 2.21 (m, 4H), 1.65 (m, 4H).

Step 4

Into a 100-mL round-bottom flask, was placed a solution of (2-phenylcyclohex-1-en-1-yl)methanol (4 g, 21.25 mmol, 1.00 equiv) in thionyl chloride (10 mL). The resulting solution was stirred for 2 h at 65° C., and then it was concentrated under vacuum. This resulted in 3.5 g (80%) of [2-(chloromethyl)cyclohex-1-en-1-yl]benzene as a yellow oil.

Step 5

Into a 100-mL round-bottom flask, was placed a solution of [2-(chloromethyl)cyclohex-1-en-1-yl]benzene (1 g, 4.84 mmol, 1.00 equiv) in CH$_3$CN (30 mL). Potassium carbonate (2.03 g, 14.69 mmol, 3.00 equiv), KI (160 mg, 0.96 mmol, 0.20 equiv), and 2,6-dihydroxybenzaldehyde (1 g, 7.24 mmol, 1.50 equiv) were added to the reaction. The resulting solution was stirred for 2 h at 60° C., and then it was concentrated under vacuum. The residue was applied onto a silica gel column with EA:PE (1:100-1:50) as eluent. This resulted in 380 mg (25%) of 2-hydroxy-6-[(2-phenylcyclohex-1-en-1-yl)methoxy]benzaldehyde as a yellow oil. $^1$HNMR (300 MHz, CDCl$_3$) δ 11.94 (s, 1H), 10.38 (s, 1H), 7.17-7.39 (m, 6H), 6.48 (d, J=8.4 Hz, 1H), 6.12 (d, J=8.4 Hz, 1H), 4.41 (s, 2H), 2.36 (m, 4H), 1.79 (m, 4H); MS (ESI) m/z 309 [M+H]$^+$.

Example 7

Synthesis of 2-hydroxy-6-((2-phenylcyclohexyl)methoxy)benzaldehyde (Compound 11)

Scheme IX

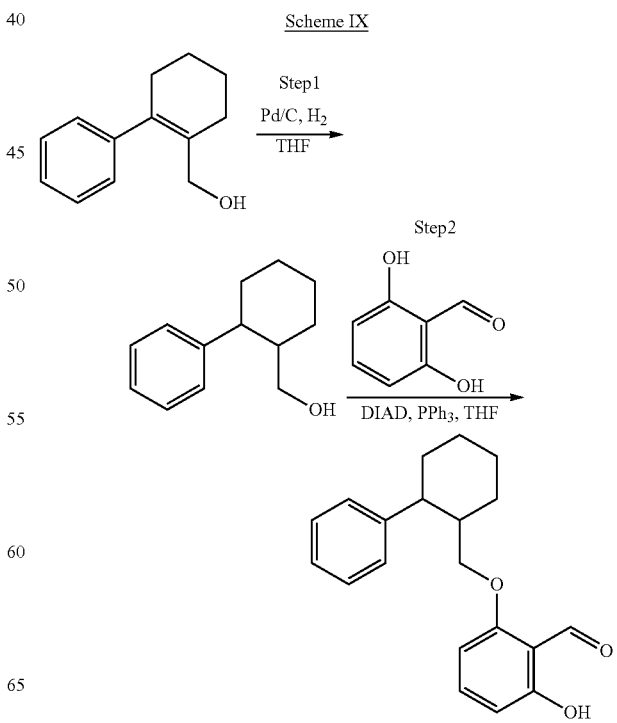

Step 1

Into a 50-mL round-bottom flask, was placed a solution of (2-phenylcyclohex-1-en-1-yl)methanol (1 g, 5.31 mmol, 1.00 equiv) in methanol (20 mL). 10% Palladium on carbon (1 g) was added to the reaction mixture. The resulting solution was stirred overnight at room temperature under hydrogen atmosphere (1 atm). The solids were filtered out. The filtrate was concentrated under vacuum. This resulted in 1 g (89%) of (2-phenylcyclohexyl)methanol as a yellow oil.

Step 2

Into a 50-mL round-bottom flask, was placed a solution of (2-phenylcyclohexyl)methanol (550 mg, 2.89 mmol, 1.00 equiv) in tetrahydrofuran (30 mL). PPh$_3$ (1.14 g, 4.35 mmol, 1.50 equiv), 2,6-dihydroxybenzaldehyde (480 mg, 3.48 mmol, 1.20 equiv) were added to the reaction mixture. This was followed by the addition of a solution of DIAD (877 mg, 4.34 mmol, 1.50 equiv) in tetrahydrofuran (5 mL) dropwise with stirring at 0° C. The resulting solution was stirred overnight at room temperature, and then it was concentrated under vacuum. The residue was applied onto a silica gel column with ethyl acetate/petroleum ether (1:100-1:10) as eluent. This resulted in 190 mg (21%) of 2-hydroxy-6-[(2-phenylcyclohexyl)methoxy]benzaldehyde as a light yellow oil. $^1$HNMR (300 MHz, CDCl$_3$) δ 9.91 (s, 1H), 7.32 (m, 6H), 6.43 (d, J=8.4 Hz, 1H), 6.09 (d, J=8.4 Hz, 1H), 4.01 (m, 1H), 3.75 (m, 1H), 3.02 (m, 1H), 2.51 (m, 1H), 1.42-2.09 (m, 8H); MS (ESI) m/z 311 [M+H]$^+$.

Example 8

Synthesis of 2-hydroxy-6-((2-(1-isopropyl-1H-pyrazol-5-yl)cyclohex-1-en-1-yl)methoxy)benzaldehyde Step 1

Into a 1000-mL 3-necked round-bottom flask, was placed a solution of ethyl2-oxocyclohexane-1-carboxylate (40 g, 235.01 mmol, 1.00 equiv) in dichloromethane (400 mL). This was followed by the addition of DIPEA (92 mL, 2.40 equiv) dropwise with stirring at −78° C. The mixture was stirred for 10 min at −78° C. To this was added Tf$_2$O (44.4 mL, 1.20 equiv) dropwise at −78° C. The resulting solution was stirred overnight at room temperature, and then it was washed with 3×300 mL of brine. The resulting mixture was concentrated under vacuum. The residue was applied onto a silica gel column with ethyl acetate/petroleum ether (1:100-1:10) as eluent. This resulted in 70 g (crude) of ethyl2-[(trifluoromethane)sulfonyloxy]cyclohex-1-ene-1-carboxylate as a yellow oil.

Step 2

Into a 1000-mL round-bottom flask, which was purged and maintained with an inert atmosphere of nitrogen, was placed a solution of 1-(propan-2-yl)-5-(tetramethyl-1,3,2-dioxaborolan-2-yl)-1H-pyrazole (19 g, 80.47 mmol, 1.00 equiv) in toluene (363 mL). Pd(dppf)Cl$_2$ (2.98 g, 4.07 mmol, 0.05 equiv), sodium carbonate(2M) (121 mL, 3.00 equiv), and ethyl2-[(trifluoromethane)sulfonyloxy]cyclohex-1-ene-1-carboxylate (26.74 g, 88.46 mmol, 1.10 equiv) in ethanol (121 mL) were added to the reaction mixture. The resulting solution was stirred for 2 h at 80° C. in an oil bath, and then it was diluted with 200 mL of ethyl acetate. The resulting mixture was washed with 2×200 mL of brine, dried over anhydrous sodium sulfate and concentrated under vacuum. The residue was applied onto a silica gel column with ethyl acetate/petroleum ether (1:100-1:20) as eluent to furnish 12.73 g (51%) of ethyl2-[1-(propan-2-yl)-1H-pyrazol-5-yl]cyclohex-1-ene-1-carboxylate as a red oil.

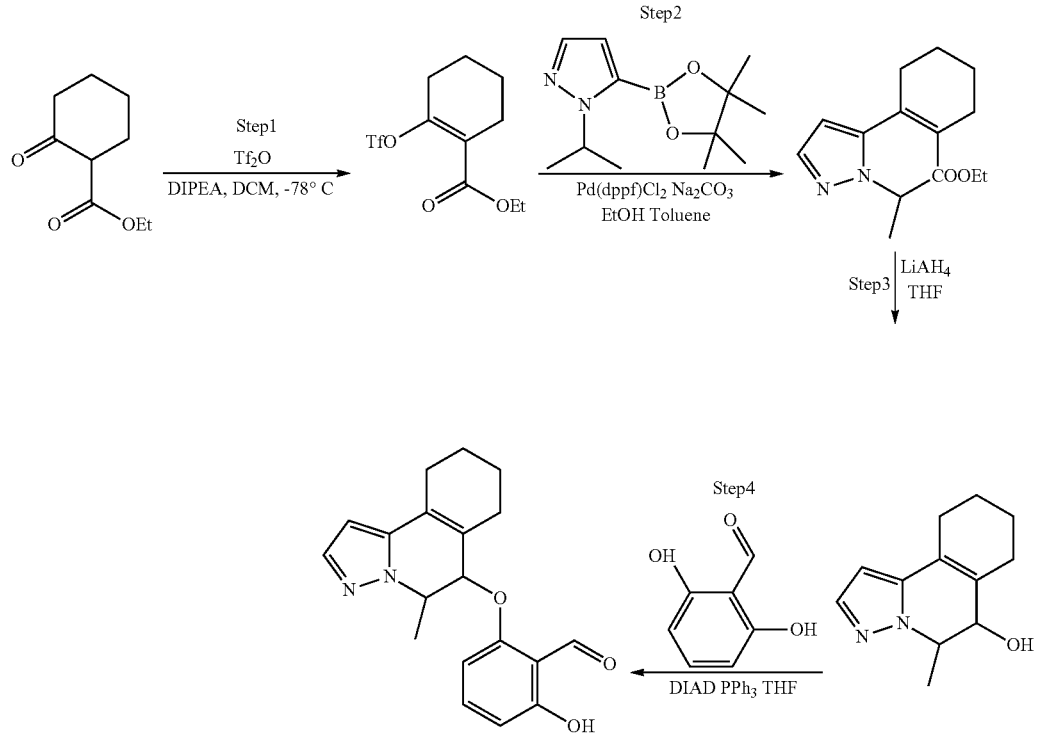

Scheme X

Step 3

Into a 500-mL round-bottom flask, was placed a suspension of LiAlH$_4$ (5.52 g, 145.26 mmol, 3.00 equiv) in tetrahydrofuran (200 mL). This was followed by the addition of a solution of ethyl2-[1-(propan-2-yl)-1H-pyrazol-5-yl]cyclohex-1-ene-1-carboxylate (12.73 g, 48.52 mmol, 1.00 equiv) in tetrahydrofuran (100 mL) dropwise with stirring at 0° C. The resulting solution was stirred for 2 h at 0° C. in an ice/salt bath. The reaction was then quenched by the addition of 5.52 mL of water and 5.52 mL of 10% aq.NaOH. The solids were filtered out. The resulting mixture was concentrated under vacuum. The residue was applied onto a silica gel column with PE:EA (20:1-5:1) as eluent to yield 6.6 g (59%) of [2-[1-(propan-2-yl)-1H-pyrazol-5-yl]cyclohex-1-en-1-yl]methanol as a white solid.

Step 4

Into a 100-mL round-bottom flask, which was purged and maintained with an inert atmosphere of nitrogen, was placed a solution of [2-[1-(propan-2-yl)-1H-pyrazol-5-yl]cyclohex-1-en-1-yl]methanol (700 mg, 3.18 mmol, 1.00 equiv) in tetrahydrofuran (20 mL). 2,6-Dihydroxybenzaldehyde (445 mg, 3.22 mmol, 1.00 equiv) and triphenylphosphine (1.08 g, 4.12 mmol, 1.30 equiv) were added to the reaction mixture. This was followed by the addition of DIAD (838 mg, 3.20 mmol, 1.30 equiv) dropwise with stirring at 0° C. The resulting solution was stirred for 4 h at room temperature, and then it was concentrated under vacuum. The crude product (300 mg) was purified by Prep-HPLC with the following conditions (Prep-HPLC-010): Column, SunFire Prep C18 OBD Column, 5 um, 19*150 mm; mobile phase, water with 0.1% TFA and MeCN (65% MeCN up to 85% in 8 min, up to 95% in 2 min, down to 65% in 1 min); Detector, Waters2545 UvDector 254&220 nm. This resulted in 415.6 mg (28%) of 2-hydroxy-6-([2-[1-(propan-2-yl)-1H-pyrazol-5-yl]cyclohex-1-en-1-yl]methoxy)benzaldehyde as a white solid. $^1$H-NMR (300 MHz, DMSO-d$_6$) δ 10.26 (s, 1H), 7.43 (m, 2H), 6.47 (d, J=8.4 Hz, 1H), 6.35 (d, J=8.4 Hz, 1H), 6.04 (d, J=1.5 Hz, 1H), 4.35 (m, 1H), 4.29 (s, 2H), 2.31 (m, 2H), 2.19 (m, 2H), 1.72 (m, 4H), 1.26 (d, J=6.6 Hz, 6H); MS (ESI) m/z 341 [M+H]$^+$.

Example 9

Synthesis of cis-3-[[2-(2-propylpyrazol-3-yl)cyclohexyl]methoxy]pyridine-2-carbaldehyde (Compound 174a), trans-3-[[2-(2-propylpyrazol-3-yl)cyclohexyl]methoxy]pyridine-2-carbaldehyde (Compound 174b), and 3-[[2-(2-propylpyrazol-3-yl)cyclohexen-1-yl]methoxy]pyridine-2-carbaldehyde (Compound 374)

The title compounds are prepared according to scheme XI below.

Ethyl2-oxocyclohexane-1-carboxylate 11.5 is converted to the triflate intermediate 11.6 by treating with a triflic anhydride in the presence of Hunig's base (Step 1). Suzuki coupling of triflate 11.6 with boronic ester 11.7 affords cyclohexene carboxylate 11.8 (Step 2). "Ar" in Scheme XI represents 2-propylpyrazol-3-yl. The cyclohexene carboxylate 11.8 is divided in two portions. Using the first portion, subsequent reduction of the ester group by DIBAL gives the corresponding alcohol 11.9-OH (Step 3). Further reaction of the alcohol 11.9-OH with mesyl chloride produces the corresponding 10-OMs mesylate (Step 5).

Using the second portion of cyclohexene carboxylate 11.8, the double bond is reduced first to give the cis-cyclohexane 11.11-cis carboxylate under palladium catalyzed hydrogenation conditions (Step 4). Reduction of the ester group of 11.11-cis by LAH yields cis-alcohol 11.12-OH-cis (Step 7). Conversion of the alcohol 11.12-OH-cis the corresponding chloride 11.13-Cl-cis is conducted via reaction with thionyl chloride (Step 8). The cis-cyclohexane carboxylate 11.11-cis can also be isomerized to the thermodynamically more stable trans-isomer 11.11-trans by the treatment with an alcoholic ethoxide solution. Analogously, transformation of 11.11-trans ester to 11.12-trans alcohol and 11.13-Cl-trans is conducted by applying conditions of Step 7 and Step 8 as for the corresponding cis-isomers.

Scheme XI

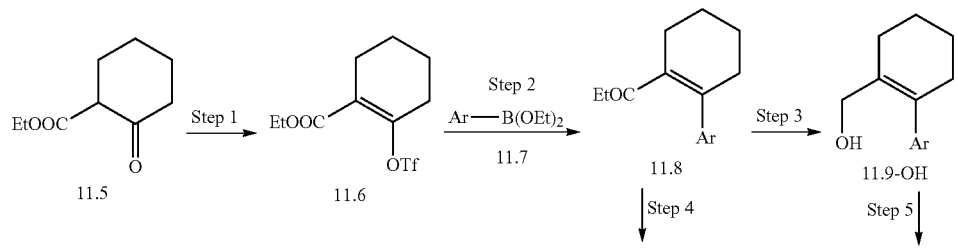

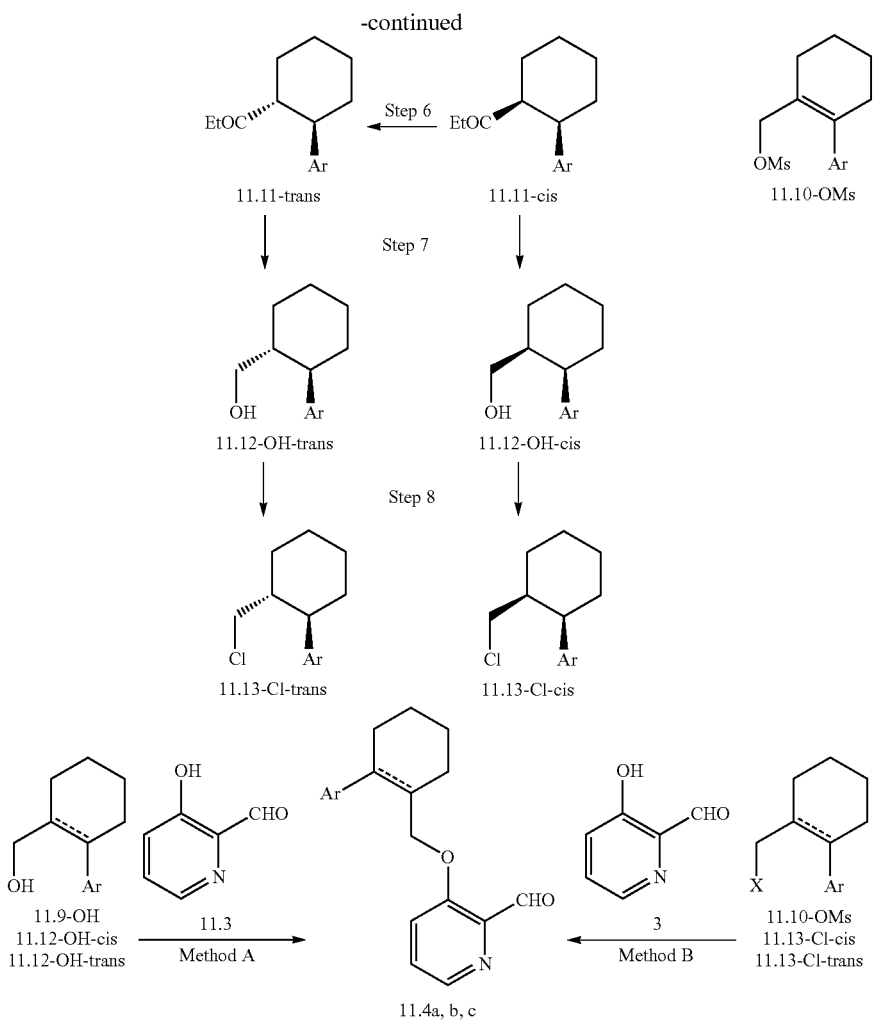

3-hydroxypicolinaldehyde 11.3 (0.1-2 mmol) is combined with with substituted methylene alcohol 11.9-OH (0.8 to 1.2 eq) and PPh₃ (1-1.5 eq) in anhydrous THF (1-10 mL) and stirred under nitrogen until complete dissolution occurs. The solution is cooled to 0° C. in an ice bath and DIAD (1.1 eq) in THF is added dropwise over a 20 min period (Method A). The ice bath is allowed to room temperature over 90 min and the mixture is stirred at room temperature for 2-48 hours. The mixture is stirred for an additional 10 min, and is then filtered through a pad of silica. The silica is washed with ethyl acetate 2-20 mL. The combined filtrates are evaporated and the residue is dried in vacuo. The residue is purified by flash silica gel chromatography to provide 3-[[2-(2-propylpyrazol-3-yl)cyclohexen-1-yl]methoxy]pyridine-2-carbaldehyde (Compound 374).

3-hydroxypicolinaldehyde 11.3 (0.1-2 mmol, 1-4 eq.), substituted methylene chloride 11.13-Cl-cis (1 eq), and K₂CO₃ (2-5 eq.) in acetonitrile (5 mL) is stirred at RT or heated up to 120° C. for 0.5-8 h under nitrogen atmosphere. Aqeuous NH₄Cl is added at 0° C. and pH is adjusted to ~7. The reaction mixture is partitioned between dichloromethane and aqueous sodium chloride. The organic layer is separated and dried, and the solvent is removed under vacuum to afford crude product. The crude product is purified by automated silica gel column chromatography using ethyl acetate/hexanes to afford cis-3-[[2-(2-propylpyrazol-3-yl)cyclohexyl]methoxy]pyridine-2-carbaldehyde (Compound 174a). The same procedure is used to prepare trans-3-[[2-(2-propylpyrazol-3-yl)cyclohexyl]methoxy]pyridine-2-carbaldehyde (Compound 174b) and other cis- and trans-cyclohexane substituted pyridine-carbaldehydes listed in Table 1.

Example 10

Preparation of Compound Intermediates

General method A—Mitsunobu coupling. A hydroxyl (hetero)arylaldehyde derivative (0.1-2 mmol) mixture with substituted methylene alcohol (0.8 to 1.2 eq) and (polymer-supported) PPh₃ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was filtered through a pad of silica. The silica was washed with ethyl acetate 2-20 mL. The combined filtrates were evaporated and the residue was dried on highvac. The residue was purified by preparative HPLC or flash silica gel chromatography.

Preparation of 2,6-dihydroxybenzaldehyde (INT-1)

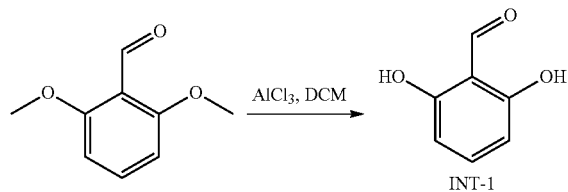

INT-1

Into a 3000-mL three neck round-bottom flask, was placed a solution of AlCl$_3$ (240 g, 1.80 mol, 3.00 equiv) in dichloromethane (1200 mL). A solution of 2,6-dimethoxybenzaldehyde (100 g, 601.78 mmol, 1.00 equiv) in dichloromethane (800 ml) was added to the reaction mixture dropwise at 0° C. The resulting solution was stirred overnight at room temperature, and then it was quenched with 200 mL of diluted HCl (2M). The resulting solution was extracted with 2×200 mL of dichloromethane. The combined organic layers were concentrated under vacuum. The residue was applied onto a silica gel column with ethyl acetate/petroleum ether (1:200-1:50) as eluent to furnish 40 g (48%) of 2,6-dihydroxybenzaldehyde as a yellow solid. $^1$HNMR (300 MHz, DMSO-d$_6$) δ 11.25 (s, 2H), 10.25 (s, 1H), 7.36 (m, 1H), 6.36 (d, J=8.4 Hz 2H); MS (ESI) m/z 139 [M+H]$^+$.

Preparation of 2-hydroxy-6-(methoxymethoxy)benzaldehyde (INT-2)

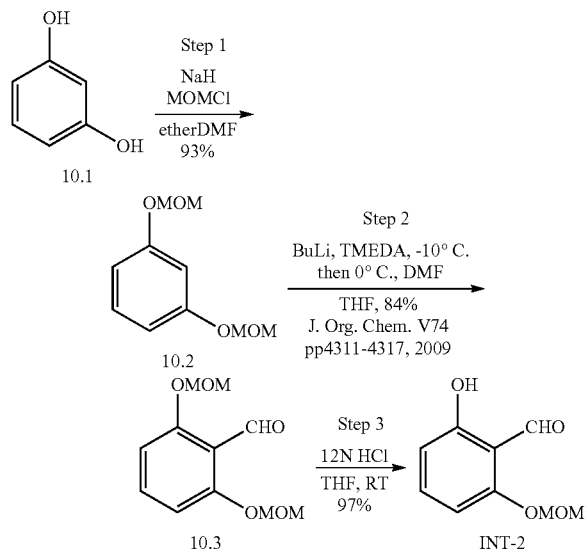

Step 1.

A three-necked round-bottom flask equipped with mechanical stirrer was charged with 0.22 mol of NaH (50% suspension in mineral oil) under nitrogen atmosphere. NaH was washed with 2 portions (100 mL) of n-hexane and then with 300 mL of dry diethyl ether; then 80 mL of anhydrous DMF was added. Then 0.09 mol of resorcinol 10.1, dissolved in 100 mL of diethyl ether was added dropwise and the mixture was left under stirring at rt for 30 min. Then 0.18 mol of MOMCl was slowly added. After 1 h under stirring at rt, 250 mL of water was added and the organic layer was extracted with diethyl ether. The extracts were washed with brine, dried (Na$_2$SO$_4$), then concentrated to give the crude product that was purified by silica gel chromatography to give compound 10.2 (93% yield).

Step 2.

A three-necked round-bottom flask was charged with 110 mL of n-hexane, 0.79 mol of BuLi and 9.4 mL of tetramethylethylendiamine (TMEDA) under nitrogen atmosphere. The mixture was cooled to −10° C. and 0.079 mol of bis-phenyl ether 10.2 was slowly added. The resulting mixture was left under magnetic stirring at −10° C. for 2 h. Then the temperature was raised to 0° C. and 0.067 mol of DMF was added dropwise. After 1 h, aqueous HCl was added until the pH was acidic; the mixture was then extracted with ethyl ether. The combined extracts were washed with brine, dried (Na$_2$SO$_4$), and concentrated to give aldehyde 10.3 (84%). 2,6-bis(methoxymethoxy)benzaldehyde (10.3): mp 58-59° C. (n-hexane); IR (KBr) n: 1685 (C=O) cm$^{-1}$; $^1$H-NMR (400 MHz, CDCl$_3$) δ 3.51 (s, 6H, 2OCH$_3$), 5.28 (s, 4H, 2OCH$_2$O), 6.84 (d, 2H, J=8.40 Hz, H-3, H-5), 7.41 (t, 1H, J=8.40 Hz, H-4), 10.55 (s, 1H, CHO); MS, m/e (relative intensity) 226 (M+, 3), 180 (4), 164 (14), 122 (2), 92 (2), 45 (100); Anal. Calc'd for C$_{11}$H$_{14}$O$_5$: C, 58.40; H, 6.24. Found: C, 57.98; H, 6.20.

Step 3.

To a solution of 2,6-bis(methoxymethoxy)benzaldehyde 10.3 (15.3 g, 67.6 mmol) in THF (105 mL) (solvent was purged with N$_2$) was added conc HCl (12N, 7 mL) under N$_2$, then it was further stirred under N$_2$ for 1.5 h. To the solution were added brine (100 mL) and ether (150 ml). The organic layer was separated and the aqueous layer was further extracted with ether (2×200 mL). The combined organics were washed with brine, dried and concentrated to give crude product, which was purified by column (300 g, hexanes/EtOAc=85:15) to give the desired product (9.9 g, 97%) as a yellow liquid.

Example 11

Preparation of 2-hydroxy-6-((2-(1-isopropyl-1H-pyrazol-5-yl)cyclopent-1-en-1-yl)methoxy)benzaldehyde (compound 571) and 2,6-dihydroxy-3-((2-(1-isopropyl-1H-pyrazol-5-yl)cyclopent-1-en-1-yl)methyl)benzaldehyde (compound 572)

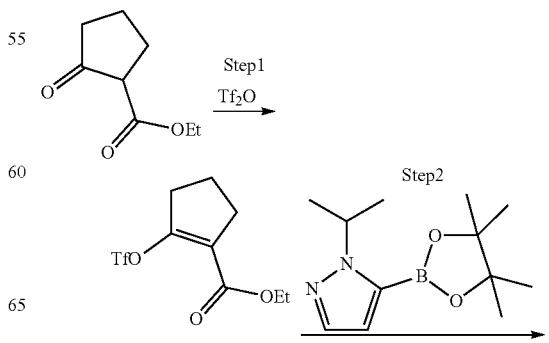

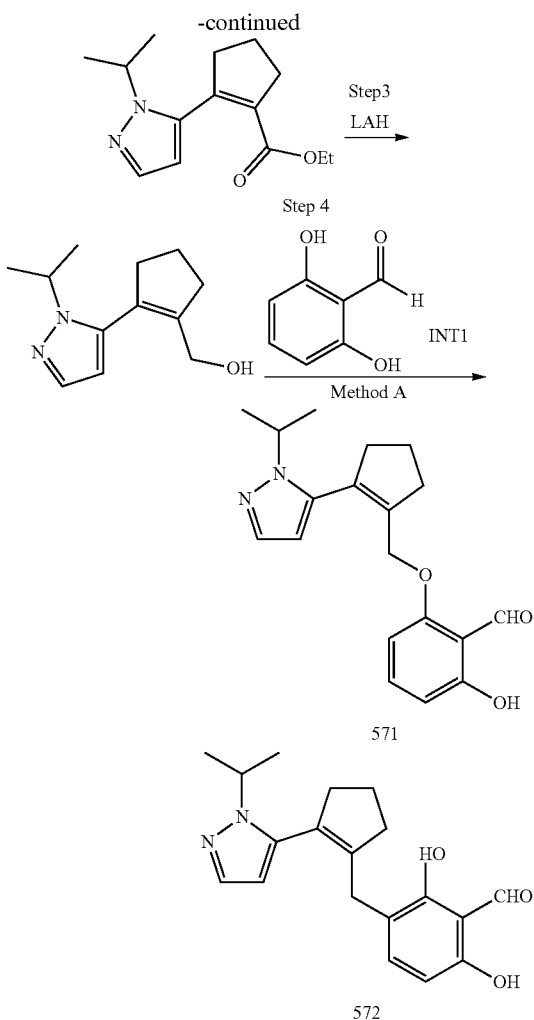

Step 1.

Into a 500-mL three neck round-bottom flask, which was purged and maintained with an inert atmosphere of nitrogen, was placed a solution of ethyl2-oxocyclopentane-1-carboxylate (46.8 g, 299.66 mmol, 1.00 equiv) in dichloromethane (200 mL). This was followed by the addition of TEA (43.8 mL) dropwise with stirring at −78° C. in 30 min. To this was added (trifluoromethane)sulfonyl trifluoromethanesulfonate (52.2 mL) dropwise with stirring at −78° C. in 1 h. The resulting solution was stirred for 5 h at room temperature, and then it was quenched by the addition of 100 mL of water. The resulting solution was extracted with 2×50 mL of dichloromethane. The combined organic layers were dried over anhydrous sodium sulfate and concentrated under vacuum to provide 82.3 g (95%) of ethyl2-[(trifluoromethane)sulfonyloxy]cyclopent-1-ene-1-carboxylate as a light yellow oil.

Step 2.

Into a 250-mL round-bottom flask, which was purged and maintained with an inert atmosphere of nitrogen, was placed a solution of ethyl2-[(trifluoromethane)sulfonyloxy]cyclopent-1-ene-1-carboxylate (3.0 g, 10.41 mmol, 1.00 equiv) in toluene (60 mL). 1-(Propan-2-yl)-5-(tetramethyl-1,3,2-dioxaborolan-2-yl)-1H-pyrazole (2.95 g, 12.49 mmol, 1.20 equiv), Pd(dppf)Cl$_2$ (425 mg, 0.58 mmol, 0.06 equiv), 2N sodium carbonate aqueous solution (20 mL) and ethanol (20 mL) were added to the reaction. The resulting solution was stirred for 5 h at 80° C., and then it was quenched with 30 mL of water. The resulting solution was extracted with 3×30 mL of dichloromethane. The combined organic layers were dried over anhydrous sodium sulfate and concentrated under vacuum. The residue was applied onto a silica gel column with ethyl acetate/petroleum ether (1:10) as eluent to yield 1.38 g (53%) of ethyl2-[1-(propan-2-yl)-1H-pyrazol-5-yl]cyclopent-1-ene-1-carboxylate as a light yellow oil.

Step 3.

Into a 30-mL round-bottom flask, was placed a solution of ethyl2-[1-(propan-2-yl)-1H-pyrazol-5-yl]cyclopent-1-ene-1-carboxylate (600 mg, 2.42 mmol, 1.00 equiv) in tetrahydrofuran (30 mL). LAH (186 mg, 4.90 mmol, 2.03 equiv) was added to the reaction solution. The resulting solution was stirred for 3 h at room temperature, and then it was quenched by the addition of 20 mL of water. The resulting solution was extracted with 3×20 mL of dichloromethane. The combined organic layers were dried over anhydrous sodium sulfate and concentrated under vacuum. The residue was applied onto a silica gel column with ethyl acetate/petroleum ether (1:3) as eluent to yield 0.492 g (99%) of [2-[1-(propan-2-yl)-1H-pyrazol-5-yl]cyclopent-1-en-1-yl]methanol as a light yellow oil.

Step 4 (Method A).

Into a 50-mL round-bottom flask, which was purged and maintained with an inert atmosphere of nitrogen, was placed a solution of [2-[1-(propan-2-yl)-1H-pyrazol-5-yl]cyclopent-1-en-1-yl]methanol (300 mg, 1.45 mmol, 1.00 equiv) in tetrahydrofuran (20 mL). 2,6-Dihydroxybenzaldehyde (201 mg, 1.46 mmol, 1.00 equiv) and PPh$_3$ (458 mg, 1.75 mmol, 1.20 equiv) were added to the reaction. This was followed by the addition of DIAD (353 mg, 1.75 mmol, 1.20 equiv) dropwise with stirring at 0° C. The resulting solution was stirred for 5 h at room temperature, and then it was quenched by the addition of 20 mL of water. The resulting solution was extracted with 3×15 mL of dichloromethane. The combined organic layers were dried over anhydrous sodium sulfate and concentrated under vacuum. The crude product (200 mg) was purified by Prep-HPLC with the following conditions (Prep-HPLC-010): Column, SunFire Prep C18 OBD Column, 5 um, 19*150 mm; mobile phase, water with 0.05% TFA and MeCN (65.0% MeCN up to 85.0% in 10 min, up to 95.0% in 3 min, down to 65.0% in 2 min); Detector, Waters2545 UvDector 254&220 nm. This provided 26.5 mg (4%) of 2-hydroxy-6-([2-[1-(propan-2-yl)-1H-pyrazol-5-yl]cyclopent-1-en-1-yl]methoxy)benzaldehyde (compound 571) trifluoroacetic acid salt as a white solid and 58.5 mg (9%) of 2,6-dihydroxy-3-([2-[1-(propan-2-yl)-1H-pyrazol-5-yl]cyclopent-1-en-1-yl]methyl)benzaldehyde trifluoroacetic acid salt as a yellow solid (compound 572).

Compound 571: $^1$H NMR (400 MHz, DMSO-d$_6$) δ 11.74 (s, 1H), 10.10 (s, 1H), 7.45-7.49 (t, 2H), 6.47-6.53 (m, 2H), 6.12 (s, 1H), 4.64 (s, 2H), 4.35-4.41 (t, 1H), 2.67-2.70 (t, 4H), 1.98-2.05 (s, 2H), 1.31 (s, 6H); MS (ESI) m/z 327 [M+H]$^+$.

Compound 572: $^1$H NMR (400 MHz, DMSO-d$_6$) δ 11.92 (s, 1H), 10.77 (s, 1H), 10.24 (s, 1H), 7.44 (s, 1H), 7.09 (s, 1H), 6.38 (d, 1H), 6.07 (s, 1H), 4.32-4.39 (t, 1H), 3.19 (s, 2H), 2.60 (s, 2H), 2.33 (s, 2H), 1.90 (s, 3H), 1.34 (s, 6H); MS (ESI) m/z 327 [M+H]$^+$.

Example 12

Preparation of 2-hydroxy-6-((2-(1-isopropyl-1H-pyrazol-5-yl)cyclopentyl)-methoxy)benzaldehyde (Compound 573)

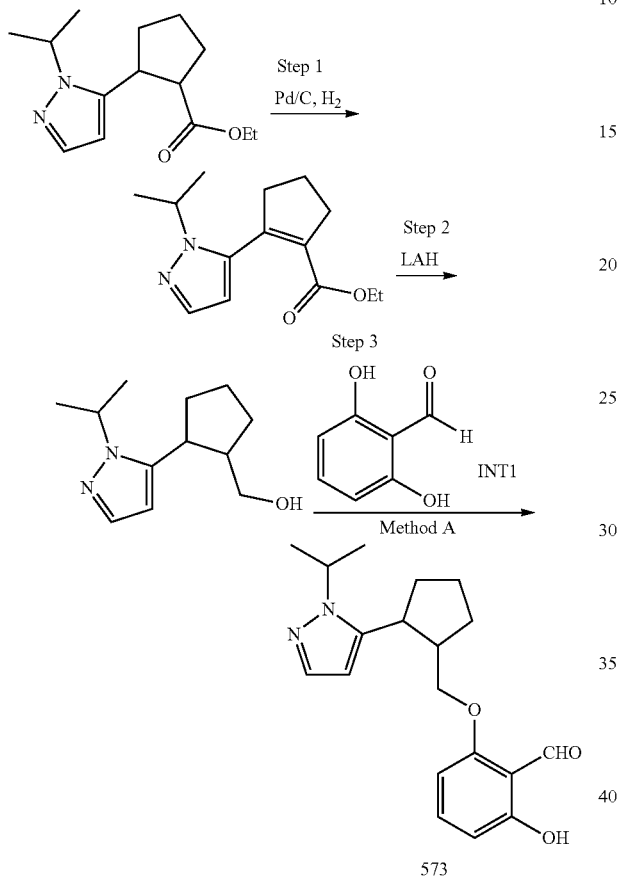

Step 1.

Into a 50-mL round-bottom flask, was placed a solution of ethyl2-[1-(propan-2-yl)-1H-pyrazol-5-yl]cyclopent-1-ene-1-carboxylate (780 mg, 3.14 mmol, 1.00 equiv) in ethanol (20 mL). 10% Palladium on carbon (0.5 g) was added to the reaction mixture. The resulting solution was stirred for 48 h at room temperature under 1 atm of hydrogen gas. The solids were filtered out. The resulting mixture was concentrated under vacuum. This provided 0.6375 g (81%) of ethyl2-[1-(propan-2-yl)-1H-pyrazol-5-yl]cyclopentane-1-carboxylate as a yellow oil.

Step 2.

Into a 50-mL round-bottom flask, which was purged and maintained with an inert atmosphere of nitrogen, was placed a solution of ethyl2-[1-(propan-2-yl)-1H-pyrazol-5-yl]cyclopentane-1-carboxylate (637.5 mg, 2.55 mmol, 1.00 equiv) in tetrahydrofuran (20 mL). LAH (194 mg, 5.11 mmol, 2.01 equiv) was added to the reaction. The resulting solution was stirred for 2 h at room temperature, and then it was quenched by the addition of 5 mL of water. The resulting solution was extracted with 3×5 mL of dichloromethane and the combined organic layers were dried over anhydrous sodium sulfate and concentrated under vacuum. This provided 0.446 g (84%) of [2-[1-(propan-2-yl)-1H-pyrazol-5-yl]cyclopentyl]methanol as a yellow oil.

Step 3 (Method A).

Into a 50-mL round-bottom flask, which was purged and maintained with an inert atmosphere of nitrogen, was placed a solution of [2-[1-(propan-2-yl)-1H-pyrazol-5-yl]cyclopentyl]methanol (446 mg, 2.14 mmol, 1.00 equiv), 2,6-dihydroxybenzaldehyde (296 mg, 2.14 mmol, 1.00 equiv), and $PPh_3$ (674 mg, 2.57 mmol, 1.20 equiv) in tetrahydrofuran (30 mL). This was followed by the addition of DIAD (519 mg, 2.57 mmol, 1.20 equiv) dropwise with stirring at 0° C. The resulting solution was stirred for 5 h at room temperature. The reaction was then quenched by the addition of 20 mL of water. The resulting solution was extracted with 3×15 mL of dichloromethane and the combined organic layers were dried over anhydrous sodium sulfate and concentrated under vacuum. The crude product (500 mg) was purified by Prep-HPLC with the following conditions (Prep-HPLC-010): Column, SunFire Prep C18 OBD Column, 5 um, 19*150 mm; mobile phase, water with 0.05% TFA and MeCN (65.0% MeCN up to 85.0% in 10 min, up to 95.0% in 2 min, down to 65.0% in 2 min); Detector, Waters2545 UvDector 254&220 nm. This provided 189.5 mg (20%) of 2-hydroxy-6-([2-[1-(propan-2-yl)-1H-pyrazol-5-yl]cyclopentyl]methoxy)benzaldehyde; trifluoroacetic acid as a white solid. $^1$H NMR (400 MHz, DMSO-$d_6$) δ 11.74 (s, 1H), 10.05 (s, 1H), 7.45 (t, 1H), 7.32 (s, 1H), 6.47 (d, J=8.4 Hz, 1H), 6.35 (d, J=8.4 Hz, 1H), 6.04 (s, 1H), 4.64 (s, 1H), 3.76 (t, 1H), 3.62 (t, 1H), 3.48 (m, 1H), 2.71 (s, 1H), 2.00 (m, 2H), 1.98 (s, 2H), 1.88 (Ss, 2H), 1.33 (s, 6H); MS (ESI) m/z 329 [M+H]$^+$.

Example 13

Preparation of 2-hydroxy-6-((2-(2-methoxypyridin-3-yl)cyclopent-1-en-1-yl)methoxy)benzaldehyde (Compound 574)

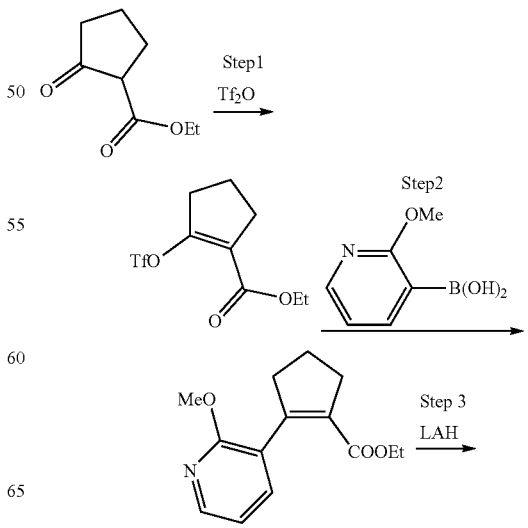

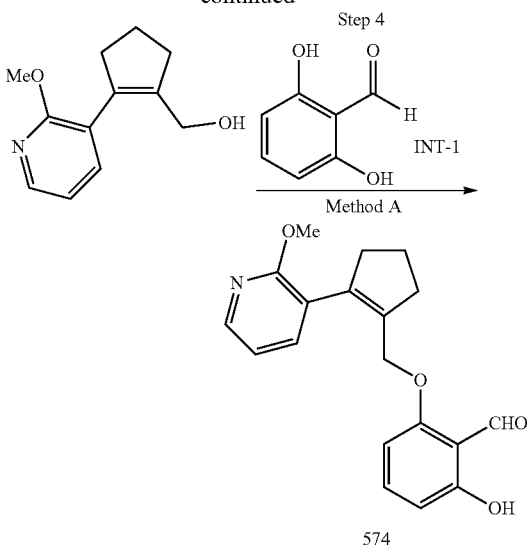

Step 1.

Into a 100-mL round-bottom flask, which was purged and maintained with an inert atmosphere of nitrogen, was placed ethyl2-[(trifluoromethane)sulfonyloxy]cyclopent-1-ene-1-carboxylate (1.44 g, 5.00 mmol, 1.00 equiv), (2-methoxypyridin-3-yl)boronic acid (1.07 g, 7.00 mmol, 1.40 equiv), toluene (30 mL), ethanol (10 mL), and sodium carbonate (2M in $H_2O$) (10 mL). This was followed by the addition of Pd(dppf)(DCM)$Cl_2$ (327 mg, 0.08 equiv). The resulting solution was stirred for 3 h at 100° C. The reaction was then quenched by the addition of 20 mL of water. The resulting solution was extracted with 3×30 mL of ethyl acetate. The combined organic layers were washed with 2×80 mL of water and 1×80 mL of brine. The mixture was dried over anhydrous sodium sulfate and concentrated under vacuum. The residue was applied onto a silica gel column with ethyl acetate/petroleum ether (1:20-1:8) as eluent to furnish 1.12 g (91%) of ethyl2-(2-methoxypyridin-3-yl)cyclopent-1-ene-1-carboxylate as a colorless oil.

Step 2.

Into a 50-mL round-bottom flask, was placed a solution of ethyl2-(2-methoxypyridin-3-yl)cyclopent-1-ene-1-carboxylate (570 mg, 2.30 mmol, 1.00 equiv) in tetrahydrofuran (20 mL). This was followed by the addition of LAH (220 mg, 5.80 mmol, 2.50 equiv) at 0° C. The resulting solution was stirred for 3 h at room temperature, and then it was quenched with 10 mL of 2.5M NaOH aq. The resulting solution was extracted with 3×30 mL of ethyl acetate. The combined organic layers were washed with 1×40 mL of water and 1×40 mL of brine. The mixture was dried over anhydrous sodium sulfate and concentrated under vacuum. The residue was applied onto a silica gel column with ethyl acetate/petroleum ether (1:10-1:6) as eluent to furnish 428 mg (90%) of [2-(2-methoxypyridin-3-yl)cyclopent-1-en-1-yl]methanol as a colorless oil.

Step 3 (Method A).

Into a 50-mL round-bottom flask, was placed a solution of [2-(2-methoxypyridin-3-yl)cyclopent-1-en-1-yl]methanol (428 mg, 2.09 mmol, 1.00 equiv), 2,6-dihydroxybenzaldehyde (374 mg, 2.71 mmol, 1.30 equiv), $PPh_3$ (709 mg, 2.70 mmol, 1.30 equiv) in tetrahydrofuran (20 mL). This was followed by the addition of DIAD (546 mg, 2.70 mmol, 1.30 equiv) dropwise with stirring at 0° C. The resulting solution was stirred for 30 min at 0° C. and for an additional hour at room temperature. The reaction was then quenched by the addition of 20 mL of water. The resulting solution was extracted with 3×40 mL of ethyl acetate. The combined organic layers were washed with 1×30 mL of water and 1×30 mL of brine, dried over anhydrous sodium sulfate and concentrated under vacuum. The residue was applied onto a silica gel column with ethyl acetate/petroleum ether (1:10-1:8) as eluent. The crude product was purified by Prep-HPLC with the following conditions (Prep-HPLC-010): Column, XBridge Shield RP18 OBD Column, 5 um, 19*150 mm; mobile phase, water with 0.05% TFA and MeCN (50.0% MeCN up to 75.0% in 10 min, up to 95.0% in 2 min, down to 50.0% in 2 min); Detector, Waters2545 UvDector 254&220 nm. This provided 140 mg (21%) of 2-hydroxy-6-[[2-(2-methoxypyridin-3-yl)cyclopent-1-en-1-yl]methoxy]benzaldehyde as a light yellow solid. $^1$H NMR (400 MHz, DMSO-$d_6$) δ 9.98 (s, 1H), 8.08 (dd, J=5.4 Hz, 2.0 Hz, 1H), 7.51 (dd, J=5.4 Hz, 2.0 Hz, 1H), 7.43 (d, J=8.4 Hz, 1H), 6.69-6.96 (m, 1H), 6.44 (dd, J=16.0 Hz, 8.4 Hz, 1H), 6.73 (s, 2H), 3.80 (s, 3H), 2.72-2.61 (m, 4H), 1.98-1.92 (m, 2H); MS (ESI) m/z 326.2 [M+H]$^+$.

Example 14

Preparation of 2-hydroxy-6-((2-(2-methoxypyridin-3-yl)cyclopentyl)methoxy)-benzaldehyde (Compound 575)

Scheme XVII

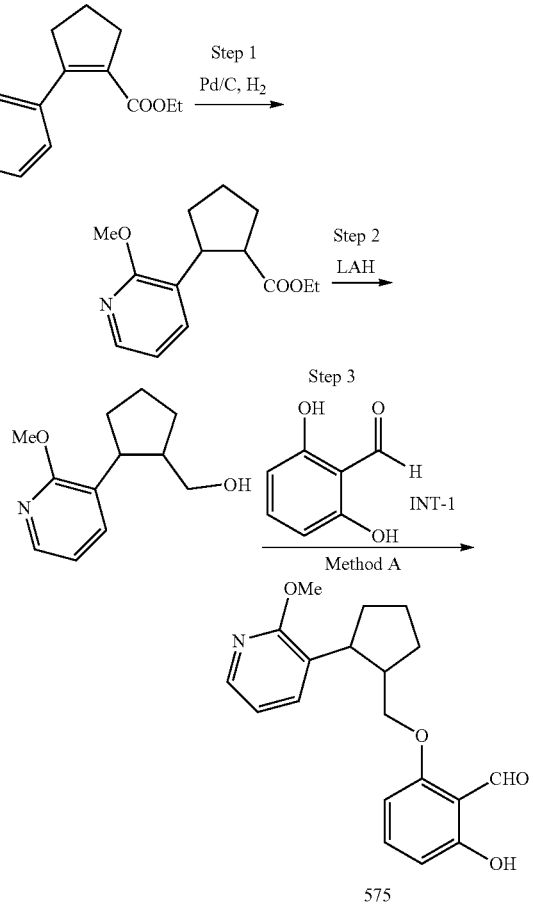

Step 1.

Into a 50-mL round-bottom flask, was placed ethyl2-(2-methoxypyridin-3-yl)cyclopent-1-ene-1-carboxylate (530 mg, 2.14 mmol, 1.00 equiv), Palladium on carbon (200 mg) and ethanol (15 mL). The resulting solution was stirred for 18 h at room temperature under hydrogen atmosphere. The solids were filtered out. The resulting mixture was concentrated under vacuum. This provided 534 mg (100%) of ethyl2-(2-methoxypyridin-3-yl)cyclopentane-1-carboxylate as a colorless oil.

Step 2.

Into a 50-mL round-bottom flask, was placed a solution of ethyl2-(2-methoxypyridin-3-yl)cyclopentane-1-carboxylate (534 mg, 2.14 mmol, 1.00 equiv) in tetrahydrofuran (20 mL). This was followed by the addition of LAH (200 mg, 5.27 mmol, 2.50 equiv), in one portion at 0° C. The resulting solution was stirred for 30 min at 0° C. and for an additional 3 h at room temperature. The reaction was then quenched by the addition of 15 mL of 2.5M NaOH aq. The resulting solution was extracted with 3×40 mL of ethyl acetate. The combined organic layers were washed with 1×40 mL of water and 1×40 mL of brine, dried over anhydrous sodium sulfate and concentrated under vacuum. The residue was applied onto a silica gel column with ethyl acetate/petroleum ether (1:6) as eluent to yield 415 mg (93%) of [2-(2-methoxypyridin-3-yl)cyclopentyl]methanol as a colorless oil.

Step 3 (Method A).

Into a 50-mL round-bottom flask, was placed a solution of 2,6-dihydroxybenzaldehyde (416 mg, 3.01 mmol, 1.30 equiv), [2-(2-methoxypyridin-3-yl)cyclopentyl]methanol (480 mg, 2.32 mmol, 1.00 equiv), PPh$_3$ (787 mg, 3.00 mmol, 1.30 equiv) in tetrahydrofuran (20 mL). This was followed by the addition of DIAD (607 mg, 3.00 mmol, 1.30 equiv) dropwise with stirring at 0° C. The resulting solution was stirred for 30 min at 0° C. and for an additional 1 h at room temperature. The reaction was then quenched by the addition of 20 mL of water. The resulting solution was extracted with 3×40 mL of ethyl acetate. The combined organic layers were washed with 1×40 mL of water and 1×20 mL of brine. The mixture was dried over anhydrous sodium sulfate and concentrated under vacuum. The residue was applied onto a silica gel column with ethyl acetate/petroleum ether (1:15). The crude product was purified by Prep-HPLC with the following conditions (Prep-HPLC-010): Column, XBridge Shield RP18 OBD Column, 5 um, 19*150 mm; mobile phase, water with 0.05% TFA and MeCN (61.0% MeCN up to 77.0% in 8 min, up to 95.0% in 2 min, down to 61.0% in 2 min); Detector, Waters2545 UvDector 254&220 nm. This provided 264 mg (35%) of 2-hydroxy-6-[[2-(2-methoxy-pyridin-3-yl)cyclopentyl]methoxy]benzaldehyde as a light yellow semi-solid. $^1$H NMR (400 MHz, CDCl$_3$) δ 11.91 (s, 1H), 10.04 (s, 1H), 7.98 (d, J=1.6 Hz, 1H), 7.43 (d, J=8.4 Hz), 7.26 (d, J=8.4 Hz, 2H), 6.80-6.70 (m, 1H), 6.42 (d, J=8.4 Hz, 1H), 6.05 (d, J=8.4 Hz, 1H), 3.93 (s, 3H), 3.67-3.60 (m, 1H), 3.58-3.40 (m, 2H), 4.00-3.85 (m, 1H), 2.20-1.50 (m, 6H); MS (ESI) m/z 328.2 [M+H]$^+$.

Example 15

Preparation of 2-((2-(8-oxa-3-azabicyclo[3.2.1]octan-3-yl)cyclohexyl)-methoxy)-6-hydroxybenzaldehyde (Compound 576)

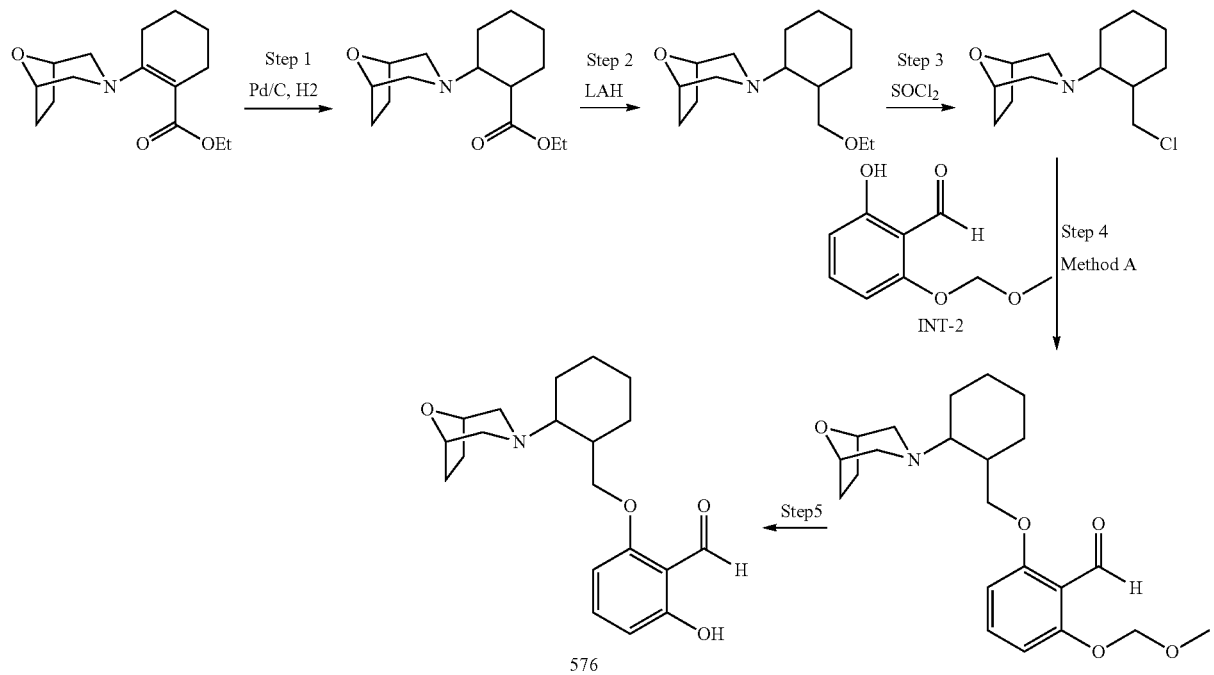

Step 1.

trans-Ethyl2-(8-oxa-3-azabicyclo[3.2.1]octan-3-yl)cyclohexanecarboxylate. To a cooled (0° C.) solution of ethyl2-oxocyclohexanecarboxylate (0.64 g, 4.0 mmol) in dichloromethane (5 mL) was added triacetoxyborohydride (1.7 g, 8.0 mmol) followed by acetic acid (0.26 g, 4.4 mmol). The mixture was stirred at ambient temperature for 12 hours and then washed with saturated aqueous NaHCO$_3$. The aqueous layer was extracted two times with CH2Cl2 and the combined organic layers were washed with brine, dried over MgSO$_4$ and concentrated in vacuo. Purification by silica gel chromatography yielded trans-ethyl 2-(8-oxa-3-azabicyclo[3.2.1]octan-3-yl)cyclohexanecarboxylate (0.65 g, 61% yield) as a clear oil. MS (ES) for $C_{15}H_{25}NO_3$: 268 (MH$^+$).

Step 2.

trans-2-(8-oxa-3-azabicyclo[3.2.1]octan-3-yl)cyclohexyl)methanol. To a cooled (0° C.) solution of trans-ethyl2-(8-oxa-3-azabicyclo[3.2.1]octan-3-yl)cyclohexanecarboxylate (0.28 g, 1.0 mmol) in THF (5 mL) was added a solution of lithium aluminum hydride (3.2 mL, 1M in THF). The reaction mixture was stirred for 1 h and then 120 µL of H$_2$O was added followed by 120 µL of 15% NaOH (aq) and then 360 µL of additional H$_2$O. The slurry was stirred for 1 h, filtered and the resulting residue was washed with ether. The combined organic layers were dried over MgSO$_4$ and concentrated in vacuo. Purification by column chromotography (EtOAc/hexanes, 0-100%) provided trans-2-(8-oxa-3-azabicyclo[3.2.1]octan-3-yl)cyclohexyl)methanol (0.20 g, 85% yield). MS (ES) for $C_{13}H_{23}NO_2$: 226 (MH$^+$).

Step 3.

trans-3-(2-(chloromethyl)cyclohexyl)-8-oxa-3-azabicyclo[3.2.1]octane. To a cooled (0° C.) solution of trans-2-(8-oxa-3-azabicyclo[3.2.1]octan-3-yl)cyclohexyl)methanol (0.220 g, 0.98 mmol) in dichloromethane was added SOCl$_2$ (0.58 g, 4.9 mmol) and the reaction mixture was allowed to warm to ambient temperature. After 1 h, the reaction mixture was concentrated and azeotroped with toluene to provide trans-3-(2-(chloromethyl)cyclohexyl)-8-oxa-3-azabicyclo[3.2.1]octane (0.24 g, 99%) as a clear oil. MS (ES) for $C_{13}H_{22}ClNO$: 244 (MH$^+$).

Step 4 (Method A).

2-((trans-2-(8-oxa-3-azabicyclo[3.2.1]octan-3-yl)cyclohexyl)methoxy)-6-(methoxymethoxy)benzaldehyde. To a solution of 2-hydroxy-6-(methoxymethoxy)benzaldehyde (0.24 g, 1.5 mmol) in DMF was added trans-3-(2-(chloromethyl)cyclohexyl)-8-oxa-3-azabicyclo[3.2.1]octane (0.24 g, 0.97 mmol) and potassium carbonate (0.67 g, 4.8 mmol). The reaction mixture was heated (90° C.) for 30 minutes and partitioned between EtOAc and saturated aqueous NaHCO$_3$. The aqueous layer was extracted with EtOAc and the combined organic layers were washed with brine, dried over MgSO$_4$ and concentrated in vacuo. Purification by silica gel chromatography provided 2-((trans-2-(8-oxa-3-azabicyclo[3.2.1]octan-3-yl)cyclohexyl)methoxy)-6-(methoxymethoxy)benzaldehyde (0.23 g, 62%) as a clear oil. MS (ES) for $C_{22}H_{31}NO_5$: 390 (MH$^+$).

Step 5.

2-(trans-2-(8-oxa-3-azabicyclo[3.2.1]octan-3-yl)cyclohexyl)methoxy)-6-hydroxybenzaldehyde. To a solution of 2-((trans-2-(8-oxa-3-azabicyclo[3.2.1]octan-3-yl)cyclohexyl)methoxy)-6-(methoxymethoxy)benzaldehyde (0.23 g, 0.59 mmol) in THF (5 mL) was added concentrated HCl (1 mL). The resulting solution was heated (50° C.) for 30 minutes and partitioned between EtOAc and saturated aqueous NaHCO$_3$. The aqueous layer was extracted with EtOAc two times and the combined organic layers were washed with brine, dried over MgSO$_4$ and concentrated in vacuo. Purification by silica gel chromatography provided 2-(trans-2-(8-oxa-3-azabicyclo[3.2.1]octan-3-yl)cyclohexyl)methoxy)-6-hydroxybenzaldehyde (0.180 mg, 88% yield) as a white powder. $^1$H NMR (400 MHz, Chloroform-d) δ 11.95 (s, 1H), 10.34 (d, J=0.6 Hz, 1H), 7.41 (t, J=8.4 Hz, 1H), 6.51 (dt, J=8.5, 0.7 Hz, 1H), 6.43 (dd, J=8.4, 0.8 Hz, 1H), 4.33-4.20 (m, 3H), 4.04 (dd, J=10.4, 9.3 Hz, 1H), 2.78 (dt, J=11.2, 1.8 Hz, 1H), 2.70 (dt, J=10.9, 1.7 Hz, 1H), 2.51 (dt, J=10.8, 4.1 Hz, 1H), 2.32-2.17 (m, 3H), 2.14-1.71 (m, 8H), 1.51-1.20 (m, 4H), 1.19-1.02 (m, 1H). MS (ES) for $C_{20}H_{27}NO_4$: 346 (MH$^+$).

Example 16

Preparation of 2-hydroxy-6-((2-(1-isopropyl-1H-pyrazol-5-yl)cyclohept-1-en-1-yl)methoxy)-benzaldehyde (Compound 577)

Scheme XIX

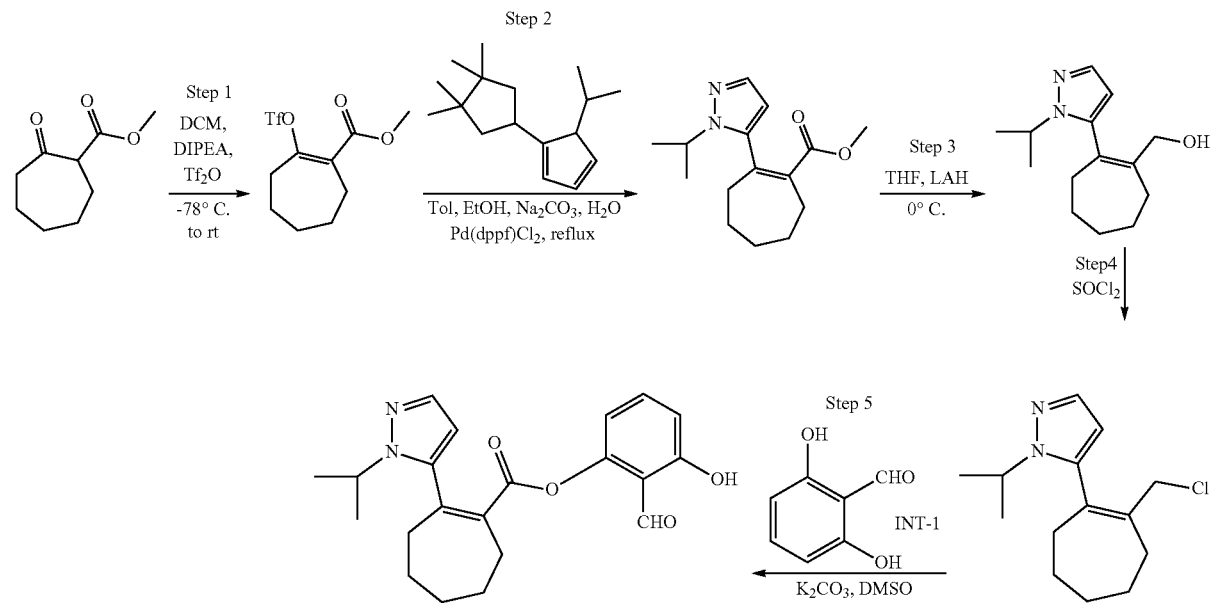

577

Step 1.

Into a 50-mL 3-necked round-bottom flask, was placed a solution of methyl2-oxocycloheptane-1-carboxylate (1 g, 5.88 mmol, 1.00 equiv) in dichloromethane (10 mL). This was followed by the addition of DIPEA (2.3 mL, 2.40 equiv) dropwise with stirring at −78° C. The mixture was stirred for 10 mins at −78° C. To this was added Tf2O (1.1 mL, 1.20 equiv) dropwise with stirring at −78° C. The resulting solution was stirred overnight at room temperature. The resulting solution was diluted with 100 mL of dichloromethane. The resulting mixture was washed with 2×50 mL of brine, dried over anhydrous sodium sulfate and concentrated under vacuum. The residue was applied onto a silica gel column with ethyl acetate/petroleum ether (1:40~1:4) as eluent. This provided 1.1 g (62%) of methyl2-[(trifluoromethane)sulfonyloxy]cyclohept-1-ene-1-carboxylate as a brown oil.

Step 2.

Into a 50-mL round-bottom flask, which was purged and maintained with an inert atmosphere of nitrogen, was placed 1-(propan-2-yl)-5-(tetramethyl-1,3,2-dioxaborolan-2-yl)-1H-pyrazole (771 mg, 3.27 mmol, 1.10 equiv), methyl2-[(trifluoromethane)sulfonyloxy]cyclohept-1-ene-1-carboxylate (900 mg, 2.98 mmol, 1.00 equiv), Tol (19.8 mL), ethanol (6.6 mL), water (6.6 mL), sodium carbonate (940.6 mg, 8.87 mmol, 2.98 equiv), and Pd(dppf)Cl2 (183.2 mg, 0.25 mmol, 0.08 equiv). The resulting solution was stirred overnight at 90° C. in an oil bath. The resulting mixture was concentrated under vacuum. The residue was applied onto a silica gel column with ethyl acetate/petroleum ether (1:10) as eluent. This provided 632 mg (81%) of methyl2-[1-(propan-2-yl)-1H-pyrazol-5-yl]cyclohept-1-ene-1-carboxylate as a brown oil.

Step 3.

Into a 50-mL round-bottom flask, which was purged and maintained with an inert atmosphere of nitrogen, was placed a solution of methyl2-[1-(propan-2-yl)-1H-pyrazol-5-yl]cyclohept-1-ene-1-carboxylate (553 mg, 2.11 mmol, 1.00 equiv) in tetrahydrofuran (9.2 mL). This was followed by the addition of LAH (243.2 mg, 6.41 mmol, 3.04 equiv) at 0° C. The resulting solution was stirred for 0.5 h at 0° C. in a water/ice bath. The reaction was then quenched by the addition of 2.3 mL of EA. The resulting solution was diluted with 50 mL of H$_2$O. The resulting solution was extracted with 3×100 mL of dichloromethane and the organic layers combined and dried over anhydrous sodium sulfate and concentrated under vacuum. The residue was applied onto a silica gel column with ethyl acetate/petroleum ether (1:2) as eluent. This provided 464 mg (94%) of [2-[1-(propan-2-yl)-1H-pyrazol-5-yl]cyclohept-1-en-1-yl]methanol as a yellow oil.

Step 4.

Into a 50-mL round-bottom flask purged and maintained with an inert atmosphere of nitrogen, was placed [2-[1-(propan-2-yl)-1H-pyrazol-5-yl]cyclohept-1-en-1-yl]methanol (273 mg, 1.16 mmol, 1.00 equiv) in dichloromethane (10 mL). This was followed by the addition of thionyl chloride (0.25 mL) dropwise with stirring at 0° C. The resulting solution was stirred for 0.5 h at 0° C. in a water/ice bath. The resulting mixture was concentrated under vacuum. This provided 295 mg (100%) of 5-[2-(chloromethyl)cyclohept-1-en-1-yl]-1-(propan-2-yl)-1H-pyrazole as a yellow oil.

Step 5.

Into a 100-mL round-bottom flask, was placed 2,6-dihydroxybenzaldehyde (241.5 mg, 1.75 mmol, 1.50 equiv), 5-[2-(chloromethyl)cyclohept-1-en-1-yl]-1-(propan-2-yl)-1H-pyrazole (295.2 mg, 1.17 mmol, 1.00 equiv), potassium carbonate (194.5 mg, 1.41 mmol, 1.21 equiv), DMSO (3.2 mL), NaI (16.2 mg, 0.10 equiv). The resulting solution was stirred for 1.5 h at 55° C. and overnight at room temperature. The resulting solution was diluted with 100 mL of 1M HCl. The resulting solution was extracted with 3×200 mL of dichloromethane and the organic layers combined and dried over anhydrous sodium sulfate and concentrated under vacuum. The crude product (200 mg) was purified by Prep-HPLC with the following conditions (Prep-HPLC-010): Column, Gemini-NX C18 AXAI Packed, 21.2*150 mm 5 um 11 nm; mobile phase, WATER WITH 0.05% TFA and MeCN (5.0% MeCN up to 35.0% in 10 min); Detector, nm. This provided 100.3 mg (24%) of 2-hydroxy-6-([2-[1-(propan-2-yl)-1H-pyrazol-5-yl]cyclohept-1-en-1-yl]methoxy)benzaldehyde as a brown oil. $^1$H NMR (400 MHz, CDCl$_3$) δ 10.37 (s, 1H), 7.76 (s, 1H), 7.36 (t, 1H, J=8.4 Hz), 6.55 (d, 1H, J=8.4 Hz), 6.16 (d, 1H, J=8.0 Hz), 6.10 (s, 1H), 4.52-4.46 (m, 1H), 4.32-4.25 (brs, 1H), 2.62-2.50 (m, 3H), 2.45-2.41 (m, 1H), 1.95-1.91 (m, 2H), 1.68-1.66 (m, 4H), 1.53 (d, 3H, J=6.8 Hz), 1.45 (d, 3H, J=6.4 Hz); MS (ESI) m/z 355.4 [M+H]$^+$.

In Vitro Testing

Example 17

Modulation of Hemoglobin Oxygen Affinity by Substituted Benzaldehyde Compounds—Assay Procedure Oxygen equilibrium curves (OEC) in purified Hemoglobin S (HbS) were measured by the change in p50, the partial pressure of oxygen at which the heme binding sites in the HbS sample are 50% saturated with oxygen. HbS was purified by a modified procedure (Antonini and Brunori, 1971; Hemoglobin and Myoglobin in their Reactions with Ligands; North Holland Publishing Company; Amsterdam, London) from blood obtained from homozygous sickle cell patients though the Hemoglobinopathy Center at Children's Hospital Oakland Research Institute (CHORI) with Institutional Review Board approval. Oxygen equilibrium curves were carried out with a HEMOX analyzer, (TCS Scientific, New Hope, Pa.). Five hundred μL of 250 μM purified HbS were diluted into 4.5 mL of HEMOX buffer (30 mM TES, 130 mM NaCl, 5 mM KCl, pH=7.4) resulting in a final hemoglobin concentration of 25 μM. The compounds were added at the final desired concentrations. The mixture was incubated for 45 min at 37° C. and then transferred to the Hemox sample chamber. The samples were saturated with oxygen by flushing with compressed air for 10 minutes. The samples were then flushed with pure nitrogen and the absorbance of deoxy-Hb was recorded as a function of the solution pO$_2$. The oxygen equilibrium data was then fit to the Hill Model to obtain values for p50. The deoxygenation curves for both HbS alone (control) and HbS in the presence of compound were collected with the TCS software. The p50 for purified Hbs was typically 13.8±1.6. Delta p50 values were obtained from the p50 value for control minus the p50 value for HbS treated with compound divided by the p50 value for the control. A positive delta p50 value corresponds to a left shifted curve and a lower p50 value relative to control, indicating that the compound acts to modulate HbS to increase its affinity for oxygen.

Example 18

Modulation of Hemoglobin Oxygen Affinity by Substituted Benzaldehyde Compounds—Assay Results The compounds of Table 1 that were where tested in the assay above were all found to have positive delta p50 values.

Delta p50% is calculated from [[p50(HbS)-p50(HbS treated with compound)]/p50(HbS)]×100. Table 2 below lists the delta p50% values where + indicates a delta p50% of between 0 and 29 and ++ indicates a delta p50% of 30 or greater. Unless noted otherwise, the compounds in Table 2 were tested at 30 µM.

TABLE 2

| Compound | delta p50 |
|---|---|
| 1 | ++ |
| 2 | ++ |
| 3 | ++ |
| 4 | ++ |
| 5 | ++ |
| 6 | ++ |
| 7 | ++ |
| 8 | + |
| 9 | + |

Example 19

Polymerization Assay

Polymerization assays are carried out in vitro using purified HBS exchanged into 1.8 M potassium phosphate buffer at pH 7.4. Using a slightly modified protocol (Antonini and Brunori, 1971), HbS is purified by the CRO VIRUSYS, from blood obtained from homozygous sickle cell patients through the Hemoglobinopathy Center at Children's Hospital Oakland Research Institute (CHORI) with Institutional Review Board approval. Compounds are prepared in 100% DMSO and a desired amount is added to 50 µM of purified HBS at a final DMSO concentration of 0.3%. Final potassium phosphate concentration is adjusted to 1.8 M using a combination of 2.5 M potassium phosphate stock solution and water at pH 7.4. The reaction mixture is incubated for an hour at 37° C. and then transferred into a 24-well plate for deoxygenation in a glove box containing 99.5% nitrogen and 0.5% oxygen. The 24-well plate is not covered and incubated at 4° C. on a plate cooler inside the glove box for one and a half hours. Fifty µL of the reaction mixture is transferred into a 96-well plate and the absorbance at 700 nm is measured every minute for one hour at 37° C. in a plate reader located inside the glove box. A plot of the absorbance against time is fitted using a Boltzman sigmoidal fit and the delay time (from zero to time at half Vmax) is measured. To compare and rank compounds, delay times are expressed as percent delay (% DT), which is defined as the difference in delay times for HBS/compound and HBS alone multiplied by 100 and divided by the delay time for HBS alone.

Compounds listed below have been tested in the polymerization assay. Activity ranges are defined by the number of dagger (†) symbols indicated. † denotes activity ≥40% but ≤80%; †† denotes activity >80% but ≤120%; ††† denotes activity >120% but ≤140%; †††† denotes activity >160%.

TABLE 3

| Compound | % delta Delay |
|---|---|
| 1 | †† |
| 2 | †††† |
| 3 | †† |

TABLE 3-continued

| Compound | % delta Delay |
|---|---|
| 4 | ††† |
| 5 | †††† |
| 6 | †† |
| 7 | †† |
| 8 | † |
| 10 | †† |
| 11 | † |

Example 20

R/T Assay

A relaxed-to-tense transition assay ("R/T assay") was used to determine the ability of substituted benzaldehyde compounds to maintain the high-oxygen affinity relaxed (R) state of hemoglobin under deoxygenated conditions. This ability can be expressed as a "delta R" value (i.e., the change in the time-period of the R state after hemoglobin is treated with a compound, as compared to the period without treatment with the compound). Delta R is the % R to remaining after the compounds treatment compared with no treatment (e.g. if R % without treatment is 8% while with treatment with a target compound is 48% R at 30 µM, then % R is 40% for that compound.

A mixture of HbS/A was purified from blood obtained from homozygous sickle cell patients though the Hemoglobinopathy Center at Children's Hospital Oakland Research Institute (CHORI) with Institutional Review Board approval. HbS/A (at a final concentration of 3 µM) was incubated for 1 hr at 37° C. in presence or absence of compounds in 50 µM potassium phosphate buffer, pH=7.4 and 30 µM 2, 3 diphosphoglycerate (DPG) in 96 well plates in a final volume of 160 µl. Compounds were added at different concentrations (3 µM to 100 µM final concentrations). Plates were covered with a Mylar film. After incubation was completed the Mylar cover was removed and the plates were placed in a Spectrostar Nano plate reader previously heated at 37° C. Five minutes later, $N_2$ (flow rate=20 L/min) was flowed through the spectrophotometer. Spectroscopic measurements (300 nm to 700 nm) were taken every 5 min for 2 hours. Data analysis was performed by using linear regression from the data retrieved for all wavelengths.

Table 4 below lists the delta R values where + indicates a delta R of between 0 and 30, ++ indicates a delta R of between 30 and 50, and +++ indicates a delta R of 50 or greater. Unless noted otherwise, the compounds in Table 2 were tested at 9 µM.

TABLE 4

| Compound | delta R (%) |
|---|---|
| 1 | +++ |
| 2 | ++ |
| 3 | +++ |
| 4 | +++ |
| 5 | +++ |
| 8 | + |
| 9 | +++ |
| 10 | ++ |
| 11 | ++ |

Example 21

Whole Blood Assay

Oxygen Equilibrium Curves (OEC) of whole blood before and after treatment with different concentrations of substituted benzaldehyde compounds were performed as follows using a HEMOX analyzer (TCS Scientific, New Hope, Pa.). Blood samples from homozygous sickle cell patients were obtained though the Hemoglobinopathy Center at Children's Hospital Oakland Research Institute (CHORI) with Institutional Review Board approval. The hematocrit was adjusted to 20% using autologous plasma and the blood samples were incubated for 1 hour at 37° C. in absence or presence of compounds. 100 µl of these samples were added to 5 mL of Hemox buffer (30 mM TES, 130 mM NaCl, 5 mM KCl, pH=7.4) at 37° C. and then transferred to the Hemox sample chamber. The samples were saturated with oxygen by flushing with compressed air for 10 minutes. The samples were then flushed with pure nitrogen and the respective absorbances of oxy- and deoxy-Hb are recorded as a function of the solution pO2. The oxygen equilibrium data were then fitted to the Hill Model to obtain values for p50. The deoxygenation curves for both whole blood alone (control) and whole blood in the presence of the compound were collected with the TCS software.

Table 5 below lists the delta p50% values where + indicates a delta p50% of between 0 and 29, ++ indicates a delta p50% of between 30 and 50, and +++ indicates a delta p50% of 50 or greater. The compounds in Table 2 were tested at 1000 µM. A positive delta p50 value corresponds to a left shifted curve and a lower p50 value relative to control, indicating that the compound acts to modulate HbS to increase its affinity for oxygen.

TABLE 5 delta p50% Values for Whole Blood Assay

| Compound | delta p50% |
| --- | --- |
| 1 | + |
| 2 | ++ |
| 3 | + |
| 4 | + |
| 5 | ++ |
| 6 | + |
| 7 | + |
| 10 | ++ |

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound of Formula (I):

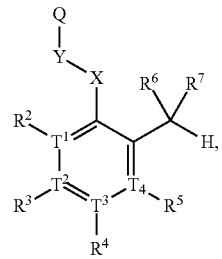

a tautomer, a stereoisomer, a mixture of stereoisomers, or a pharmaceutically acceptable salt thereof, wherein:

Q is cycloalkyl or cycloalkenyl, each of which is substituted with one to three $R^a$;

Y is $CR^{1a}R^{1b}$, wherein
$R^{1a}$ is H or halo, and
$R^{1b}$ is H or halo;

X is O;

$T^1$, $T^2$, $T^3$, and $T^4$ are independently C or N provided that at least one of $T^1$, $T^2$, $T^3$, and $T^4$ is C; wherein when $T^1$, $T^2$, $T^3$, or $T^4$ are N, then $R^2$, $R^3$, $R^4$, or $R^5$, respectively, are absent;

$R^2$, $R^3$, and $R^4$ are independently hydrogen, halo, $R^b$, $OR^d$, or $NR^dNR^d$;

$R^5$ is selected from the group consisting of hydrogen, halo, $R^b$, $OR^d$, —$O(CH_2)_zOR^d$, —$O(CH_2)_zNR^dR^d$, $OC(O)R^e$, $SR^d$, $CN$, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$; wherein z is 0, 1, 2, 3, 4, 5, or 6; or $R^5$ is —$(CH_2)_pR^{5a}$, wherein p is 0 or 1 and $R^{5a}$ is OH;

$R^6$ and $R^7$ together form oxo or an aldehyde protecting group, or $R^6$ together with $R^{1b}$ or $R^5$ forms a cyclic ether, wherein one of $R^{1b}$ or $R^{5a}$ is O, $R^6$ is a bond, and $R^7$ is selected from the group consisting of OH, $C_{1-8}$alkoxy, and halo$C_{1-8}$alkoxy;

each $R^a$ is independently selected from the group consisting of halo, $R^b$, $OR^d$, —$(CH_2)_kCO_2(C_{1-8}$alkyl)OH, —$(CH_2)_kCO_2R^d$, —$(CH_2)_kCONR^dR^d$, —$(CH_2)_kC(O)R^d$, —$(CH_2)_k$aryl optionally substituted with one to three $R^c$, —$(CH_2)_k$heteroaryl optionally substituted with one to three $R^c$, and —$(CH_2)_k$heterocycloalkyl optionally substituted with one to three $R^c$; wherein k is 0, 1, 2, 3, 4, 5, or 6; and wherein at least one of $R^a$ is selected from the group consisting of $OR^d$, —$(CH_2)_kCO_2(C_{1-8}$alkyl)OH, —$(CH_2)_kCO_2R^d$, —$(CH_2)_kCONR^dR^d$, —$(CH_2)_kC(O)R^d$, —$(CH_2)_k$aryl optionally substituted with one to three $R^c$, —$(CH_2)_k$heteroaryl optionally substituted with one to three $R^c$, —$(CH_2)_k$heterocycloalkyl optionally substituted with one to three $R^c$, substituted $C_{1-8}$alkyl, substituted $C_{2-8}$alkenyl, and substituted $C_{2-8}$ alkynyl; wherein the substituted $C_{1-8}$alkyl, substituted $C_{2-8}$alkenyl, and substituted $C_{2-8}$ alkynyl are each substituted with one to three halo, $OR^d$, or $NR^dR^d$;

each $R^b$ is independently selected from the group consisting of $C_{1-8}$alkyl, $C_{2-8}$alkenyl, and $C_{2-8}$ alkynyl, each optionally independently substituted with one to three halo, $OR^d$, or $NR^dR^d$;

each $R^c$ is independently selected from the group consisting of halo, $C_{1-8}$alkyl, halo$C_{1-8}$alkyl, $C_{2-8}$alkenyl, halo$C_{2-8}$ alkenyl, $C_{2-8}$alkynyl, halo$C_{2-8}$alkynyl, $(CH_2)_mOR^f$, heteroaryl, cycloalkyl, and heterocycloalkyl; wherein m is selected from the group consisting of 0, 1, 2, 3, 4, 5, and 6;

each $R^d$ is independently selected from the group consisting of hydrogen, $C_{1-8}$ alkyl, halo$C_{1-8}$alkyl, $C_{2-8}$ alkenyl, halo$C_{2-8}$alkenyl, $C_{2-8}$ alkynyl, halo$C_{2-8}$alkynyl, —$(CH_2)_k$heterocycloalkyl, and —$(CH_2)_uO$—$(CH_2)_uH$; wherein k is 0, 1, 2, 3, 4, 5, or 6 and each u is independently 1, 2, 3, 4, 5, or 6;

each $R^f$ is independently selected from the group consisting of hydrogen, $C_{1-8}$ alkyl, halo$C_{1-8}$alkyl, $C_{2-8}$ alkenyl, halo$C_{2-8}$alkenyl, $C_{2-8}$ alkynyl, and halo$C_{2-8}$alkynyl; and $R^e$ is $C_{1-8}$alkyl, halo$C_{1-8}$alkyl, $C_{2-8}$ alkenyl, halo$C_{2-8}$alkenyl, $C_{2-8}$alkynyl, or halo$C_{2-8}$alkynyl;

provided that:
at least one of $R^4$ and $R^5$ is other than hydrogen or $T^1$ and $T^3$ are C; $T^2$ is N and $T^4$ is C, or $T^2$ is C and $T^4$ is N.

2. The compound according to claim 1, a tautomer, a stereoisomer, a mixture of stereoisomers, or a pharmaceutically acceptable salt thereof, wherein:
$T^1$, $T^2$, $T^3$, and $T^4$ are C.

3. The compound according to claim 2, a tautomer, a stereoisomer, a mixture of stereoisomers, or a pharmaceutically acceptable salt thereof, wherein:
$R^2$, $R^3$, $R^4$, and $R^5$ are independently hydrogen, halo, $R^b$, or $OR^d$.

4. The compound according to claim 3, a tautomer, a stereoisomer, a mixture of stereoisomers, or a pharmaceutically acceptable salt thereof, wherein Y is $CH_2$.

5. The compound according to claim 1, a tautomer, a stereoisomer, a mixture of stereoisomers, or a pharmaceutically acceptable salt thereof, wherein $R^5$ is OH; and $R^2$, $R^3$ and $R^4$ are hydrogen.

6. The compound according to claim 5, a tautomer, a stereoisomer, a mixture of stereoisomers, or a pharmaceutically acceptable salt thereof, wherein Q is cyclopentyl or cyclohexyl.

7. The compound according to claim 6, a tautomer, a stereoisomer, a mixture of stereoisomers, or a pharmaceutically acceptable salt thereof, wherein each $R^a$ is independently selected from the group consisting of $R^b$, $OR^d$, —$(CH_2)_kCO_2R^d$, —$(CH_2)_k$aryl optionally substituted with one to three $R^c$, —$(CH_2)k$heteroaryl optionally substituted with one to three $R^c$, and —$(CH_2)_k$heterocycloalkyl optionally substituted with one to three $R^c$; wherein k is 0, 1, 2, 3, 4, 5, or 6; and wherein at least one of $R^a$ is selected from the group consisting of $OR^d$, —$(CH_2)_kCO_2R^d$, —$(CH_2)k$aryl optionally substituted with one to three $R^c$, —$(CH_2)_k$heteroaryl optionally substituted with one to three $R^c$, —$(CH_2)_k$heterocycloalkyl optionally substituted with one to three $R^c$, substituted $C_{1-8}$alkyl, substituted $C_{2-8}$alkenyl, and substituted $C_{2-8}$ alkynyl, wherein the substituted $C_{1-8}$alkyl, substituted $C_{2-8}$alkenyl, and substituted $C_{2-8}$ alkynyl are each substituted with one to three halo, $OR^d$, or $NR^dR^d$.

8. The compound according to claim 6, a tautomer, a stereoisomer, a mixture of stereoisomers, or a pharmaceutically acceptable salt thereof, wherein Q is substituted with one $R^a$ which is heteroaryl optionally substituted with one to three $R^c$.

9. The compound according to claim 8, a tautomer, a stereoisomer, a mixture of stereoisomers, or a pharmaceutically acceptable salt thereof, wherein $R^a$ is selected from the group consisting of pyridinyl, pyrazolyl, and imidazolyl, and wherein each $R^c$ is independently selected from the group consisting of halo, $OR^f$, $C_{1-8}$alkyl, halo$C_{1-8}$alkyl, cycloalkyl, and heterocycloalkyl.

10. A compound according to claim 8, a tautomer, a stereoisomer, a mixture of stereoisomers, a pharmaceutically acceptable salt thereof, wherein $R^a$ is selected from the group consisting of 2-chloropyridin-3-yl, 2-methoxypyridin-3-yl, 2-cyclobutylpyrazol-3-yl, 2-cyclopentylpyrazol-3-yl, 2-cyclopropylpyrazol-3-yl, 2-ethylpyrazol-3-yl, 2-propan-2-ylpyrazol-3-yl, 2-propylpyrazol-3-yl, 2-(2,2,2-trifluoroethyl)pyrazol-3-yl, 2-(2,2-difluoroethyl)pyrazol-3-yl, 2-(3,3,3-trifluoropropyl)pyrazol-3-yl, 2-(oxetan-3-yl)pyrazol-3-yl, 2-propan-2-ylpyrazol-3-yl, 2-propylpyrazol-3-yl, and 3-propan-2-ylimidazol-4yl.

11. The compound according to claim 5, a tautomer, a stereoisomer, a mixture of stereoisomers, or a pharmaceutically acceptable salt thereof, wherein Q is cyclopentenyl or cyclohexenyl.

12. The compound according to claim 11, a tautomer, a stereoisomer, a mixture of stereoisomers, or a pharmaceutically acceptable salt thereof, wherein each $R^a$ is independently selected from the group consisting of $R^b$, $OR^d$, —$(CH_2)_kCO_2R^d$, —$(CH_2)_k$aryl optionally substituted with one to three $R^c$, —$(CH_2)_k$heteroaryl optionally substituted with one to three $R^c$, and —$(CH_2)_k$heterocycloalkyl optionally substituted with one to three $R^c$; wherein k is 0, 1, 2, 3, 4, 5, or 6; and wherein at least one of $R^a$ is selected from the group consisting of $OR^d$, —$(CH_2)_kCO_2R^d$, —$(CH_2)_k$aryl optionally substituted with one to three $R^c$, —$(CH_2)_k$heteroaryl optionally substituted with one to three $R^c$, —$(CH_2)_k$heterocycloalkyl optionally substituted with one to three $R^c$, substituted $C_{1-8}$alkyl, substituted $C_{2-8}$alkenyl, and substituted $C_{2-8}$ alkynyl; wherein the substituted $C_{1-8}$alkyl, substituted $C_{2-8}$alkenyl, and substituted $C_{2-8}$ alkynyl are each substituted with one to three halo, $OR^d$, or $NR^dR^d$.

13. The compound according to claim 12, a tautomer, a stereoisomer, a mixture of stereoisomers, or a pharmaceutically acceptable salt thereof, wherein Q is substituted with one $R^a$ which is heteroaryl optionally substituted with one to three $R^c$.

14. The compound according to claim 13, a tautomer, a stereoisomer, a mixture of stereoisomers, or a pharmaceutically acceptable salt thereof, wherein $R^a$ is selected from the group consisting of pyridinyl, pyrazolyl, and imidazolyl, and wherein each $R^c$ is independently selected from the group consisting of halo, $OR^f$, $C_{1-8}$alkyl, halo$C_{1-8}$alkyl, cycloalkyl, and heterocycloalkyl.

15. The compound according to claim 14, a tautomer, a stereoisomer, a mixture of stereoisomers, or a pharmaceutically acceptable salt thereof, wherein $R^a$ is selected from the group consisting of 2-chloropyridin-3-yl, 2-methoxypyridin-3-yl, 2-cyclobutylpyrazol-3-yl, 2-cyclopentylpyrazol-3-yl, 2-cyclopropylpyrazol-3-yl, 2-ethylpyrazol-3-yl, 2-propan-2-ylpyrazol-3-yl, 2-propylpyrazol-3-yl, 2-(2,2,2-trifluoroethyl)pyrazol-3-yl, 2-(2,2-difluoroethyl)pyrazol-3-yl, 2-(3,3,3-trifluoropropyl)pyrazol-3-yl, 2-(oxetan-3-yl)pyrazol-3-yl, 2-propan-2-ylpyrazol-3-yl, 2-propylpyrazol-3-yl, and 3-propan-2-ylimidazol-4 -yl.

16. The compound according to claim 1, a tautomer, a stereoisomer, a mixture of stereoisomers, a pharmaceutically acceptable salt thereof, wherein at least one of $T^1$, $T^2$, $T^3$, and $T^4$ is N.

17. The compound according to claim 16, a tautomer, a stereoisomer, a mixture of stereoisomers, or a pharmaceutically acceptable salt thereof, wherein:

$T^1$ and $T^3$ are C;

$T^2$ is N and $T^4$ is C, or $T^2$ is C and $T^4$ is N;

$R^2$, $R^3$, $R^4$, and $R^5$ are independently hydrogen, halo, $R^b$, or $OR^d$.

18. The compound according to claim 17, a tautomer, a stereoisomer, a mixture of stereoisomers, or a pharmaceutically acceptable salt thereof, wherein:

$T^2$ is N and $T^4$ is C;

$R^2$, $R^3$, and $R^4$ are hydrogen; and $R^5$ is $OR^d$ wherein $R^d$ is hydrogen.

19. The compound according to claim 17, a tautomer, a stereoisomer, a mixture of stereoisomers, or a pharmaceutically acceptable salt thereof, wherein Q is cyclopentyl or cyclohexyl.

20. The compound according to claim 19, a tautomer, a stereoisomer, a mixture of stereoisomers, or a pharmaceutically acceptable salt thereof, wherein each $R^c$ is independently selected from the group consisting of $R^b$, $OR^d$, —$(CH_2)_k CO_2 R^d$, —$(CH_2)_k$aryl optionally substituted with one to three $R^c$, —$(CH_2)_k$heteroaryl optionally substituted with one to three $R^c$, and —$(CH_2)_k$heterocycloalkyl optionally substituted with one to three $R^c$; wherein k is 0, 1, 2, 3, 4, 5, or 6; and wherein at least one of $R^a$ is selected from the group consisting of $OR^d$, —$(CH_2)_k CO_2 R^d$, —$(CH_2)_k$aryl optionally substituted with one to three $R^c$, —$(CH_2)_k$heteroaryl optionally substituted with one to three $R^c$, —$(CH_2)_k$heterocycloalkyl optionally substituted with one to three $R^c$, substituted $C_{1-8}$alkyl, substituted $C_{2-8}$alkenyl, and substituted $C_{2-8}$ alkynyl; wherein the substituted $C_{1-8}$alkyl, substituted $C_{2-8}$alkenyl, and substituted $C_{2-8}$ alkynyl are each substituted with one to three halo, $OR^d$, or $NR^d R^d$.

21. The compound according to claim 20, a tautomer, a stereoisomer, a mixture of stereoisomers, or a pharmaceutically acceptable salt thereof, wherein Q is substituted with one $R^a$ which is heteroaryl optionally substituted with one to three $R^c$.

22. The compound according to claim 21, a tautomer, a stereoisomer, a mixture of stereoisomers, or a pharmaceutically acceptable salt thereof, wherein $R^a$ is selected from the group consisting of pyridinyl, pyrazolyl, and imidazolyl, and wherein each $R^c$ is independently selected from the group consisting of halo, $OR^f$, $C_{1-8}$alkyl, halo$C_{1-8}$alkyl, cycloalkyl, and heterocycloalkyl.

23. The compound according to claim 21, a tautomer, a stereoisomer, a mixture of stereoisomers, or a pharmaceutically acceptable salt thereof, wherein $R^a$ is selected from the group consisting of 2-chloropyridin-3-yl, 2-methoxypyridin-3-yl, 2-cyclobutylpyrazol-3-yl, 2-cyclopentylpyrazol-3-yl, 2-cyclopropylpyrazol-3-yl, 2-ethylpyrazol-3-yl, 2-propan-2-ylpyrazol-3-yl, 2-propylpyrazol-3-yl, 2-(2,2,2-trifluoroethyl)pyrazol-3-yl, 2-(2,2-difluoroethyl)pyrazol-3-yl, 2-(3,3,3-trifluoropropyl)pyrazol-3-yl, 2-(oxetan-3-yl)pyrazol-3-yl, 2-propan-2-ylpyrazol-3-yl, 2-propylpyrazol-3-yl, and 3-propan-2-ylimidazol-4 -yl.

24. A compound selected from the group consisting of cis-methyl4-((2-formyl-3-hydroxyphenoxy)methyl)cyclohexanecarboxylate;

cis-4((2-formyl-3-hydroxyphenoxy)methyl)cyclohexanecarboxylic acid;

(1R,3S)-3-((2-formyl-3-hydroxyphenoxy)methyl)cyclohexanecarboxylic acid;

trans-methyl4-((2-formyl-3-hydroxyphenoxy)methyl)cyclohexanecarboxylate;

trans-4-((2-formyl-3-hydroxyphenoxy)methyl)cyclohexanecarboxylic acid;

methyl3-((2-formyl-3-hydroxyphenoxy)methyl)cyclohexanecarboxylate;

trans-methyl4-((2-formyl-3-methoxyphenoxy)methyl)cyclohexanecarboxylate;

2-hydroxy-6-((3,4,5,6-tetrahydro-[1,1'-biphenyl]-2-yl)methoxy)benzaldehyde;

2-hydroxy-6-((2-phenylcyclohexyl)methoxy)benzaldehyde;

2-hydroxy-6-((2-(1-isopropyl-1H-pyrazol-5-yl)cyclohex-1-en-1-yl)methoxy)benzaldehyde;

2-hydroxy-6-[[2-(2-hydroxypropan-2-yl)cyclohexyl]methoxy]benzaldehyde;

2-hydroxy-6-[[2-(2-hydroxybutan-2-yl)cyclohexyl]methoxy]benzaldehyde;

2-hydroxy-6-[[2-(2-hydroxypentan-2-yl)cyclohexyl]methoxy]benzaldehyde;

2-hydroxy-6-[[2-[2-(3,3,3-trifluoropropyl)pyrazol-3-yl]cyclohexyl]methoxy]benzaldehyde;

2-[[2-(2-chlorophenyl)cyclohexyl]methoxy]-6-hydroxybenzaldehyde;

2-hydroxy--[[2-(3-propan-2-ylimidazol-4-yl)cyclohexyl]methoxy]benzaldehyde;

2-hydroxy-6-[(2-phenylcyclohexyl)methoxy]benzaldehyde;

2-[[2-[2-(2,2-difluoroethyl)pyrazol-3-yl]cyclohexyl]methoxy]-6-hydroxybenzaldehyde;

2-[[2-(2-fluorophenyl)cyclohexyl]methoxy]-6-hydroxybenzaldehyde;

2-[[2-(2-cyclobutylpyrazol-3-yl)cyclohexyl]methoxy]-6-hydroxybenzaldehyde;

2-hydroxy-6-[[2-(2-methoxypyridin-3-yl)cyclohexyl]methoxy]benzaldehyde;

2-hydroxy-6-[[2-(2-propan-2-ylpyrazol-3-yl)cyclohexyl]methoxy]benzaldehyde;

2-[[2-(2-cyclopentylpyrazol-3-yl)cyclohexyl]methoxy]-6-hydroxybenzaldehyde;

2-hydroxy-6-[[2-(2-propylpyrazol-3-yl)cyclohexyl]methoxy]benzaldehyde;

2-[[2-(2-chloropyridin-3-yl)cyclohexyl]methoxy]-6-hydroxybenzaldehyde;

2-[[2-(2-cyclopropylpyrazol-3-yl)cyclohexyl]methoxy]-6-hydroxybenzaldehyde;

2-hydroxy-6-[[2-(2-methoxyphenyl)cyclohexyl]methoxy]benzaldehyde;

2-hydroxy-6-[[2-(2,2,2-trifluoroethyl)pyrazol-3-yl]cyclohexyl]methoxy]benzaldehyde;

2-hydroxy-6-[[2-(oxetan-3-yl)pyrazol-3-yl]cyclohexyl]methoxy]benzaldehyde;

2-[[2-(2-ethylpyrazol-3-yl)cyclohexyl]methoxy]-6-hydroxybenzaldehyde;

2-hydroxy-6-[[2-(2-hydroxypentan-2-yl)cyclohexyl]methoxy]-3-methylbenzaldehyde;

2-hydroxy-6-[[2-(2-hydroxybutan-2-yl)cyclohexyl]methoxy]-3-methylbenzaldehyde;

2-hydroxy-6-[[2-(2-hydroxypropan-2-yl)cyclohexyl]methoxy]-3-methylbenzaldehyde;

6-[[2-(2-cyclobutylpyrazol-3-yl)cyclohexyl]methoxy]-2-hydroxy-3-methylbenzaldehyde;

2-hydroxy-3-methyl-64[2-(2-propan-2-ylpyrazol-3-yl)cyclohexyl]methoxy]benzaldehyde;

6-[[2-(2-chloropyridin-3-yl)cyclohexyl]methoxy]-2-hydroxy-3-methylbenzaldehyde;
6-[[2-[2-(2,2-difluoroethyl)pyrazol-3-yl]cyclohexyl]methoxy]-2-hydroxy-3-methylbenzaldehyde;
6-[[2-(2-fluorophenyl)cyclohexyl]methoxy]-2-hydroxy-3-methylbenzaldehyde;
6-[[2-(2-cyclopropylpyrazol-3-yl)cyclohexyl]methoxy]-2-hydroxy-3-methylbenzaldehyde;
2-hydroxy-6-[[2-(2-methoxyphenyl)cyclohexyl]methoxy]-3-methylbenzaldehyde;
2-hydroxy-3-methyl-6-[[2-[2-(3,3,3-trifluoropropyl)pyrazol-3-yl]cyclohexyl]methoxy]benzaldehyde;
2-hydroxy-3-methyl-6-[[2-[2-(oxetan-3-yl)pyrazol-3-yl]cyclohexyl]methoxy]benzaldehyde;
6-[[2-(2-chlorophenyl)cyclohexyl]methoxy]-2-hydroxy-3-methylbenzaldehyde;
2-hydroxy-3-methyl-6-[[2-(2-propylpyrazol-3-yl)cyclohexyl]methoxy]benzaldehyde;
2-hydroxy-3-methyl-6-[[2-(3-propan-2-ylimidazol-4-yl)cyclohexyl]methoxy]benzaldehyde;
2-hydroxy-3-methyl-6-[(2-phenylcyclohexyl)methoxy]benzaldehyde;
2-hydroxy-3-methyl-6-[[2-[2-(2,2,2-trifluoroethyl)pyrazol-3-yl]cyclohexyl]methoxy]benzaldehyde;
2-hydroxy-6-[[2-(2-methoxypyridin-3-yl)cyclohexyl]methoxy]-3-methylbenzaldehyde;
6-[[2-(2-ethylpyrazol-3-yl)cyclohexyl]methoxy]-2-hydroxy-3-methylbenzaldehyde;
6-[[2-(2-cyclopentylpyrazol-3-yl)cyclohexyl]methoxy]-2-hydroxy-3-methylbenzaldehyde;
3-chloro-2-hydroxy-6-[[2-(2-hydroxybutan-2-yl)cyclohexyl]methoxy]benzaldehyde;
3-chloro-2-hydroxy-6-[[2-(2-hydroxypropan-2-yl)cyclohexyl]methoxy]benzaldehyde;
3-chloro-2-hydroxy-6-[[2-(2-hydroxypentan-2-yl)cyclohexyl]methoxy]benzaldehyde;
3-chloro-6-[[2-[2-(2,2-difluoroethyl)pyrazol-3-yl]cyclohexyl]methoxy]-2-hydroxybenzaldehyde;
3-chloro-2-hydroxy-6-[[2-[2-(oxetan-3-yl)pyrazol-3-yl]cyclohexyl]methoxy]benzaldehyde;
3-chloro-2-hydroxy-6-[[2-(2-propylpyrazol-3-yl)cyclohexyl]methoxy]benzaldehyde;
3-chloro-6-[[2-(2-chloropyridin-3-yl)cyclohexyl]methoxy]-2-hydroxybenzaldehyde;
3-chloro-2-hydroxy-6-[[2-(3-propan-2-ylimidazol-4-yl)cyclohexyl]methoxy]benzaldehyde;
3-chloro-2-hydroxy-6-[(2-phenylcyclohexyl)methoxy]benzaldehyde;
3-chloro-2-hydroxy-6-[[2-(2-methoxyphenyl)cyclohexyl]methoxy]benzaldehyde;
3-chloro-2-hydroxy-6-[[2-[2-(2,2,2-trifluoroethyl)pyrazol-3-yl]cyclohexyl]methoxy]benzaldehyde;
3-chloro-6-[[2-(2-cyclobutylpyrazol-3-yl)cyclohexyl]methoxy]-2-hydroxybenzaldehyde;
3-chloro-6-[[2-(2-ethylpyrazol-3-yl)cyclohexyl]methoxy]-2-hydroxybenzaldehyde;
3-chloro-6-[[2-(2-chlorophenyl)cyclohexyl]methoxy]-2-hydroxybenzaldehyde;
3-chloro-2-hydroxy-6-[[2-(2-propan-2-ylpyrazol-3-yl)cyclohexyl]methoxy]benzaldehyde;
3-chloro-6-[[2-(2-cyclopentylpyrazol-3-yl)cyclohexyl]methoxy]-2-hydroxybenzaldehyde;
3-chloro-6-[[2-(2-fluorophenyl)cyclohexyl]methoxy]-2-hydroxybenzaldehyde;
3-chloro-6-[[2-(2-cyclopropylpyrazol-3-yl)cyclohexyl]methoxy]-2-hydroxybenzaldehyde;
3-chloro-2-hydroxy-6-[[2-(2-methoxypyridin-3-yl)cyclohexyl]methoxy]benzaldehyde;
3-chloro-2-hydroxy-6-[[2-[2-(3,3,3-trifluoropropyl)pyrazol-3-yl]cyclohexyl]methoxy]benzaldehyde;
2-fluoro-6-[[2-(2-hydroxypropan-2-yl)cyclohexyl]methoxy]benzaldehyde;
2-fluoro-6-[[2-(2-hydroxypentan-2-yl)cyclohexyl]methoxy]benzaldehyde;
2-fluoro-6-[[2-(2-hydroxybutan-2-yl)cyclohexyl]methoxy]benzaldehyde;
2-fluoro-6-[[2-(2-propylpyrazol-3-yl)cyclohexyl]methoxy]benzaldehyde;
2-[[2-(2-chloropyridin-3-yl)cyclohexyl]methoxy]-6-fluorobenzaldehyde;
2-fluoro-6-[[2-(2-methoxyphenyl)cyclohexyl]methoxy]benzaldehyde;
2-fluoro-6[[2-[2-(2,2,2-trifluoroethyl)pyrazol-3-yl]cyclohexyl]methoxy]benzaldehyde;
2-fluoro-6[[2-[2-(oxetan-3-yl)pyrazol-3-yl]cyclohexyl]methoxyThenzaldehyde;
2-[[2-(2-ethylpyrazol-3-yl)cyclohexyl]methoxy]-6-fluorobenzaldehyde;
2-[[2-(2-chlorophenyl)cyclohexyl]methoxy]-6-fluorobenzaldehyde;
2-fluoro-6-[[2-(2-propan-2-ylpyrazol-3-yl)cyclohexyl]methoxy]benzaldehyde;
2-fluoro-6-[(2-phenylcyclohexyl)methoxy]benzaldehyde;
2-[[2-[2-(2,2-difluoroethyl)pyrazol-3-yl]cyclohexyl]methoxy]-6-fluorobenzaldehyde;
2-fluoro-6-[[2-(2-fluorophenyl)cyclohexyl]methoxy]benzaldehyde;
2-[[2-(2-cyclopropylpyrazol-3-yl)cyclohexyl]methoxy]-6-fluorobenzaldehyde;
2-[[2-(2-cyclobutylpyrazol-3-yl)cyclohexyl]methoxy]-6-fluorobenzaldehyde;
2-fluoro-6-[[2-(2-methoxypyridin-3-yl)cyclohexyl]methoxy]benzaldehyde;
2-fluoro-6-[[2-[2-(3,3,3-trifluoropropyl)pyrazol-3-yl]cyclohexyl]methoxy]benzaldehyde;
2-[[2-(2-cyclopentylpyrazol-3-yl)cyclohexyl]methoxy]-6-fluorobenzaldehyde;
2-fluoro-6-[[2-(3-propan-2-ylimidazol-4-yl)cyclohexyl]methoxy]benzaldehyde;
2-hydroxy-6-[[2-(2-hydroxypropan-2-yl)cyclohexen-1-yl]methoxy]benzaldehyde;
2-hydroxy-6-[[2-(2-hydroxybutan-2-yl)cyclohexen-1-yl]methoxy]benzaldehyde;
2-hydroxy-6-[[2-(2-hydroxypentan-2-yl)cyclohexen-1-yl]methoxy]benzaldehyde;
2-hydroxy-6-[[2-[2-(3,3,3-trifluoropropyl)pyrazol-3-yl]cyclohexen-1-yl]methoxy]benzaldehyde;
2-[[2-(2-chlorophenyl)cyclohexen-1-yl]methoxy]-6-hydroxybenzaldehyde;
2-hydroxy-6-[[2-(3-propan-2-ylimidazol-4-yl)cyclohexen-1-yl]methoxy]benzaldehyde;
2-[[2-(2-fluorophenyl)cyclohexen-1-yl]methoxy]-6-hydroxybenzaldehyde;
2-[[2-(2-cyclobutylpyrazol-3-yl)cyclohexen-1-yl]methoxy]-6-hydroxybenzaldehyde;
2-hydroxy-6-[[2-(2-methoxypyridin-3-yl)cyclohexen-1-yl]methoxy]benzaldehyde;
2-hydroxy-6-[[2-(2-propan-2-ylpyrazol-3-yl)cyclohexen-1-yl]methoxy]benzaldehyde;
2-[[2-(2-cyclopentylpyrazol-3-yl)cyclohexen-1-yl]methoxy]-6-hydroxybenzaldehyde;
2-hydroxy-6-[[2-(2-propylpyrazol-3-yl)cyclohexen-1-yl]methoxy]benzaldehyde;

2-[[2-(2-chloropyridin-3-yl)cyclohexen-1-yl]methoxy]-6-hydroxybenzaldehyde;
2-[[2-(2-cyclopropylpyrazol-3-yl)cyclohexen-1-yl]methoxy]-6-hydroxybenzaldehyde;
2-hydroxy-6-[[2-(2-methoxyphenyl)cyclohexen-1-yl]methoxy]benzaldehyde;
2-hydroxy-6-[[2-[2-(2,2,2-trifluoroethyl)pyrazol-3-yl]cyclohexen-1-yl]methoxy]benzaldehyde;
2-hydroxy-6-[[2-(oxetan-3-yl)pyrazol-3-yl]cyclohexen-1-yl]methoxy]benzaldehyde;
2-[[2-(2-ethylpyrazol-3-yl)cyclohexen-1-yl]methoxy]-6-hydroxybenzaldehyde;
2-hydroxy-6-[[2-(2-hydroxypentan-2-yl)cyclohexen-1-yl]methoxy]-3-methylbenzaldehyde;
2-hydroxy-6-[[2-(2-hydroxybutan-2-yl)cyclohexen-1-yl]methoxy]-3-methylbenzaldehyde;
2-hydroxy-6-[[2-(2-hydroxypropan-2-yl)cyclohexen-1-yl]methoxy]-3-methylbenzaldehyde;
6-[[2-(2-cyclobutylpyrazol-3-yl)cyclohexen-1-yl]methoxy]-2-hydroxy-3-methylbenzaldehyde;
2-hydroxy-3-methyl-6-[[2-(2-propan-2-ylpyrazol-3-yl)cyclohexen-1-yl]methoxy]benzaldehyde;
6-[[2-(2-chloropyridin-3-yl)cyclohexen-1-yl]methoxy]-2-hydroxy-3-methylbenzaldehyde;
6-[[2-[2-(2,2-difluoroethyl)pyrazol-3-yl]cyclohexen-1-yl]methoxy]-2-hydroxy-3-methylbenzaldehyde;
6-[[2-(2-fluorophenyl)cyclohexen-1-yl]methoxy]-2-hydroxy-3-methylbenzaldehyde;
6-[[2-(2-cyclopropylpyrazol-3-yl)cyclohexen-1-yl]methoxy]-2-hydroxy-3-methylbenzaldehyde;
2-hydroxy-6-[[2-(2-methoxyphenyl)cyclohexen-1-yl]methoxy]-3-methylbenzaldehyde;
2-hydroxy-3-methyl-6-[[2-[2-(3,3,3-trifluoropropyl)pyrazol-3-yl]cyclohexen-1-yl]methoxy]benzaldehyde;
2-hydroxy-3-methyl-6-[[2-[2-(oxetan-3-yl)pyrazol-3-yl]cyclohexen-1-yl]methoxy]benzaldehyde;
6-[[2-(2-chlorophenyl)cyclohexen-1-yl]methoxy]-2-hydroxy-3-methylbenzaldehyde;
2-hydroxy-3-methyl-6-[[2-(2-propylpyrazol-3-yl)cyclohexen-1-yl]methoxy]benzaldehyde;
2-hydroxy-3-methyl-6-[[2-(3-propan-2-ylimidazol-4-yl)cyclohexen-1-yl]methoxy]benzaldehyde;
2-hydroxy-3-methyl-6-[(2-phenylcyclohexen-1-yl)methoxy]benzaldehyde;
2-hydroxy-3-methyl-6-[[2-[2-(2,2,2-trifluoroethyl)pyrazol-3-yl]cyclohexen-1-yl]methoxy]benzaldehyde;
2-hydroxy-6-[[2-(2-methoxypyridin-3-yl)cyclohexen-1-yl]methoxy]-3-methylbenzaldehyde;
6-[[2-(2-ethylpyrazol-3-yl)cyclohexen-1-yl]methoxy]-2-hydroxy-3-methylbenzaldehyde;
6-[[2-(2-cyclopentylpyrazol-3-yl)cyclohexen-1-yl]methoxy]-2-hydroxy-3-methylbenzaldehyde;
3-chloro-2-hydroxy-6-[[2-(2-hydroxybutan-2-yl)cyclohexen-1-yl]methoxy]benzaldehyde;
3-chloro-2-hydroxy-6-[[2-(2-hydroxypropan-2-yl)cyclohexen-1-yl]methoxy]benzaldehyde;
3-chloro-2-hydroxy-6-[[2-(2-hydroxypentan-2-yl)cyclohexen-1-yl]methoxy]benzaldehyde;
3-chloro-6-[[2-[2-(2,2-difluoroethyl)pyrazol-3-yl]cyclohexen-1-yl]methoxy]-2-hydroxybenzaldehyde;
3-chloro-2-hydroxy-6-[[2-[2-(oxetan-3-yl)pyrazol-3-yl]cyclohexen-1-yl]methoxy]benzaldehyde;
3-chloro-2-hydroxy-6-[[2-(2-propylpyrazol-3-yl)cyclohexen-1-yl]methoxy]benzaldehyde;
3-chloro-6-[[2-(2-chloropyridin-3-yl)cyclohexen-1-yl]methoxy]-2-hydroxybenzaldehyde;
3-chloro-2-hydroxy-6-[[2-(3-propan-2-ylimidazol-4-yl)cyclohexen-1-yl]methoxy]benzaldehyde;
3-chloro-2-hydroxy-6-[(2-phenylcyclohexen-1-yl)methoxy]benzaldehyde;
3-chloro-2-hydroxy-6-[[2-(2-methoxyphenyl)cyclohexen-1-yl]methoxy]benzaldehyde;
3-chloro-2-hydroxy-6-[[2-[2-(2,2,2-trifluoroethyl)pyrazol-3-yl]cyclohexen-1-yl]methoxy]benzaldehyde;
3-chloro-6-[[2-(2-cyclobutylpyrazol-3-yl)cyclohexen-1-yl]methoxy]-2-hydroxybenzaldehyde;
3-chloro-6-[[2-(2-ethylpyrazol-3-yl)cyclohexen-1-yl]methoxy]-2-hydroxybenzaldehyde;
3-chloro-6-[[2-(2-chlorophenyl)cyclohexen-1-yl]methoxy]-2-hydroxybenzaldehyde;
3-chloro-2-hydroxy-6-[[2-(2-propan-2-ylpyrazol-3-yl)cyclohexen-1-yl]methoxy]benzaldehyde;
3-chloro-6-[[2-(2-cyclopentylpyrazol-3-yl)cyclohexen-1-yl]methoxy]-2-hydroxybenzaldehyde;
3-chloro-6-[[2-(2-fluorophenyl)cyclohexen-1-yl]methoxy]-2-hydroxybenzaldehyde;
3-chloro-6-[[2-(2-cyclopropylpyrazol-3-yl)cyclohexen-1-yl]methoxy]-2-hydroxybenzaldehyde;
3-chloro-2-hydroxy-6-[[2-(2-methoxypyridin-3-yl)cyclohexen-1-yl]methoxy]benzaldehyde;
3-chloro-2-hydroxy-6-[[2-[2-(3,3,3-trifluoropropyl)pyrazol-3-yl]cyclohexen-1-yl]methoxy]benzaldehyde;
2-fluoro-6-[[2-(2-hydroxypropan-2-yl)cyclohexen-1-yl]methoxy]benzaldehyde;
2-fluoro-6-[[2-(2-hydroxypentan-2-yl)cyclohexen-1-yl]methoxy]benzaldehyde;
2-fluoro-6-[[2-(2-hydroxybutan-2-yl)cyclohexen-1-yl]methoxy]benzaldehyde;
2-fluoro-6-[[2-(2-propylpyrazol-3-yl)cyclohexen-1-yl]methoxy]benzaldehyde;
2-[[2-(2-chloropyridin-3-yl)cyclohexen-1-yl]methoxy]-6-fluorobenzaldehyde;
2-fluoro-6-[[2-(2-methoxyphenyl)cyclohexen-1-yl]methoxy]benzaldehyde;
2-fluoro-6-[[2-[2-(2,2,2-trifluoroethyl)pyrazol-3-yl]cyclohexen-1-yl]methoxy]benzaldehyde;
2-fluoro-6-[[2-[2-(oxetan-3-yl)pyrazol-3-yl]cyclohexen-1-yl]methoxy]benzaldehyde;
2-[[2-(2-ethylpyrazol-3-yl)cyclohexen-1-yl]methoxy]-6-fluorobenzaldehyde;
2-[[2-(2-chlorophenyl)cyclohexen-1-yl]methoxy]-6-fluorobenzaldehyde;
2-fluoro-6-[[2-(2-propan-2-ylpyrazol-3-yl)cyclohexen-1-yl]methoxy]benzaldehyde;
2-fluoro-6-[(2-phenylcyclohexen-1-yl)methoxy]benzaldehyde;
2-[[2-[2-(2,2-difluoroethyl)pyrazol-3-yl]cyclohexen-1-yl]methoxy]-6-fluorobenzaldehyde;
2-fluoro-6-[[2-(2-fluorophenyl)cyclohexen-1-yl]methoxy]benzaldehyde;
2-[[2-(2-cyclopropylpyrazol-3-yl)cyclohexen-1-yl]methoxy]-6-fluorobenzaldehyde;
2-[[2-(2-cyclobutylpyrazol-3-yl)cyclohexen-1-yl]methoxy]-6-fluorobenzaldehyde;
2-fluoro-6-[[2-(2-methoxypyridin-3-yl)cyclohexen-1-yl]methoxy]benzaldehyde;
2-fluoro-6-[[2-[2-(3,3,3-trifluoropropyl)pyrazol-3-yl]cyclohexen-1-yl]methoxy]benzaldehyde;
2-[[2-(2-cyclopentylpyrazol-3-yl)cyclohexen-1-yl]methoxy]-6-fluorobenzaldehyde;
2-fluoro-6-[[2-(3-propan-2-ylimidazol-4-yl)cyclohexen-1-yl]methoxy]benzaldehyde;

3-[[2-(2-hydroxypentan-2-yl)cyclohexyl]methoxy]pyridine-2-carbaldehyde;
3-[[2-(2-hydroxybutan-2-yl)cyclohexyl]methoxy]pyridine-2-carbaldehyde;
3-[[2-(2-hydroxypropan-2-yl)cyclohexyl]methoxy]pyridine-2-carbaldehyde;
3-[[2-(2-propylpyrazol-3-yl)cyclohexyl]methoxy]pyridine-2-carbaldehyde;
3-[[2-(2-chloropyridin-3-yl)cyclohexyl]methoxy]pyridine-2-carbaldehyde;
3-[[2-(2-methoxyphenyl)cyclohexyl]methoxy]pyridine-2-carbaldehyde;
3-[[2-[2-(3,3,3-trifluoropropyl)pyrazol-3-yl]cyclohexyl]methoxy]pyridine-2-carbaldehyde;
3-[[2-[2-(oxetan-3-yl)pyrazol-3-yl]cyclohexyl]methoxy]pyridine-2-carbaldehyde;
3-[[2-(2-ethylpyrazol-3-yl)cyclohexyl]methoxy]pyridine-2-carbaldehyde;
3-[[2-(2-chlorophenyl)cyclohexyl]methoxy]pyridine-2-carbaldehyde;
3-[[2-(3-propan-2-ylimidazol-4-yl)cyclohexyl]methoxy]pyridine-2-carbaldehyde;
3-[(2-phenylcyclohexyl)methoxy]pyridine-2-carbaldehyde;
3-[[2-[2-(2,2-difluoroethyl)pyrazol-3-yl]cyclohexyl]methoxy]pyridine-2-carbaldehyde;
3-[[2-(2-fluorophenyl)cyclohexyl]methoxy]pyridine-2-carbaldehyde;
3-[[2-(2-cyclobutylpyrazol-3-yl)cyclohexyl]methoxy]pyridine-2-carbaldehyde;
3-[[2-(2-methoxypyridin-3-yl)cyclohexyl]methoxy]pyridine-2-carbaldehyde;
3-[[2-(2-propan-2-ylpyrazol-3-yl)cyclohexyl]methoxy]pyridine-2-carbaldehyde;
3-[[2-(2-cyclopentylpyrazol-3-yl)cyclohexyl]methoxy]pyridine-2-carbaldehyde;
3-[[2-(2-cyclopropylpyrazol-3-yl)cyclohexyl]methoxy]pyridine-2-carbaldehyde;
3-[[2-[2-(2,2,2-trifluoroethyl)pyrazol-3-yl]cyclohexyl]methoxy]pyridine-2-carbaldehyde;
3-[[2-(2-hydroxybutan-2-yl)cyclohexyl]methoxy]-6-methylpyridine-2-carbaldehyde;
3-[[2-(2-hydroxypropan-2-yl)cyclohexyl]methoxy]-6-methylpyridine-2-carbaldehyde;
3-[[2-(2-hydroxypentan-2-yl)cyclohexyl]methoxy]-6-methylpyridine-2-carbaldehyde;
3-[[2-(2-cyclobutylpyrazol-3-yl)cyclohexyl]methoxy]-6-methylpyridine-2-carbaldehyde;
3-[[2-(2-cyclopentylpyrazol-3-yl)cyclohexyl]methoxy]-6-methylpyridine-2-carbaldehyde;
6-methyl-3-[[2-(2-propylpyrazol-3-yl)cyclohexyl]methoxy]pyridine-2-carbaldehyde;
3-[[2-(2-chloropyridin-3-yl)cyclohexyl]methoxy]-6-methylpyridine-2-carbaldehyde;
6-methyl-3-[[2-(3-propan-2-ylimidazol-4-yl)cyclohexyl]methoxy]pyridine-2-carbaldehyde;
3-[[2-(2-methoxyphenyl)cyclohexyl]methoxy]-6-methylpyridine-2-carbaldehyde;
6-methyl-3-[[242-(2,2,2-trifluoroethyl)pyrazol-3-yl]cyclohexyl]methoxy]pyridine-2-carbaldehyde;
6-methyl-3-[[2-[2-(oxetan-3-yl)pyrazol-3-yl]cyclohexyl]methoxy]pyridine-2-carbaldehyde;
3-[[2-(2-ethylpyrazol-3-yl)cyclohexyl]methoxy]-6-methylpyridine-2-carbaldehyde;
3-[[2-(2-chlorophenyl)cyclohexyl]methoxy]-6-methylpyridine-2-carbaldehyde;
6-methyl-3-[[2-(2-propan-2-ylpyrazol-3-yl)cyclohexyl]methoxy]pyridine-2-carbaldehyde;
6-methyl-3-[(2-phenylcyclohexyl)methoxy]pyridine-2-carbaldehyde;
3-[[2-[2-(2,2-difluoroethyl)pyrazol-3-yl]cyclohexyl]methoxy]-6-methylpyridine-2-carbaldehyde;
3-[[2-(2-fluorophenyl)cyclohexyl]methoxy]-6-methylpyridine-2-carbaldehyde;
3-[[2-(2-cyclopropylpyrazol-3-yl)cyclohexyl]methoxy]-6-methylpyridine-2-carbaldehyde;
3-[[2-(2-methoxypyridin-3-yl)cyclohexyl]methoxy]-6-methylpyridine-2-carbaldehyde;
6-methyl-3-[[2-[2-(3,3,3-trifluoropropyl)pyrazol-3-yl]cyclohexyl]methoxy]pyridine-2-carbaldehyde;
3-chloro-5-[[2-(2-hydroxypropan-2-yl)cyclohexyl]methoxy]pyridine-4-carbaldehyde;
3-chloro-5-[[2-(2-hydroxypentan-2-yl)cyclohexyl]methoxy]pyridine-4-carbaldehyde;
3-chloro-5-[[2-(2-hydroxybutan-2-yl)cyclohexyl]methoxy]pyridine-4-carbaldehyde;
3-chloro-5-[[2-[2-(oxetan-3-yl)pyrazol-3-yl]cyclohexyl]methoxy]pyridine-4-carbaldehyde;
3-chloro-5-[[2-(3-propan-2-ylimidazol-4-yl)cyclohexyl]methoxy]pyridine-4-carbaldehyde;
3-chloro-5-[[2-(2-methoxyphenyl)cyclohexyl]methoxy]pyridine-4-carbaldehyde;
3-chloro-5-[[2-[2-(2,2,2-trifluoroethyl)pyrazol-3-yl]cyclohexyl]methoxy]pyridine-4-carbaldehyde;
3-chloro-5-[[2-(2-cyclobutylpyrazol-3-yl)cyclohexyl]methoxy]pyridine-4-carbaldehyde;
3-chloro-5-[[2-(2-ethylpyrazol-3-yl)cyclohexyl]methoxy]pyridine-4-carbaldehyde;
3-chloro-5-[[2-(2-chlorophenyl)cyclohexyl]methoxy]pyridine-4-carbaldehyde;
3-chloro-5-[[2-(2-propan-2-ylpyrazol-3-yl)cyclohexyl]methoxy]pyridine-4-carbaldehyde;
3-chloro-5-[[2-(2-cyclopentylpyrazol-3-yl)cyclohexyl]methoxy]pyridine-4-carbaldehyde;
3-chloro-5-[[2-[2-(2,2-difluoroethyl)pyrazol-3-yl]cyclohexyl]methoxy]pyridine-4-carbaldehyde;
3-chloro-5-[[2-(2-fluorophenyl)cyclohexyl]methoxy]pyridine-4-carbaldehyde;
3-chloro-5-[[2-(2-cyclopropylpyrazol-3-yl)cyclohexyl]methoxy]pyridine-4-carbaldehyde;
3-chloro-5-[[2-(2-methoxypyridin-3-yl)cyclohexyl]methoxy]pyridine-4-carbaldehyde;
3-chloro-5-[[2-[2-(3,3,3-trifluoropropyl)pyrazol-3-yl]cyclohexyl]methoxy]pyridine-4-carbaldehyde;
3-chloro-5-[[2-(2-propylpyrazol-3-yl)cyclohexyl]methoxy]pyridine-4-carbaldehyde;
3-chloro-5-[[2-(2-chloropyridin-3-yl)cyclohexyl]methoxy]pyridine-4-carbaldehyde;
3-chloro-5-[(2-phenylcyclohexyl)methoxy]pyridine-4-carbaldehyde;
3-[[2-(2-hydroxypentan-2-yl)cyclohexyl]methoxy]-5-methylpyridine-4-carbaldehyde;
3-[[2-(2-hydroxybutan-2-yl)cyclohexyl]methoxy]-5-methylpyridine-4-carbaldehyde;
3-[[2-(2-hydroxypropan-2-yl)cyclohexyl]methoxy]-5-methylpyridine-4-carbaldehyde;
3-[[2-(2-methoxyphenyl)cyclohexyl]methoxy]-5-methylpyridine-4-carbaldehyde;
3-methyl-5-[[2-[2-(2,2,2-trifluoroethyl)pyrazol-3-yl]cyclohexyl]methoxy]pyridine-4-carbaldehyde;
3-methyl-5-[[2-[2-(oxetan-3-yl)pyrazol-3-yl]cyclohexyl]methoxy]pyridine-4-carbaldehyde;

3-[[2-(2-ethylpyrazol-3-yl)cyclohexyl]methoxy]-5-methylpyridine-4-carbaldehyde;
3-methyl-5-[(2-phenylcyclohexyl)methoxy]pyridine-4-carbaldehyde;
3-[[2-(2,2-difluoroethyl)pyrazol-3-yl]cyclohexyl]methoxy]-5-methylpyridine-4-carbaldehyde;
3-[[2-(2-fluorophenyl)cyclohexyl]methoxy]-5-methylpyridine-4-carbaldehyde;
3-[[2-(2-cyclopropylpyrazol-3-yl)cyclohexyl]methoxy]-5-methylpyridine-4-carbaldehyde;
3-[[2-(2-cyclobutylpyrazol-3-yl)cyclohexyl]methoxy]-5-methylpyridine-4-carbaldehyde;
3-[[2-(2-methoxypyridin-3-yl)cyclohexyl]methoxy]-5-methylpyridine-4-carbaldehyde;
3-methyl-5-[[2-[2-(3,3,3-trifluoropropyl)pyrazol-3-yl]cyclohexyl]methoxy]pyridine-4-carbaldehyde;
3-[[2-(2-cyclopentylpyrazol-3-yl)cyclohexyl]methoxy]-5-methylpyridine-4-carbaldehyde;
3-methyl-5-[[2-(2-propylpyrazol-3-yl)cyclohexyl]methoxy]pyridine-4-carbaldehyde;
3-[[2-(2-chloropyridin-3-yl)cyclohexyl]methoxy]-5-methylpyridine-4-carbaldehyde;
3-methyl-5-[[2-(3-propan-2-ylimidazol-4-yl)cyclohexyl]methoxy]pyridine-4-carbaldehyde;
3-[[2-(2-chlorophenyl)cyclohexyl]methoxy]-5-methylpyridine-4-carbaldehyde;
3-methyl-5-[[2-(2-propan-2-ylpyrazol-3-yl)cyclohexyl]methoxy]pyridine-4-carbaldehyde;
3-hydroxy-5-[[2-(2-hydroxypentan-2-yl)cyclohexyl]methoxy]pyridine-4-carbaldehyde;
3-hydroxy-5-[[2-(2-hydroxybutan-2-yl)cyclohexyl]methoxy]pyridine-4-carbaldehyde;
3-hydroxy-5-[[2-(2-hydroxypropan-2-yl)cyclohexyl]methoxy]pyridine-4-carbaldehyde;
3-hydroxy-5-[[2-(3-propan-2-ylimidazol-4-yl)cyclohexyl]methoxy]pyridine-4-carbaldehyde;
3-[[2-[2-(2,2-difluoroethyl)pyrazol-3-yl]cyclohexyl]methoxy]-5-hydroxypyridine-4-carbaldehyde;
3-[[2-(2-fluorophenyl)cyclohexyl]methoxy]-5-hydroxypyridine-4-carbaldehyde;
3-hydroxy-5-[[2-(2-methoxypyridin-3-yl)cyclohexyl]methoxy]pyridine-4-carbaldehyde;
3-hydroxy-5-[[2-(2-propan-2-ylpyrazol-3-yl)cyclohexyl]methoxy]pyridine-4-carbaldehyde;
3-[[2-(2-cyclopentylpyrazol-3-yl)cyclohexyl]methoxy]-5-hydroxypyridine-4-carbaldehyde;
3-hydroxy-5-[[2-(2-propylpyrazol-3-yl)cyclohexyl]methoxy]pyridine-4-carbaldehyde;
3-[[2-(2-chloropyridin-3-yl)cyclohexyl]methoxy]-5-hydroxypyridine-4-carbaldehyde;
3-[[2-(2-cyclopropylpyrazol-3-yl)cyclohexyl]methoxy]-5-hydroxypyridine-4-carbaldehyde;
3-hydroxy-5-[[2-(2-methoxyphenyl)cyclohexyl]methoxy]pyridine-4-carbaldehyde;
3-hydroxy-5-[[2-[2-(2,2,2-trifluoroethyl)pyrazol-3-yl]cyclohexyl]methoxy]pyridine-4-carbaldehyde;
3-hydroxy-5-[[2-[2-(3,3,3-trifluoropropyl)pyrazol-3-yl]cyclohexyl]methoxy]pyridine-4-carbaldehyde;
3-hydroxy-5-[[2-(oxetan-3-yl)pyrazol-3-yl]cyclohexyl]methoxy]pyridine-4-carbaldehyde;
3-[[2-(2-ethylpyrazol-3-yl)cyclohexyl]methoxy]-5-hydroxypyridine-4-carbaldehyde;
3-[[2-(2-chlorophenyl)cyclohexyl]methoxy]-5-hydroxypyridine-4-carbaldehyde;
3-hydroxy-5-[(2-phenylcyclohexyl)methoxy]pyridine-4-carbaldehyde;
3-[[2-(2-cyclobutylpyrazol-3-yl)cyclohexyl]methoxy]-5-hydroxypyridine-4-carbaldehyde;
3-[[2-(2-hydroxybutan-2-yl)cyclohexyl]methoxy]-5-methoxypyridine-4-carbaldehyde;
3-[[2-(2-hydroxypropan-2-yl)cyclohexyl]methoxy]-5-methoxypyridine-4-carbaldehyde;
3-[[2-(2-hydroxypentan-2-yl)cyclohexyl]methoxy]-5-methoxypyridine-4-carbaldehyde;
3-[[2-(2-fluorophenyl)cyclohexyl]methoxy]-5-methoxypyridine-4-carbaldehyde;
3-[[2-(2-cyclopropylpyrazol-3-yl)cyclohexyl]methoxy]-5-methoxypyridine-4-carbaldehyde;
3-methoxy-5-[[2-[2-(3,3,3-trifluoropropyl)pyrazol-3-yl]cyclohexyl]methoxy]pyridine-4-carbaldehyde;
3-methoxy-5-[[2-[2-(oxetan-3-yl)pyrazol-3-yl]cyclohexyl]methoxy]pyridine-4-carbaldehyde;
3-[[2-(2-chlorophenyl)cyclohexyl]methoxy]-5-methoxypyridine-4-carbaldehyde;
3-methoxy-5-[[2-(2-propylpyrazol-3-yl)cyclohexyl]methoxy]pyridine-4-carbaldehyde;
3-methoxy-5-[[2-(3-propan-2-ylimidazol-4-yl)cyclohexyl]methoxy]pyridine-4-carbaldehyde;
3-methoxy-5-[(2-phenylcyclohexyl)methoxy]pyridine-4-carbaldehyde;
3-methoxy-5-[[2-[2-(2,2,2-trifluoroethyl)pyrazol-3-yl]cyclohexyl]methoxy]pyridine-4-carbaldehyde;
3-[[2-(2-cyclobutylpyrazol-3-yl)cyclohexyl]methoxy]-5-methoxypyridine-4-carbaldehyde;
3-methoxy-5-[[2-(2-methoxypyridin-3-yl)cyclohexyl]methoxy]pyridine-4-carbaldehyde;
3-[[2-(2-ethylpyrazol-3-yl)cyclohexyl]methoxy]-5-methoxypyridine-4-carbaldehyde;
3-methoxy-5-[[2-(2-propan-2-ylpyrazol-3-yl)cyclohexyl]methoxy]pyridine-4-carbaldehyde;
3-[[2-(2-cyclopentylpyrazol-3-yl)cyclohexyl]methoxy]-5-methoxypyridine-4-carbaldehyde;
3-[[2-(2-chloropyridin-3-yl)cyclohexyl]methoxy]-5-methoxypyridine-4-carbaldehyde;
3-[[2-(2,2-difluoroethyl)pyrazol-3-yl]cyclohexyl]methoxy]-5-methoxypyridine-4-carbaldehyde;
3-methoxy-5-[[2-(2-methoxyphenyl)cyclohexyl]methoxy]pyridine-4-carbaldehyde;
2-hydroxy-5-[[2-(2-hydroxybutan-2-yl)cyclohexyl]methoxy]pyridine-4-carbaldehyde;
2-hydroxy-5-[[2-(2-hydroxypropan-2-yl)cyclohexyl]methoxy]pyridine-4-carbaldehyde;
2-hydroxy-5-[[2-(2-hydroxypentan-2-yl)cyclohexyl]methoxy]pyridine-4-carbaldehyde;
5-[[2-(2-ethylpyrazol-3-yl)cyclohexyl]methoxy]-2-hydroxypyridine-4-carbaldehyde;
5-[[2-(2-chlorophenyl)cyclohexyl]methoxy]-2-hydroxypyridine-4-carbaldehyde;
2-hydroxy-5-[(2-phenylcyclohexyl)methoxy]pyridine-4-carbaldehyde;
5-[[2-(2-cyclopropylpyrazol-3-yl)cyclohexyl]methoxy]-2-hydroxypyridine-4-carbaldehyde;
5-[[2-(2-cyclobutylpyrazol-3-yl)cyclohexyl]methoxy]-2-hydroxypyridine-4-carbaldehyde;
2-hydroxy-5-[[2-(2-methoxypyridin-3-yl)cyclohexyl]methoxy]pyridine-4-carbaldehyde;
2-hydroxy-5-[[2-[2-(3,3,3-trifluoropropyl)pyrazol-3-yl]cyclohexyl]methoxy]pyridine-4-carbaldehyde;
5-[[2-(2-cyclopentylpyrazol-3-yl)cyclohexyl]methoxy]-2-hydroxypyridine-4-carbaldehyde;
2-hydroxy-5-[[2-(2-propylpyrazol-3-yl)cyclohexyl]methoxy]pyridine-4-carbaldehyde;

5-[[2-(2-chloropyridin-3-yl)cyclohexyl]methoxy]-2-hydroxypyridine-4-carbaldehyde;
2-hydroxy-5-[[2-(3-propan-2-ylimidazol-4-yl)cyclohexyl]methoxy]pyridine-4-carbaldehyde;
2-hydroxy-5-[[2-(2-methoxyphenyl)cyclohexyl]methoxy]pyridine-4-carbaldehyde;
2-hydroxy-5-[[2-[2-(2,2,2-trifluoroethyl)pyrazol-3-yl]cyclohexyl]methoxy]pyridine-4-carbaldehyde;
2-hydroxy-5-[[2-[2-(oxetan-3-yl)pyrazol-3-yl]cyclohexyl]methoxy]pyridine-4-carbaldehyde;
2-hydroxy-5-[[2-[2-(2-propan-2-ylpyrazol-3-yl)cyclohexyl]methoxy]pyridine-4-carbaldehyde;
5-[[2-[2-(2,2-difluoroethyl)pyrazol-3-yl]cyclohexyl]methoxy]-2-hydroxypyridine-4-carbaldehyde;
5-[[2-(2-fluorophenyl)cyclohexyl]methoxy]-2-hydroxypyridine-4-carbaldehyde;
5-[[2-(2-hydroxypropan-2-yl)cyclohexyl]methoxy]-2-methoxypyridine-4-carbaldehyde;
5-[[2-(2-hydroxypentan-2-yl)cyclohexyl]methoxy]-2-methoxypyridine-4-carbaldehyde;
5-[[2-(2-hydroxybutan-2-yl)cyclohexyl]methoxy]-2-methoxypyridine-4-carbaldehyde;
2-methoxy-5-[[2-(2-methoxypyridin-3-yl)cyclohexyl]methoxy]pyridine-4-carbaldehyde;
5-[[2-(2-cyclopentylpyrazol-3-yl)cyclohexyl]methoxy]-2-methoxypyridine-4-carbaldehyde;
2-methoxy-5-[[2-(2-propylpyrazol-3-yl)cyclohexyl]methoxy]pyridine-4-carbaldehyde;
5-[[2-(2-chloropyridin-3-yl)cyclohexyl]methoxy]-2-methoxypyridine-4-carbaldehyde;
5-[[2-(2-cyclopropylpyrazol-3-yl)cyclohexyl]methoxy]-2-methoxypyridine-4-carbaldehyde;
2-methoxy-5-[[2-(2-methoxyphenyl)cyclohexyl]methoxy]pyridine-4-carbaldehyde;
2-methoxy-5-[[2-(2,2,2-trifluoroethyl)pyrazol-3-yl]cyclohexyl]methoxy]pyridine-4-carbaldehyde;
2-methoxy-5-[[2-[2-(3,3,3-trifluoropropyl)pyrazol-3-yl]cyclohexyl]methoxy]pyridine-4-carbaldehyde;
2-methoxy-5-[[2-[2-(oxetan-3-yl)pyrazol-3-yl]cyclohexyl]methoxy]pyridine-4-carbaldehyde;
5-[[2-(2-ethylpyrazol-3-yl)cyclohexyl]methoxy]-2-methoxypyridine-4-carbaldehyde;
5-[[2-(2-chlorophenyl)cyclohexyl]methoxy]-2-methoxypyridine-4-carbaldehyde;
2-methoxy-5-[[2-(3-propan-2-ylimidazol-4-yl)cyclohexyl]methoxy]pyridine-4-carbaldehyde;
2-methoxy-5-[(2-phenylcyclohexyl)methoxy]pyridine-4-carbaldehyde;
5-[[2-(2,2-difluoroethyl)pyrazol-3-yl]cyclohexyl]methoxy]-2-methoxypyridine-4-carbaldehyde;
5-[[2-(2-fluorophenyl)cyclohexyl]methoxy]-2-methoxypyridine-4-carbaldehyde;
5-[[2-(2-cyclobutylpyrazol-3-yl)cyclohexyl]methoxy]-2-methoxypyridine-4-carbaldehyde;
2-methoxy-5-[[2-(2-propan-2-ylpyrazol-3-yl)cyclohexyl]methoxy]pyridine-4-carbaldehyde;
5-[[2-(2-hydroxypropan-2-yl)cyclohexyl]methoxy]-2-(2-methoxyethoxy)pyridine-4-carbaldehyde;
5-[[2-(2-hydroxypentan-2-yl)cyclohexyl]methoxy]-2-(2-methoxyethoxy)pyridine-4-carbaldehyde;
5-[[2-(2-hydroxybutan-2-yl)cyclohexyl]methoxy]-2-(2-methoxyethoxy)pyridine-4-carbaldehyde;
2-(2-methoxyethoxy)-5-[(2-phenylcyclohexyl)methoxy]pyridine-4-carbaldehyde;
5-[[2-(2-cyclobutylpyrazol-3-yl)cyclohexyl]methoxy]-2-(2-methoxyethoxy)pyridine-4-carbaldehyde;
5-[[2-(2-chlorophenyl)cyclohexyl]methoxy]-2-(2-methoxyethoxy)pyridine-4-carbaldehyde;
2-(2-methoxyethoxy)-5-[[2-(2-propan-2-ylpyrazol-3-yl)cyclohexyl]methoxy]pyridine-4-carbaldehyde;
5-[[2-(2-cyclopentylpyrazol-3-yl)cyclohexyl]methoxy]-2-(2-methoxyethoxy)pyridine-4-carbaldehyde;
5-[[2-[2-(2,2-difluoroethyl)pyrazol-3-yl]cyclohexyl]methoxy]-2-(2-methoxyethoxy)pyridine-4-carbaldehyde;
5-[[2-(2-fluorophenyl)cyclohexyl]methoxy]-2-(2-methoxyethoxy)pyridine-4-carbaldehyde;
5-[[2-(2-cyclopropylpyrazol-3-yl)cyclohexyl]methoxy]-2-(2-methoxyethoxy)pyridine-4-carbaldehyde;
2-(2-methoxyethoxy)-5-[[2-(2-methoxypyridin-3-yl)cyclohexyl]methoxy]pyridine-4-carbaldehyde;
2-(2-methoxyethoxy)-5-[[2-[2-(3,3,3-trifluoropropyl)pyrazol-3-yl]cyclohexyl]methoxy]pyridine-4-carbaldehyde;
2-(2-methoxyethoxy)-5-[[2-(oxetan-3-yl)pyrazol-3-yl]cyclohexyl]methoxy]pyridine-4-carbaldehyde;
2-(2-methoxyethoxy)-5-[[2-(2-propylpyrazol-3-yl)cyclohexyl]methoxy]pyridine-4-carbaldehyde;
5-[[2-(2-chloropyridin-3-yl)cyclohexyl]methoxy]-2-(2-methoxyethoxy)pyridine-4-carbaldehyde;
2-(2-methoxyethoxy)-5-[[2-(3-propan-2-ylimidazol-4-yl)cyclohexyl]methoxy]pyridine-4-carbaldehyde;
2-(2-methoxyethoxy)-5-[[2-(2-methoxyphenyl)cyclohexyl]methoxy]pyridine-4-carbaldehyde;
2-(2-methoxyethoxy)-5-[[2-[2-(2,2,2-trifluoroethyl)pyrazol-3-yl]cyclohexyl]methoxy]pyridine-4-carbaldehyde;
5-[[2-(2-ethylpyrazol-3-yl)cyclohexyl]methoxy]-2-(2-methoxyethoxy)pyridine-4-carbaldehyde;
5-[[2-(2-hydroxybutan-2-yl)cyclohexyl]methoxy]-2-(2-morpholin-4-ylethoxy)pyridine-4-carbaldehyde;
5-[[2-(2-hydroxypropan-2-yl)cyclohexyl]methoxy]-2-(2-morpholin-4-ylethoxy)pyridine-4-carbaldehyde;
5-[[2-(2-hydroxypentan-2-yl)cyclohexyl]methoxy]-2-(2-morpholin-4-ylethoxy)pyridine-4-carbaldehyde;
2-(2-morpholin-4-ylethoxy)-5-[[2-[2-(3,3,3-trifluoropropyl)pyrazol-3-yl]cyclohexyl]methoxy]pyridine-4-carbaldehyde;
5-[[2-(2-chlorophenyl)cyclohexyl]methoxy]-2-(2-morpholin-4-ylethoxy)pyridine-4-carbaldehyde;
2-(2-morpholin-4-ylethoxy)-54[2-(2-propylpyrazol-3-yl)cyclohexyl]methoxy]pyridine-4-carbaldehyde;
2-(2-morpholin-4-ylethoxy)-5-[(2-phenylcyclohexyl)methoxy]pyridine-4-carbaldehyde;
2-(2-morpholin-4-ylethoxy)-5-[[2-(2,2,2-trifluoroethyl)pyrazol-3-yl]cyclohexyl]methoxy]pyridine-4-carbaldehyde;
5-[[2-(2-cyclobutylpyrazol-3-yl)cyclohexyl]methoxy]-2-(2-morpholin-4-ylethoxy)pyridine-4-carbaldehyde;
5-[[2-(2-methoxypyridin-3-yl)cyclohexyl]methoxy]-2-(2-morpholin-4-ylethoxy)pyridine-4-carbaldehyde;
5-[[2-(2-ethylpyrazol-3-yl)cyclohexyl]methoxy]-2-(2-morpholin-4-ylethoxy)pyridine-4-carbaldehyde;
2-(2-morpholin-4-ylethoxy)-5-[[2-(2-propan-2-ylpyrazol-3-yl)cyclohexyl]methoxy]pyridine-4-carbaldehyde;
5-[[2-(2-cyclopentylpyrazol-3-yl)cyclohexyl]methoxy]-2-(2-morpholin-4-ylethoxy)pyridine-4-carbaldehyde;
5-[[2-(2-chloropyridin-3-yl)cyclohexyl]methoxy]-2-(2-morpholin-4-ylethoxy)pyridine-4-carbaldehyde;
5-[[2-(2,2-difluoroethyl)pyrazol-3-yl]cyclohexyl]methoxy]-2-(2-morpholin-4-ylethoxy)pyridine-4-carbaldehyde;

5-[[2-(2-fluorophenyl)cyclohexyl]methoxy]-2-(2-morpholin-4-ylethoxy)pyridine-4-carbaldehyde;
5-[[2-(2-cyclopropylpyrazol-3-yl)cyclohexyl]methoxy]-2-(2-morpholin-4-ylethoxy)pyridine-4-carbaldehyde;
5-[[2-(2-methoxyphenyl)cyclohexyl]methoxy]-2-(2-morpholin-4-ylethoxy)pyridine-4-carbaldehyde;
2-(2-morpholin-4-ylethoxy)-5-[[2-[2-(oxetan-3-yl)pyrazol-3-yl]cyclohexyl]methoxy]pyridine-4-carbaldehyde;
2-(2-morpholin-4-ylethoxy)-5-[[2-(3-propan-2-ylimidazol-4-yl)cyclohexyl]methoxy]pyridine-4-carbaldehyde;
3-[[2-(2-hydroxypentan-2-yl)cyclohexen-1-yl]methoxy]pyridine-2-carbaldehyde;
3-[[2-(2-hydroxybutan-2-yl)cyclohexen-1-yl]methoxy]pyridine-2-carbaldehyde;
3-[[2-(2-hydroxypropan-2-yl)cyclohexen-1-yl]methoxy]pyridine-2-carbaldehyde;
3-[[2-(2-propylpyrazol-3-yl)cyclohexen-1-yl]methoxy]pyridine-2-carbaldehyde;
3-[[2-(2-chloropyridin-3-yl)cyclohexen-1-yl]methoxy]pyridine-2-carbaldehyde;
3-[[2-(2-methoxyphenyl)cyclohexen-1-yl]methoxy]pyridine-2-carbaldehyde;
3-[[2-[2-(3,3,3-trifluoropropyl)pyrazol-3-yl]cyclohexen-1-yl]methoxy]pyridine-2-carbaldehyde;
3-[[2-[2-(oxetan-3-yl)pyrazol-3-yl]cyclohexen-1-yl]methoxy]pyridine-2-carbaldehyde;
3-[[2-(2-ethylpyrazol-3-yl)cyclohexen-1-yl]methoxy]pyridine-2-carbaldehyde;
3-[[2-(2-chlorophenyl)cyclohexen-1-yl]methoxy]pyridine-2-carbaldehyde;
3-[[2-(3-propan-2-ylimidazol-4-yl)cyclohexen-1-yl]methoxy]pyridine-2-carbaldehyde;
3-[(2-phenylcyclohexen-1-yl)methoxy]pyridine-2-carbaldehyde;
3-[[2-(2,2-difluoroethyl)pyrazol-3-yl]cyclohexen-1-yl]methoxy]pyridine-2-carbaldehyde;
3-[[2-(2-fluorophenyl)cyclohexen-1-yl]methoxy]pyridine-2-carbaldehyde;
3-[[2-(2-cyclobutylpyrazol-3-yl)cyclohexen-1-yl]methoxy]pyridine-2-carbaldehyde;
3-[[2-(2-methoxypyridin-3-yl)cyclohexen-1-yl]methoxy]pyridine-2-carbaldehyde;
3-[[2-(2-propan-2-ylpyrazol-3-yl)cyclohexen-1-yl]methoxy]pyridine-2-carbaldehyde;
3-[[2-(2-cyclopentylpyrazol-3-yl)cyclohexen-1-yl]methoxy]pyridine-2-carbaldehyde;
3-[[2-(2-cyclopropylpyrazol-3-yl)cyclohexen-1-yl]methoxy]pyridine-2-carbaldehyde;
3-[[2-(2,2,2-trifluoroethyl)pyrazol-3-yl]cyclohexen-1-yl]methoxy]pyridine-2-carbaldehyde;
3-[[2-(2-hydroxybutan-2-yl)cyclohexen-1-yl]methoxy]-6-methylpyridine-2-carbaldehyde;
3-[[2-(2-hydroxypropan-2-yl)cyclohexen-1-yl]methoxy]-6-methylpyridine-2-carbaldehyde;
3-[[2-(2-hydroxypentan-2-yl)cyclohexen-1-yl]methoxy]-6-methylpyridine-2-carbaldehyde;
3-[[2-(2-cyclobutylpyrazol-3-yl)cyclohexen-1-yl]methoxy]-6-methylpyridine-2-carbaldehyde;
3-[[2-(2-cyclopentylpyrazol-3-yl)cyclohexen-1-yl]methoxy]-6-methylpyridine-2-carbaldehyde;
6-methyl-3-[[2-(2-propylpyrazol-3-yl)cyclohexen-1-yl]methoxy]pyridine-2-carbaldehyde;
3-[[2-(2-chloropyridin-3-yl)cyclohexen-1-yl]methoxy]-6-methylpyridine-2-carbaldehyde;
6-methyl-3-[[2-(3-propan-2-ylimidazol-4-yl)cyclohexen-1-yl]methoxy]pyridine-2-carbaldehyde;
3-[[2-(2-methoxyphenyl)cyclohexen-1-yl]methoxy]-6-methylpyridine-2-carbaldehyde;
6-methyl-3-[[2-(2,2,2-trifluoroethyl)pyrazol-3-yl]cyclohexen-1-yl]methoxy]pyridine-2-carbaldehyde;
6-methyl-3-[[2-(oxetan-3-yl)pyrazol-3-yl]cyclohexen-1-yl]methoxy]pyridine-2-carbaldehyde;
3-[[2-(2-ethylpyrazol-3-yl)cyclohexen-1-yl]methoxy]-6-methylpyridine-2-carbaldehyde;
3-[[2-(2-chlorophenyl)cyclohexen-1-yl]methoxy]-6-methylpyridine-2-carbaldehyde;
6-methyl-3-[[2-(2-propan-2-ylpyrazol-3-yl)cyclohexen-1-yl]methoxy]pyridine-2-carbaldehyde;
6-methyl-3-[(2-phenylcyclohexen-1-yl)methoxy]pyridine-2-carbaldehyde;
3-[[2-[2-(2,2-difluoroethyl)pyrazol-3-yl]cyclohexen-1-yl]methoxy]-6-methylpyridine-2-carbaldehyde;
3-[[2-(2-fluorophenyl)cyclohexen-1-yl]methoxy]-6-methylpyridine-2-carbaldehyde;
3-[[2-(2-cyclopropylpyrazol-3-yl)cyclohexen-1-yl]methoxy]-6-methylpyridine-2-carbaldehyde;
3-[[2-(2-methoxypyridin-3-yl)cyclohexen-1-yl]methoxy]-6-methylpyridine-2-carbaldehyde;
6-methyl-3-[[2-[2-(3,3,3-trifluoropropyl)pyrazol-3-yl]cyclohexen-1-yl]methoxy]pyridine-2-carbaldehyde;
3-chloro-5-[[2-(2-hydroxypropan-2-yl)cyclohexen-1-yl]methoxy]pyridine-4-carbaldehyde;
3-chloro-5-[[2-(2-hydroxypentan-2-yl)cyclohexen-1-yl]methoxy]pyridine-4-carbaldehyde;
3-chloro-5-[[2-(2-hydroxybutan-2-yl)cyclohexen-1-yl]methoxy]pyridine-4-carbaldehyde;
3-chloro-5-[[2-(oxetan-3-yl)pyrazol-3-yl]cyclohexen-1-yl]methoxy]pyridine-4-carbaldehyde;
3-chloro-5-[[2-(3-propan-2-ylimidazol-4-yl)cyclohexen-1-yl]methoxy]pyridine-4-carbaldehyde;
3-chloro-5-[[2-(2-methoxyphenyl)cyclohexen-1-yl]methoxy]pyridine-4-carbaldehyde;
3-chloro-5-[[2[2-(2,2,2-trifluoroethyl)pyrazol-3-yl]cyclohexen-1-yl]methoxy]pyridine-4-carbaldehyde;
3-chloro-5-[[2-(2-cyclobutylpyrazol-3-yl)cyclohexen-1-yl]methoxy]pyridine-4-carbaldehyde;
3-chloro-5-[[2-(2-ethylpyrazol-3-yl)cyclohexen-1-yl]methoxy]pyridine-4-carbaldehyde;
3-chloro-5-[[2-(2-chlorophenyl)cyclohexen-1-yl]methoxy]pyridine-4-carbaldehyde;
3-chloro-5-[[2-(2-propan-2-ylpyrazol-3-yl)cyclohexen-1-yl]methoxy]pyridine-4-carbaldehyde;
3-chloro-5-[[2-(2-cyclopentylpyrazol-3-yl)cyclohexen-1-yl]methoxy]pyridine-4-carbaldehyde;
3-chloro-5-[[2-[2-(2,2-difluoroethyl)pyrazol-3-yl]cyclohexen-1-yl]methoxy]pyridine-4-carbaldehyde;
3-chloro-5-[[2-(2-fluorophenyl)cyclohexen-1-yl]methoxy]pyridine-4-carbaldehyde;
3-chloro-5-[[2-(2-cyclopropylpyrazol-3-yl)cyclohexen-1-yl]methoxy]pyridine-4-carbaldehyde;
3-chloro-5-[[2-(2-methoxypyridin-3-yl)cyclohexen-1-yl]methoxy]pyridine-4-carbaldehyde;
3-chloro-5-[[2-(3,3,3-trifluoropropyl)pyrazol-3-yl]cyclohexen-1-yl]methoxy]pyridine-4-carbaldehyde;
3-chloro-5-[[2-(2-propylpyrazol-3-yl)cyclohexen-1-yl]methoxy]pyridine-4-carbaldehyde;
3-chloro-5-[[2-(2-chloropyridin-3-yl)cyclohexen-1-yl]methoxy]pyridine-4-carbaldehyde;
3-chloro-5-[(2-phenylcyclohexen-1-yl)methoxy]pyridine-4-carbaldehyde;

3-[[2-(2-hydroxypentan-2-yl)cyclohexen-1-yl]methoxy]-5-methylpyridine-4-carbaldehyde;
3-[[2-(2-hydroxybutan-2-yl)cyclohexen-1-yl]methoxy]-5-methylpyridine-4-carbaldehyde;
3-[[2-(2-hydroxypropan-2-yl)cyclohexen-1-yl]methoxy]-5-methylpyridine-4-carbaldehyde;
3-[[2-(2-methoxyphenyl)cyclohexen-1-yl]methoxy]-5-methylpyridine-4-carbaldehyde;
3-methyl-5-[[2-[2-(2,2,2-trifluoroethyl)pyrazol-3-yl]cyclohexen-1-yl]methoxy]pyridine-4-carbaldehyde;
3-methyl-5-[[2-(oxetan-3-yl)pyrazol-3-yl]cyclohexen-1-yl]methoxy]pyridine-4-carbaldehyde;
3-[[2-(2-ethylpyrazol-3-yl)cyclohexen-1-yl]methoxy]-5-methylpyridine-4-carbaldehyde;
3-methyl-5-[(2-phenylcyclohexen-1-yl)methoxy]pyridine-4-carbaldehyde;
3-[[2-(2,2-difluoroethyl)pyrazol-3-yl]cyclohexen-1-yl]methoxy]-5-methylpyridine-4-carbaldehyde;
3-[[2-(2-fluorophenyl)cyclohexen-1-yl]methoxy]-5-methylpyridine-4-carbaldehyde;
3-[[2-(2-cyclopropylpyrazol-3-yl)cyclohexen-1-yl]methoxy]-5-methylpyridine-4-carbaldehyde;
3-[[2-(2-cyclobutylpyrazol-3-yl)cyclohexen-1-yl]methoxy]-5-methylpyridine-4-carbaldehyde;
3-[[2-(2-methoxypyridin-3-yl)cyclohexen-1-yl]methoxy]-5-methylpyridine-4-carbaldehyde;
3-methyl-5-[[2-[2-(3,3,3-trifluoropropyl)pyrazol-3-yl]cyclohexen-1-yl]methoxy]pyridine-4-carbaldehyde;
3-[[2-(2-cyclopentylpyrazol-3-yl)cyclohexen-1-yl]methoxy]-5-methylpyridine-4-carbaldehyde;
3-methyl-5-[[2-(2-propylpyrazol-3-yl)cyclohexen-1-yl]methoxy]pyridine-4-carbaldehyde;
3-[[2-(2-chloropyridin-3-yl)cyclohexen-1-yl]methoxy]-5-methylpyridine-4-carbaldehyde;
3-methyl-5-[[2-(3-propan-2-yhmidazol-4-yl)cyclohexen-1-yl]methoxy]pyridine-4-carbaldehyde;
3-[[2-(2-chlorophenyl)cyclohexen-1-yl]methoxy]-5-methylpyridine-4-carbaldehyde;
3-methyl-5-[[2-(2-propan-2-ylpyrazol-3-yl)cyclohexen-1-yl]methoxy]pyridine-4-carbaldehyde;
3-hydroxy-5-[[2-(2-hydroxypentan-2-yl)cyclohexen-1-yl]methoxy]pyridine-4-carbaldehyde;
3-hydroxy-5-[[2-(2-hydroxybutan-2-yl)cyclohexen-1-yl]methoxy]pyridine-4-carbaldehyde;
3-hydroxy-5-[[2-(2-hydroxypropan-2-yl)cyclohexen-1-yl]methoxy]pyridine-4-carbaldehyde;
3-hydroxy-5-[[2-(3-propan-2-yhmidazol-4-yl)cyclohexen-1-yl]methoxy]pyridine-4-carbaldehyde;
3-[[2-[2-(2,2-difluoroethyl)pyrazol-3-yl]cyclohexen-1-yl]methoxy]-5-hydroxypyridine-4-carbaldehyde;
3-[[2-(2-fluorophenyl)cyclohexen-1-yl]methoxy]-5-hydroxypyridine-4-carbaldehyde;
3-hydroxy-5-[[2-(2-methoxypyridin-3-yl)cyclohexen-1-yl]methoxy]pyridine-4-carbaldehyde;
3-hydroxy-5-[[2-(2-propan-2-ylpyrazol-3-yl)cyclohexen-1-yl]methoxy]pyridine-4-carbaldehyde;
3-[[2-(2-cyclopentylpyrazol-3-yl)cyclohexen-1-yl]methoxy]-5-hydroxypyridine-4-carbaldehyde;
3-hydroxy-5-[[2-(2-propylpyrazol-3-yl)cyclohexen-1-yl]methoxy]pyridine-4-carbaldehyde;
3-[[2-(2-chloropyridin-3-yl)cyclohexen-1-yl]methoxy]-5-hydroxypyridine-4-carbaldehyde;
3-[[2-(2-cyclopropylpyrazol-3-yl)cyclohexen-1-yl]methoxy]-5-hydroxypyridine-4-carbaldehyde;
3-hydroxy-5-[[2-(2-methoxyphenyl)cyclohexen-1-yl]methoxy]pyridine-4-carbaldehyde;
3-hydroxy-5-[[2-(2,2,2-trifluoroethyl)pyrazol-3-yl]cyclohexen-1-yl]methoxy]pyridine-4-carbaldehyde;
3-hydroxy-5-[[2-[2-(3,3,3-trifluoropropyl)pyrazol-3-yl]cyclohexen-1-yl]methoxy]pyridine-4-carbaldehyde;
3-hydroxy-5-[[2-[2-(oxetan-3-yl)pyrazol-3-yl]cyclohexen-1-yl]methoxy]pyridine-4-carbaldehyde;
3-[[2-(2-ethylpyrazol-3-yl)cyclohexen-1-yl]methoxy]-5-hydroxypyridine-4-carbaldehyde;
3-[[2-(2-chlorophenyl)cyclohexen-1-yl]methoxy]-5-hydroxypyridine-4-carbaldehyde;
3-hydroxy-5-[(2-phenylcyclohexen-1-yl)methoxy]pyridine-4-carbaldehyde;
3-[[2-(2-cyclobutylpyrazol-3-yl)cyclohexen-1-yl]methoxy]-5-hydroxypyridine-4-carbaldehyde;
3-[[2-(2-hydroxybutan-2-yl)cyclohexen-1-yl]methoxy]-5-methoxypyridine-4-carbaldehyde;
3-[[2-(2-hydroxypropan-2-yl)cyclohexen-1-yl]methoxy]-5-methoxypyridine-4-carbaldehyde;
3-[[2-(2-hydroxypentan-2-yl)cyclohexen-1-yl]methoxy]-5-methoxypyridine-4-carbaldehyde;
3-[[2-(2-fluorophenyl)cyclohexen-1-yl]methoxy]-5-methoxypyridine-4-carbaldehyde;
3-[[2-(2-cyclopropylpyrazol-3-yl)cyclohexen-1-yl]methoxy]-5-methoxypyridine-4-carbaldehyde;
3-methoxy-5-[[2-[2-(3,3,3-trifluoropropyl)pyrazol-3-yl]cyclohexen-1-yl]methoxy]pyridine-4-carbaldehyde;
3-methoxy-5-[[2-[2-(oxetan-3-yl)pyrazol-3-yl]cyclohexen-1-yl]methoxy]pyridine-4-carbaldehyde;
3-[[2-(2-chlorophenyl)cyclohexen-1-yl]methoxy]-5-methoxypyridine-4-carbaldehyde;
3-methoxy-5-[[2-(2-propylpyrazol-3-yl)cyclohexen-1-yl]methoxy]pyridine-4-carbaldehyde;
3-methoxy-5-[[2-(3-propan-2-ylimidazol-4-yl)cyclohexen-1-yl]methoxy]pyridine-4-carbaldehyde;
3-methoxy-5-[(2-phenylcyclohexen-1-yl)methoxy]pyridine-4-carbaldehyde;
3-methoxy-5-[[2-[2-(2,2,2-trifluoroethyl)pyrazol-3-yl]cyclohexen-1-yl]methoxy]pyridine-4-carbaldehyde;
3-[[2-(2-cyclobutylpyrazol-3-yl)cyclohexen-1-yl]methoxy]-5-methoxypyridine-4-carbaldehyde;
3-methoxy-5-[[2-(2-methoxypyridin-3-yl)cyclohexen-1-yl]methoxy]pyridine-4-carbaldehyde;
3-[[2-(2-ethylpyrazol-3-yl)cyclohexen-1-yl]methoxy]-5-methoxypyridine-4-carbaldehyde;
3-methoxy-5-[[2-(2-propan-2-ylpyrazol-3-yl)cyclohexen-1-yl]methoxy]pyridine-4-carbaldehyde;
3-[[2-(2-cyclopentylpyrazol-3-yl)cyclohexen-1-yl]methoxy]-5-methoxypyridine-4-carbaldehyde;
3-[[2-(2-chloropyridin-3-yl)cyclohexen-1-yl]methoxy]-5-methoxypyridine-4-carbaldehyde;
3-[[2-[2-(2,2-difluoroethyl)pyrazol-3-yl]cyclohexen-1-yl]methoxy]-5-methoxypyridine-4-carbaldehyde;
3-methoxy-5-[[2-(2-methoxyphenyl)cyclohexen-1-yl]methoxy]pyridine-4-carbaldehyde;
2-hydroxy-5-[[2-(2-hydroxybutan-2-yl)cyclohexen-1-yl]methoxy]pyridine-4-carbaldehyde;
2-hydroxy-5-[[2-(2-hydroxypropan-2-yl)cyclohexen-1-yl]methoxy]pyridine-4-carbaldehyde;
2-hydroxy-5-[[2-(2-hydroxypentan-2-yl)cyclohexen-1-yl]methoxy]pyridine-4-carbaldehyde;
5-[[2-(2-ethylpyrazol-3-yl)cyclohexen-1-yl]methoxy]-2-hydroxypyridine-4-carbaldehyde;
5-[[2-(2-chlorophenyl)cyclohexen-1-yl]methoxy]-2-hydroxypyridine-4-carbaldehyde;
2-hydroxy-5-[(2-phenylcyclohexen-1-yl)methoxy]pyridine-4-carbaldehyde;

5-[[2-(2-cyclopropylpyrazol-3-yl)cyclohexen-1-yl]
methoxy]-2-hydroxypyridine-4-carbaldehyde;
5-[[2-(2-cyclobutylpyrazol-3-yl)cyclohexen-1-yl]
methoxy]-2-hydroxypyridine-4-carbaldehyde;
2-hydroxy-5-[[2-(2-methoxypyridin-3-yl)cyclohexen-1-
yl]methoxy]pyridine-4-carbaldehyde;
2-hydroxy-5-[[2-[2-(3,3,3-trifluoropropyl)pyrazol-3-yl]
cyclohexen-1-yl]methoxy]pyridine-4-carbaldehyde;
5-[[2-(2-cyclopentylpyrazol-3-yl)cyclohexen-1-yl]
methoxy]-2-hydroxypyridine-4-carbaldehyde;
2-hydroxy-5-[[2-(2-propylpyrazol-3-yl)cyclohexen-1-yl]
methoxy]pyridine-4-carbaldehyde;
5-[[2-(2-chloropyridin-3-yl)cyclohexen-1-yl]methoxy]-
2-hydroxypyridine-4-carbaldehyde;
2-hydroxy-5-[[2-(3-propan-2-ylimidazol-4-yl)cyclo-
hexen-1-yl]methoxy]pyridine-4-carbaldehyde;
2-hydroxy-5-[[2-(2-methoxyphenyl)cyclohexen-1-yl]
methoxy]pyridine-4-carbaldehyde;
2-hydroxy-5-[[2-(2,2,2-trifluoroethyl)pyrazol-3-yl]cyclo-
hexen-1-yl]methoxy]pyridine-4-carbaldehyde;
2-hydroxy-5-[[2-[2-(oxetan-3-yl)pyrazol-3-yl]cyclo-
hexen-1-yl]methoxy]pyridine-4-carbaldehyde;
2-hydroxy-5-[[2-(2-propan-2-ylpyrazol-3-yl)cyclohexen-
1-yl]methoxy]pyridine-4-carbaldehyde;
5-[[2-(2,2-difluoroethyl)pyrazol-3-yl]cyclohexen-1-yl]
methoxy]-2-hydroxypyridine-4-carbaldehyde;
5-[[2-(2-fluorophenyl)cyclohexen-1-yl]methoxy]-2-hy-
droxypyridine-4-carbaldehyde;
5-[[2-(2-hydroxypropan-2-yl)cyclohexen-1-yl]methoxy]-
2-methoxypyridine-4-carbaldehyde;
5-[[2-(2-hydroxypentan-2-yl)cyclohexen-1-yl]methoxy]-
2-methoxypyridine-4-carbaldehyde;
5-[[2-(2-hydroxybutan-2-yl)cyclohexen-1-yl]methoxy]-
2-methoxypyridine-4-carbaldehyde;
2-methoxy-5-[[2-(2-methoxypyridin-3-yl)cyclohexen-1-
yl]methoxy]pyridine-4-carbaldehyde;
5-[[2-(2-cyclopentylpyrazol-3-yl)cyclohexen-1-yl]
methoxy]-2-methoxypyridine-4-carbaldehyde;
2-methoxy-5-[[2-(2-propylpyrazol-3-yl)cyclohexen-1-yl]
methoxy]pyridine-4-carbaldehyde;
5-[[2-(2-chloropyridin-3-yl)cyclohexen-1-yl]methoxy]-
2-methoxypyridine-4-carbaldehyde;
5-[[2-(2-cyclopropylpyrazol-3-yl)cyclohexen-1-yl]
methoxy]-2-methoxypyridine-4-carbaldehyde;
2-methoxy-5-[[2-(2-methoxyphenyl)cyclohexen-1-yl]
methoxy]pyridine-4-carbaldehyde;
2-methoxy-5-[[2-[2-(2,2,2-trifluoroethyl)pyrazol-3-yl]
cyclohexen-1-yl]methoxy]pyridine-4-carbaldehyde;
2-methoxy-5-[[2-[2-(3,3,3-trifluoropropyl)pyrazol-3-yl]
cyclohexen-1-yl]methoxy]pyridine-4-carbaldehyde;
2-methoxy-5-[[2-[2-(oxetan-3-yl)pyrazol-3-yl]cyclo-
hexen-1-yl]methoxy]pyridine-4-carbaldehyde;
5-[[2-(2-ethylpyrazol-3-yl)cyclohexen-1-yl]methoxy]-2-
methoxypyridine-4-carbaldehyde;
5-[[2-(2-chlorophenyl)cyclohexen-1-yl]methoxy]-2-
methoxypyridine-4-carbaldehyde;
2-methoxy-5-[[2-(3-propan-2-ylimidazol-4-yl)cyclo-
hexen-1-yl]methoxy]pyridine-4-carbaldehyde;
2-methoxy-5-[(2-phenylcyclohexen-1-yl)methoxy]pyri-
dine-4-carbaldehyde;
5-[[2-[2-(2,2-difluoroethyl)pyrazol-3-yl]cyclohexen-1-
yl]methoxy]-2-methoxypyridine-4-carbaldehyde;
5-[[2-(2-fluorophenyl)cyclohexen-1-yl]methoxy]-2-
methoxypyridine-4-carbaldehyde;
5-[[2-(2-cyclobutylpyrazol-3-yl)cyclohexen-1-yl]
methoxy]-2-methoxypyridine-4-carbaldehyde;
2-methoxy-5-[[2-(2-propan-2-ylpyrazol-3-yl)cyclo-
hexen-1-yl]methoxy]pyridine-4-carbaldehyde;
5-[[2-(2-hydroxypropan-2-yl)cyclohexen-1-yl]methoxy]-
2-(2-methoxyethoxy)pyridine-4-carbaldehyde;
5-[[2-(2-hydroxypentan-2-yl)cyclohexen-1-yl]methoxy]-
2-(2-methoxyethoxy)pyridine-4-carbaldehyde;
5-[[2-(2-hydroxybutan-2-yl)cyclohexen-1-yl]methoxy]-
2-(2-methoxyethoxy)pyridine-4-carbaldehyde;
2-(2-methoxyethoxy)-5-[(2-phenylcyclohexen-1-yl)
methoxy]pyridine-4-carbaldehyde;
5-[[2-(2-cyclobutylpyrazol-3-yl)cyclohexen-1-yl]
methoxy]-2-(2-methoxyethoxy)pyridine-4-carbalde-
hyde;
5-[[2-(2-chlorophenyl)cyclohexen-1-yl]methoxy]-2-(2-
methoxyethoxy)pyridine-4-carbaldehyde;
2-(2-methoxyethoxy)-5-[[2-(2-propan-2-ylpyrazol-3-yl)
cyclohexen-1-yl]methoxy]pyridine-4-carbaldehyde;
5-[[2-(2-cyclopentylpyrazol-3-yl)cyclohexen-1-yl]
methoxy]-2-(2-methoxyethoxy)pyridine-4-carbalde-
hyde;
5-[[2-[2-(2,2-difluoroethyl)pyrazol-3-yl]cyclohexen-1-
yl]methoxy]-2-(2-methoxyethoxy)pyridine-4-carbal-
dehyde;
5-[[2-(2-fluorophenyl)cyclohexen-1-yl]methoxy]-2-(2-
methoxyethoxy)pyridine-4-carbaldehyde;
5-[[2-(2-cyclopropylpyrazol-3-yl)cyclohexen-1-yl]
methoxy]-2-(2-methoxyethoxy)pyridine-4-carbalde-
hyde;
2-(2-methoxyethoxy)-5-[[2-(2-methoxypyridin-3-yl)cy-
clohexen-1-yl]methoxy]pyridine-4-carbaldehyde;
2-(2-methoxyethoxy)-5-[[2-[2-(3,3,3-trifluoropropyl)
pyrazol-3-yl]cyclohexen-1-yl]methoxy]pyridine-4-car-
baldehyde;
2-(2-methoxyethoxy)-5-[[2-[2-(oxetan-3-yl)pyrazol-3-yl]
cyclohexen-1-yl]methoxy]pyridine-4-carbaldehyde;
2-(2-methoxyethoxy)-5-[[2-(2-propylpyrazol-3-yl)cyclo-
hexen-1-yl]methoxy]pyridine-4-carbaldehyde;
5-[[2-(2-chloropyridin-3-yl)cyclohexen-1-yl]methoxy]-
2-(2-methoxyethoxy)pyridine-4-carbaldehyde;
2-(2-methoxyethoxy)-5-[[2-(3-propan-2-ylimidazol-4-yl)
cyclohexen-1-yl]methoxy]pyridine-4-carbaldehyde;
2-(2-methoxyethoxy)-5-[[2-(2-methoxyphenyl)cyclo-
hexen-1-yl]methoxy]pyridine-4-carbaldehyde;
2-(2-methoxyethoxy)-5-[[2-[2-(2,2,2-trifluoroethyl)pyra-
zol-3-yl]cyclohexen-1-yl]methoxy]pyridine-4-carbal-
dehyde;
5-[[2-(2-ethylpyrazol-3-yl)cyclohexen-1-yl]methoxy]-2-
(2-methoxyethoxy)pyridine-4-carbaldehyde;
5-[[2-(2-hydroxybutan-2-yl)cyclohexen-1-yl]methoxy]-
2-(2-morpholin-4-ylethoxy)pyridine-4-carbaldehyde;
5-[[2-(2-hydroxypropan-2-yl)cyclohexen-1-yl]methoxy]-
2-(2-morpholin-4-ylethoxy)pyridine-4-carbaldehyde;
5-[[2-(2-hydroxypentan-2-yl)cyclohexen-1-yl]methoxy]-
2-(2-morpholin-4-ylethoxy)pyridine-4-carbaldehyde;
2-(2-morpholin-4-ylethoxy)-5-[[2-[2-(3,3,3-trifluoropro-
pyl)pyrazol-3-yl]cyclohexen-1-yl]methoxy]pyridine-
4-carbaldehyde;
5-[[2-(2-chlorophenyl)cyclohexen-1-yl]methoxy]-2-(2-
morpholin-4-ylethoxy)pyridine-4-carbaldehyde;
2-(2-morpholin-4-ylethoxy)-5-[[2-(2-propylpyrazol-3-yl)
cyclohexen-1-yl]methoxy]pyridine-4-carbaldehyde;
2-(2-morpholin-4-ylethoxy)-5-[(2-phenylcyclohexen-1-
yl)methoxy]pyridine-4-carbaldehyde;
2-(2-morpholin-4-ylethoxy)-5[[2-[2-(2,2,2-trifluoroethyl)
pyrazol-3-yl]cyclohexen-1-yl]methoxy]pyridine-4-car-
baldehyde;

5-[[2-(2-cyclobutylpyrazol-3-yl)cyclohexen-1-yl]methoxy]-2-(2-morpholin-4-ylethoxy)pyridine-4-carbaldehyde;

5-[[2-(2-methoxypyridin-3-yl)cyclohexen-1-yl]methoxy]-2-(2-morpholin-4-ylethoxy)pyridine-4-carbaldehyde;

5-[[2-(2-ethylpyrazol-3-yl)cyclohexen-1-yl]methoxy]-2-(2-morpholin-4-ylethoxy)pyridine-4-carbaldehyde;

2-(2-morpholin-4-ylethoxy)-5-[[2-(2-propan-2-ylpyrazol-3-yl)cyclohexen-1-yl]methoxy]pyridine-4-carbaldehyde;

5-[[2-(2-cyclopentylpyrazol-3-yl)cyclohexen-1-yl]methoxy]-2-(2-morpholin-4-ylethoxy)pyridine-4-carbaldehyde;

5-[[2-(2-chloropyridin-3-yl)cyclohexen-1-yl]methoxy]-2-(2-morpholin-4-ylethoxy)pyridine-4-carbaldehyde;

5-[[2-[2-(2,2-difluoroethyl)pyrazol-3-yl]cyclohexen-1-yl]methoxy]-2-(2-morpholin-4-ylethoxy)pyridine-4-carbaldehyde;

5-[[2-(2-fluorophenyl)cyclohexen-1-yl]methoxy]-2-(2-morpholin-4-ylethoxy)pyridine-4-carbaldehyde;

5-[[2-(2-cyclopropylpyrazol-3-yl)cyclohexen-1-yl]methoxy]-2-(2-morpholin-4-ylethoxy)pyridine-4-carbaldehyde;

5-[[2-(2-methoxyphenyl)cyclohexen-1-yl]methoxy]-2-(2-morpholin-4-ylethoxy)pyridine-4-carbaldehyde;

2-(2-morpholin-4-ylethoxy)-5-[[2-[2-(oxetan-3-yl)pyrazol-3-yl]cyclohexen-1-yl]methoxy]pyridine-4-carbaldehyde; and 2-(2-morpholin-4-ylethoxy)-5-[[2-(3-propan-2-ylimidazol-4-yl)cyclohexen-1-yl]methoxy]pyridine-4-carbaldehyde, or a tautomer, a stereoisomer, a mixture of stereoisomers, or a pharmaceutically acceptable salt thereof.

25. A compound according to claim 24, selected from the group consisting of cis-methyl 4-((2-formyl-3-hydroxyphenoxy)methyl)cyclohexanecarboxylate;

cis-4-((2-formyl-3-hydroxyphenoxy)methyl)cyclohexanecarboxylic acid;

(1R,3S)-3-((2-formyl-3-hydroxyphenoxy)methyl)cyclohexanecarboxylic acid;

trans-methyl 4-((2-formyl-3-hydroxyphenoxy)methyl)cyclohexanecarboxylate;

trans-4-((2-formyl-3-hydroxyphenoxy)methyl)cyclohexanecarboxylic acid;

methyl 3-((2-formyl-3-hydroxyphenoxy)methyl)cyclohexanecarboxylate;

trans-methyl 4-((2-formyl-3-methoxyphenoxy)methyl)cyclohexanecarboxylate;

2-hydroxy-6-((3,4,5,6-tetrahydro-[1,1'-biphenyl]-2-yl)methoxy)benzaldehyde;

2-hydroxy-6-((2-phenylcyclohexyl)methoxy)benzaldehyde; and 2-hydroxy-6-((2-(1-isopropyl-1H-pyrazol-5-yl)cyclohex-1-en-1-yl)methoxy)benzaldehyde, or a tautomer, a stereoisomer, a mixture of stereoisomers, or a pharmaceutically acceptable salt thereof.

26. A pharmaceutical composition comprising a compound of claim 1, a tautomer, a stereoisomer, a mixture of stereoisomers, or a pharmaceutically acceptable salt thereof.

\* \* \* \* \*

UNITED STATES PATENT AND TRADEMARK OFFICE
CERTIFICATE OF CORRECTION

PATENT NO. : 10,100,043 B2
APPLICATION NO. : 14/776723
DATED : October 16, 2018
INVENTOR(S) : Brian Metcalf et al.

It is certified that error appears in the above-identified patent and that said Letters Patent is hereby corrected as shown below:

In the Claims

In Claim 1, Column 316, Line 25, please replace "X is 0;" with --X is O;--.

In Claim 7, Column 317, Line 56, please replace "–(CH$_2$)kheteroaryl" with -- –(CH$_2$)$_k$heteroaryl--.

In Claim 7, Column 317, Line 60, please replace "–(CH$_2$)karyl" with -- –(CH$_2$)$_k$aryl--.

In Claim 24, Column 319, Line 64, please replace "cis-methyl4-((2-formyl-3-hydroxyphenoxy)" with --*cis*-methyl 4-((2-formyl-3-hydroxyphenoxy)--.

In Claim 24, Column 320, Line 3, please replace "trans-methyl4-((2-formyl-3-hydroxyphenoxy)" with --*trans*-methyl 4-((2-formyl-3-hydroxyphenoxy)--.

In Claim 24, Column 320, Line 7, please replace "methyl3-((2-formyl-3-hydroxyphenoxy)" with --methyl 3-((2-formyl-3-hydroxyphenoxy)--.

In Claim 24, Column 320, Line 9, please replace "trans-methyl4-((2-formyl-3-methoxyphenoxy)" with --*trans*-methyl 4-((2-formyl-3-methoxyphenoxy)--.

In Claim 24, Column 320, Line 28, please replace "2-hydroxy--[[2-(3-propan-2-ylimidazol-4-yl)" with --2-hydroxy-6-[[2-(3-propan-2-ylimidazol-4-yl)--.

In Claim 24, Column 320, Line 52, please replace "2-hydroxy-6-[[2-(2,2,2-trifluoroethyl)" with --2-hydroxy-6-[[2-[2-(2,2,2-trifluoroethyl)--.

In Claim 24, Column 320, Line 54, please replace "2-hydroxy-6-[[2-(oxetan-3-yl)" with --2-hydroxy-6-[[2-[2-(oxetan-3-yl)--.

In Claim 24, Column 320, Line 66, please replace "2-hydroxy-3-methyl-64[2-(2-propan-2-ylpyrazol- Signed and Sealed this
Twenty-seventh Day of December, 2022

Katherine Kelly Vidal
*Director of the United States Patent and Trademark Office*

3-yl)" with --2-hydroxy-3-methyl-6-[[2-(2-propan-2-ylpyrazol-3-yl)--.

In Claim 24, Column 322, Line 17, please replace "2-fluoro-6[[2-[2-(2,2,2-trifluoroethyl)" with --2-fluoro-6-[[2-[2-(2,2,2-trifluoroethyl)--.

In Claim 24, Column 322, Line 19, please replace "2-fluoro-6[[2-[2-(oxetan-3-yl)" with --2-fluoro-6-[[2-[2-(oxetan-3-yl)--.

In Claim 24, Column 322, Line 20, please replace "methoxyThenzaldehyde;" with --methoxy]benzaldehyde;--.

In Claim 24, Column 323, Line 9, please replace "2-hydroxy-6-[[2-(oxetan-3-yl)" with --2-hydroxy-6-[[2-[2-(oxetan-3-yl)--.

In Claim 24, Column 325, Line 60, please replace "6-methyl-3-[[242-(2,2,2-trifluoroethyl)" with --6-methyl-3-[[2-[2-(2,2,2-trifluoroethyl)--.

In Claim 24, Column 327, Line 5, please replace "3-[[2-(2,2-difluoroethyl)" with --3-[[2-[2-(2,2-difluoroethyl)--.

In Claim 24, Column 327, Line 40, please replace "methoxy]- 5-hydroxy" with --methoxy]-5-hydroxy--.

In Claim 24, Column 327, Line 60, please replace "3-hydroxy-5-[[2-(oxetan-3-yl)" with --3-hydroxy-5-[[2-[2-(oxetan-3-yl)--.

In Claim 24, Column 329, Line 11, please replace "2-hydroxy-5-[[2-[2-(2-propan-2-ylpyrazol-3-yl)" with --2-hydroxy-5-[[2-(2-propan-2-ylpyrazol-3-yl)--.

In Claim 24, Column 329, Line 36, please replace "2-methoxy-5-[[2-(2,2,2-trifluoroethyl)" with --2-methoxy-5-[[2-[2-(2,2,2-trifluoroethyl)--.

In Claim 24, Column 329, Line 50, please replace "5-[[2-(2,2-difluoroethyl)" with --5-[[2-[2-(2,2-difluoroethyl)--.

In Claim 24, Column 330, Line 19, please replace "2-(2-methoxyethoxy)-5-[[2-(oxetan-3-yl)" with --2-(2-methoxyethoxy)-5-[[2-[2-(oxetan-3-yl)--.

In Claim 24, Column 330, Line 45, please replace "2-(2-morpholin-4-ylethoxy)-54[2-(2-propylpyrazol-3-yl)" with --2-(2-morpholin-4-ylethoxy)-5-[[2-(2-propylpyrazol-3-yl)--.

In Claim 24, Column 330, Line 49, please replace "2-(2-morpholin-4-ylethoxy)-5-[[2-(2,2,2-trifluoroethyl)" with --2-(2-morpholin-4-ylethoxy)-5-[[2-[2-(2,2,2-trifluoroethyl)--.

In Claim 24, Column 330, Line 65, please replace "5-[[2-(2,2-difluoroethyl)" with --5-[[2-[2-(2,2-difluoroethyl)--.

In Claim 24, Column 331, Line 38, please replace "3-[[2-(2,2-difluoroethyl)" with --3-[[2-[2-(2,2-difluoroethyl)--.

In Claim 24, Column 331, Line 52, please replace "3-[[2-(2,2,2-trifluoroethyl)" with --3-[[2-[2-(2,2,2-trifluoroethyl)--.

In Claim 24, Column 332, Line 5, please replace "6-methyl-3-[[2-(2,2,2-trifluoroethyl)" with --6-methyl-3-[[2-[2-(2,2,2-trifluoroethyl)--.

In Claim 24, Column 332, Line 7, please replace "6-methyl-3-[[2-(oxetan-3-yl)" with --6-methyl-3-[[2-[2-(oxetan-3-yl)--.

In Claim 24, Column 332, Line 34, please replace "3-chloro-5-[[2-(oxetan-3-yl)" with --3-chloro-5-[[2-[2-(oxetan-3-yl)--.

In Claim 24, Column 332, Line 40, please replace "3-chloro-5-[[2[2-(2,2,2-trifluoroethyl)" with --3-chloro-5-[[2-[2-(2,2,2-trifluoroethyl)--.

In Claim 24, Column 332, Line 60, please replace "3-chloro-5-[[2-(3,3,3-trifluoropropyl)" with --3-chloro-5-[[2-[2-(3,3,3-trifluoropropyl)--.

In Claim 24, Column 333, Line 11, please replace "3-methyl-5-[[2-(oxetan-3-yl)" with --3-methyl-5-[[2-[2-(oxetan-3-yl)--.

In Claim 24, Column 333, Line 17, please replace "3-[[2-(2,2-difluoroethyl)" with --3-[[2-[2-(2,2-difluoroethyl)--.

In Claim 24, Column 333, Line 36, please replace "(3-propan-2-yhmidazol-4-yl)" with --(3-propan-2-ylimidazol-4-yl)--.

In Claim 24, Column 333, Line 48, please replace "(3-propan-2-yhmidazol-4-yl)" with --(3-propan-2-ylimidazol-4-yl)--.

In Claim 24, Column 334, Line 1, please replace "3-hydroxy-5-[[2-(2,2,2-trifluoroethyl)" with --3-hydroxy-5-[[2-[2-(2,2,2-trifluoroethyl)--.

In Claim 24, Column 335, Line 20, please replace "2-hydroxy-5-[[2-(2,2,2-trifluoroethyl)" with --2-hydroxy-5-[[2-[2-(2,2,2-trifluoroethyl)--.

In Claim 24, Column 335, Line 26, please replace "5-[[2-(2,2-difluoroethyl)" with --5-[[2-[2-(2,2-difluoroethyl)--.

In Claim 24, Column 336, Line 65, please replace "2-(2-morpholin-4-ylethoxy)-5[[2-[2-(2,2,2-trifluoroethyl)" with --2-(2-morpholin-4-ylethoxy)-5-[[2-[2-(2,2,2-trifluoroethyl)--.

In Claim 25, Column 338, Line 5, please replace "cis-methyl4-((2-formyl-3-hydroxyphenoxy)" with --*cis*-methyl 4-((2-formyl-3-hydroxyphenoxy)--.

In Claim 25, Column 338, Line 11, please replace "trans-methyl4-((2-formyl-3-hydroxyphenoxy)" with --*trans*-methyl 4-((2-formyl-3-hydroxyphenoxy)--.

In Claim 25, Column 338, Line 15, please replace "methyl3-((2-formyl-3-hydroxyphenoxy)" with --methyl 3-((2-formyl-3-hydroxyphenoxy)--.

In Claim 25, Column 338, Line 17, please replace "trans-methyl4-((2-formyl-3-methoxyphenoxy)" with --*trans*-methyl 4-((2-formyl-3-methoxyphenoxy)--.